US011008559B2

(12) United States Patent
Kolkman et al.

(10) Patent No.: US 11,008,559 B2
(45) Date of Patent: May 18, 2021

(54) METHODS OF MAKING *BACILLUS AKIBAI* SERINE PROTEASES

(71) Applicant: DANISCO US INC., Palo Alto, CA (US)

(72) Inventors: Marc Kolkman, Oegstgeest (NL); Rie Mejldal, Ostbirk (DK); Anja Hemmingsen Kellett Smith, Arhuc (DK); Lilia Maria Babe, Emerald Hills, CA (US); Richard R. Bott, Burlingame, CA (US)

(73) Assignee: DANISCO US INC, Palo Alto, CA (US)

( * ) Notice: Subject to any disclaimer, the term of this patent is extended or adjusted under 35 U.S.C. 154(b) by 0 days.

(21) Appl. No.: 15/984,464

(22) Filed: May 21, 2018

(65) Prior Publication Data
US 2018/0251743 A1 Sep. 6, 2018

Related U.S. Application Data

(63) Continuation of application No. 15/103,248, filed as application No. PCT/US2014/070097 on Dec. 12, 2014, now abandoned.

(60) Provisional application No. 61/915,745, filed on Dec. 13, 2013.

(51) Int. Cl.
 *C12N 9/54* (2006.01)
 *C11D 3/386* (2006.01)
 *C11D 11/00* (2006.01)

(52) U.S. Cl.
 CPC .............. *C12N 9/54* (2013.01); *C11D 3/386* (2013.01); *C11D 3/38681* (2013.01); *C11D 11/0017* (2013.01); *C12Y 304/21062* (2013.01); *C07K 2319/02* (2013.01)

(58) Field of Classification Search
 CPC ................... C12Y 304/21062; C12P 21/00
 USPC .................................. 435/212, 71.1
 See application file for complete search history.

(56) References Cited

U.S. PATENT DOCUMENTS

| 7,449,187 B2 | 11/2008 | Weber |
| 7,569,226 B2 | 8/2009 | Weber |

FOREIGN PATENT DOCUMENTS

| WO | 2003054185 A1 | 7/2003 |
| WO | 2003055974 A2 | 7/2003 |

OTHER PUBLICATIONS

English Abstract of WO2003054185. Publication Date: Jul. 3, 2003.
English Abstract of WO2003055974. Publication Date: Jul. 10, 2003.
International Search Report of International Application No. PCTUS2014070097, Publication No. WO2015089441.
International Preliminary Report International Application No. PCTUS2014070097, Publication No. WO2015089441.
Nielsen, P. et al. "Phenetic Diversity of Alkaliphilic Bacillus Strains: Proposal for Nine New Species," Microbiology, Society for General Microbiology, vol. 141, No. 7, Apr. 1, 1995.
Nogi, Y. "Characterization of alkaliphilic Bacillus strains used in industry: proposal of five novel species," International Journal of Systematic and Evolutionary Microbiology, vol. 55, No. 6, Nov. 1, 2005.
Yuki, Masahiro et al. "Draft Genome Sequences o Three Alkaliphilic Bacillus Strains, Bacillus wakoensis JCM 9140T, Bacillus akibai JCM 9157T, and Bacillus hemicellulosilyticus JCM 9152T," Genome Announements Journal, vol. 2, Issue 1. Jan./Feb. 2014.
NPL8_DatabaseGeneseq_ABR63645.
DatabaseGeneseq_ABR63734.
EBI Database Accession No. AYA40066, Jul. 8, 2010, *Bacillus* sp. Mature APRM serine protease protein, Seq ID 3, XP002790365.
EBI Database Accession No. DJ087558, Aug. 24, 2012, Alkaline keratinase and DNA code for them and method for using the same, XP002790366.
Extended European Search Report—EP Application No. 18212235.8—dated Apr. 5, 2019.

*Primary Examiner* — Sheridan Swope

(57) ABSTRACT

The present disclosure relates to serine proteases cloned from *Bacillus Akibai* and *Bacillus Clarkii*, and variants thereof. Compositions containing the serine proteases are suitable for use in cleaning fabrics and hard surfaces, as well as in a variety of industrial applications.

7 Claims, 25 Drawing Sheets

Specification includes a Sequence Listing.

BspAl02518

```
                                        1                                                50
              BspAI02518      (1) -AQSTPWGISRINAPAVHSTGNFGQGVRVAVLDSGVAS-HEDLRIAGGVS
                BspU02193    (1) -TQTVPWGINHVKAPTVHNWGNVGTGVKVAVLDTGIAS-HPDLRVSGGAS
      B_pseudofirmus_ADC49870 (1) -AQTVPWGIPYIYSDVVHRQGYFGNGVKVAVLDTGVAP-HPDLHIRGGVS
         Bacillus_sp_ADD64465 (1) -SQTVPWGISFISTQQAHNRGIFGNGARVAVLDTGIAS-HPDLRIAGGAS
         B_halodurans_BAB04574 (1) -SQTVPWGISFINTQQAHNRGIFGNGARVAVLDTGIAS-HPDLRIAGGAS
         Bacillus_sp_BAA05540 (1) -SQTVPWGISFINTQQAHNRGIFGNGARVAVLDTGIAS-HPDLRIAGGAS
            B_clausii_ABI26631 (1) -SQTVPWGISFINTQQAHNRGIFGNGARVAVLDTGIAS-HPDLRIAGGAS
           B_gibsonii_AGS78407 (1) -QQTVPWGITRVQAPAVHNRGITGSGVRVAILDSGISA-HSDLNIRGGAS
         Bacillus_sp_BAA25184 (1) -MQTVPWGINRVQAPIAQSRGFTGTGVRVAVLDTGISN-HADLRIRGGAS
            B_sp_Sendai_BAA06157 (1) -NQVTPWGITRVQAPTAWTRGYTGTGVRVAVLDTGIST-HPDLNIRGGVS
            B_subtilis_AAA87324 (1) -MQTVPWGINRVQAPIAQSRGFTGTGVRVAVLDTGISN-HADLRIRGGAS
            B_lehensis_AFK08970 (1) -MQTVPWGINRVQAPIAQSRGFTGTGVRVAVLDTGISN-HADLRIRGGAS
            B_clausii_BAD63300 (1) -AQSVPWGISRVQAPAAHNRGLTGSGVKVAVLDTGIST-HPDLNIRGGAS
              B_lentus_P29600 (1) -AQSVPWGISRVQAPAAHNRGLTGSGVKVAVLDTGIST-HPDLNIRGGAS
          B_alcalophilus_AAA22212 (1) -AQSVPGISRVQAPAAHNRGLTGSGVKVAVLDTGIST-HPDLNIRGGAS
         Bacillus_sp_sprC_AAC43580 (1) -AQTVPWGIPHIKADKAHAAGVTGSSGVKVAILDTGIDANHADLNVKGGAS
         Bacillus_sp_BAD21128 (1) -SQTVPYGVPHIKADVAHSQNVTGNGVKVAILDTGIDAAHEDLRVVGGAS
         Bacillus_sp_BAD11988 (1) -AQTTPWGVTHINAHRAHSSGVTGSGVKVAILDTGIHASHPDLNVRGGAS
         B_sp_sprD_AAC43581 (1) -AQTVPYGVPHIKADVAHAQNVTGSSGVKVAVLDTGIDASHEDLRVVGGAS
       B_sonorensis_WP_006636716 (1) -AQTVPYGIPLIKADKVQAQGYKGANVKVGIIDTGIASSHTDLKVVGGAS
         B_licheniformis_CAJ70731.1 (1) -AQTVPYGIPLIKADKVQAQGFKGANVKVAVLDTGIQASHPDLNVVGGAS
              B_pumilus_ADK11996 (1) -AQTVPYGIPQIKAPAVHAQGYKGANVKVAVLDTGIHAAHPDLNVAGGAS
           B_circulans_ADN04910 (1) -AQTVPYGIPQIKAFAVHAQGYKGANVKVAVLDTGIHAAHPDLNVAGGAS
      B_stratosphericus_WP_007497196 (1) -AQTVPYGIPQIKAPAVHAQGYKGANVKVAVLDTGIHAAHPDLNVAGGAS
           B_lehensis_AFP23380.1 (1) MAQTVPYGIPQIKAPAVHAQGYKGANVKVAVLDTGIHAAHPDLNVAGGAS
           B_atrophaeus_YP003972439 (1) -AQSVPYGISQIKAPAVHSQGYTGSNVKVAVIDSGIDSSHPDLKVSGGAS
        B_amyloliquefaciens_CAA24990 (1) -AQSVPYGVSQIKAPALHSQGYTGSNVKVAVIDSGIDSSHPDLKVAGGAS
        G_stearothermophilus_ABY25856 (1) -AQSVPYGVSQIKAPALHSQGFTGSNVKVAVIDSGIDSSHPDLKVAGGAS
       B_methylotrophicus_AGC81872.1 (1) -AQSVPYGVSQIKAPALHSQGFTGSNVKVAVIDSGIDSSHPDLKVAGGAS
         B_vallismortis_WP010329279 (1) -AQSVPYGISQIKAPALHSQGYTGSNVKVAVIDSGIDSSHPDLNVRGGAS
         B_subtilis_str168_CAA74536.1 (1) -AQSVPYGISQIKAPALHSQGYTGSNVKVAVIDSGIDSSHPDLNVRGGAS
             B_subtilis_BAN09118 (1) -AQSVPYGISQIKAPALHSQGYTGSNVKVAVIDSGIDSSHPDLNVRGGAS
         B_mojavensis_WP010333625 (1) -AQSVPYGISQIKAPALHSQGYTGSNVKVAVIDSGIDSSHPDLNVRGGAS
         B_marmarensis_ERN52602.1 (1) -AQTVPWGIPYIYSDVVHRQGYFGNGVKVAVLDTGVAP-HPDLHIRGGVS
                        Consensus (1)  AQTVPWGIS IKAPAVHSQGYTGSGVKVAVLDTGIASSHPDL V GGAS
```

FIG. 7A

```
                                    51                                                        100
              BspAI02518       (49) FVASEP-SYQDYNGHGTHVAGTIAGLNNSVGVLGVAPSVQLYAVKVLDRN
              BspU02193        (49) FIPSEP-TIQDFNGHGTHVAGTVAALNNSIGVLGVAPNVQLYGVKVLDRN
       B_pseudofirmus_ADC49870 (49) FISTEN-TYVDYNGHGTHVAGTVAALNNSYGVLGVAPGAELYAVKVLDRN
         Bacillus_sp_ADD64465  (49) FISSEP-SYHDNNGHGTHVAGTIAALNNSIGVLGVAPSADLYAVKVLDRN
         B_halodurans_BAB04574 (49) FISSEP-SYHDNNGHGTHVAGTIAALNNSIGVLGVAPSADLYAVKVLDRN
         Bacillus_sp_BAA05540  (49) FISSEP-SYHDNNGHGTHVAGTIAALNNSIGVLGVAPSADLYAVKVLDRN
           B_clausii_ABI26631  (49) FISSEP-SYHDNNGHGTHVAGTIAALNNSIGVLGVAPSADLYAVKVLDRN
           B_gibsonii_AGS78407 (49) FVPGEP-TTADLNGHGTHVAGTVAALNNSIGVIGVAPNAELYAVKVLGAN
         Bacillus_sp_BAA25184  (49) FVPGEP-NISDGNGHGTHVAGTIAALNNSIGVLGVAPNVDLYGVKVLGAS
           B_sp_Sendai_BAA06157 (49) FVPGEP-SYQDGNGHGTHVAGTIAALNNSIGVVGVAPNAELYAVKVLGAN
           B_subtilis_AAA87324 (49) FVPGEP-NISDGNGHGTQVAGTIAALNNSIGVLGVAPNVDLYGVKVLGAS
           B_lehensis_AFK08970 (49) FVPGEP-NISDGNGHGTHVAGTIAALNNSIGVIGVAPNVDLYGVKVLGAS
           B_clausii_BAD63300  (49) FVPGEP-STQDGNGHGTHVAGTIAALNNSIGVLGVAPSAELYAVKVLGAS
             B_lentus_P29600   (49) FVPGEP-STQDGNGHGTHVAGTIAALNNSIGVLGVAPSAELYAVKVLGAS
         B_alcalophilus_AAA22212 (49) FVPGEP-STQDGNGHGTHVAGTIAALNNSIGVLGVAPNAELYAVKVLGAS
       Bacillus_sp_sprC_AAC43580 (50) FVSGEPNALQDGNGHGTHVAGTVAALNNTTGVLGVAYNADLYAVKVLSAS
         Bacillus_sp_BAD21128  (50) FVAGEPNALQDGNGHGTHVAGTVAALNNQVGVLGVAYDVDLYAVKVLGAD
         Bacillus_sp_BAD11988  (50) FISGESNPYIDSNGHGTHVAGTVAALNNTVGVLGVAYNAELYAVKVLSAS
             B_sp_sprD_AAC43581 (50) FVSEEPDALTDGNGHGTHVAGTIAALNNNVGVLGVSYDVDLYAVKVLSAG
         B_sonorensis_WP_006636716 (50) FVSGES-YNTDGNGHGTHVAGTVAALDNTTGVLGVAPNVSLYAIKVLNSS
         B_licheniformis_CAJ70731.1 (50) FVAGEA-YNTDGNGHGTHVAGTVAALDNTTGVLGVAPSVSLYAVKVLNSS
             B_pumilus_ADK11996 (50) FVPSEPNATQDFQSHGTHVAGTIAALDNTIGVLGVAPSASLYAVKVLDRN
           B_circulans_ADN04910 (50) FVPSEPNATQDFQSHGTHVAGTIAALDNTIGVLGVAPSASLYAVKVLDRN
       B_stratosphericus_WP_007497196 (50) FVPSEPNATQDFQSHGTHVAGTIAALDNTIGVLGVAPSASLYAVKVLDRN
           B_lehensis_AFP23380.1 (51) FVPSEPNATQDFQSHGTHVAGTIAALDNTIGVLGVAPSASLYAVKVLDRY
         B_atrophaeus_YP003972439 (50) FVPSEPNPFQDGNSHGTHVAGTVAALNNSVGVLGVAPSASLYAVKVLSSS
       B_amyloliquefaciens_CAA24990 (50) MVPSETNPFQDNNSHGTHVAGTVAALNNSIGVLGVAPSASLYAVKVLGAD
       G_stearothermophilus_ABY25856 (50) MVPSETNPFQDNNSHGTHVAGTVAALNNSVGVLGVAPSASLYAVKVLGAD
       B_methylotrophicus_AGC81872.1 (50) MVPSETNPFQDRNSHGTHVAGTVAALNNSVGVLGVAPSASLYAVKVLGAD
       B_vallismortis_WP010329279 (50) FVPSETNPYQDGSSHGTHVAGTVAALNNSIGVLGVAPNASLYAVKVLDST
       B_subtilis_str168_CAA74536.1 (50) FVPSETNPYQDGSSHGTHVAGTIAALNNSIGVLGVSPSASLYAVKVLDST
             B_subtilis_BAN09118 (50) FVPSETNPYQDGSSHGTHVAGTVAALNNTIGVLGVAPSASLYAVKVLDST
         B_mojavensis_WP010333625 (50) FVPSETNPYQDGSSHGTHVAGTVAALNNTIGVLGVAPSASLYAVKVLDST
         B_marmarensis_ERN52602.1 (49) FIPTEN-TYVDYNGHGTHVAGTVAALNNSYGVLGVAPGAELYAVKVLDRN
                      Consensus (51) FVPSEP YQDGNGHGTHVAGTIAALNNSIGVLGVAPSADLYAVKVL A
```

FIG. 7B

```
                                          101                                           150
              BspAI02518   (98)  GGGNHSDIARGIEWSVNNGMHVVNMSLGGPTGSTTLQRAADNAYNRGVLL
              BspU02193    (98)  GGGSHSAIAQGIEWSISNGMDVVNMSLGGATSSTALSQAVANASNRGILL
     B_pseudofirmus_ADC49870 (98) GSGSHASIAQGIEWAMNNGMDIANMSLGPSGSTTLQLAADRARNAGVLL
         Bacillus_sp_ADD64465 (98) GSGSLASVAQGIEWAINNNMHIINMSLGSTSGSSTLELAVNRGNNAGILL
         B_halodurans_BAB04574 (98) GSGSLASVAQGIEWAINNNMHIINMSLGSTSGSSTLELAVNRANNAGILL
         Bacillus_sp_BAA05540 (98) GSGSLASVAQGIEWAINNNMHIINMSLGSTSGSSTLELAVNRANNAGILL
             B_clausii_ABI26631 (98) GSGSLASVAQGIEWAINNNMHIINMSLGSTSGSSTLELAVNRANNAGILL
             B_gibsonii_AGS78407 (98) GSGSVSGIAQGLEWAATNNMHIANMSLGSDFPSSTLERAVNYATSRDVLV
         Bacillus_sp_BAA25184 (98) GSGSISGIAQGLQWAANNGMHIANMSLGSSAGSATMEQAVNQATASGVLV
           B_sp_Sendai_BAA06157 (98) GSGSVSSIAQGLQWTAQNNIHVANLSLGSPVGSQTLELAVNQATNAGVLV
            B_subtilis_AAA87324 (98) GSGSISGIAQGLQWAANNGMHIANMSLGSSAGSATMEQAVNQATASGVLV
            B_lehensis_AFK08970 (98) GCGSISGIAQGLQWAANNGMHIANMSLGSSAGSATMEQAVNQATASGVLV
             B_clausii_BAD63300 (98) GSGSVSSIAQGLEWAGNNGMHVANLSLGSPSPSATLEQAVNSATSRGVLV
              B_lentus_P29600   (98) GSGSVSSIAQGLEWAGNNGMHVANLSLGSPSPSATLEQAVNSATSRGVLV
        B_alcalophilus_AAA22212 (98) GSGSVSSIAQGLEWAGNNGMHVANLSLGSPSPSATLEQAVNSATSRGVLV
    Bacillus_sp_sprC_AAC43580 (100) GSGTLSGIAQGIEWSISNGMNVINMSLGGSSGSTALQQACNNAYNRGIVV
         Bacillus_sp_BAD21128 (100) GSGTLSGIAQGIEWSIANNMDVINMSLGGSTGSTTLKQAADNAYNSGLVV
         Bacillus_sp_BAD11988 (100) GSGTLSGIAQGVEWSIANKMDVINMSLGGSSGSTALQRAVDNAYRNNIVV
             B_sp_sprD_AAC43581 (100) GSGTLAGIAQGIEWAIDNNMDVINMSLGGSTGSTTLKQASDNAYNSGIVV
     B_sonorensis_WP_006636716 (99) GSGTYSAIVSGIEWATQNGLDVINMSLGGPSGSTALKQAVDKAYASGIVV
     B_licheniformis_CAJ70731.1 (99) GSGSYSGIVSGIEWATTNGMDVINMSLGGASGSTAMKQAVDNAYARGVVV
              B_pumilus_ADK11996 (100) GDGQYSWIISGIEWAVANNNMDVINMSLGGASGSTALKNAVDTANNRGVVV
             B_circulans_ADN04910 (100) GDGQYSWIISGIEWAVANNNMDVINMSLGGPNGSTALKNAVDTANNRGVVV
     B_stratosphericus_WP_007497196 (100) GDGQYSWIISGIEWAVANNNMDVINMSLGGPSGSTALKNAVDTANNRGVVV
            B_lehensis_AFP23380.1 (101) GDGQYSWIISGIEWAVANNNMDVINMSLGGPNGSTALKNAVDTANNRGVVV
          B_atrophaeus_YP003972439 (100) GSGDYSWIINGIEWAISNNMDVINMSLGGPQGSTALKAVVDKAVSQGIVV
     B_amyloliquefaciens_CAA24990 (100) GSGQYSWIINGIEWAIANNMDVINMSLGGPSGSAALKAAVDKAVASGVVV
     G_stearothermophilus_ABY25856 (100) GSGQYSWIINGIEWAIAYNMDVINMSLGGPSGSAALKAAVDKAVASGIVV
     B_methylotrophicus_AGC81872.1 (100) GSGQYSWIINGIEWAIANNMDVINMSLGGPSGSAALKAAVDKAVASGVVV
        B_vallismortis_WP010329279 (100) GNGQYSWIINGIEWAISNKMDVINMSLGGPSGSTALKSVVDRAVASGIVV
      B_subtilis_str168_CAA74536.1 (100) GSGQYSWIINGIEWAISNNMDVINMSLGGPTGSTALKTVVDKAVSSGIVV
              B_subtilis_BAN09118 (100) GSGQYSWIINGIEWAISNNMDVINMSLGGPTGSTALKTVVDKAVASGIVV
        B_mojavensis_WP010333625 (100) GSGQYSWIINGIEWAISNNMDVINMSLGGPTGSTALKTVVDKAVASGIVV
        B_marmarensis_ERN52602.1 (98)  GSGSHASIAQGIEWAMNNGMDIANMSLGSPSGSTTLQLAADRARNAGVLL
                     Consensus  (101) GSGSYS IAQGIEWAI NNMDVINMSLGGPSGSTTL  AVD A ASGVVV
```

FIG. 7C

```
                                            151                                               200
                    BspAI02518   (148)   IAAAGNTG-TSG----VSFPARYSSVMAVAATDSNNNRASFSTYGSQIEI
                    BspU02193    (148)   IAASGNTG------RAGIQFPARYSQVMAVGAVDQNNRLASFSTFGNEQEI
           B_pseudofirmus_ADC49870 (148) IGAAGNSG-QQGGSNNMGYPARYASVMAVGAVDQNGNRANFSSYGSELEI
                 Bacillus_sp_ADD64465 (148) VGAAGNTG-RQG----VNYPARYSGVMAVAAVDQNGQRASFSTYGPEIEI
                B_halodurans_BAB04574 (148) VGAAGNTG------RQGVNYPARYSGVMAVAAVDQNGQRASFSTYGPEIEI
                 Bacillus_sp_BAA05540 (148) VGAAGNTG-RQG----VNYPARYSGVMAVAAVDQNGQRASFSTYGPEIEI
                    B_clausii_ABI26631 (148) VGAAGNTG-RQG-----VNYPARYSGVMAAAVDQNGQRASFSTYGPEIEI
                    B_gibsonii_AGS78407 (148) IAATGNNG------SGSVGYPARYANAMAVGATDQNNRRANFSQYGTGIDI
                 Bacillus_sp_BAA25184 (148) VAASGNSG-AGN----VGFPARYANAMAVGATDQNNNRASFSQYGAGLDI
                B_sp_Sendai_BAA06157 (148) VAATGNNG-SGT-----VSYPARYANALAVGATDQNNNRASFSQYGTGLNI
                B_subtilis_AAA87324 (148) VAASGNSG-AGN----VGFPARYANAMAVGATDQNNNRATFSQYGAGLDI
                B_lehensis_AFK08970 (148) VAASGNSG-AGN----VGFPARYANAMAVGATDQNNNRASFSQYGAGLDI
                B_clausii_BAD63300 (148) VAASGNSG-AGS-----ISYPARYANAMAVGATDQNNNRASFSQYGAGLDI
                    B_lentus_P29600 (148) VAASGNSG-AGS-----ISYPARYANAMAVGATDQNNNRASFSQYGAGLDI
             B_alcalophilus_AAA22212 (148) VAASGNSG-AGS-----ISYPARYANAMAVGATDQNNNRASFSQYGAGLDI
           Bacillus_sp_sprC_AAC43580 (150) IAAAGNSG-SSGNRNTMGYPARYSSVIAVGAVSSNNTRASFSSVGSELEV
                 Bacillus_sp_BAD21128 (150) VAAAGNSGDFFGLINTIGYPARYDSVIAVGAVDSNNRRASFSSVGSQLEV
                 Bacillus_sp_BAD11988 (150) VAAAGNSG-AQGNRNTIGYPARYSSVIAVGAVDSNNNRASFSSVGSELEV
                    B_sp_sprD_AAC43581 (150) IAAAGNSGSVLGLVNTIGYPARYDSVIAVGAVDSNNNRASFSSVGSQLEV
           B_sonorensis_WP_006636716 (149) VAAAGNSG-SSGSQNTIGYPAKYDSVIAVGAVDSNKNRASFSSVGSELEV
           B_licheniformis_CAJ70731.1 (149) VAAAGNSG-SSGNTNTIGYPAKYDSVIAVGAVDSNSNRASFSSVGAELEV
                    B_pumilus_ADK11996 (150) VAAAGNSG-SSGSRSTVGYPAKYESTIAVANVNSNNVRNSSSSAGPELDV
                 B_circulans_ADN04910 (150) VAAAGNSG-STGSTSTVGYPAKYDSTIAVANVNSNNVRNSSSSAGPELDV
         B_stratosphericus_WP_007497196 (150) VAAAGNSG-STGSTSTVGYPAKYDSTIAVANVNSNNVRNSSSSAGPELDV
              B_lehensis_AFP23380.1 (151) VAAAGNSG-STGSTSTVGYPAKYDSTIAVANVNSNNVRNSSSSAGPELDV
              B_atrophaeus_YP003972439 (150) VAAAGNSG-SSGSTSTVGYPAKYPSVIAVGAVDSNNQRASFSSAGSELDV
         B_amyloliquefaciens_CAA24990 (150) VAAAGNEG-TSGSSSTVGYPGKYPSVIAVGAVDSSNQRASFSSVGPELDV
         G_stearothermophilus_ABY25856 (150) VAAAGNEG-TSGSSSTVGYPGKYPSVIAVGAVNSSNQRASFSSVGSELDV
         B_methylotrophicus_AGC81872.1 (150) VAAAGNEG-TSGSSSTVGYPGKYPSVIAVGAVNSSNQRASFSSVGSELDV
           B_vallismortis_WP010329279 (150) VAAAGNEG-TSGSSSTIGYPAKYPSTIAVGAVNSSNQRGSFSSVGPELDV
           B_subtilis_str168_CAA74536.1 (150) AAAAGNEG-SSGSTSTVGYPAKYPSTIAVGAVNSSNQRASFSSAGSELDV
                 B_subtilis_BAN09118 (150) VAAAGNEG-SSGSTSTVGYPAKYPSTIAVGAVNSSNQRASFSSAGSELDV
              B_mojavensis_WP010333625 (150) VAAAGNEG-SSGSTSTVGYPAKYPSTIAVGAVNSSNQRASFSSAGSELDV
           B_marmarensis_ERN52602.1 (148) IGAAGNSG-QQGGSNNMGYPARYASVMAVGAVDQNGNRANFSSYGSELEI
                         Consensus (151) VAAAGNSG S G   TVGYPARYASVIAVGAVDSNNNRASFSS GSELDV
```

FIG. 7D

```
                                            201                                              250
            BspAI02518    (193) SAPGVGINSTYPTNGYSSLNGTSMASPHVAGVAALVKARYPSATNAQIRQ
              BspU02193   (193) VAPGVGIQSTYLNNGYSSLNGTSMAAPHVAGVAALVMSEYPWATAPQVRG
    B_pseudofirmus_ADC49870 (197) MAPGVNINSTYLNNGYRSLNGTSMASPHVAGVAALVKQKHPHLTAAQIRN
       Bacillus_sp_ADD64465 (193) SAPGVNVYSTYTGNRYVSLSGTSMAAPHVAGTAALVKSRYPSYTNNQIRQ
         B_halodurans_BAB04574 (193) SAPGVNVNSTYTGNRYVSLSGTSMATPHVAGVAALVKSRYPSYTNNQIRQ
          Bacillus_sp_BAA05540 (193) SAPGVNVNSTYTGNRYVSLSGTSMATPHVAGVAALVKSRYPSYTNNQIRQ
              B_clausii_ABI26631 (193) SAPGVNINSTYTGNRYESLSGTSMATPHVAGVAALVKSRYPSYTNNQIRQ
            B_gibsonii_AGS78407 (193) VAPGVNVQSTYPGNRYVSMNGTSMATPHVAGAAALVKQRYPSWNATQIRN
          Bacillus_sp_BAA25184 (193) VAPGVGVQSTVPGNGYSSFNGTSMATPHVAGVAALVKQKNPSWSNVQIRN
             B_sp_Sendai_BAA06157 (193) VAPGVGIQSTYPGNRYASLSGTSMATPHVAGVAALVKQKNPSWSNTQIRQ
             B_subtilis_AAA87324 (193) VAPGVGVQSTVPGNGYASFNGTSMATPHVAGVAALVKQKNPSWSNVQIRN
              B_lehensis_AFK08970 (193) VAPGVGVQSTVPGNGYASFNGTSMATPHVAGVAALVKQKNPSWSNVQIRN
             B_clausii_BAD63300 (193) VAPGVNVQSTYPGSTYASLNGTSMATPHVAGVAALVKQKNPSWSNVQIRN
                B_lentus_P29600 (193) VAPGVNVQSTYPGSTYASLNGTSMATPHVAGAAALVKQKNPSWSNVQIRN
         B_alcalophilus_AAA22212 (193) VAPGVNVQSTYPGSTYASLNGTSMATPHVAGAAALVKQKNPSWSNVQIRN
          Bacillus_sp_sprC_AAC43580 (199) MAPGVNILSTTPGNNYASFNGTSMAAPHVAGAAALIKAKYPSMTNVQIRE
            Bacillus_sp_BAD21128 (200) MAPGVNILSTLPGNSYGSLNGTSMASPHVAGAAALLLAQDPTLTNVQVRE
            Bacillus_sp_BAD11988 (199) MAPGVSILSTVPGSSYASYNGTSMASPHVAGAAALLKAKYPNWSAAQIRN
               B_sp_sprD_AAC43581 (200) MAPGVAINSTLPGNQYGELNGTSMASPHVAGAAALLLAQNPNLTNVQVRE
          B_sonorensis_WP_006636716 (198) MAPGVSVYSTYPSNTYTSLNGTSMASPHVAGAAALILSKYPTLSASQVRN
         B_licheniformis_CAJ70731.1 (198) MAPGAGVYSTYPTNTYATLNGTSMASPHVAGAAALILSKHPNLSASQVRN
              B_pumilus_ADK11996 (199) SAPGTSILSTVPSSGYTSYTGTSMASPHVAGAAALILSKNPNLTNSQVRQ
             B_circulans_ADN04910 (199) SAPGTSILSTVPSRGYTSYTGTSMASPHVAGAAALILSKNPNLSNSQVRQ
       B_stratosphericus_WP_007497196 (199) SAPGTSILSTVPSSGYTSYTGTSMASPHVAGAAALILSKYPNLSTSQVRQ
              B_lehensis_AFP23380.1 (200) SAPGTSILSTVPSSGYTSYTGTSMASPHVAGAAALILSKYPNLSTSQVRQ
           B_atrophaeus_YP003972439 (199) MAPGVSIQSTLPGSSYGSYNGTSMASPHVAGAAALVLSKHPNWTNSQVRN
      B_amyloliquefaciens_CAA24990 (199) MAPGVSIQSTLPGNKYGAYNGTSMASPHVAGAAALILSKHPNWTNTQVRS
     G_stearothermophilus_ABY25856 (199) MAPGVSIQSTLPGNKYGAYNGTSMASPHVAGAAALILSKHPNWTNTQVRS
       B_methylotrophicus_AGC81872.1 (199) MAPGVSIQSTLPGNKYGAYNGTSMASPHVAGAAALILSKHPNWTNTQVRS
          B_vallismortis_WP010329279 (199) MAPGVSIQSTLPGGTYGSYNGTSMATPHVAGAAALILSKHPTWTNTQVRN
         B_subtilis_str168_CAA74536.1 (199) MAPGVSIQSTLPGGTYGSYNGTSMATPHVAGAAALILSKHPTWTNAQVRD
              B_subtilis_BAN09118 (199) MAPGVSIQSTLPGGTYGSYNGTSMATPHVAGAAALILSKHPTWSNAQVRD
         B_mojavensis_WP010333625 (199) MAPGVSIQSTLPGGTYGAYNGTSMATPHVAGAAALILSKHPTWTNAQVRD
            B_marmarensis_ERN52602.1 (197) MAPGVNINSTYLNNGYRSLNGTSMASPHVAGVAALVKQKHPHLTAAQIRN
                     Consensus (201) MAPGV IQSTLPGN YGSYNGTSMASPHVAGAAALVKSKYPSWTN QIRN
```

FIG. 7E

```
                                                    251                  277
                        BspAI02518   (243)  HLRSTSTYLGNSTYYGSGLVDAQRATN  (SEQ ID NO:3)
                         BspU02193   (243)  RLNDTAIPLGNAYYFGNGLVDASRAAY  (SEQ ID NO:6)
            B_pseudofirmus_ADC49870  (247)  RMNQTAIPLGNSTYYGNGLVDAEYAAQ  (SEQ ID NO:49)
                 Bacillus_sp_ADD64465 (243)  RINQTATYLGSSNLYGNGLVHAGRATQ  (SEQ ID NO:50)
                  B_halodurans_BAB04574 (243) RINQTATYLGSPSLYGNGLVHAGRATQ  (SEQ ID NO:51)
                  Bacillus_sp_BAA05540 (243) RINQTATYLGSPSLYGNGLVHAGRATQ  (SEQ ID NO:52)
                    B_clausii_ABI26631 (243) RINQTATYLGSPSLYGNGLVHAGRATQ  (SEQ ID NO:53)
                    B_gibsonii_AGS78407 (243) HLKNTATNLGNSSQFGSGLVNAEAATR  (SEQ ID NO:54)
                  Bacillus_sp_BAA25184 (243) HLKNTATNLGNTNQFGSGLVNAEAATR  (SEQ ID NO:55)
                   B_sp_Sendai_BAA06157 (243) HLTSTATSLGNSNQFGSGLVNAEAATR  (SEQ ID NO:56)
                    B_subtilis_AAA87324 (243) HLKNTATNLGNTTQFGSGLVNAEAATR  (SEQ ID NO:57)
                    B_lehensis_AFK08970 (243) HLKNTATNLGNTTQFGSGLVNAEAATR  (SEQ ID NO:58)
                    B_clausii_BAD63300  (243) HLKNTATGLGNTNLYGSGLVNAEAATR  (SEQ ID NO:59)
                      B_lentus_P29600  (243) HLKNTATSTNLYGSGLVNAEAATR     (SEQ ID NO:60)
                B_alcalophilus_AAA22212 (243) HLKNTATSLGSTNLYGSGLVNAEAATR  (SEQ ID NO:61)
              Bacillus_sp_sprC_AAC43580 (249) RLKNTATNLGDPFFYGKGVINVESALQ  (SEQ ID NO:62)
                  Bacillus_sp_BAD21128 (250) ILRDTATNLGSSFYYGNGVIDVEKALQ  (SEQ ID NO:63)
                  Bacillus_sp_BAD11988 (249) KLNSTTTYLGSSFYYGNGVINVERALQ  (SEQ ID NO:64)
                   B_sp_sprD_AAC43581  (250) RLRDTATNLGSAFNYGHGVINLERALQ  (SEQ ID NO:65)
                B_sonorensis_WP_006636716 (248) RLSSTATNLGDSFYYGKGLINVEAAAQ (SEQ ID NO:66)
              B_licheniformis_CAJ70731.1 (248) RLSSTATYLGSSFYYGKGLINVEAAAQ (SEQ ID NO:67)
                     B_pumilus_ADK11996 (249) RLENTATPLGDSFYYGKGLINVQAASN  (SEQ ID NO:68)
                    B_circulans_ADN04910 (249) RLENTATPLGNSFYYGKGLINVQAASN (SEQ ID NO:69)
             B_stratosphericus_WP_007497196 (249) RLENTATPLGNSFYYGKGLINVQAASN (SEQ ID NO:70)
                   B_lehensis_AFP23380.1 (250) RLENTATPLGNSFYYGKGLINVQAASN (SEQ ID NO:71)
                 B_atrophaeus_YP003972439 (249) SLESTATNLGNSFYYGKGLINVQAAAQ (SEQ ID NO:72)
             B_amyloliquefaciens_CAA24990 (249) SLENTTTKLGDSFYYGKGLINVQAAAQ (SEQ ID NO:73)
             G_stearothermophilus_ABY25856 (249) SLENTTTKLGDAFYYGKGLINVQAAAQ (SEQ ID NO:74)
             B_methylotrophicus_AGC81872.1 (249) SLENTTTKLGDAFYYGKGLINVQAAAQ (SEQ ID NO:75)
                B_vallismortis_WP010329279 (249) RLESTTTYLGSSFYYGKGLINVQAAAQ (SEQ ID NO:76)
               B_subtilis_str168_CAA74536.1 (249) RLESTATYLGNSFYYGKGLINVQAAAQ (SEQ ID NO:77)
                      B_subtilis_BAN09118 (249) RLESTATNLGSSFYYGKGLINVQAAAQ (SEQ ID NO:78)
                B_mojavensis_WP010333625 (249) RLESTATYLGSSFYYGKGLINVQAAAQ (SEQ ID NO:79)
                 B_marmarensis_ERN52602.1 (247) RMNQTAIPLGNSTYYGNGLVDAEYAAQ (SEQ ID NO:80)
                               Consensus (251) RL NTAT LG SFYYG GLINV AATQ  (SEQ ID NO:81)
```

FIG. 7F

```
                              1                                                50
SWT66_254731                  SQTVPWGINRVQAPTVHSWGARGNGVRVAVLDTGI-ASHEDLRISGGASF
Bcl04009                      SQTIPWGINRVQAPTVHSWGARGNGVRVAVLDTGI-ASHEDLRISGGASF
Bakn00315                     SQTVPWGINHIQAPTVHSWGNRGNGVRVAVLDSGV-ASHEDLRISGGRSF
BspAI02518                    AQSTPWGISRINAPAVHSTGNFQGVRVAVLDSGV-ASHEDLRIAGGVSF
BspU02193                     TQTVPWGINHVKAPTVHNWGNVGTGVKVAVLDTGI-ASHPDLRVSGGASF
B_pseudofirmus_ADC49870       AQTVPWGIPYIYSDVVHRQGYFGNGVKVAVLDTGV-APHPDLHIRGGVSF
B_lentus_P29600               AQSVPWGISRVQAPAAHNRGLTGSGVKVAVLDTGI-STHPDLNIRGGASF
B_amyloliquefaciens_CAA24990  AQSVPYGVSQIKAPALHSQGYTGSNVKVAVIDSGIDSSHPDLKVAGGASM
B_licheniformis_CAJ70731.1    AQTVPYGIPLIKADKVQAQGFKGANVKVAVLDTGIQASHPDLNVVGGASF
Bacillus_sp_sprC_AAC43580     AQTVPWGIPHIKADKAHAAGVTGSGVKVAILDTGIDANHADLNVKGGASF
                              :*: *:*:   : :    :  *   * .*:**::*:*:   * **.: ** *:

Consensus  (1) AQTVPWGI  I AP VHS G  G GVKVAVLDTGIAS HPDLRI GGASF 51                                               100
SWT66_254731                  ISSEPSY-NDLNGHGTHVAGTIAARDNSYGVLGVAPNVNLYAVKVLDRNG
Bcl04009                      ISSEPSY-NDLNGHGTHVAGTIAARDNSYGVLGVAPNVDLYAVKVLDRNG
Bakn00315                     ITSEPSY-QDYNGHGTHVAGTIAGLNNSYGVLGVAPNVNLYAVKVLDRNG
BspAI02518                    VASEPSY-QDYNGHGTHVAGTIAGLNNSVGVLGVAPSVQLYAVKVLDRNG
BspU02193                     IPSEPTI-QDFNGHGTHVAGTVAALNNSIGVLGVAPNVQLYGVKVLDRNG
B_pseudofirmus_ADC49870       ISTENTY-VDYNGHGTHVAGTVAALNNSYGVLGVAPGAELYAVKVLDRNG
B_lentus_P29600               VPGEPST-QDGNGHGTHVAGTIAALNNSIGVLGVAPSAELYAVKVLGASG
B_amyloliquefaciens_CAA24990  VPSETNPFQDNNSHGTHVAGTVAALNNSIGVLGVAPSASLYAVKVLGADG
B_licheniformis_CAJ70731.1    VAGEAYN-TDGNGHGTHVAGTVAALDNTTGVLGVAPSVSLYAVKVLNSSG
Bacillus_sp_sprC_AAC43580     VSGEPNALQDGNGHGTHVAGTVAALNNTTGVLGVAYNADLYAVKVLSASG
                              :. *        * *.********:*. :*: ****** ...**.****. .*

Consensus  (51)    SEP SYQD NGHGTHVAGT AALNNS GVLGVAPNV LYAVKVLDRNG 101                                              150
SWT66_254731                  SGSLSGIARGIEWAITNNMDIVNMSLGGSTGSTALRQAADNAYNRGILLV
Bcl04009                      SGSLSGIARGIEWAITNNMDIVNMSLGGSTGSTALRQAADNAYNRGILLV
Bakn00315                     SGSHSAIAQGIEWSVSNGMHIVNMSLGGPTGSTTLQRAADNAYNRGVLLI
BspAI02518                    GGNHSDIARGIEWSVNNGMHVVNMSLGGPTGSTTLQRAADNAYNRGVLLI
BspU02193                     GGSHSAIAQGIEWSISNGMDVVNMSLGGATSSTALSQAVANASNRGILLI
B_pseudofirmus_ADC49870       SGSHASIAQGIEWAMNNGMDIANMSLGSPSGSTTLQLAADRARNAGVLLI
B_lentus_P29600               SGSVSSIAQGLEWAGNNGMHVANLSLGSPSPSATLEQAVNSATSRGVLVV
B_amyloliquefaciens_CAA24990  SGQYSWIINGIEWAIANNMDVINMSLGGPSGSAALKAAVDKAVASGVVVV
B_licheniformis_CAJ70731.1    SGSYSGIVSGIEWATTNGMDVINMSLGGASGSTAMKQAVDNAYARGVVVV
Bacillus_sp_sprC_AAC43580     SGTLSGIAQGIEWSISNGMNVINMSLGGSSGSTALQQACNNAYNRGIVVI
                              .*   :   *  *:**:  *.*.: *:***...: *::: *   *   *::::

Consensus (101) SGS S IAQGIEWAI NGMDVVNMSLGGP GSTAL QAADNAYNRGVLL
```

FIG. 9A

```
                                      151                                                 200
SWT66_254731                          AAAGNTGSAG-----ISFPARYNSVMAVGATDSNNNRASFSTFGNELEIMA
Bcl04009                              AAAGNTGSAG-----ISFPARYNSVMAVGATDSNNNRASFSTFGNELEIMA
Bakn00315                             AAAGNTGSAG-----ISYPARYNSVMAVGAVDSNNNRASFSTFGNELEIMA
BspAI02518                            AAAGNTGTSG-----VSFPARYSSVMAVAATDSNNNRASFSTYGSQIEISA
BspU02193                             AASGNTGRAG-----IQFPARYSQVMAVGAVDQNNRLASFSTFGNEQEIVA
B_pseudofirmus_ADC49870               GAAGNSGQQGGSNNMGYPARYASVMAVGAVDQNGNRANFSSYGSELEIMA
B_lentus_P29600                       AASGNSGAGS-----ISYPARYANAMAVGATDQNNNRASFSQYGAGLDIVA
B_amyloliquefaciens_CAA24990          AAAGNEGTSGSSSTVGYPGKYPSVIAVGAVDSSNQRASFSSVGPELDVMA
B_licheniformis_CAJ70731.1            AAAGNSGSSGNTNTIGYPAKYDSVIAVGAVDSNSNRASFSSVGAELEVMA
Bacillus_sp_sprC_AAC43580             AAAGNSGSSGNRNTMGYPARYSSVIAVGAVSSNNTRASFSSVGSELEVMA
                                      .*:** *   .    :  :*.:*  ..::**.*.....  *.**   *   :: *
                     Consensus (151)  AAAGNTGS G     ISYPARY SVMAVGAVDSNNNRASFST G ELEIMA 201                                                 250
SWT66_254731                          PGVSVLSTYPTNRYVSLNGTSMASPHVAGVAALVKSRYPHATNVQIRNRL
Bcl04009                              PGVSVLSTYPTNRYVSLNGTSMASPHVAGVAALVKSRYPNATNVQIRNRL
Bakn00315                             PGVSILSTHLSNQYVSLNGTSMASPHVAGVAALVKAQYPSATNAQIRQRL
BspAI02518                            PGVGINSTYPTNGYSSLNGTSMASPHVAGVAALVKARYPSATNAQIRQHL
BspU02193                             PGVGIQSTYLNNGYSSLNGTSMAAPHVAGVAALVMSEYPWATAPQVRGRL
B_pseudofirmus_ADC49870               PGVNINSTYLNNGYRSLNGTSMASPHVAGVAALVKQKHPHLTAAQIRNRM
B_lentus_P29600                       PGVNVQSTYPGSTYASLNGTSMATPHVAGAAALVKQKNPSWSNVQIRNHL
B_amyloliquefaciens_CAA24990          PGVSIQSTLPGNKYGAYNGTSMASPHVAGAAALILSKHPNWTNTQVRSSL
B_licheniformis_CAJ70731.1            PGAGVYSTYPTNTYATLNGTSMASPHVAGAAALILSKHPNLSASQVRNRL
Bacillus_sp_sprC_AAC43580             PGVNILSTTPGNNYASFNGTSMAAPHVAGAAALIKAKYPSMTNVQIRERL
                                      **..: **   .  * : ******:*****.***:  . *   *:*   :
                     Consensus (201)  PGV I STYP N Y SLNGTSMASPHVAGVAALVKSKYP ATN QIRNRL 251            275
SWT66_254731                          NSTATNLGSSYYFGNGLVNAARAAN (SEQ ID NO:17)
Bcl04009                              NSTATNLGSSYYFGNGLVNAARAAN (SEQ ID NO:14)
Bakn00315                             RDTATPLGSSYYFGNGLVHAARAAN (SEQ ID NO:11)
BspAI02518                            RSTSTYLGNSTYYGSGLVDAQRATN (SEQ ID NO:3)
BspU02193                             NDTAIPLGNAYYFGNGLVDASRAAY (SEQ ID NO:6)
B_pseudofirmus_ADC49870               NQTAIPLGNSTYYGNGLVDAEYAAQ (SEQ ID NO:49)
B_lentus_P29600                       KNTATSLGSTNLYGSGLVNAEAATR (SEQ ID NO:60)
B_amyloliquefaciens_CAA24990          ENTTTKLGDSFYYGKGLINVQAAAQ (SEQ ID NO:73)
B_licheniformis_CAJ70731.1            SSTATYLGSSFYYGKGLINVEAAAQ (SEQ ID NO:67)
Bacillus_sp_sprC_AAC43580             KNTATNLGDPFFYGKGVINVESALQ (SEQ ID NO:62)
                                      .*:   **..  :*.*::..   *
                     Consensus (251)     TAT LGSS YYGNGLVNA RAA (SEQ ID NO: 83)
```

FIG. 9B

|                     |      | 1                                                    50 |
|---------------------|------|---------------------------------------------------------|
| Bsp_AAC43580        | (1)  | Q E G PH   DK  AA G VT G    V VA  D G DANHADL V GGAS    |
| Bam_CAA24990        | (1)  | Q S E G SQ   AL  Q G YT G   V VA  D G TD SHPDLKVAGGAS   |
| Bli_CAJ70731        | (1)  | Q E G PL   DK  AQ G FKGA V VA  D G QASHPDL V GGAS       |
| Ble_P29600          | (1)  | Q S E G SRVQ A  R G LT G   V VA  D G ST -HPDL RGGAS     |
| Bps_ADC49870        | (1)  | Q E G PY YSDV  RQ G YFG  V VA  D G  -HPDL RGGVS         |
| BspU02193           | (1)  | Q E G NHV   T  W G VG  V VA  D G  -HPDL VSGGAS          |
| ACB102_2847966      | (1)  | Q S E G SR N A  T G FG  V VA  D G  -HDL AGGVS           |
| BspAI02518          | (1)  | Q S E G SR N A  T G FG  V VA  D G  -HDL AGGVS           |
| COG104_4065768      | (1)  | Q S E G SR N A  T G FG  V VA  D G  -HDL AGGVS           |
| ACB83_2687815       | (1)  | Q S E G SR N A  T G LG  V VA  D G  -HDL AGGVS           |
| ACB90_2720294       | (1)  | Q S E G SR N A  T G LG  V VA  D G  -HDL AGGVS           |
| Bcl04009            | (1)  | S Q E G NRVQ T  W G AR G  V VA  D G  -HDL SGGAS         |
| SWT66_254731        | (1)  | S Q E G NRVQ T  W G AR G  V VA  D G  -HDL SGGAS         |
| ACB82_2683104       | (1)  | S Q E G NH Q T  W G RG  V VA  D G  -HDL SGGRS           |
| ACB89_2715301       | (1)  | S Q E G NH Q T  W G RG  V VA  D G  -HDL FGGRS           |
| ACB92_2732966       | (1)  | S Q E G NH Q T  W G RG  V VA  D G  -HDL SGGRS           |
| DETPh35_2828044     | (1)  | S Q E G NH Q T  W G RG  V VA  D G  -HDL SGGRS           |
| Bakn00315           | (1)  | S Q E G NH Q T  W G RG  V VA  D G  -HDL SGGRS           |
| Consensus           | (1)  | AQTVPWGI  IQAP VHS GN GNGVRVAVLDSGVAS HEDLRISGG SF       |

|                     |      | 51                                                   100 |
|---------------------|------|---------------------------------------------------------|
| Bsp_AAC43580        | (51) | VS E AL DGN HGTHVAGT AA  N TGVLGVAY  LY VKV A G         |
| Bam_CAA24990        | (51) | V E P DNN HGTHVAGT AA  N IGVLGVA  LY VKV A G            |
| Bli_CAJ70731        | (51) | V AY-NT DGN HGTHVAGT AA  N TGVLGVA  LY VKV S G          |
| Ble_P29600          | (50) | V -T DGN HGTHVAGT AA  N IGVLGVA  LY VKV A G             |
| Bps_ADC49870        | (50) | IS NT- VD N HGTHVAGT AA  N YGVLGVA  LY VKV  G           |
| BspU02193           | (50) | I E T-I DN HGTHVAGT AA  N IGVLGVA  LY VKV G             |
| ACB102_2847966      | (50) | VA E - D N HGTHVAGT A  N VGVLGVA  LY VKV G              |
| BspAI02518          | (50) | VA E - D N HGTHVAGT A  N VGVLGVA  LY VKV G              |
| COG104_4065768      | (50) | VA E - D N HGTHVAGT A  N VGVLGVA  LY VKV G              |
| ACB83_2687815       | (50) | VA E - D N HGTHVAGT A  N VGVLGVA  LY VKV G              |
| ACB90_2720294       | (50) | VA E - D N HGTHVAGT A  N VGVLGVA F LY VKV G             |
| Bcl04009            | (50) | IS E -NDLN HGTHVAGT AAR N YGVLGVA  LY VKV G             |
| SWT66_254731        | (50) | IS E -NDLN HGTHVAGT AAR N YGVLGVA  LY VKV G             |
| ACB82_2683104       | (50) | I E - D N HGTHVAGT A  N YGVLGVA  LY VKV G               |
| ACB89_2715301       | (50) | I E - D N HGTHVAGT A  N YGVLGVA  LY VKV G               |
| ACB92_2732966       | (50) | I E - D N HGTHVAGT A  N YGVLGVA  LY VKV G               |
| DETPh35_2828044     | (50) | I E - D N HGTHVAGT A  N YGVLGVA  LY VKV G               |
| Bakn00315           | (50) | I E - D N HGTHVAGT A  N YGVLGVA  LY VKV G               |
| Consensus           | (51) | IASEPS YQDYNGHGTHVAGTIAGLNNS GVLGVAPNVNLYAVKV DRN G      |

FIG. 12A

|                    |       | 101                                                  150 |
|--------------------|-------|-----------------------------------------------------------|
| Bsp_AAC43580       | (101) |                                                           |
| Bam_CAA24990       | (101) |                                                           |
| Bli_CAJ70731       | (100) |                                                           |
| Ble_P29600         | (99)  |                                                           |
| Bps_ADC49870       | (99)  |                                                           |
| BspU02193          | (99)  |                                                           |
| ACB102_2847966     | (99)  |                                                           |
| BspAI02518         | (99)  |                                                           |
| COG104_4065768     | (99)  |                                                           |
| ACB83_2687815      | (99)  |                                                           |
| ACB90_2720294      | (99)  |                                                           |
| Bcl04009           | (99)  |                                                           |
| SWT66_254731       | (99)  |                                                           |
| ACB82_2683104      | (99)  |                                                           |
| ACB89_2715301      | (99)  |                                                           |
| ACB92_2732966      | (99)  |                                                           |
| DETPh35_2828044    | (99)  |                                                           |
| Bakn00315          | (99)  |                                                           |
| Consensus          | (101) | SGSHSAIAQGIEWSVSNGMHVVNMSLGGPTGSTTLQRAADNAYNRGVLLI        |

|                    |       | 151                                                  200 |
|--------------------|-------|-----------------------------------------------------------|
| Bsp_AAC43580       | (151) |                                                           |
| Bam_CAA24990       | (151) |                                                           |
| Bli_CAJ70731       | (150) |                                                           |
| Ble_P29600         | (149) |                                                           |
| Bps_ADC49870       | (149) |                                                           |
| BspU02193          | (149) |                                                           |
| ACB102_2847966     | (149) |                                                           |
| BspAI02518         | (149) |                                                           |
| COG104_4065768     | (149) |                                                           |
| ACB83_2687815      | (149) |                                                           |
| ACB90_2720294      | (149) |                                                           |
| Bcl04009           | (149) |                                                           |
| SWT66_254731       | (149) |                                                           |
| ACB82_2683104      | (149) |                                                           |
| ACB89_2715301      | (149) |                                                           |
| ACB92_2732966      | (149) |                                                           |
| DETPh35_2828044    | (149) |                                                           |
| Bakn00315          | (149) |                                                           |
| Consensus          | (151) | AAAGNTGSAG ISYPARYSSVMAVGAVDSNNRASFSTFG ELEIMA            |

FIG. 12B

```
                       201                                              250
Bsp_AAC43580    (201)  PG N LST T  NYA NGTSMA PHVAG AAL  K P M  Q R
Bam_CAA24990    (201)  PG S QST L  KY AY NGTSMA PHVAG AAL LSKH  W  QVR S
Bli_CAJ70731    (200)  PG GVYST  T YAT NGTSMA PHVAG AAL LSKH LSAS QVRN
Ble_P29600      (195)  PG NVQST   TYA NGTSMA PHVAG AAL QKN  WS   QRN
Bps_ADC49870    (199)  PG N ST L GYR NGTSMA PHVAG AAL QKH PHL A Q RN M
BspU02193       (195)  PG G QST L GYS NGTSMA PHVAG AAL MS  W  AP QVRG
ACB102_2847966  (195)  PG G ST  RYS NGTSMA PHVAG AAL   R P   Q R
BspAI02518      (195)  PG G ST  GYS NGTSMA PHVAG AAL   R P   Q R
COG104_4065768  (195)  PG G ST  RYS NGTSMA PHVAG AAL   R P   Q R
ACB83_2687815   (195)  PG G ST  RYS NGTSMA PHVAG AAL   R P   Q R
ACB90_2720294   (195)  PG G ST  RYS NGTSMA PHVAG AAL   R P   Q R
Bc104009        (195)  PG SVLST  RY NGTSMA PHVAG AAL  SR P   Q RN
SWT66_254731    (195)  PG SVLST  RY NGTSMA PHVAG AAL  SR PH   Q RN
ACB82_2683104   (195)  PG S LST LS QY NGTSMA PHVAG AAL   P   Q R
ACB89_2715301   (195)  PG S LST LS QY NGTSMA PHVAG AAL   P   Q R
ACB92_2732966   (195)  PG S LST LS QYI NGTSMA PHVAG AAL   P   Q R
DETPh35_2828044 (195)  PG S LST LS QY NGTSMA PHVAG AAL   P   Q R
Bakn00315       (195)  PG S LST LS QY NGTSMA PHVAG AAL   P   Q R
Consensus       (201)  PGV INSTYPTN YSSLNGTSMASPHVAGVAALVKARYPSATNAQIRQRL
                       251                    275
Bsp_AAC43580    (251)  KNT NLG  FF G GVIN ESA LQ
Bam_CAA24990    (251)   NT KLG  F  G G IN QAA Q
Bli_CAJ70731    (250)  SST YLG  F  G G IN EAA Q
Ble_P29600      (245)  KNT SLG  NL G G N EAA
Bps_ADC49870    (249)   QT IPLG  T  G G D EYA Q
BspU02193       (245)   DT IPLG AY  G G D S A Y
ACB102_2847966  (245)   ST YLG  T  G G D Q A
BspAI02518      (245)   ST YLG  T  G G D Q A
COG104_4065768  (245)   ST YLG  T  G G D Q A
ACB83_2687815   (245)   ST NLG  T  G G N Q A
ACB90_2720294   (245)   ST NLG  T  G G N Q A
Bc104009        (245)   ST NLG  Y  G G N A A
SWT66_254731    (245)   ST NLG  Y  G G N A A
ACB82_2683104   (245)   DT PLG  Y  G G H T A
ACB89_2715301   (245)   DT PLG  Y  G G H A A
ACB92_2732966   (245)   DT PLG  Y  G G H A A
DETPh35_2828044 (245)   DT PLG  Y  G G H A A
Bakn00315       (245)   DT PLG  Y  G G H A A
Consensus       (251)  R TAT LGSSYYYGNGLV A RAAN
```

1: BspAl2518   AQSTPWGISRINAPAVHSTGNFGQGVRVAVLDSGVEASHEDLRIAGGVSFVASEPSYEQDYNGHGTHVAGTIAGLNNSVGVLGVAPSVQLYAVKVLDRNGGGNHS
 2: Bakn315     SQTVPWGINHIQAPTVHSWGNRGNGVRVAVLDSGVEASHEDLRISGGRSFITSEPSYEQDYNGHGTHVAGTIAGLNNSYGVLGVAPNVNLYAVKVLDRNGSGSHS
 3: Bcl04009    SQTIPWGINRVQAPTVHSWGARGNGVRVAVLDTGIEASHEDLRISGGASFISSEPSYENDLNGHGTHVAGTIAARDNSYGVLGVAPNVDLYAVKVLDRNGSGSLS
 4: swi66       SQTVPWGINRVQAPTVHSWGARGNGVRVAVLDTGIEASHEDLRISGGASFISSEPSYENDLNGHGTHVAGTIAARDNSYGVLGVAPNVNLYAVKVLDRNGSGSLS
 5: BspU2193    TQTVPWGINHVKAPTVHNWGNVGTGVRVAVLETGIEASHPDLRVSGGASFIPSEPTIEQDFNGHGTHVAGTVAALNNSIGVLGVAPNVQLYGVKVLDRNGSGSHS
 6: ACB82       SQTVPWGINHIQAPTVHSWGNRGNGVRVAVLDSGVEASHEDLRISGGRSFITSEPSYEQDYNGHGTHVAGTIAGLNNSYGVLGVAPNVNLYAVKVLDRNGSGSHS
 7: ACB92       SQTVPWGINHIQAPTVHSWGNRGNGVRVAVLDSGVEASHEDLRISGGRSFITSEPSYEQDYNGHGTHVAGTIAGLNNSYGVLGVAPNVNLYAVKVLDRNGSGSHS
 8: ACB83       AQSTPWGISRINAPAVHSTGNLGQGVRVAVLDSGVEASHEDLRIAGGVSFVASEPSYEQDYNGHGTHVAGTIAGLNNSVGVLGVAPNVNLYAVKVLDRNGGGNHS
 9: ACB89       SQTVPWGINHIQAPTVHSWGNRGNGVRVAVLDSGVEASHEDLRISGGRSFITSEPSYEQDYNGHGTHVAGTIAGLNNSYGVLGVAPNVNLYAVKVLDRNGSGSHS
10: ACB90       AQSTPWGISRINAPAVHSTGNFGQGVRVAVLDSGVEASHEDLRIAGGVSFVASEPSYEQDYNGHGTHVAGTIAGLNNSVGVLGVAPFVQLYAVKVLDRNGGGNHS
11: ACB102      AQSTPWGISRINAPAVHSTGNFGQGVRVAVLDSGVEASHEDLRIAGGVSFVASEPSYEQDYNGHGTHVAGTIAGLNNSVGVLGVAPSVQLYAVKVLDRNGGGNHS
12: COG104      AQSTPWGISRINAPAVHSTGNFGQGVRVAVLDSGVEASHEDLRISGGRSFITSEPSYEQDYNGHGTHVAGTIAGLNNSYGVLGVAPNVNLYAVKVLDRNGGGNHS
13: DETPh35     SQTVPWGINHIQAPTVHSWGNRGNGVRVAVLDSGVEASHEDLRISGGRSFITSEPSYEQDYNGHGTHVAGTIAGLNNSYGVLGVAPNVNLYAVKVLDRNGSGSHS
14: 1JEA        AQSVPWGISRVQAPAAHNRGLTGSSGVKVAVLDTGIS-THPDLNIRGGASFVPGEPS-TQDGNGHGTHVAGTIAALNNSIGVLGVAPSAELYAVKVLGASGSGSVS
15: 2ST1.A      AQSVPVYGVSQIKAPALHSQGYTGSNVKVAVIDSGIDSSHPDLKVAGGASMVPSETNPFQDNNSHGTHVAGTVAALNNSIGVLGVAPSASLYAVKVLGADGSGQYS
16: 3UNX.A      AQTVPYGIPLIKADKVQAQGFKGANVKVAVLDTGIQASHPDLNVVGGASFVAGE-AYNTDGNGHGTHVAGTVAALDNTTGVLGVAPSVSLYAVKVLNSSGSGSYS
17: LG12        AQTVPWGIPHIKADKAHAAGVTGSSGVKVAILDTGIDANHADLMVKGGASFVSGEPNALQDGNGHGTHVAGTVAALMNTTGVLGVAYNADLYAVKVLSASGSGTLS
```

FIG. 14A

```
           105       110       115       120       125       130       135       140       145       150       155       160       165       170       175       180       185       190       195       200
            |         |         |         |         |         |         |         |         |         |         |         |         |         |         |         |         |         |         |         |
 1: BspAl2518 DIARGIEWSVNNGMHVNMSLGGPTGSTTLQRAADNAYNRGVLLIAAAGNGTEEEESGVSFPARYSSVMAVAATDSNNNRASFSTYGSQIEISAPGVGINSTYP
 2: Bakn315   AIAQGIEWSVSNGMHIVNMSLGGPTGSTTLQRAADNAYNRGVLLIAAAGNGSRRRRAGISYPARYNSVMAVGAVDSNNNRASFSTFGNELEIMAPGVSILSTHL
 3: Bcl04009  GIARGIEWAITNNMDIVNMSLGGSTGSTALRQAADNAYNRGILLVAAAGNGSEEEEAGISFPARYNSVMAVGATDSNNNRASFSTFGNELEIMAPGVSLSTYP
 4: sw66      GIARGIEWAITNNMDIVNMSLGGSTGSTALRQAADNAYNRGILLIAAAGNGSEEEEAGISFPARYNSVMAVGATDSNNNRASFSTFGNELEIMAPGVSLSTYP
 5: BspU2193  AIAQGIEWSISNGMDVVNMSLGGATSSTALSQAVANASNRGILLIAASGNGRRRRRAGIQFPARYSQVMAVGAVDQNNRLASFSTFGNEQEIVAPGVGIQSTYL
 6: ACB82    AIAQGIEWSVSNGMHIVNMSLGGPTGSTTLQRAADNAYNRGVLLIAAAGNGSRRRRAGISYPARYNSVMAVGAVDSNNNRASFSTFGNELEIMAPGVSILSTHL
 7: ACB92    AIAQGIEWSVSNGMHIVNMSLGGPTGSTTLQRAADNAYNRGVLLIAAAGNGSEEEEAGISFPARYSSVMAVGAVDSNNNRASFSTYGPEIEISAPGVGINSTYP
 8: ACB83    DIARGIEWSVNNGMHVNMSLGGPTGSTTLQRAADNAYNRGVLLIAAAGNGTEEEESGVSFPARYSSVMAVAATDSNNNRASFSTYGPEIEISAPGVGINSTYP
 9: ACB89    AIAQGIEWSVSNGMHIVNMSLGGPTGSTTLQRAADNAYNRGVLLIAAAGNGSEEEEAGISFPARYSSVMAVGAVDSNNNRASFSTYGTQIEISAPGVGINSTYP
10: ACB90    DIARGIEWSVNNGMHVNMSLGGPTGSTTLQRAADNAYNRGVLLIAAAGNGTEEEESGVSFPARYSSVMAVAATDSNNNRASFSTYGPEIEISAPGVGINSTYP
11: ACB102   DIARGIEWSVNNGMHVNMSLGGPTGSTTLQRAADNAYNRGVLLIAAAGNGTEEEESGVSFPARYSSVMAVAATDSNNNRASFSTYGPEIEISAPGVGINSTYP
12: COG104   DIARGIEWSVNNGMHVNMSLGGPTGSTTLQRAADNAYNRGVLLIAAAGNGTEEEESGVSFPARYSSVMAVAATDSNNNRASFSTYGTQIEISAPGVGINSTYP
13: DETPh35  AIAQGIEWSVSNGMHIVNMSLGGPTGSATLQRAADNAYNRGVLLIAAAGNGSEEEEAGISYPARYNSVMAVGAVDSNNNRASFSTFGNELEIMAPGVSILSTHL
14: 1JEA     SIAQGLEWAGNGMHVANLSLGSPSPSATLEQAVNSATSRGVLVVAASGNSGA----GSISYPARYANAMAVGATDQNNNRASFSQYGAGLDIVAPGVNVQSTYP
15: 2ST1_A   WITNGIEWAIANNMDVINMSLGGPSGSAALKAAVDKAVASGVVVAAAGNECTSGSSSTVGYPGKYPSVIAVGAVDSSNQRASFSSVGPELDVMAPGVSIQSTLP
16: 3UNX_A   GIVSGIEWATTNCGMDVINMSLGGASGSTAMKQAVDNAYARGVVVVAAAGNSGSSSGSTNTIGYPAKYDSVIAVGAVDSNSNRASFSSVGAELEVMAPGAGVYSTYP
17: LG12     GIAQGIEWSISNGMNVINMSLGGSSSGSTALQQACNMAYNRGIVVIAAAGNSGSSGNRNTMGYPARYSSVIAVGAVSSNNTRASFSSVGSELEVMAPGVNILSTTP
```

*FIG. 14B*

```
          205       210       215       220       225       230       235       240       245       250       255       260       265
           |         |         |         |         |         |         |         |         |         |         |         |         |
 1: BspAl2518  TNGYSSLNGTS MASPHVAGVAALVKARYPSATNAQIRQHLRSTSTYLGNSTYYGSGLVDAQRATAEN
 2: Bakn315    SNQYVSLNGTS MASPHVAGVAALVKAQYPSATNAQIRQRLRDTATPLGSSYYFGNGLVHAARAAEN
 3: Bcl04609   TNRYVSLNGTS MASPHVAGVAALVKSRYPNATNVQIRNRLNSTATNLGSSYYFGNGLVNAARAAEN
 4: sw66      TNRYVSLNGTS MASPHVAGVAALVKSRYPHATNVQIRNRLNSTATNLGSSYYFGNGLVNAARAAEN
 5: BspU2193   NNGYSSLNGTS MAAPHVAGVAALVMSEYPWATAPQVRGRLNDTAIPLGNAYYFGNGLVDASRAAY
 6: ACB82      SNQYVSLNGTS MASPHVAGVAALVKAQYPSATNAQIRQRLRDTATPLGSSYYFGNGLVHATRAAEN
 7: ACB92      SNQYISLNGTS MASPHVAGVAALVKAQYPSATNAQIRQRLRDTATPLGSSYYFGNGLVHAARAAEN
 8: ACB83      TNRYSSLNGTS MASPHVAGVAALVKARYPSATNAQIRQHLRSTSTNLGNSTYYGSGLVNAQRAAEN
 9: ACB89      SNQYVSLNGTS MASPHVAGVAALVKAQYPSATNAQIRQHLRSTSTNLGNSTYYGSGLVDAQRAAEN
10: ACB90     TNRYSSLNGTS MASPHVAGVAALVKARYPSATNAQIRQHLRSTSTYLGNSTYYGSGLVHAARAAEN
11: ACB102    TNRYSSLNGTS MASPHVAGVAALVKARYPSATNAQIRQHLRSTSTYLGNSTYYGSGLVDARAAEN
12: COG104    TNRYSSLNGTS MASPHVAGVAALVKARYPSATNAQIRQLRDTATPLGSSYYFGNGLVDAQRAAEN
13: DETPh35   SNQYVSLNGTS MASPHVAGVAALVKAQYPSATNAQIRQRLRDTATPLGSSYYFGNGLVHAARAAEN
14: 1JEA      GSTYASLNGTS MATPHVAGAAALVKQKNPSWSNVQIRNHLKNTATSLGSTNLYGSGLVNAEAATR
15: 2ST1.A    GMKYGAYNGTS MASPHVAGAAALILSKHPNWTNTQVRSSLENTTTKLGDSFYYGKGLINVQAAAQ
16: 3UNX.A    TNTYATLNGTS MASPHVAGAAALILSKHPNLSASQVRNRLSSTATYLGSSFYYGKGLINVEAAAQ
17: LG12      GNNYASFNGTS MAAPHVAGAAALIKAKYPSMTNVQIRERLKNTATMLGDPFFYGKGVINVESALQ
```

*FIG. 14C*

METHODS OF MAKING *BACILLUS AKIBAI* SERINE PROTEASES

CROSS REFERENCE TO RELATED APPLICATION

This application is a Continuation of U.S. application Ser. No. 15/103,248, filed Oct. 27, 2016, which is a 371 filing of International Application No. PCT/US14/70097, filed Dec. 12, 2014, which claims the benefit of U.S. Provisional Patent Application No. 61/915,745, filed Dec. 13, 2013, the contents of which are hereby incorporated herein by reference in their entirety.

SEQUENCE LISTING

The sequence listing submitted via EFS, in compliance with 37 C.F.R. § 1.52(e), is incorporated herein by reference. The sequence listing text file submitted via EFS contains the file "20180521_NB40497USPCN_SeqLst.txt" created on May 21, 2018, which is 186 kilobytes in size.

FIELD

The present disclosure relates to serine proteases cloned from *Bacillus* spp., and variants thereof. Compositions containing the serine proteases are suitable for use in cleaning fabrics and hard surfaces, as well as in a variety of industrial applications.

BACKGROUND

Serine proteases are enzymes (EC No. 3.4.21) possessing an active site serine that initiates hydrolysis of peptide bonds of proteins. There are two broad categories of serine proteases, based on their structure: chymotrypsin-like (trypsin-like) and subtilisin-like. The prototypical subtilisin (EC No. 3.4.21.62) was initially obtained from *Bacillus subtilis*. Subtilisins and their homologues are members of the S8 peptidase family of the MEROPS classification scheme. Members of family S8 have a catalytic triad in the order Asp, His and Ser in their amino acid sequence.

Although serine proteases have long been known in the art of industrial enzymes, there remains a need for further serine proteases that are suitable for particular conditions and uses.

SUMMARY

The present compositions and methods relate to recombinant serine proteases cloned from *Bacillus* spp., and variants thereof. Compositions containing the serine proteases are suitable for use in cleaning fabrics and hard surfaces, as well as in a variety of industrial applications.

In some embodiments, the invention is a recombinant polypeptide of a *B. akibai/clarkii*-clade subtilisin, or an active fragment thereof, wherein the recombinant polypeptide or the active fragment thereof has proteolytic activity.

In another embodiment, the invention is a recombinant polypeptide of a *B. akibai/clarkii*-clade subtilisin, or an active fragment thereof, wherein the recombinant polypeptide or the active fragment thereof has proteolytic activity and comprises an amino acid sequence of SEQ ID NO:42, 43, 44, 45, 46, 47, or 48.

In a further embodiment, the invention is a recombinant polypeptide of a *B. akibai/clarkii*-clade subtilisin, or an active fragment thereof, wherein the recombinant polypeptide or the active fragment thereof having proteolytic activity and comprising an amino acid sequence of SEQ ID NO:42, 43, 44, 45, 46, 47, or 48, further comprises an amino acid sequence having at least: (i) 72% identity to an amino acid sequence of SEQ ID NO:3, 6, 11, 14, 17, 20, 23, 26, 29, 32, 35, 38, 41, or 84; (ii) 72% identity to an amino acid sequence of SEQ ID NO: 3, 6, 11, 14, or 17; (iii) 72% identity to the amino acid sequence of SEQ ID NO:20, SEQ ID NO:23, SEQ ID NO:26, SEQ ID NO:29, SEQ ID NO:32, SEQ ID NO:35, SEQ ID NO:38 or SEQ ID NO:41; (iv) 70% identity to an amino acid sequence of SEQ ID NO:3, 6, 11, 14, 17, 20, 23, 26, 29, 32, 35, 38, 41, or 84; (v) 70% identity to an amino acid sequence of SEQ ID NO:3, 6, 14, 17, 20, 23, 26, or 29; or (vi) 70% identity to an amino acid sequence of SEQ ID NO:3, 6, 14, or 17.

In some embodiments, the invention is a recombinant polypeptide, or an active fragment thereof having proteolytic activity and comprising an amino acid sequence having at least: (i) 70% identity to the amino acid sequence of SEQ ID NO:3, SEQ ID NO:6, SEQ ID NO:14, SEQ ID NO:17, SEQ ID NO:20, SEQ ID NO:23, SEQ ID NO:26, SEQ ID NO:29, or SEQ ID NO:84; (ii) 70% identity to the amino acid sequence of SEQ ID NO:3, SEQ ID NO:6, SEQ ID NO:14, or SEQ ID NO:17; (iii) 72% identity to the amino acid sequence of SEQ ID NO:3, SEQ ID NO:6, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41 or SEQ ID NO:84; (iv) 72% identity to the amino acid sequence of SEQ ID NO:3, SEQ ID NO:6, SEQ ID NO:11, SEQ ID NO:14 or SEQ ID NO:17; or (v) 72% identity to the amino acid sequence of SEQ ID NO:20, SEQ ID NO:23, SEQ ID NO:26, SEQ ID NO:29, SEQ ID NO:32, SEQ ID NO:35, SEQ ID NO:38, SEQ ID NO:41, or SEQ ID NO:84.

In some embodiments, the invention is a recombinant polypeptide comprising an amino acid sequence having at least 72% identity to the amino acid sequence of SEQ ID NO:3, SEQ ID NO:6, SEQ ID NO:11, SEQ ID NO:14 or SEQ ID NO:17.

In yet a further embodiment, the invention is a recombinant polypeptide comprising an amino acid sequence having at least 70% identity to the amino acid sequence of SEQ ID NO:3, SEQ ID NO:6, SEQ ID NO:14, or SEQ ID NO:17.

In some embodiments, at least one of the foregoing recombinant polypeptides has protease activity, specifically casein hydrolysis. In some embodiments, at least one of the foregoing recombinant polypeptides retains at least 50% of its maximal protease activity at a pH range of 8 to 12. In some embodiments, at least one of the foregoing recombinant polypeptides retains at least 50% of its maximal protease activity at a temperature range of 50° C. to 75° C. In some embodiments, at least one of the foregoing recombinant polypeptides has cleaning activity in a detergent composition, including an automatic dish washing detergent and a laundry detergent.

In some embodiments, the invention is a composition comprising a surfactant and at least one of the recombinant polypeptides stated above. In some embodiments, the surfactant is selected from the group consisting of a non-ionic surfactant, an anionic surfactant, a cationic surfactant, a zwitterionic surfactant, an ampholytic surfactant, a semi-polar non-ionic surfactant, and a combination thereof. In some embodiments, the composition is a detergent composition, such as a laundry detergent, a fabric softening detergent, a dishwashing detergent, and a hard-surface cleaning detergent. In some embodiments, the composition further comprises at least one calcium ion and/or zinc ion, at least one stabilizer, at least one bleaching agent, phosphate, or borate. In some embodiments the composition is phosphate-free and/or borate-free. In some embodiments, the composition is a granular, powder, solid, bar, liquid, tablet, gel, paste or unit dose composition. In some embodiments, the composition further comprising one or more additional enzymes or enzyme derivatives selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, metalloproteases, additional serine proteases, and combinations thereof.

In some embodiments, the invention is a method of cleaning, comprising contacting a surface or an item with a composition listed above. In some embodiments, the invention is a method for producing a recombinant polypeptide comprising stably transforming a host cell with an expression vector comprising a polynucleotide encoding at least one of the recombinant polypeptide above.

BRIEF DESCRIPTION OF THE DRAWINGS

FIG. 7A-F provides an alignment of the amino acid sequences of the mature forms of BspAI02518 (SEQ ID NO:3) and BspU02193 (SEQ ID NO:6) with the amino acid sequences of various bacterial serine proteases (SEQ ID NOs:49-79). A consensus sequence is shown below the alignment (SEQ ID NO:81).

FIG. 9A-B provides an alignment of the amino acid sequences of the mature forms of BspAI02518 (SEQ ID NO:3), BspU02193 (SEQ ID NO:6), Bakn00315 (SEQ ID NO:11), Bcl04009 (SEQ ID NO:14), and SWT66_254731 (SEQ ID NO:17) with the sequences of several other bacterial serine proteases. The amino acid sequences of subtilisins from B. pseudofirmus (SEQ ID NO:49), B. lentus (SEQ ID NO:600), Bacillus sp. LG12 (SEQ ID NO:62), B. licheniformis (SEQ ID NO:67), and B. amyloliquefaciens (SEQ ID NO:73) correspond to NCBI Accession Nos. ADC49870, P29600, AAC43580, CAJ70731, and CAA24990.

FIG. 12 A-C provides an alignment of 18 amino acid sequences corresponding to the mature forms of: BspAI02518 (SEQ ID NO:3), BspU02193 (SEQ ID NO:6), Bakn00315 (SEQ ID NO:11), Bcl04009 (SEQ ID NO:14), SWT66_254731 (SEQ ID NO:17), ACB102 (SEQ ID NO:20), COG104 (SEQ ID NO:23), ACB83 (SEQ ID NO:26), ACB90 (SEQ ID NO:29), ACB82 (SEQ ID NO:32), ACB89 (SEQ ID NO:35), ACB92 (SEQ ID NO:38), DETPh35 (SEQ ID NO:41), and the mature forms of subtilisins from B.s amyloliquefaciens, B. lentus, B. licheniformis, Bacillus sp. LG12, and B. pseudofirmus (NCBI Accession Nos. CAA24990 (SEQ ID NO: 73), P29600 (SEQ ID NO:600), CAJ70731 (SEQ ID NO: 67), AAC43580 (SEQ ID NO: 62, and ADC49870 (SEQ ID NO: 49), respectively).

FIG. 14 A-C provides a structure-based sequence alignment of BspAI02518 (SEQ ID NO: 3), BspU02193 (SEQ ID NO: 6), Bakn00315 (SEQ ID NO: 11), Bcl04009 (SEQ ID NO: 14), SWT66_254731 (SEQ ID NO: 17), ACB102 (SEQ ID NO: 20), COG104 (SEQ ID NO: 23), ACB83 (SEQ ID NO: 26), ACB90 (SEQ ID NO: 29), ACB82 (SEQ ID NO: 32), ACB89 (SEQ ID NO: 35), ACB92 (SEQ ID NO: 38), and DETPh35 (SEQ ID NO: 41) (i.e. B. akibai/clarkii-clade subtilisins) with BPN' subtilisin from B. amyloliquefaciens (pdb entry 2ST1) (SEQ ID NO: 73), Carlsberg from B. licheniformis (pdb entry 3UNX) (SEQ ID NO: 67), B. lentus subtilisin (pdb entry 1JEA) (SEQ ID NO: 600) and the proprietary structure of subtilisin LG12 (SEQ ID NO: 62). Highlighted is the active site triad Asp32, H62 and S215 and N153 that contributes to the oxyanion hole (BspAI02518 numbering) of the Bacillus subtilisins. Also highlighted is a region of the structure-based alignment in which the B. akibai/clarkii-clade subtilisin sequences have a common motif from Val (V) 91 through Gly (G) 99 or Ser (S) 99.

DETAILED DESCRIPTION

Figure 1:
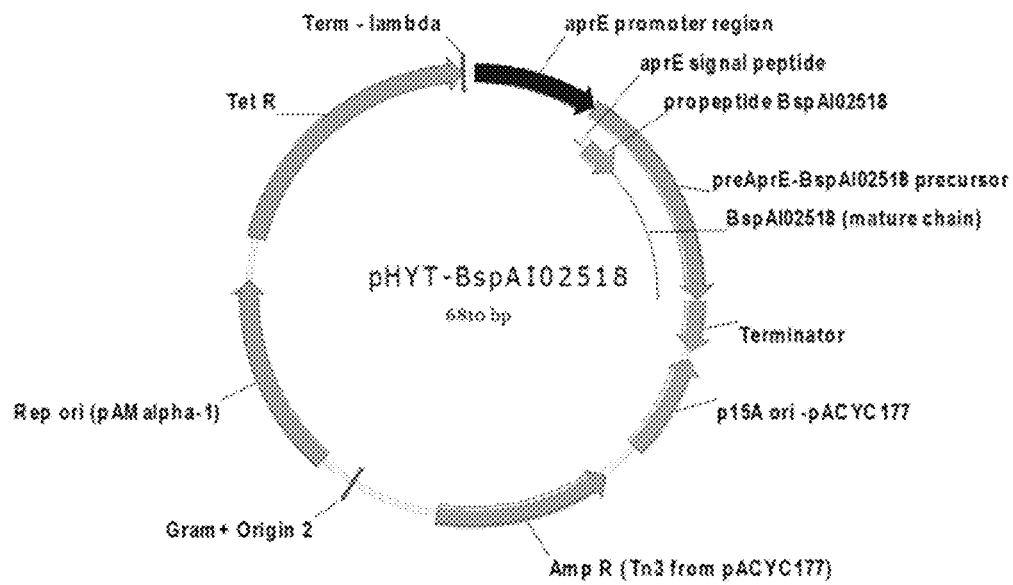
FIG. 1 provides a plasmid map of pHYT-BspAI02518 for expression of the BspAI02518 serine protease.

Described are compositions and methods relating to recombinant serine proteases from *B. akibai/clarkii*-clade strains from C-M2-3, GICC 2089392, ATCC No. 43226, DSM 8720, ACB102_2847966, COG104_4065768, ACB83_2687815, ACB90_2720294, ACB82_2683104, ACB89_2715301, ACB92_2732966, and DETPh35_2828044. The compositions and methods are based, in part, on the observation that recombinant BspAI02518, and BspU02193 have protease activity in the presence of a surfactant, in basic reaction conditions, and at elevated temperatures. These features of BspAI02518 and BspU02193, which are predicted to be shared by Bakn00315, Bcl04009, SWT66_254731, ACB102, COG104, ACB83, ACB90, ACB82, ACB89, ACB92, and DETPh35 make these proteases well suited for use in cleansing fabrics and hard surfaces, as well as in textile, leather, and feather processing. As a result, at least BspAI02518 and BspU02193, as well as Bakn00315, Bcl04009, SWT66_254731, ACB102, COG104, ACB83, ACB90, ACB82, ACB89, ACB92, and DETPh35 are well suited to inclusion in compositions for protein degradation, including but not limited to laundry and dish washing detergents. BspAI02518 and BspU02193, as well as Bakn00315, Bcl04009, SWT66_254731, ACB102, COG104, ACB83, ACB90, ACB82, ACB89, ACB92, and DETPh35 are also suited for inclusion in personal care compositions, as well as human food and animal feed applications.

I. Definitions

Prior to describing the present compositions and methods in detail, the following terms are defined for clarity. Terms and abbreviations not defined should be accorded their ordinary meaning as used in the art. Unless defined otherwise herein, all technical and scientific terms used herein have the same meaning as commonly understood by one of ordinary skill in the art. Unless otherwise indicated, the practice of the present disclosure involves conventional techniques commonly used in molecular biology, protein engineering, and microbiology. Although any methods and materials similar or equivalent to those described herein find use in the practice of the present disclosure, some suitable methods and materials are described herein. The terms defined immediately below are more fully described by reference to the Specification as a whole.

As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. It is to be understood that this disclosure is not limited to the particular methodology, protocols, and reagents described herein, absent an indication to the contrary.

It is intended that every maximum numerical limitation given throughout this Specification includes every lower numerical limitation, as if such lower numerical limitations were expressly written herein. Every minimum numerical limitation given throughout this Specification will include every higher numerical limitation, as if such higher numerical limitations were expressly written herein. Every numerical range given throughout this Specification will include every narrower numerical range that falls within such broader numerical range, as if such narrower numerical ranges were all expressly written herein.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

As used herein, the terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity. For example, proteolytic activity may be ascertained by comparative assays that analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011 and U.S. Pat. No. 6,376,450). The pNA peptidyl assay (See e.g., Del Mar et al., Anal Biochem, 99:316-320, 1979) also finds use in determining the active enzyme concentration. This assay measures the rate at which p-nitroaniline is released as the enzyme hydrolyzes a soluble synthetic substrate, such as succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration in a sample of purified protein. The activity on substrate/protein concentration gives the enzyme specific activity.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. gibsonii, B. agaradhaerens, B akibai, B. clarkii* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores under stressful environmental conditions is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus Halobacillus, Paenibacillus, Salibacillus, Thermobacillus, Ureibacillus,* and *Virgibacillus.*

The terms "polynucleotide" and "nucleic acid," which are used interchangeably herein, refer to a polymer of any length of nucleotide monomers covalently bonded in a chain. DNA (deoxyribonucleic acid), a polynucleotide comprising deoxyribonucleotides, and RNA (ribonucleic acid), a polymer of ribonucleotides, are examples of polynucleotides or nucleic acids having distinct biological functions. Polynucleotides or nucleic acids include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, expressed sequence tag(s) (EST(s)), exons, introns, messenger RNA (mRNA), transfer RNA (tRNA), ribosomal RNA (rRNA), ribozymes, complementary DNA (cDNA), recombinant polynucleotides, branched polynucleotides, plasmids, vectors, isolated DNA of any sequence, isolated RNA of any sequence, nucleic acid probes, and primers.

As used herein, the term "mutation" refers to changes made to a reference amino acid or nucleic acid sequence. It is intended that the term encompass substitutions, insertions and deletions.

As used herein, the term "vector" refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multicloning site, and a selectable marker. The process of inserting a vector into a target cell is typically referred to as transformation. The present invention includes, in some embodiments, a vector that comprises a DNA sequence encoding a serine protease polypeptide (e.g., precursor or mature serine protease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

As used herein, the term "expression cassette," "expression plasmid" or "expression vector" refers to a nucleic acid construct or vector generated recombinantly or synthetically for the expression of a nucleic acid of interest in a target cell. An expression vector or expression cassette typically comprises a promoter nucleotide sequence that drives expression of the foreign nucleic acid. The expression vector or cassette also typically includes any other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Many prokaryotic and eukaryotic expression vectors are commercially available.

As used herein, a "plasmid" refers to an extrachromosomal DNA molecule which is capable of replicating independently from the chromosomal DNA. A plasmid is double stranded (ds) and may be circular and is typically used as a cloning vector.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction. Transformation refers to the genetic alteration of a cell which results from the uptake, optional genomic incorporation, and expression of genetic material (e.g., DNA).

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein the term "gene" refers to a polynucleotide (e.g., a DNA segment), that encodes a polypeptide and includes regions preceding and following the coding regions. In some instances a gene includes intervening sequences (introns) between individual coding segments (exons).

As used herein, "recombinant" when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) that has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination" and "recombining" of polynucleotides or nucleic acids refer generally to the assembly or combining of two or more nucleic acid or polynucleotide strands or fragments to generate a new polynucleotide or nucleic acid.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

The terms "host strain" and "host cell" refer to a suitable host for an expression vector comprising a DNA sequence of interest.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S". When describing modifications, a position followed by amino acids listed in parentheses indicates a list of substitutions at that position by any of the listed amino acids. For example, 6(L,I) means position 6 can be substituted with a leucine or isoleucine. At times, in a sequence, a slash (/) is used to define substitutions, e.g. F/V, indicates that the particular position may have a phenylalanine or valine at that position.

A "prosequence" or "propeptide sequence" refers to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Bacterial serine proteases are often expressed as pro-enzymes.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from Bacillus" refers to those enzymes having proteolytic activity that are naturally produced by Bacillus, as well as to serine proteases like those produced by Bacillus sources but which through the use of genetic engineering techniques are produced by other host cells transformed with a nucleic acid encoding the serine proteases.

The term "identical" in the context of two polynucleotide or polypeptide sequences refers to the residues in the two sequences that are the same when aligned for maximum correspondence, as measured using sequence comparison or analysis algorithms.

As used herein, "% identity" or percent identity" or "PID" refers to sequence identity. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous proteases" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25(17):3389-402). Using this information, proteins sequences can be grouped. A phylogenetic tree can be built using the amino acid sequences. Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system.

The CLUSTAL W algorithm is another example of a sequence alignment algorithm (See, Thompson et al., Nucleic Acids Res, 22:4673-4680, 1994). Default parameters for the CLUSTAL W algorithm include: Gap opening penalty=10.0; Gap extension penalty=0.05; Protein weight matrix=BLOSUM series; DNA weight matrix=IUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

A nucleic acid or polynucleotide is "isolated" when it is at least partially or completely separated from other components, including but not limited to for example, other proteins, nucleic acids, cells, etc. Similarly, a polypeptide, protein or peptide is "isolated" when it is at least partially or completely separated from other components, including but not limited to for example, other proteins, nucleic acids, cells, etc. On a molar basis, an isolated species is more abundant than are other species in a composition. For example, an isolated species may comprise at least about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

As used herein, the term "functional assay" refers to an assay that provides an indication of a protein's activity. In some embodiments, the term refers to assay systems in which a protein is analyzed for its ability to function in its usual capacity. For example, in the case of a protease, a functional assay involves determining the effectiveness of the protease to hydrolyze a proteinaceous substrate.

The term "cleaning activity" refers to a cleaning performance achieved by a serine protease polypeptide or reference protease under conditions prevailing during the proteolytic, hydrolyzing, cleaning, or other process of the disclosure. In some embodiments, cleaning performance of a serine protease polypeptide or reference protease may be determined by using various assays for cleaning one or more various enzyme sensitive stains on an item or surface (e.g., a stain resulting from food, grass, blood, ink, milk, oil, and/or egg protein). Cleaning performance of a variant or reference protease can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO 99/34011 and U.S. Pat. No. 6,605,458, both of which are herein incorporated by reference, as well as those cleaning assays and methods included in the Examples provided below.

The term "cleaning effective amount" of a serine protease polypeptide or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than a serine protease polypeptide of the disclosure. In some embodiments, the cleaning compositions of the present disclosure include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwashing compositions (e.g., "hand" or "manual" dishwashing detergents) and automatic dishwashing compositions (e.g., "automatic dishwashing detergents"). Single dosage unit forms also find use with the present invention, including but not limited to pills, tablets, gelcaps, or other single dosage units such as pre-measured powders or liquids.

Cleaning composition or cleaning formulations, as used herein, include, unless otherwise indicated, granular or powder-form all-purpose or heavy-duty washing agents, especially cleaning detergents; liquid, granular, gel, solid, tablet, paste, or unit dosage form all-purpose washing agents, especially the so-called heavy-duty liquid (HDL) detergent or heavy-duty dry (HDD) detergent types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, contact lens cleaning compositions, wound debridement compositions, and personal cleansing compositions.

As used herein, the term "detergent composition" or "detergent formulation" is used in reference to a composition intended for use in a wash medium for the cleaning of soiled or dirty objects, including particular fabric and/or non-fabric objects or items. Such compositions of the present disclosure are not limited to any particular detergent composition or formulation. Indeed, in some embodiments, the detergents of the disclosure comprise at least one serine protease polypeptide of the disclosure and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the disclosure, such as, but not limited to, cleaning compositions or detergent compositions, do not contain any phosphate (e.g., phosphate salt or phosphate builder).

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc.

As used herein, "wash performance" of a protease (e.g., a serine protease polypeptide of the disclosure) refers to the contribution of a serine protease polypeptide to washing that provides additional cleaning performance to the detergent as compared to the detergent without the addition of the serine protease polypeptide to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

As used herein, the term "disinfecting" refers to the removal of contaminants from the surfaces, as well as the inhibition or killing of microbes on the surfaces of items. It is not intended that the present disclosure be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

II. Serine Protease Polypeptides

The present disclosure provides novel serine protease enzymes. The serine protease polypeptides of the present disclosure include isolated, recombinant, substantially pure, or non-naturally occurring polypeptides. In some embodiments, the polypeptides are useful in cleaning applications and can be incorporated into cleaning compositions that are useful in methods of cleaning an item or a surface in need thereof.

In some embodiments, the invention is a *B. akibai/clarkii*-clade of subtilisins. In other embodiments the invention is a recombinant polypeptide of a *B. akibai/clarkii*-clade subtilisin, or active fragment thereof, comprising a DRN motif. In some embodiments, the DRN motif is VKVLDRNGR$^1$G, wherein $R^1$ is selected from G or S (SEQ ID NO:42). In other embodiments, the DRN motif is VKVLDRNGGG (SEQ ID NO:43). In yet still other embodiments, the DRN motif is VKVLDRNGSG (SEQ ID NO:44). In another embodiment, the DRN motif is D95R96N97 (SEQ ID NO:45). In a further embodiment, the DRN motif is V91K92V93L94D95R96N97G98G/S99G100 (SEQ ID NO:46). In a still further embodiment, the DRN motif is V91K92V93L94D95R96N97G98G99G100 (SEQ ID NO:47). In another embodiment the DRN motif is V91K92V93L94D95R96N97G98S99G100 (SEQ ID NO:48). In an even further embodiment, the DRN motif is selected from VKVLDRNGR$^1$G, wherein R$^1$ is selected from G or S (SEQ ID NO:42); VKVLDRNGGG (SEQ ID NO:43); VKVLDRNGSG (SEQ NO:44); D95R96N97 (SEQ ID NO:45); V91K92V93L94D95R96N97G98G/S99G100 (SEQ ID NO:46); V91K92V93L94D95R96N97G98G99G100 (SEQ ID NO:47); and V91K92V93L94D95R96N97G98S99G100 (SEQ ID NO:48). The sequence numbering set forth in SEQ ID NOs:45, 46, 47, and 48 is based on BspAI02518 SEQ ID NO:3 sequence numbering.

In some embodiments, the polypeptide of the present invention, is a polypeptide having a specified degree of amino acid sequence homology to the exemplified polypeptides, e.g., 70%, 72%, 74%, 76%, 78%, 80%, 85%, 90%, 95%, 96%, 97%, 98%, 99% or 100% sequence identity to the amino acid sequence selected from the group consisting of SEQ ID NO:3, SEQ ID NO:6, SEQ ID NO:11, SEQ ID NO:14 and SEQ ID NO:17. In a still further embodiment, the polypeptide of the present invention, is a polypeptide having a specified degree of amino acid sequence homology to the exemplified polypeptides, e.g., 70%, 72%, 74%, 76%, 78%, 80%, 85%, 90%, 95%, 96%, 97%, 98%, 99% or 100% sequence identity to an amino acid sequence of SEQ ID NO:3, SEQ ID NO:6, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, or SEQ ID NO:84. Homology can be determined by amino acid sequence alignment, e.g., using a program such as BLAST, ALIGN, or CLUSTAL, as described herein. In some embodiments, the polypeptide is an isolated, recombinant, substantially pure, or non-naturally occurring enzyme having protease activity.

In other embodiments, the polypeptide of the present invention, or an active fragment thereof, is from a *B. akibai/clarkii*-clade subtilisin, wherein the polypeptide or the active fragment thereof has proteolytic activity.

In another embodiment, the polypeptide of the present invention, or an active fragment thereof, is from a *B. akibai/clarkii*-clade subtilisin, wherein the polypeptide or the active fragment thereof has proteolytic activity and comprises an amino acid sequence of SEQ ID NO:42, 43, 44, 45, 46, 47, or 48.

In a further embodiment, the polypeptide of the present invention, or an active fragment thereof, is from a *B. akibai/clarkii*-clade subtilisin, wherein the polypeptide or the active fragment thereof having proteolytic activity and comprising an amino acid sequence of SEQ ID NO:42, 43, 44, 45, 46, 47, or 48, further comprises an amino acid sequence having at least: (i) 72% identity to an amino acid sequence of SEQ ID NO:3, 6, 11, 14, 17, 20, 23, 26, 29, 32, 35, 38, 41, or 84; (ii) 72% identity to an amino acid sequence of SEQ ID NO: 3, 6, 11, 14, or 17; (iii) 70% identity to an amino acid sequence of SEQ ID NO:3, 6, 11, 14, 17, 20, 23, 26, 29, 32, 35, 38, 41, or 84; or (iv) 70% identity to an amino acid sequence of SEQ ID NO:3, 6, 14, 17, 20, 23, 26, 29, or 84.

In some embodiments, the polypeptide of the present invention, or an active fragment thereof, has proteolytic activity and comprises an amino acid sequence having at least: (i) 70% identity to the amino acid sequence of SEQ ID NO:3, SEQ ID NO:6, SEQ ID NO:14, SEQ ID NO:17, SEQ ID NO:20, SEQ ID NO:23, SEQ ID NO:26, SEQ ID NO:29 or SEQ ID NO:84; (ii) 70% identity to the amino acid sequence of SEQ ID NO:3, SEQ ID NO:6, SEQ ID NO:14, SEQ ID NO:17, or SEQ ID NO:84; (iii) 72% identity to the amino acid sequence of SEQ ID NO:3, SEQ ID NO:6, SEQ ID NO:11, SEQ ID NO:14, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, or SEQ ID NO:84; (iv) 72% identity to the amino acid sequence of SEQ ID NO:3, SEQ ID NO:6, SEQ ID NO:11, SEQ ID NO:14 or SEQ ID NO:17; or (v) 72% identity to the amino acid sequence of SEQ ID NO:20, SEQ ID NO:23, SEQ ID NO:26, SEQ ID NO:29, SEQ ID NO:32, SEQ ID NO:35, SEQ ID NO:38, SEQ ID NO:41, or SEQ ID NO:84.

Also provided is a polypeptide enzyme of the present invention, having protease activity, such as alkaline protease activity, said enzyme comprising an amino acid sequence which differs from the amino acid sequence of SEQ ID NO: 3, 6, 11, 14, 17, 20, 23, 26, 29, 32, 35, 38, 41 or 84 by no more than 50, no more than 40, no more than 30, no more than 25, no more than 20, no more than 15, no more than 10, no more than 9, no more than 8, no more than 7, no more than 6, no more than 5, no more than 4, no more than 3, no more than 2, or no more than 1 amino acid residue(s), when aligned using any of the previously described alignment methods.

As noted above, the variant enzyme polypeptides of the invention have enzymatic activities (e.g., protease activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more variant serine protease enzyme polypeptides of the invention are described infra. The enzymatic activity (e.g., protease enzyme activity) of an enzyme polypeptide of the invention can be determined readily using procedures well known to those of ordinary skill in the art. The Examples presented infra describe methods for evaluating the enzymatic activity and cleaning performance. The performance of polypeptide enzymes of the invention in removing stains (e.g., a protein stain such as blood/milk/ink or egg yolk), cleaning hard surfaces, or cleaning laundry, dishware or tableware item(s) can be readily determined using procedures well known in the art and/or by using procedures set forth in the Examples. In some embodiments, the invention is a recombinant polypeptide or active fragment thereof of the invention, wherein the polypeptide has protease activity in the presence of a surfactant. In some embodiments, the protease activity comprises casein hydrolysis activity. In some embodiments, the protease activity comprises dimethylcasein hydrolysis activity.

The serine protease polypeptides of the present invention can have protease activity over a broad range of pH conditions. In some embodiments, the serine protease polypeptides have protease activity on azo-casein as a substrate, as demonstrated in Example 4. In some embodiments, the serine protease polypeptides have protease activity at a pH of from about 4.0 to about 12.0. In some embodiments, the serine protease polypeptides have protease activity at a pH of from about 8.0 to about 12.0. In some embodiments, the serine protease polypeptides have at least 50%, 60%, 70%, 80% or 90% of maximal protease activity at a pH of from about 8.0 to about 12.0. In some embodiments, the serine protease polypeptides have protease activity at a pH above 8.0, 8.5, 9.0, 9.5, 10.0, 10.5, 11.0 or 11.5. In some embodiments, the serine protease polypeptides have protease activity at a pH below 12.0, 11.5, 11.0, 10.5, 10.0, 9.5, 9.0 or 8.5.

In some embodiments, the serine protease polypeptides of the present invention have protease activity at a temperature range from about 10° C. to about 90° C. In some embodiments, the serine protease polypeptides of the present invention have protease activity at a temperature range of from about 50° C. to about 75° C. In some embodiments, the serine protease polypeptides have at least 50%, 60%, 70%, 80% or 90% of maximal protease activity at a temperature of from about 50° C. to about 75° C. In some embodiments, the serine proteases have activity at a temperature above 50° C., 55° C., 60° C., 65° C., or 70° C. In some embodiments, the serine proteases have activity at a temperature below 75° C., 70° C., 65° C., 60° C., or 55° C.

In some embodiments, the serine protease polypeptides of the present invention demonstrate cleaning performance in a cleaning composition. Cleaning compositions often include ingredients harmful to the stability and performance of enzymes, making cleaning compositions a harsh environment for enzymes, e.g. serine proteases, to retain function. Thus, it is not trivial for an enzyme to be put in a cleaning composition and expect enzymatic function (e.g. serine protease activity, such as demonstrated by cleaning performance). In some embodiments, the serine protease polypeptides of the present invention demonstrate cleaning performance in automatic dishwashing (ADW) detergent compositions. In some embodiments, the cleaning performance in automatic dishwashing (ADW) detergent compositions includes cleaning of egg yolk stains. In some embodiments, the serine protease polypeptides of the present invention demonstrate cleaning performance in laundry detergent compositions. In some embodiments, the cleaning performance in laundry detergent compositions includes cleaning of blood/milk/ink stains. In each of the cleaning compositions, the serine protease polypeptides of the present invention demonstrate cleaning performance with or without a bleach component.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleotides in one or more codons such that a particular codon encodes the same or a different amino acid, resulting in either a silent variation (e.g., when the encoded amino acid is not altered by the nucleotide mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded polypeptide enzyme compared to the polypeptide enzyme encoded by the original nucleic acid sequence. A nucleic acid sequence of the invention can also be modified to include one or more codons that provide for optimum expression in an expression system (e.g., bacterial expression system), while, if desired, said one or more codons still encode the same amino acid(s).

In some embodiments, the present invention provides a genus of enzyme polypeptides having the desired enzymatic activity (e.g., protease enzyme activity or cleaning performance activity) which comprise sequences having the amino acid substitutions described herein and also which comprise one or more additional amino acid substitutions, such as conservative and non-conservative substitutions, wherein the polypeptide exhibits, maintains, or approximately maintains the desired enzymatic activity (e.g., proteolytic activity, as reflected in the cleaning activity or performance of the polypeptide enzyme of SEQ ID NO:3, SEQ ID NO:6, SEQ ID NO:11, SEQ ID NO:14 or SEQ ID NO:17). In some embodiments, the proteolytic activity is reflected in the cleaning activity or performance of the polypeptide enzyme of SEQ ID NO:20, 23, 26, 29, 32, 35, 38, 41, or 84. Amino acid substitutions in accordance with the invention may include, but are not limited to, one or more non-conservative substitutions and/or one or more conservative amino acid substitutions. A conservative amino acid residue substitution typically involves exchanging a member within one functional class of amino acid residues for a residue that belongs to the same functional class (conservative amino acid residues are considered functionally homologous or conserved in calculating percent functional homology). A conservative amino acid substitution typically involves the substitution of an amino acid in an amino acid sequence with a functionally similar amino acid. For example, alanine, glycine, serine, and threonine are functionally similar and thus may serve as conservative amino acid substitutions for one another. Aspartic acid and glutamic acid may serve as conservative substitutions for one another. Asparagine and glutamine may serve as conservative substitutions for one another. Arginine, lysine, and histidine may serve as conservative substitutions for one another. Isoleucine, leucine, methionine, and valine may serve as conservative substitutions for one another. Phenylalanine, tyrosine, and tryptophan may serve as conservative substitutions for one another.

Other conservative amino acid substitution groups can be envisioned. For example, amino acids can be grouped by similar function or chemical structure or composition (e.g., acidic, basic, aliphatic, aromatic, sulfur-containing). For instance, an aliphatic grouping may comprise: Glycine (G), Alanine (A), Valine (V), Leucine (L), Isoleucine (I). Other groups containing amino acids that are considered conservative substitutions for one another include: aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E); non-polar uncharged residues, Cysteine (C), Methionine (M), and Proline (P); hydrophilic uncharged residues: Serine (S), Threonine (T), Asparagine (N), and Glutamine (Q). Additional groupings of amino acids are well-known to those of skill in the art and described in various standard textbooks. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine.

Conservatively substituted variations of a polypeptide sequence of the invention (e.g., variant serine proteases of the invention) include substitutions of a small percentage, sometimes less than 5%, 4%, 3%, 2%, or 1%, or less than 10, 9, 8, 7, 6, 5, 4, 3, 2, or 1 amino acid substitutions of the amino acids of the polypeptide sequence, with a conservatively selected amino acid of the same conservative substitution group.

III. Nucleic Acids Encoding Serine Proteases

The invention provides isolated, non-naturally occurring, or recombinant nucleic acids which may be collectively referred to as "nucleic acids of the invention" or "polynucleotides of the invention", which encode polypeptides of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include serine protease polypeptides having enzymatic activity (e.g., proteolytic activity) which are useful in cleaning applications and cleaning compositions for cleaning an item or a surface (e.g., surface of an item) in need of cleaning.

In some embodiments, the polynucleotide of the present invention is a polynucleotide having a specified degree of nucleic acid homology to the exemplified polynucleotide. In some embodiments, the polynucleotide comprises a nucleic acid sequence selected from the group consisting of SEQ ID NO:1, SEQ ID NO:4, SEQ ID NO:9, SEQ ID NO:12, and SEQ ID NO:15. In other embodiments, the polynucleotide comprises a nucleic acid sequence having at least 50, 60, 65, 70, 72, 73, 74, 75, 80, 85, 90, 91, 92, 93, 94, 95, 96, 97, 98, 99 or 100% identity to SEQ ID NO:1, 4, 9, 12, 15, 18, 21, 24, 27, 30, 33, 36, or 39. In other embodiments, the polynucleotide of the present invention may also have a complementary nucleic acid sequence to a nucleic acid sequence selected from the group consisting of SEQ ID NO:1, SEQ ID NO:4, SEQ ID NO:9, SEQ ID NO:12, and SEQ ID NO:15. In a further embodiment, the polynucleotide of the present invention may also have a complementary nucleic acid sequence to SEQ ID NO: 1, 4, 9, 12, 15, 18, 21, 24, 27, 30, 33, 36, or 39. In some embodiments, a polynucleotide of the present invention has a nucleic acid sequence that encodes an amino acid sequence having at least 70%, 71%, 72%, 73%, 74%, 75%, 80%, 85%, 90%, 95%, 96%, 97%, 98%, 99% or 100% sequence identity to the amino acid sequence of SEQ ID NO: 3, 6, 11, 14, 17, 20, 23, 26, 29, 32, 35, 38, or 41. Homology can be determined by amino acid sequence alignment, e.g., using a program such as BLAST, ALIGN, or CLUSTAL, as described herein.

In a further embodiment, the polynucleotide of the present invention encodes an amino acid sequence of SEQ ID NO:42, 43, 44, 45, 46, 47, or 48 and further encodes an amino acid sequence having 70% identity to an amino acid sequence of SEQ ID NO:3, 6, 14, 17, 20, 23, 26, or 29. In another embodiment, the polynucleotide of the present invention encodes an amino acid sequence of SEQ ID NO:42, 43, 44, 45, 46, 47, or 48 and further encodes an amino acid sequence having 70% identity to an amino acid sequence of SEQ ID NO:3, 6, 14, or 17. In a still further embodiment, the polynucleotide of the present invention encodes an amino acid sequence of SEQ ID NO:42, 43, 44, 45, 46, 47, or 48 and further encodes an amino acid sequence having 72% identity to an amino acid sequence of SEQ ID NO:3, 6, 11, 14, 17, 20, 23, 26, 29, 32, 35, 38, or 41. In yet a further embodiment, the polynucleotide of the present invention encodes an amino acid sequence of SEQ ID NO:42, 43, 44, 45, 46, 47, or 48 and further encodes an amino acid sequence having 72% identity to an amino acid sequence of SEQ ID NO:3, 6, 11, 14, or 17.

In some embodiments, the invention provides an isolated, recombinant, substantially pure, or non-naturally occurring nucleic acid comprising a nucleotide sequence encoding any polypeptide (including any fusion protein, etc.) of the invention described above in the section entitled "Polypeptides of the Invention" and elsewhere herein. In some embodiments, the invention provides a synthetically derived nucleic acid comprising a nucleotide sequence encoding any polypeptide (including any fusion protein, etc.) of the invention described herein. The invention also provides an isolated, recombinant, substantially pure, or non-naturally-occurring nucleic acid comprising a nucleotide sequence encoding a combination of two or more of any polypeptides of the invention described above and elsewhere herein. The invention also provides a synthetically derived nucleic acid comprising a nucleotide sequence encoding a combination of two or more of any polypeptides of the invention described herein. The present invention provides nucleic acids encoding a serine protease polypeptide of the present invention, wherein the serine protease polypeptide is a mature form having proteolytic activity. In some embodiments, the serine protease (e.g., BspAI02518) is expressed recombinantly with a homologous pro-peptide sequence (e.g., BspAI02518 pro-peptide). In other embodiments, the serine protease is expressed recombinantly with a heterologous pro-peptide sequence (e.g., GG36 pro-peptide sequence set forth as:

(SEQ ID NO: 82))
AEEAKEKYLIGFNEQEAVSEFVEQVEANDEVAILSEEEEVEIELLHEFET

IPVLSVELSPEDVDALELDPAISYIEEDAEVTTM.

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods) to form essentially any desired continuous nucleic acid sequence. The synthesis of the nucleic acids of the invention can be also facilitated by any suitable method known in the art, including but not limited to chemical synthesis using the classical phosphoramidite method (See e.g., Beaucage et al. Tetrahedron Letters 22:1859-69 [1981]); or the method described by Matthes et al. (See, Matthes et al., EMBO J. 3:801-805 [1984], as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 [1984]; and Itakura et al., Science 198:1056 [1984]).

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. Nucleotides of the invention may also be obtained by screening cDNA libraries using one or more oligonucleotide probes that can hybridize to or PCR-amplify polynucleotides which encode a serine protease polypeptide polypeptide(s) of the invention. Procedures for screening and isolating cDNA clones and PCR amplification procedures are well known to those of skill in the art and described in standard references known to those skilled in the art. Some nucleic acids of the invention can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination). A variety of methods are known in the art that are suitable for generating modified polynucleotides of the invention that encode serine protease polypeptides of the invention, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches.

IV. Vectors, Host Cells, and Methods for Producing Serine Proteases

The present invention provides vectors comprising at least one serine protease polynucleotide of the invention described herein (e.g., a polynucleotide encoding a serine protease polypeptide of the invention described herein), expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, and compositions comprising one or more such vectors, nucleic acids, expression vectors, expression cassettes, DNA constructs, cells, cell cultures, or any combination or mixtures thereof.

In some embodiments, the invention provides recombinant cells comprising at least one vector (e.g., expression vector or DNA construct) of the invention which comprises at least one nucleic acid or polynucleotide of the invention. Some such recombinant cells are transformed or transfected with such at least one vector, although other methods are available and known in the art. Such cells are typically referred to as host cells. Some cells comprise bacterial cells, including, but are not limited to *Bacillus* sp. cells, such as *B. subtilis* cells. The invention also provides recombinant cells (e.g., recombinant host cells) comprising at least one serine protease polypeptide of the invention.

In some embodiments, the invention provides a vector comprising a nucleic acid or polynucleotide of the invention. In some embodiments, the vector is an expression vector or expression cassette in which a polynucleotide sequence of the invention which encodes a serine protease polypeptide of the invention is operably linked to one or additional nucleic acid segments required for efficient gene expression (e.g., a promoter operably linked to the polynucleotide of the invention which encodes a serine protease polypeptide of the invention). A vector may include a transcription terminator and/or a selection gene, such as an antibiotic resistance gene, that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pC194, pJH101, pE194, pHP13 (See, Harwood and Cutting [eds.], Chapter 3, Molecular Biological Methods for *Bacillus*, John Wiley & Sons [1990]; suitable replicating plasmids for *B. subtilis* include those listed on p. 92) See also, Perego, Integrational Vectors for Genetic Manipulations in *B. subtilis*, in Sonenshein et al., [eds.] *B. subtilis* and Other Gram-Positive Bacteria: Biochemistry, Physiology and Molecular Genetics, American Society for Microbiology, Washington, D.C. [1993], pp. 615-624), and p2JM103BBI.

For expression and production of a protein of interest (e.g., serine protease polypeptide) in a cell, at least one expression vector comprising at least one copy of a polynucleotide encoding the serine protease polypeptide, and in some instances comprising multiple copies, is transformed into the cell under conditions suitable for expression of the serine protease. In some embodiments of the present invention, a polynucleotide sequence encoding the serine protease polypeptide (as well as other sequences included in the vector) is integrated into the genome of the host cell, while in other embodiments, a plasmid vector comprising a polynucleotide sequence encoding the serine protease polypeptide remains as autonomous extra-chromosomal element within the cell. The invention provides both extrachromosomal nucleic acid elements as well as incoming nucleotide sequences that are integrated into the host cell genome. The vectors described herein are useful for production of the serine protease polypeptides of the invention. In some embodiments, a polynucleotide construct encoding the serine protease polypeptide is present on an integrating vector that enables the integration and optionally the amplification of the polynucleotide encoding the serine protease polypeptide into the host chromosome. Examples of sites for integration are well known to those skilled in the art. In some embodiments, transcription of a polynucleotide encoding a serine protease polypeptide of the invention is effectuated by a promoter that is the wild-type promoter for the selected precursor protease. In some other embodiments, the promoter is heterologous to the precursor protease, but is functional in the host cell. Specifically, examples of suitable promoters for use in bacterial host cells include, but are not limited to, for example, the amyE, amyQ, amyL, pstS, sacB, pSPAC, pAprE, pVeg, pHpaII promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilis* xylosidase gene, the *B. thuringiensis* cryIIIA, and the *B. licheniformis* alpha-amylase gene. Additional promoters include, but are not limited to the A4 promoter, as well as phage Lambda PR or PL promoters, and the *E. coli* lac, trp or tac promoters.

Serine protease polypeptides of the present invention can be produced in host cells of any suitable microorganism, including bacteria and fungi. In some embodiments, serine protease polypeptides of the present invention can be produced in Gram-positive bacteria. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, the serine protease polypeptides are produced by *Bacillus* sp. host cells. Examples of *Bacillus* sp. host cells that find use in the production of the serine protease polypeptides of the invention include, but are not limited to *B. licheniformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii,* and *B. megaterium,* as well as other organisms within the genus *Bacillus*. In some embodiments, *B. subtilis* host cells are used for production of serine protease polypeptides. U.S. Pat. Nos. 5,264,366 and 4,760,025 (RE 34,606) describe various *Bacillus* host strains that can be used for producing serine protease polypeptide of the invention, although other suitable strains can be used.

Several bacterial strains that can be used to produce serine protease polypeptides of the invention include non-recombinant (i.e., wild-type) *Bacillus* sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *B. subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics 73:215-228 [1973]; See also, U.S. Pat. Nos. 4,450,235 and 4,302,544, and EP 0134048, each of which is incorporated by reference in its entirety). The use of *B. subtilis* as an expression host cells is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host cell is a *Bacillus* sp. that includes a mutation or deletion in at least one of the following genes, degU, degS, degR and degQ. In some embodiments, the mutation is in a degU gene, and in some embodiments the mutation is degU(Hy)32 (See e.g., Msadek et al., J. Bacteriol. 172:824-834 [1990]; and Olmos et al., Mol. Gen. Genet. 253:562-567 [1997]). In some embodiments, the *Bacillus* host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce a serine protease polypeptide of the invention is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments, the *Bacillus* sp. host cell comprises a deletion of 9 protease genes (See e.g., U.S. Pat. Appl. Pub. No. 2005/0202535, incorporated herein by reference).

Host cells are transformed with at least one nucleic acid encoding at least one serine protease polypeptide of the invention using any suitable method known in the art. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Those of skill in the art are well aware of suitable methods for introducing nucleic acid sequences of the invention into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and transfection, transduction, and protoplast fusion are well known and suited for use in the present invention. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154:1077-1087 [1983]; and Weinrauch et al., J. Bacteriol. 169:1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding a serine protease polypeptide of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into the host genome. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art and are well described in the scientific literature. In some embodiments, the invention provides a culture (e.g., cell culture) comprising at least one serine protease polypeptide or at least one nucleic acid of the invention.

In some embodiments, host cells transformed with at least one polynucleotide sequence encoding at least one serine protease polypeptide of the invention are cultured in a suitable nutrient medium under conditions permitting the expression of the present protease, after which the resulting protease is recovered from the culture. In some embodiments, the protease produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.).

In some embodiments, a serine protease polypeptide produced by a recombinant host cell is secreted into the culture medium. A nucleic acid sequence that encodes a purification facilitating domain may be used to facilitate purification of proteins. A vector or DNA construct comprising a polynucleotide sequence encoding a serine protease polypeptide may further comprise a nucleic acid sequence encoding a purification facilitating domain to facilitate purification of the serine protease polypeptide (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system. The inclusion of a cleavable linker sequence such as Factor XA or enterokinase (e.g., sequences available from Invitrogen, San Diego, Calif.) between the purification domain and the heterologous protein also find use to facilitate purification.

Assays for detecting and measuring the enzymatic activity of an enzyme, such as a serine protease polypeptide of the invention, are well known. Various assays for detecting and measuring activity of proteases (e.g., serine protease polypeptides of the invention), are also known to those of ordinary skill in the art. In particular, assays are available for measuring protease activity that are based on the release of acid-soluble peptides from casein or hemoglobin, measured as absorbance at 280 nm or colorimetrically using the Folin method. Other exemplary assays involve the solubilization of chromogenic substrates (See e.g., Ward, "Proteinases," in Fogarty (ed.), Microbial Enzymes and Biotechnology, Applied Science, London, [1983], pp. 251-317). Other exemplary assays include, but are not limited to succinyl-Ala-Ala-Pro-Phe-para nitroanilide assay (suc-AAPF-pNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

A variety of methods can be used to determine the level of production of a mature protease (e.g., mature serine protease polypeptides of the present invention) in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (MA), fluorescent immunoassays (FIA), and fluorescent activated cell sorting (FACS). These and other assays are well known in the art (See e.g., Maddox et al., J. Exp. Med. 158:1211 [1983]).

In some other embodiments, the invention provides methods for making or producing a mature serine protease polypeptide of the invention. A mature serine protease polypeptide does not include a signal peptide or a propeptide sequence. Some methods comprise making or producing a serine protease polypeptide of the invention in a recombinant bacterial host cell, such as for example, a Bacillus sp. cell (e.g., a B. subtilis cell). In some embodiments, the invention provides a method of producing a serine protease polypeptide of the invention, the method comprising cultivating a recombinant host cell comprising a recombinant expression vector comprising a nucleic acid encoding a serine protease polypeptide of the invention under conditions conducive to the production of the serine protease polypeptide. Some such methods further comprise recovering the serine protease polypeptide from the culture.

In some embodiments the invention provides methods of producing a serine protease polypeptide of the invention, the methods comprising: (a) introducing a recombinant expression vector comprising a nucleic acid encoding a serine protease polypeptide of the invention into a population of cells (e.g., bacterial cells, such as B. subtilis cells); and (b) culturing the cells in a culture medium under conditions conducive to produce the serine protease polypeptide encoded by the expression vector. Some such methods further comprise: (c) isolating the serine protease polypeptide from the cells or from the culture medium.

V. Compositions Comprising Serine Proteases

A. Fabric and Home Care Products

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. Compositions of the invention include cleaning compositions, such as detergent compositions. In the exemplified detergent compositions, the enzymes levels are expressed by pure enzyme by weight of the total composition and unless otherwise specified, the detergent ingredients are expressed by weight of the total compositions.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the serine protease polypeptides of the present invention. The precise nature of these additional components, and levels of incorporation thereof, will depend on the physical form of the composition and the nature of the cleaning operation for which it is to be used. Suitable adjunct materials include, but are not limited to, bleach catalysts, other enzymes, enzyme stabilizing systems, chelants, optical brighteners, soil release polymers, dye transfer agents, dispersants, suds suppressors, dyes, perfumes, colorants, filler salts, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, 6,326,348, 6,610,642, 6,605,458, 5,705,464, 5,710,115, 5,698,504, 5,695,679, 5,686,014 and 5,646,101 all of which are incorporated herein by reference. In embodiments in which the cleaning adjunct materials are not compatible with the serine protease polypeptides of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.). The aforementioned adjunct ingredients may constitute the balance of the cleaning compositions of the present invention.

The cleaning compositions of the present invention are advantageously employed for example, in laundry applications, hard surface cleaning applications, dishwashing applications, including automatic dishwashing and hand dishwashing, as well as cosmetic applications such as dentures, teeth, hair and skin cleaning. The enzymes of the present invention are also suited for use in contact lens cleaning and wound debridement applications. In addition, due to the unique advantages of increased effectiveness in lower temperature solutions, the enzymes of the present invention are ideally suited for laundry applications. Furthermore, the enzymes of the present invention find use in granular and liquid compositions.

The serine protease polypeptides of the present invention also find use in cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more proteases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the serine protease polypeptides provided herein, alone or in combination with other proteases and/or additional enzymes. The required level of enzyme is achieved by the addition of one or more serine protease polypeptides of the present invention. Typically the present cleaning compositions comprise at least about 0.0001 weight percent, from about 0.0001 to about 10, from about 0.001 to about 1, or from about 0.01 to about 0.1 weight percent of at least one of the serine protease polypeptides of the present invention.

The cleaning compositions herein are typically formulated such that, during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 9 to about 11. In some embodiments, the cleaning compositions of the present invention can be formulated to have an alkaline pH under wash conditions, such as a pH of from about 8.0 to about 12.0, or from about 8.5 to about 11.0, or from about 9.0 to about 11.0. In some embodiments, the cleaning compositions of the present invention can be formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionized water at 20° C., measured using a conventional pH meter. Techniques for controlling pH at recommended usage levels include the use of buffers, alkalis, acids, etc., and are well known to those skilled in the art.

In some embodiments, when the serine protease polypeptide (s) is/are employed in a granular composition or liquid, it is desirable for the serine protease polypeptide to be in the form of an encapsulated particle to protect the serine protease polypeptide from other components of the granular composition during storage. In addition, encapsulation is also a means of controlling the availability of the serine protease polypeptide during the cleaning process. In some embodiments, encapsulation enhances the performance of the serine protease polypeptide (s) and/or additional enzymes. In this regard, the serine protease polypeptides of the present invention are encapsulated with any suitable encapsulating material known in the art. In some embodiments, the encapsulating material typically encapsulates at least part of the serine protease polypeptide (s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP 0 922 499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

There are a variety of wash conditions including varying detergent formulations, wash water volumes, wash water temperatures, and lengths of wash time, to which proteases involved in washing are exposed. A low detergent concentration system includes detergents where less than about 800 ppm of the detergent components are present in the wash water. A medium detergent concentration includes detergents where between about 800 ppm and about 2000 ppm of the detergent components are present in the wash water. A high detergent concentration system includes detergents where greater than about 2000 ppm of the detergent components are present in the wash water. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

Different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million.

TABLE I

Water Hardness

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

Accordingly, in some embodiments, the present invention provides serine protease polypeptides that show surprising wash performance in at least one set of wash conditions (e.g., water temperature, water hardness, and/or detergent concentration). In some embodiments, the serine protease polypeptides of the present invention are comparable in wash performance to other serine protease polypeptide proteases. In some embodiments of the present invention, the serine protease polypeptides provided herein exhibit enhanced oxidative stability, enhanced thermal stability, enhanced cleaning capabilities under various conditions, and/or enhanced chelator stability. In addition, the serine protease polypeptides of the present invention find use in cleaning compositions that do not include detergents, again either alone or in combination with builders and stabilizers.

In some embodiments of the present invention, the cleaning compositions comprise at least one serine protease polypeptide of the present invention at a level from about 0.00001% to about 10% by weight of the composition and the balance (e.g., about 99.999% to about 90.0%) comprising cleaning adjunct materials by weight of composition. In some other embodiments of the present invention, the cleaning compositions of the present invention comprises at least one serine protease polypeptide at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, or any combinations or mixtures thereof. In some embodiments, a combination of enzymes is used (i.e., a "cocktail") comprising conventional applicable enzymes like protease, lipase, cutinase and/or cellulase in conjunction with amylase is used.

In addition to the serine protease polypeptides provided herein, any other suitable protease finds use in the compositions of the present invention. Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147 and subtilisin 168). Additional examples include those mutant proteases described in U.S. Pat. Nos. RE 34,606; 5,955,340; 5,700,676; 6,312,936; and 6,482,628, all of which are incorporated herein by reference. Additional protease examples include, but are not limited to trypsin (e.g., of porcine or bovine origin), and the *Fusarium* protease described in WO 89/06270. In some embodiments, commercially available protease enzymes that find use in the present invention include, but are not limited to MAX-ATASE®, MAXACAL™ MAXAPEM™, OPTICLEAN®, OPTIMASE®, PROPERASE®, PURAFECT®, PURAFECT® OXP, PURAIVIAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (Genencor); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ variants (Henkel Kommanditgesellschaft auf Aktien, Duesseldorf, Germany), and KAP (*B. alkalophilus* subtilisin; Kao Corp., Tokyo, Japan). Various proteases are described in WO95/23221, WO 92/21760, WO 09/149200, WO 09/149144, WO 09/149145, WO 11/072099, WO 10/056640, WO 10/056653, WO 11/140364, WO 12/151534, U.S. Pat. Publ. No. 2008/0090747, and U.S. Pat. Nos. 5,801,039, 5,340,735, 5,500,364, 5,855,625, US RE 34,606, 5,955,340, 5,700,676, 6,312,936, 6,482,628, 8,530, 219, and various other patents. In some further embodiments, metalloproteases find use in the present invention, including but not limited to the metalloproteases described in WO1999014341, WO1999033960, WO1999014342, WO1999034003, WO2007044993, WO2009058303, WO2009058661, WO2014194032, WO2014194034, and WO2014194054. Exemplary metalloproteases include nprE, the recombinant form of neutral metalloprotease expressed in *B. subtilis* (See e.g., WO 07/044993), and PMN, the purified neutral metalloprotease from *B. amyloliquefaciens*.

In addition, any suitable lipase finds use in the present invention. Suitable lipases include, but are not limited to those of bacterial or fungal origin. Chemically or genetically modified mutants are encompassed by the present invention. Examples of useful lipases include *Humicola lanuginosa* lipase (See e.g., EP 258 068, and EP 305 216), *Rhizomucor miehei* lipase (See e.g., EP 238 023), *Candida* lipase, such as *C. antarctica* lipase (e.g., the *C. antarctica* lipase A or B; See e.g., EP 214 761), *Pseudomonas* lipases such as *P. alcaligenes* lipase and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipase polypeptide enzymes such as cutinases also find use in some embodiments of the present invention, including but not limited to the cutinase derived from *Pseudomonas mendocina* (See, WO 88/09367), and the cutinase derived from *Fusarium solani pisi* (See, WO 90/09446).

Additional suitable lipases include lipases such as M1 LIPASE™, LUMA FAST™, and LIPOMAX™ (Genencor); LIPEX®, LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from about 0.00001% to about 10% of additional lipase by weight of the composition and the balance of cleaning adjunct materials by weight of composition. In some other embodiments of the present invention, the cleaning compositions of the present invention also comprise lipases at a level of about 0.0001% to about 10%, about 0.001% to about 5%, about 0.001% to about 2%, about 0.005% to about 0.5% lipase by weight of the composition.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296, 839). Additional suitable amylases include those found in WO9510603, WO9526397, WO9623874, WO9623873, WO9741213, WO9919467, WO0060060, WO0029560, WO9923211, WO9946399, WO0060058, WO0060059, WO9942567, WO0114532, WO02092797, WO0166712, WO0188107, WO0196537, WO0210355, WO9402597, WO0231124, WO9943793, WO9943794, WO2004113551, WO2005001064, WO2005003311, WO0164852, WO2006063594, WO2006066594, WO2006066596, WO2006012899, WO2008092919, WO2008000825, WO2005018336, WO2005066338, WO2009140504, WO2005019443, WO2010091221, WO2010088447, WO0134784, WO2006012902, WO2006031554, WO2006136161, WO2008101894, WO2010059413, WO2011098531, WO2011080352, WO2011080353, WO2011080354, WO2011082425, WO2011082429, WO2011076123, WO2011087836, WO2011076897, WO94183314, WO9535382, WO9909183, WO9826078, WO9902702, WO9743424, WO9929876, WO9100353, WO9605295, WO9630481, WO9710342, WO2008088493, WO2009149419, WO2009061381, WO2009100102, WO2010104675, WO2010117511, and WO2010115021. Commercially available amylases that find use in the present invention include, but are not limited to DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P (Genencor).

In some embodiments of the present invention, the cleaning compositions of the present invention further comprise amylases at a level from about 0.00001% to about 10% of additional amylase by weight of the composition and the balance of cleaning adjunct materials by weight of composition. In some other embodiments of the present invention, the cleaning compositions of the present invention also comprise amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257). Commercially available cellulases that find use in the present include, but are not limited to CELLUZYME®, CAREZYME® (Novozymes), REVITALENZ™ 100 (Danisco US Inc), and KAC-500 (B)™ (Kao Corporation). In some embodiments, cellulases are incorporated as portions or fragments of mature wild-type or variant cellulases, wherein a portion of the N-terminus is deleted (See e.g., U.S. Pat. No. 5,874,276). Additional suitable cellulases include those found in WO2005054475, WO2005056787, U.S. Pat. Nos. 7,449, 318, and 7,833,773. In some embodiments, the cleaning compositions of the present invention further comprise cellulases at a level from about 0.00001% to about 10% of additional cellulase by weight of the composition and the balance of cleaning adjunct materials by weight of composition. In some other embodiments of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114, 6,602,842, and 6,440,991, all of which are incorporated herein by reference). Commercially available mannanases that find use in the present invention include, but are not limited to MANNASTAR®, PURABRITE™, and MANNAWAY®. In some embodiments, the cleaning compositions of the present invention further comprise mannanases at a level from about 0.00001% to about 10% of additional mannanase by weight of the composition and the balance of cleaning adjunct materials by weight of composition. In some embodiments of the present invention, the cleaning compositions of the present invention also comprise mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In some other embodiments of the present invention, the cleaning compositions of the present invention also comprise peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO2005/056782, WO2007106293, WO2008063400, WO2008106214, and WO2008106215). In addition, in some embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the serine protease polypeptide (s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

In some embodiments, an effective amount of one or more serine protease polypeptide (s) provided herein is included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the serine protease polypeptides of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use in detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the serine protease polypeptides of the present invention. Thus, in some embodiments, the compositions comprising at least one serine protease polypeptide of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one serine protease polypeptide of the present invention are fabric cleaning compositions such as those described in U.S. Pat. Nos. 6,610,642 and 6,376,450. In addition, the serine protease polypeptides of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one serine protease polypeptide provided herein. Thus, in some embodiments, the compositions comprising at least one serine protease polypeptide of the present invention is a hard surface cleaning composition such as those described in U.S. Pat. Nos. 6,610,642, 6,376,450, and 6,376,450.

In yet further embodiments, the present invention provides dishwashing compositions comprising at least one serine protease polypeptide provided herein. Thus, in some embodiments, the compositions comprising at least one serine protease polypeptide of the present invention is a hard surface cleaning composition such as those in U.S. Pat. Nos. 6,610,642 and 6,376,450. In some still further embodiments, the present invention provides dishwashing compositions comprising at least one serine protease polypeptide provided herein. In some further embodiments, the compositions comprising at least one serine protease polypeptide of the present invention comprise oral care compositions such as those in U.S. Pat. Nos. 6,376,450, and 6,376,450. The formulations and descriptions of the compounds and cleaning adjunct materials contained in the aforementioned U.S. Pat. Nos. 6,376,450, 6,605,458, 6,605,458, and 6,610,642, find use with the serine protease polypeptides provided herein.

The cleaning compositions of the present invention are formulated into any suitable form and prepared by any process chosen by the formulator (See e.g., U.S. Pat. Nos. 5,879,584, 5,691,297, 5,574,005, 5,569,645, 5,565,422, 5,516,448, 5,489,392, 5,486,303, 4,515,705, 4,537,706, 4,515,707, 4,550,862, 4,561,998, 4,597,898, 4,968,451, 5,565,145, 5,929,022, 6,294,514 and 6,376,445). When a low pH cleaning composition is desired, the pH of such composition is adjusted via the addition of a material such as monoethanolamine or an acidic material such as HCl. In some embodiments, the cleaning compositions according to the present invention comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR—N(CH$_2$COOM)$_2$ where R is C$_{1-12}$ alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl)aspartic acid (SEAS), N-(2-sulfomethyl)glutamic acid (SMGL), N-(2-sulfoethyl) glutamic acid (SEGL), IDS (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,N diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400µ to about 1200µ and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle of the invention is a highly active particle comprising a high level of amino carboxylic builder. Sulphuric acid has been found to further contribute to the stability of the final particle.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP 2 100 949).

In some embodiments, builders for use herein include phosphate builders and non-phosphate builders. In some embodiments, the builder is a phosphate builder. In some embodiments, the builder is a non-phosphate builder. If present, builders are used in a level of from 0.1% to 80%, or from 5 to 60%, or from 10 to 50% by weight of the composition. In some embodiments the product comprises a mixture of phosphate and non-phosphate builders. Suitable phosphate builders include mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition of the invention. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present invention. In some embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some embodiments, the anti-redeposition agent is a non-ionic surfactant as known in the art (See e.g., EP 2 100 949). In some embodiments, the non-ionic surfactant can be ethoxylated nonionic surfactants, epoxy-capped poly(oxyalkylated) alcohols and amine oxides surfactants.

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1% to about 20%. In some embodiments, silicates are present at a level of from about 5% to about 15% by weight of the composition.

In some still additional embodiments, the cleaning compositions of the present invention also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts, such as calcium formate. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO 07/145964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleaches, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP 2 100 949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP 2 100 949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612, 5,227,084, 4,810410, WO 99/06521, and EP 2 100 949).

In some embodiments, the cleaning compositions of the present invention contain one or more catalytic metal complexes. In some embodiments, a metal-containing bleach catalyst finds use. In some embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In some additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some embodiments, provide from about 0.005 ppm to about 25 ppm, more preferably from about 0.05 ppm to about 10 ppm, and most preferably from about 0.1 ppm to about 5 ppm, of the MRL in the wash liquor.

In some embodiments, transition-metals in the instant transition-metal bleach catalyst include, but are not limited to manganese, iron and chromium. MRLs also include, but are not limited to special ultra-rigid ligands that are cross-bridged (e.g., 5,12-diethyl-1,5,8,12-tetraazabicyclo[6.6.2]hexadecane). Suitable transition metal MRLs are readily prepared by known procedures (See e.g., WO 2000/32601, and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860 and WO 94/26859). In some embodiments, the metal care agent is a zinc salt. In some further embodiments, the cleaning compositions of the present invention comprise from about 0.1% to about 5% by weight of one or more metal care agent.

In some embodiments, the cleaning composition is a high density liquid (HDL) composition having a variant serine protease polypeptide protease. The HDL liquid laundry detergent can comprise a detersive surfactant (10%-40%% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof); and optionally non-ionic surfactant (selected from a group of linear or branched or random chain, substituted or unsubstituted alkyl alkoxylated alcohol, for example a $C_8$-$C_{18}$ alkyl ethoxylated alcohol and/or $C_6$-$C_{12}$ alkyl phenol alkoxylates), optionally wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

The composition can comprise optionally, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof.

The composition can comprise additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition can further comprise saturated or unsaturated fatty acid, preferably saturated or unsaturated $C_{12}$-$C_{24}$ fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydroxyethyl cellulose, cationic starch, cationic polyacrylamides, and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof.

The composition may optionally include enzymes (generally about 0.01 wt % active enzyme to 0.5 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may comprise an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition can further comprise silicone or fatty-acid based suds suppressors; hueing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof.

In some embodiments, the cleaning compositions of the present invention are provided in unit dose form, including tablets, capsules, sachets, pouches, and multi-compartment pouches. In some embodiments, the unit dose format is designed to provide controlled release of the ingredients within a multi-compartment pouch (or other unit dose format). Suitable unit dose and controlled release formats are known in the art (See e.g., EP 2 100 949, WO 02/102955, U.S. Pat. Nos. 4,765,916 and 4,972,017, and WO 04/111178 for materials suitable for use in unit dose and controlled release formats). In some embodiments, the unit dose form is provided by tablets wrapped with a water-soluble film or water-soluble pouches. Various unit dose formats are provided in EP 2 100 947 and WO2013/165725 (which is hereby incorporated herein by reference), and are known in the art.

In some embodiments, the cleaning composition is a high density powder (HDD) composition having a variant serine protease polypeptide protease. The HDD powder laundry detergent can comprise a detersive surfactant including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (selected from a group of linear or branched or random chain, substituted or unsubstituted $C_8$-$C_{18}$ alkyl ethoxylates, and/or $C_6$-$C_{12}$ alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants e.g., alkanolamine sulpho-betaines); ampholytic surfactants; semi-polar non-ionic surfactants and mixtures thereof; builders (phosphate free builders [for example zeolite builders examples of which include zeolite A, zeolite X, zeolite P and zeolite MAP in the range of 0 wt % to less than 10 wt %]; phosphate builders (for example, sodium tripolyphosphate in the range of 0 wt % to less than 10 wt %]; citric acid, citrate salts and nitrilotriacetic acid or salt thereof in the range of less than 15 wt %); silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 10 wt %); and bleaching agents (including photobleaches, (e.g., sulfonated zinc phthalocyanines, sulfonated aluminum phthalocyanines, xanthenes dyes, and mixtures thereof; hydrophobic or hydrophilic bleach activators (include e.g., dodecanoyl oxybenzene sulfonate, decanoyl oxybenzene sulfonate, decanoyl oxybenzoic acid or salts thereof, 3,5,5-trimethyl hexanoyl oxybenzene sulfonate, tetraacetyl ethylene diamine-TAED, and nonanoyloxybenzene sulfonate-NOBS, nitrile quats, and mixtures thereof); sources of hydrogen peroxide (e.g., inorganic perhydrate salts examples of which include mono or tetra hydrate sodium salt of perborate, percarbonate, persulfate, perphosphate, or persilicate); preformed hydrophilic and/or hydrophobic peracids (e.g., percarboxylic acids and salts, percarbonic acids and salts, perimidic acids and salts, peroxymonosulfuric acids and salts, and mixtures thereof); and/or bleach catalysts (e.g., imine bleach boosters (examples of which include iminium cations and polyions); iminium zwitterions; modified amines; modified amine oxides; N-sulphonyl imines; N-phosphonyl imines; N-acyl imines; thiadiazole dioxides; perfluoroimines; cyclic sugar ketones and mixtures thereof; and metal-containing bleach catalysts (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid) and water-soluble salts thereof).

The composition preferably includes enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition can further comprise additional detergent ingredients including perfume microcapsules, starch encapsulated perfume accord, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an automatic dishwashing (ADW) detergent composition having a serine protease of the present invention. The ADW detergent composition can comprise two or more non-ionic surfactants selected from a group of ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% comprising either phosphate (mono-phosphates, di-phosphates, tri-polyphosphates or oligomeric-polyphosphates, preferred sodium tripolyphosphate-STPP or phosphate-free builders [amino acid based compounds, examples of which include MGDA (methyl-glycine-diacetic acid), and salts and derivatives thereof, GLDA (glutamic-N,N diacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), B-alaninediacetic acid (B-ADA) and their salts], homopolymers and copolymers of polycarboxylic acids and their partially or completely neutralized salts, monomeric polycarboxylic acids and hydroxycarboxylic acids and their salts in the range of 0.5% to 50% by weight; sulfonated/carboxylated polymers (provide dimensional stability to the product) in the range of about 0.1% to about 50% by weight; drying aids in the range of about 0.1% to about 10% by weight (selected from polyesters, especially anionic polyesters optionally together with further monomers with 3 to 6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1% to about 20% by weight (sodium or potassium silicates for example sodium disilicate, sodium meta-silicate and crystalline phyllosilicates); bleach-inorganic (for example perhydrate salts such as perborate, percarbonate, perphosphate, persulfate and persilicate salts) and organic (for example organic peroxyacids including diacyl and tetraacylperoxides, especially diperoxydodecanedioc acid, diperoxytetradecanedioc acid, and diperoxyhexadecanedioc acid); bleach activators—organic peracid precursors in the range from about 0.1% to about 10% by weight; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1% to 5% by weight (selected from benzatriazoles, metal salts and complexes, and/or silicates); enzymes in the range from about 0.01 to 5.0 mg of active enzyme per gram of automatic dishwashing detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, and any mixture thereof); and enzyme stabilizer components (selected from oligosaccharides, polysaccharides and inorganic divalent metal salts).

In some embodiments, the cleaning composition is borate-free. In some embodiments, the cleaning composition is phosphate-free. In some embodiments, the cleaning composition can have less than 10 ppm, or less than 5 ppm or less than 1 ppm of borates and/or phosphates in the composition.

Representative detergent formulations that beneficially include a serine protease polypeptide of the present invention include the detergent formulations found in WO2013063460, pages 78-152, and in particular the tables of pages 94 to 152 are hereby incorporated by reference. The serine proteases are normally incorporated into the detergent composition at a level of from 0.00001% to 10% of enzyme protein by weight of the composition. In some embodiments, the detergent composition comprises more than 0.0001%, 0.001%, 0.01%, or 0.1% of the serine protease by weight of the composition. In some embodiments, the detergent composition comprises less than 1%, 0.1%, 0.01%, or 0.001% of the serine protease by weight of the composition.

B. Textile Processing

Also provided are compositions and methods of treating fabrics (e.g., to desize a textile) using a serine protease polypeptide of the present invention. Fabric-treating methods are well known in the art (see, e.g., U.S. Pat. No. 6,077,316). For example, the feel and appearance of a fabric can be improved by a method comprising contacting the fabric with a serine protease in a solution. The fabric can be treated with the solution under pressure.

A serine protease of the present invention can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. A serine protease of the present invention can be applied during or after the weaving to remove these sizing starch or starch derivatives. After weaving, the serine protease can be used to remove the size coating before further processing the fabric to ensure a homogeneous and wash-proof result.

A serine protease of the present invention can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. The serine protease can be used in methods of finishing denim garments (e.g., a "bio-stoning process"), enzymatic desizing and providing softness to fabrics, and/or finishing process.

C. Leather and Feather Processing

The serine protease polypeptides described herein find further use in the enzyme aided removal of proteins from animals and their subsequent degradation or disposal, such as feathers, skin, hair, hide, and the like. In some instances, immersion of the animal carcass in a solution comprising a serine protease polypeptide of the present invention can act to protect the skin from damage in comparison to the traditional immersion in scalding water or the defeathering process. In one embodiment, feathers can be sprayed with an isolated serine protease polypeptide of the present invention under conditions suitable for digesting or initiating degradation of the plumage. In some embodiments, a serine protease of the present invention can be used, as above, in combination with an oxidizing agent.

In some embodiments, removal of the oil or fat associated with raw feathers is assisted by using a serine protease polypeptide of the present invention. In some embodiments, the serine protease polypeptides are used in compositions for cleaning the feathers as well as to sanitize and partially dehydrate the fibers. In yet other embodiments, the disclosed serine protease polypeptides find use in recovering protein from plumage. In some other embodiments, the serine protease polypeptides are applied in a wash solution in combination with 95% ethanol or other polar organic solvent with or without a surfactant at about 0.5% (v/v).

D. Animal Feed Applications

In a further aspect of the invention, the serine protease polypeptides of the present invention can be used as a component of an animal feed composition, animal feed additive and/or pet food comprising a serine protease and variants thereof. The present invention further relates to a method for preparing such an animal feed composition, animal feed additive composition and/or pet food comprising mixing the serine protease polypeptide with one or more animal feed ingredients and/or animal feed additive ingredients and/or pet food ingredients. Furthermore, the present invention relates to the use of the serine protease polypeptide in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to, dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

E. Paper Pulp Bleaching

The protease polypeptides described herein find further use in the enzyme aided bleaching of paper pulps such as chemical pulps, semi-chemical pulps, kraft pulps, mechanical pulps or pulps prepared by the sulfite method. In general terms, paper pulps are incubated with a protease polypeptide of the present invention under conditions suitable for bleaching the paper pulp.

In some embodiments, the pulps are chlorine free pulps bleached with oxygen, ozone, peroxide or peroxyacids. In some embodiments, the protease polypeptides are used in enzyme aided bleaching of pulps produced by modified or continuous pulping methods that exhibit low lignin contents. In some other embodiments, the protease polypeptides are applied alone or preferably in combination with xylanase and/or endoglucanase and/or alpha-galactosidase and/or cellobiohydrolase enzymes.

F. Protein Degradation

The protease polypeptides described herein find further use in the enzyme aided removal of proteins from animals and their subsequent degradation or disposal, such as feathers, skin, hair, hide, and the like. In some instances, immersion of the animal carcass in a solution comprising a protease polypeptide of the present invention can act to protect the skin from damage in comparison to the traditional immersion in scalding water or the defeathering process. In one embodiment, feathers can be sprayed with an isolated protease polypeptide of the present invention under conditions suitable for digesting or initiating degradation of the plumage. In some embodiments, a protease of the present invention can be used, as above, in combination with an oxidizing agent.

In some embodiments, removal of the oil or fat associated with raw feathers is assisted by using a protease polypeptide of the present invention. In some embodiments, the protease polypeptides are used in compositions for cleaning the feathers as well as to sanitize and partially dehydrate the fibers. In some other embodiments, the protease polypeptides are applied in a wash solution in combination with 95% ethanol or other polar organic solvent with or without a surfactant at about 0.5% (v/v). In yet other embodiments, the disclosed protease polypeptides find use in recovering protein from plumage. The disclosed protease polypeptides may be used alone or in combination in suitable feather processing and proteolytic methods, such as those disclosed in PCT/EP2013/065362, PCT/EP2013/065363, and PCT/EP2013/065364, which are hereby incorporated by reference. In some embodiments, the recovered protein can be subsequently used in animal or fish feed.

G. Tissue Debridement

The protease polypeptides described herein find further use in the enzyme aided debridement of tissue. This involves the removal of dead or damaged tissue, for example, removal from wounds to aid in healing.

H. Tissue Culture

The protease polypeptides described herein find further use in tissue culture. In particular, proteases of the present invention can be used to suspend or resuspend cells adherent to a cell culture wall, such as during the process of harvesting cells. Proteases of the present invention can be used to cleave protein bonds between cultured cells and the dish, allowing cells to become suspended in solution.

I. Food Applications

The protease polypeptides described herein find further use as a food additive, a digestive aide or a food processing aid.

EXAMPLES

The following examples are provided to demonstrate and illustrate certain preferred embodiments and aspects of the present disclosure and should not be construed as limiting.

In the experimental disclosure which follows, the following abbreviations apply: ADW (automatic dish washing); BMI (blood/milk/ink); BSA (bovine serum albumin); CAPS (N-cyclohexyl-3-aminopropanesulfonic acid); CHES (N-cyclohexyl-2-aminoethanesulfonic acid); DMC (dimethyl casein); HDD (heavy duty dry/powder); HDL (heavy duty liquid); HEPES (4-(2-hydroxyethyl)-1-piperazineethanesulfonic acid); MTP (microtiter plate); ND (not done); OD (optical density); PCR (polymerase chain reaction); ppm (parts per million); QS (quantity sufficient); rpm (revolutions per minute); AAPF (succinyl-Ala-Ala-Pro-Phe-p-nitroanilide); TNBSA (2,4,6-trinitrobenzene sulfonic acid); v/v (volume to volume); w/v (weight to volume).

Example 1

Cloning of *Bacillus* sp. Serine Proteases BspAI02518 and BspU02193

Serine Protease BspAI02518

The *B. akibai* C-M2-3 strain (DuPont Culture Collection) was selected as a potential source for enzymes useful in various industrial applications. The entire genome of the *Bacillus* sp. C-M2-3 strain was sequenced using ILLUMINA® sequencing by synthesis technology.

Genome sequencing and assembly of the sequence data was performed by BaseClear (Leiden, The Netherlands). Contigs were annotated by BioXpr (Namur, Belgium). One of the genes identified this way in *B. akibai* C-M-2-3 encodes a serine protease that showed homology to serine proteases of other bacteria.

The nucleotide sequence of BspAI02518n is set forth as SEQ ID NO:1:

ATGAAAATGAAATGGTCACGTTTACTTTTAACTCTAGTTCTCGTATTCAG

TTTTGTATTCCCATCTATGACAAGTGCAAACTCAGCTGTAGAAAAAGAGG

ACTATCTGATCGGTTTTAAGCAGAAAGGGAATGTTAGTGCACAAGTTGTG

AATATGAGTGGAGGAGAAGTCGTCCATGAATATGAACATATGCCAGTCTT

GCACGTTAAATTACCTCCACAAGCTGCTAAAGCTTTAGAAAAGAACCGAA

ATATTGAATACATCGAAAAAGATGAAAAAGTCCAAGCAACAGCACAATCG

ACACCTTGGGGGATTTCACGTATTAATGCTCCTGCTGTTCACTCGACTGG

TAATTTTGGACAAGGTGTCCGAGTTGCCGTTTTAGATAGTGGAGTTGCTT

CTCATGAAGACTTACGGATTGCTGGGGGAGTGAGCTTTGTCGCTTCAGAA

CCTAGTTATCAAGATTATAATGGTCACGGAACACATGTTGCTGGAACCAT

TGCTGGTTTAAATAATAGTGTTGGGGTCCTTGGTGTAGCTCCATCTGTCC

AATTATATGCGGTTAAGGTGTTGGATCGTAATGGCGGGGAAATCATAGT

GACATTGCTAGAGGAATTGAGTGGTCAGTTAATAATGGTATGCATGTGGT

GAATATGAGTTTAGGTGGACCAACAGGGTCAACCACTCTTCAACGAGCAG

CGGATAATGCTTATAATAGAGGAGTTCTTTTAATTGCTGCGGCTGGTAAC

ACGGGAACTAGTGGAGTTAGCTTCCCTGCGCGTTACAGCTCAGTAATGGC

AGTAGCCGCAACAGATTCTAATAATAACCGTGCTTCATTTTCAACTTATG

GATCACAAATTGAAATTTCAGCACCTGGAGTTGGCATTAATAGCACGTAT

CCAACGAATGGTTATTCAAGTTTAAATGGAACATCAATGGCTTCACCTCA

TGTCGCTGGTGTAGCGGCCCTAGTGAAGGCGAGATATCCAAGTGCGACGA

ATGCTCAGATTAGACAACATCTTCGTAGCACTTCTACGTATCTAGGAAAC

TCAACTTACTATGGTAGTGGTCTAGTTGATGCACAGCGTGCAACTAAC.

The amino acid sequence of the preproenzyme encoded by BspAI02518n is set forth as SEQ ID NO:2:

*MKMKWSRLLLTLVLVFSFVFPSMTSA*NSAVEKEDYLIGFKQKGNVSAQVVNMSG-GEVVHEYEHM

PVLHVKLPPQAAKALEKNRNIEYIEKDEKVQATA*QSTPWGISRINAPAVH*

STGNFGQGVRVAVLDSGVASHEDLRIAGGVSFVASEPSYQDYNGHGTHVA

GTIAGLNNSVGVLGVAPSVQLYAVKVLDRNGGGNHSDIARGIEWSVNNGM

HVVNMSLGGPTGSTTLQRAADNAYNRGVLLIAAAGNTGTSGVSFPARYSS

VMAVAATDSNNNRASFSTYGSQIEISAPGVGINSTYPTNGYSSLNGTSMA

SPHVAGVAALVKARYPSATNAQIRQHLRSTSTYLGNSTYYGSGLVDAQRA

TN.

At the N-terminus, the preproenzyme has a signal peptide with a predicted length of 26 amino acids (in bold italics in SEQ ID NO:2) as determined using SignalP-NN (Emanuelsson et al., Nature Protocols, 2:953-971, 2007). The presence of a signal peptide sequence indicates that this serine protease is a secreted enzyme. Like other serine proteases, the enzyme has a pro-sequence with a predicted length of 71 amino acids (in italics in SEQ ID NO:2). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, BspAI02518 (269 amino acids), is depicted in SEQ ID NO:3.

AQSTPWGISRINAPAVHSTGNFGQGVRVAVLDSGVASHEDLRIAGGVSFV

ASEPSYQDYNGHGTHVAGTIAGLNNSVGVLGVAPSVQLYAVKVLDRNGGG

NHSDIARGIEWSVNNGMHVVNMSLGGPTGSTTLQRAADNAYNRGVLLIAA

AGNTGTSGVSFPARYSSVMAVAATDSNNNRASFSTYGSQIEISAPGVGIN

STYPTNGYSSLNGTSMASPHVAGVAALVKARYPSATNAQIRQHLRSTSTY

LGNSTYYGSGLVDAQRATN.

Serine Protease BspU02193

The *B. akibai* GICC 2089392 strain (Dupont Culture Collection) was selected as a potential source for enzymes useful in various industrial applications. The entire genome of the *Bacillus* sp. GICC 2089392 strain was sequenced using ILLUMINA® sequencing by synthesis technology. Genome sequencing and assembly of the sequence data was performed by BaseClear (Leiden, The Netherlands). Contigs were annotated by BioXpr (Namur, Belgium). One of the genes identified this way in *B. akibai* GICC 2089392 encodes serine protease that showed homology to serine proteases of other bacteria.

The nucleotide sequence of BspU02193n is depicted in SEQ ID NO:4.

ATGAGTAAAATGAAGTTTACTAGTTTGTTGTTAGGGTTGGTTGTGGCGTT

TGTCTTTGTCTTCTCGACTCTGTCAGTCAGTGCGAATGGAAAAGGTGCTG

AGCGTCTTGATTATTTAGTTGGGTTTAAAGAGAAGCCGAATGCACAAGTG

ATGGCGCAGTCTGGTGGCGAGGTGGTTCATGAGTTTGAATATATGAATGT

CGTTCATATGAAACTTCCAGAGCAAGCAGCAAAAGCTCTTGAGAAGAACC

CGAACATTGCGTTTGTTGAGCGTGATGAGAAGGTCGAAGCGACTCAAACG

GTTCCTTGGGGAATCAATCATGTGAAAGCTCCGACTGTTCATAACTGGGG

-continued
```
CAATGTTGGAACGGGCGTGAAGGTGGCGGTGCTTGATACAGGAATCGCGT

CTCACCCGGATTTACGTGTGTCTGGTGGAGCGAGCTTCATTCCATCTGAG

CCTACGATTCAAGATTTCAACGGACACGGAACGCATGTGGCGGGGACAGT

CGCTGCGTTAAATAATAGCATTGGTGTGCTTGGTGTCGCGCCGAATGTTC

AATTATATGGTGTAAAGGTTTTAGATCGTAACGGTGGCGGATCTCATAGT

GCGATTGCTCAAGGGATTGAGTGGTCGATTTCAAATGGGATGGATGTTGT

GAATATGAGTTTAGGTGGAGCGACTAGTTCAACGGCGTTAAGCCAAGCGG

TAGCGAATGCGAGTAACCGCGGGATTTTATTAATTGCGGCGTCTGGTAAC

ACAGGGCGCGCGGGCATTCAGTTCCCTGCTCGTTATAGCCAAGTGATGGC

TGTTGGAGCGGTCGATCAGAACAACCGTCTGGCTTCATTCTCAACATTTG

GAAACGAGCAAGAAATTGTGGCTCCCGGTGTAGGTATTCAGAGCACATAC

TTAAACAACGGATATTCTTCATTAAACGGTACATCAATGGCTGCTCCTCA

CGTGGCAGGTGTCGCGGCACTTGTGATGAGCGAGTACCCATGGGCAACAG

CACCTCAAGTACGCGGACGTCTAAATGATACAGCCATTCCACTAGGTAAC

GCGTATTACTTCGGGAACGGATTGGTGGACGCTTCAAGAGCCGCGTAT.
```

The amino acid sequence of the preproenzyme encoded by BspU02193n is set forth as SEQ ID NO:5:

MSKMKFTSLLLGLVVAFVFVFSTLSVSANGKGAERLDYL-
VGFKEKPNAQVMAQSGGEVVHEFEY

MNVVHMKLPEQAAKALEKNPNIAFVERDEKVEATQTVPWGINHVKAPTVH

NWGNVGTGVKVAVLDTGIASHPDLRVSGGASFIPSEPTIQDFNGHGTHVA

GTVAALNNSIGVLGVAPNVQLYGVKVLDRNGGGSHSAIAQGIEWSISNGM

DVVNMSLGGATSSTALSQAVANASNRGILLIAASGNTGRAGIQFPARYSQ

VMAVGAVDQNNRLASFSTFGNEQEIVAPGVGIQSTYLNNGYSSLNGTSMA

APHVAGVAALVMSEYPWATAPQVRGRLNDTAIPLGNAYYFGNGLVDASRA

AY.

At the N-terminus, the preproenzyme has a signal peptide with a predicted length of 28 amino acids (in bold italics in SEQ ID NO:5) as determined using SignalP-NN (Emanuelsson et al., Nature Protocols, 2:953-971, 2007). The presence of a signal peptide sequence indicates that this serine protease is a secreted enzyme. Like other serine proteases, the enzyme has a pro-sequence with a predicted length of 69 amino acids (in italics in SEQ ID NO:5). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, BspU02193 (269 amino acids), is set forth as SEQ ID NO:6:

TQTVPWGINHVKAPTVHNWGNVGTGVKVAVLDTGIASHPDLRVSGGASFI

PSEPTIQDFNGHGTHVAGTVAALNNSIGVLGVAPNVQLYGVKVLDRNGGG

SHSAIAQGIEWSISNGMDVVNMSLGGATSSTALSQAVANASNRGILLIAA

SGNTGRAGIQFPARYSQVMAVGAVDQNNRLASFSTFGNEQEIVAPGVGIQ

STYLNNGYSSLNGTSMAAPHVAGVAALVMSEYPWATAPQVRGRLNDTAIP

LGNAYYFGNGLVDASRAAY.

Example 2

Heterologous Expression of BspAI02518 and BspU02193

The BspAI02518 protease was produced in *B. subtilis* using an expression cassette consisting of the *B. subtilis* aprE promoter, the *B. subtilis* aprE signal peptide sequence, the native BspAI02518 protease pro-peptide sequence, the mature BspAI02518 protease sequence and a BPN' terminator. The BspAI02518 expression cassette was cloned into the pHYT replicating shuttle vector and transformed into a suitable *B. subtilis* strain. The pHYT vector was derived from pHY300PLK (Takara) by adding a terminator after the tetracycline resistance gene using the BstEII and EcoRI sites (terminator sequence: GGTTACCTTG AATGTATATA AACATTCTCA AAGGGATTTC TAATAAAAAA CGCTCGGTTG CCGCCGGGCG TTTTTTATGC ATC-GATGGAA TTC set forth as SEQ ID NO:7). The HindIII site in pHY300PLK was also removed using a linker cloned into the BamHI and HindIII sites (linker sequence: GGATCCTGAC TGCCTGAGCT T set forth as SEQ ID NO:8). A map of the pHYT vector for expression of the BspAI02518 protease (pHYT—BspAI02518) is shown in FIG. 1.

Figure 2:
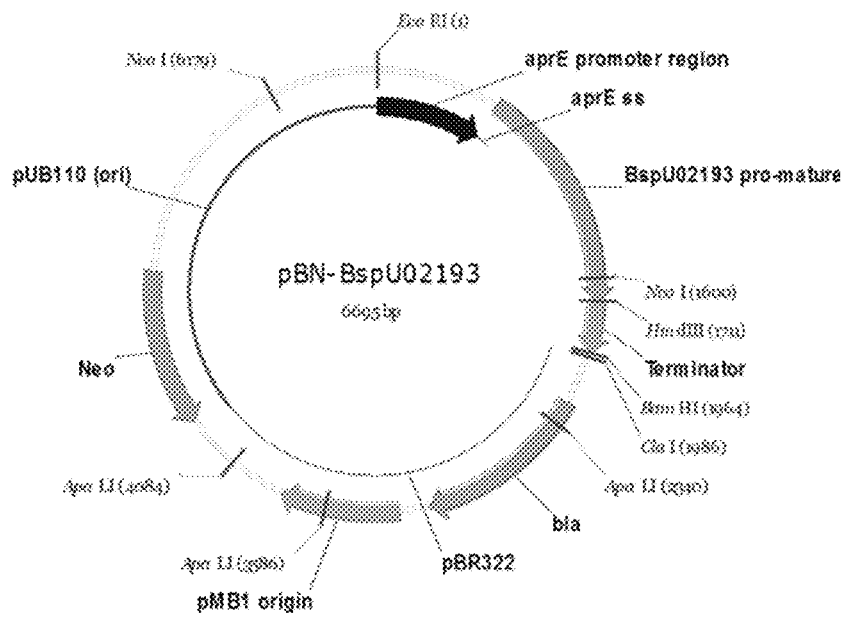
FIG. 2 provides a plasmid map of pBN-BspU02193 for expression of the BspU02193 serine protease.

To produce BspAI02518, a *B. subtilis* transformant containing pHYT-BspAI02518 was cultured in 15 ml Falcon tubes for 16 hours in TSB (broth) containing 12.5 ppm tetracycline. 300 μl of this pre-culture was added to a 500 mL flask filled with 30 mL cultivation media supplemented with 25 ppm tetracycline. The cultivation media was an enriched semi-defined media based on MOPs buffer, with urea as major nitrogen source, glucose as the main carbon source, and supplemented with 1% soytone for robust cell growth. The flasks were incubated for 2 days at 32° C. with constant rotational mixing at 180 rpm. Cultures were harvested by centrifugation at 14500 rpm for 20 min in conical tubes. The BspU02193 protease was produced in *B. subtilis* using an expression cassette consisting of the *B. subtilis* aprE promoter, the *B. subtilis* aprE signal peptide sequence, the native BspU02193 protease pro-peptide, the mature BspU02193 protease and a BPN' terminator. The BspU02193 expression cassette was cloned into a pBN-based replicating shuttle vector (Babe' et al., Biotechnol Appl Biochem, 27:117-124, 1998) and transformed into a suitable *B. subtilis* strain. A map of the pBN vector for expression of the BspU02193 protease (pBN—BspU02193) is shown in FIG. 2.

To produce BspU02193, a *B. subtilis* transformant containing pBN—BspU02193 was cultured in 15 ml Falcon tubes for 16 hours in TSB (broth) containing 10 ppm neomycin. 300 μl of this pre-culture was added to a 500 mL flask filled with 30 mL of cultivation media supplemented with 10 ppm neomycin. The cultivation media was an enriched semi-defined media based on MOPs buffer, with urea as major nitrogen source, glucose as the main carbon source, and supplemented with 1% soytone for robust cell growth. The flasks were incubated for 2 days at 32° C. with constant rotational mixing at 180 rpm. Cultures were harvested by centrifugation at 14500 rpm for 20 min in conical tubes.

Protein was quantified by the stain-free Imager Criterion method. This method is based on utilization of stain-free precast PAGE gels, where the intensity of each band depends on the amount of tryptophan residues present in the protein of interest. The CRITERION™ TGX (Tris-Glycine extended) STAIN-FREE™ precast gels for PAGE include unique trihalo compounds. This allows rapid fluorescent detection of proteins with the Gel Doc™ EZ imaging system. The trihalo compounds react with tryptophan residues in a UV-induced reaction to produce fluorescence, which can be easily detected by the Gel Doc EZ imager within the gels. Reagents used in the assay include: Concentrated (10×) Laemmli Sample Buffer (Kem-En-Tec, Catalogue No. 42556); either 18 or 26-well Criterion TGX Strain-Free Precast gels (Bio-Rad, Catalogue Nos. 567-8124 and 567-8125, respectively); and protein markers "Precision Plus Protein Standards" (Bio-Rad, Catalogue No. 161-0363). The assay was carried out as follows: 25 µl protein sample and 25 µl 0.5 M HCl were added to a 96 well-PCR plate on ice to inactivate the protease and prevent self-hydrolysis. 50 µl of the acid protein mix was added to 50 µL sample buffer containing 0.385 mg DTT in the 96 well-PCR plate. The plate was sealed with Microseal 'B' Film from Bio-Rad and was placed into a PCR machine to be heated to 70° C. for 10 min. Afterwards the chamber was filled with running buffer, and the gel cassette was set. Then 20 µL of each sample together with markers was loaded into each pocket. Electrophoresis was started at 200 V for 55 min. Following electrophoresis, the gel was transferred to an Imager, and Image Lab software was used for calculation of the intensity of each band. By knowing the protein amount and the tryptophan content of the standard sample, a calibration curve can be made. The amount of experimental sample was determined by extrapolation of the band intensity and tryptophan numbers to protein concentration. This protein quantification method was employed to prepare samples of the BspAI02518 and BspU02193 proteases for use in the assays described in subsequent examples.

Samples of isolated BspAI02518 and BspU2193 proteases were analyzed by LC-MS/MS as described subsequently. In preparation for sequence confirmation, including N- and C-terminal determination, a sample of BspAI02518 protease and BspU2193 protease were subjected to a series of chemical treatments in a 10 kDa spinfilter. The samples were denatured and reduced/alkylated by urea and DTT/Iodoacetamide treatment. A guanidination step was performed to convert lysines to homoarginines to protect lysine side chains from acetylation. The acetylation reaction using Sulfo-NHS-Acetate (Sulfosuccinimidyl Acetate) only modifies the protein N-terminal residue. The samples were then mixed with a buffer containing 40 v/v % $^{18}$O water:60 v/v % $^{16}$O water and the proteolytic enzymes used for protein digestion. The resulting peptides will contain mixtures of $^{18}$O and $^{16}$O, except for the Carboxyl terminus which will retain the native $^{16}$O, as will be apparent from the isotopic pattern of the peptides. The peptide, originating from the protein N-terminus, will appear as the only acetylated peptide. The resulting peptides were separated and analyzed using a nano-LC system followed by LTQ Orbitrap (Thermo Fisher) high resolution mass spectrometer. The amino acid sequences were deduced from the MS/MS fragment spectra of the peptides. Based on this analysis, the N-terminus of the isolated protein was confirmed to begin with A at position 1 from the predicted mature sequence. The sequence of the mature protein was determined to correspond to sequence listed in SEQ ID NO: 3, consisting of 269 amino acids. Based on this analysis, the N-terminus of the isolated BspU2193 protein was confirmed to begin with Q at position 2 from the predicted mature sequence listed in SEQ ID NO:84.

The amino acid sequence of the processed mature enzyme, BspU2193 that was purified and used for further characterization (268 amino acids), is set forth as SEQ ID NO:84:

QTVPWGINHVKAPTVHNWGNVGTGVKVAVLDTGIASHPDLRVSGGASFIP

SEPTIQDFNGHGTHVAGTVAALNNSIGVLGVAPNVQLYGVKVLDRNGGGS

HSAIAQGIEWSISNGMDVVNMSLGGATSSTALSQAVANASNRGILLIAAS

GNTGRAGIQFPARYSQVMAVGAVDQNNRLASFSTFGNEQEIVAPGVGIQS

TYLNNGYSSLNGTSMAAPHVAGVAALVMSEYPWATAPQVRGRLNDTAIPL

GNAYYFGNGLVDASRAAY.

Example 3

Protease Activity of BspAI02518 and BspU02193

Figure 3:
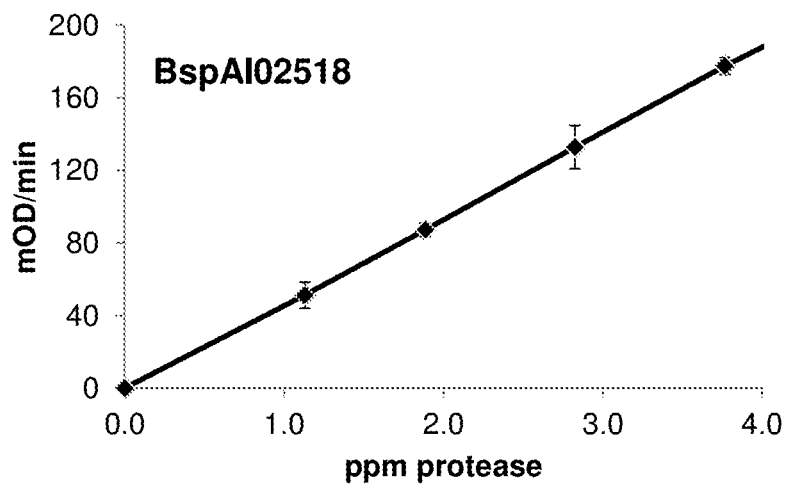
FIG. 3 provides a plot of the protease activity of BspAI02518 on a DMC substrate.
Figure 4:
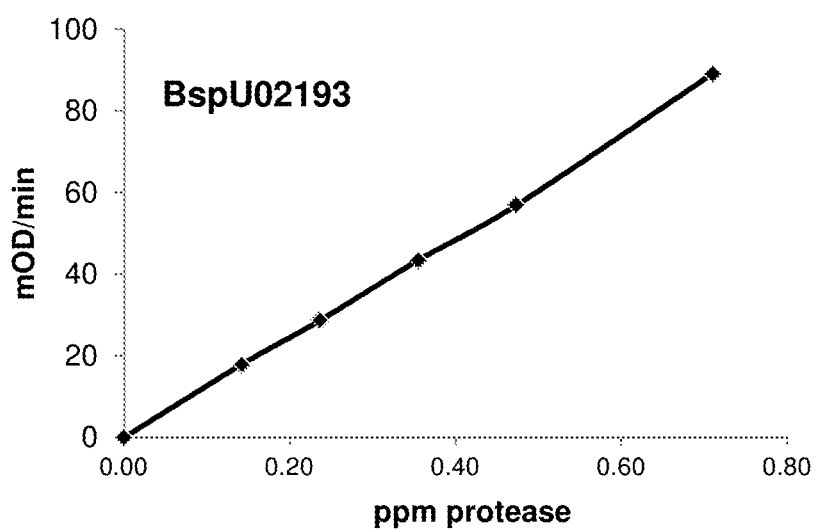
FIG. 4 provides a plot of the protease activity of BspU02193 on a DMC substrate.

The protease activities of BspAI02518 and BspU02193 were tested by measuring the hydrolysis of a dimethyl casein (DMC) substrate. The reagent solutions used for the DMC assay were: 2.5% w/v DMC (Sigma C-9801) in 100 mM sodium carbonate buffer pH 9.5, 0.075% TNBSA (Thermo Scientific) in Reagent A. Reagent A: 45.4 g $Na_2B_4O_7 \cdot 10H_2O$ (Merck) in 15 mL 4 N NaOH to reach a final volume of 1000 mL in deionised water. Protease supernatants were diluted in dilution solution: 10 mM NaCl, 0.1 mM $CaCl_2$, 0.005% Tween-80 to the desired concentration to achieve a linear response during hydrolysis over 5 min. A 96-well microtiter plate (MTP) was filled with 9Sµ1 DMC substrate followed by the addition of 5 µl diluted protease supernatant. 100⁴, of TNBSA in Reagent A was then added with slow mixing. Activity was measured at 405 nm over 5 min using a SpectraMax plate reader in kinetic mode at RT. The absorbance of a blank containing no protease was subtracted from each sample reading. The activity was expressed as mOD/min. The protease activity curve for BspAI02518 is shown in FIG. 3 and the protease activity curve for BspU02193 is shown in FIG. 4. The specific activity of the BspAI02518 protease in the DMC assay was found to be 46 mOD/min/ppm (where ppm is the final concentration of protease in the assay). The specific activity of the BspU02193 protease in the DMC assay was found to be 123 mOD/min/ppm. The specific activities of GG36 and BPN' proteases were found to be 54 and 23 mOD/min/ppm respectively under the same assay conditions.

Example 4 pH Profiles of BspAI02518 and BspU02193

The pH dependence of proteolytic activities of BspAI02518 and BspU02193 were studied using an azo-casein substrate in a 50 mM acetate/Bis-Tris/HEPES/CHES buffer including 50 mM $CaCl_2$. The effect of pH between 4 to 12 was measured in 1 pH unit increments. One Protaxyme AK tablet (Megazyme, Ireland) was added to a glass test tube together with 1.9 mL of appropriate buffer, followed by gentle hydration at 40° C. for 5 min in a temperature controlled water bath fitted with magnetic stirrer. A 100 µl sample of freshly prepared protease (diluted in deionised water to an appropriate concentration for the assay) was added to the prehydrated substrate and the reaction was carried out at 40° C. for 10 min. To stop the reaction, 10 mL of a 2% w/v Tris buffer pH 12 was added and the solution was immediately filtered through a Whatman No. 1 filter. The supernatant was collected and the absorbance at 590 nm was measured for the supernatant to quantify the product of the reaction. The absorbance from a buffer-only control was subtracted from each sample reading, and the resulting values were converted to percentages of relative activity, by defining the activity at the optimal pH as 100%. BspAI02518 was determined to maintain ≥50% activity over the pH range of 7.5-12 and BspU02193 was determined to maintain ≥50% activity over the pH range of 9-12, under the conditions of this assay.

Example 5

Temperature Profiles of BspAI02518 and BspU02193

The temperature dependence of proteolytic activities of BspAI02518 and BspU02193 were measured using an azocasein substrate in a 50 mM acetate/Bis-Tris/HEPES/CHES buffer including 50 mM $CaCl_2$ at pH 9. The activity was measured at temperatures between 30° C. and 80° C. in 10° C. increments. One Protaxyme AK tablet (Megazyme, Ireland) was added to a glass test tube together with 1.9 mL of an appropriate buffer, followed by gentle hydration at set temperatures for 5 min in a temperature controlled water bath fitted with a magnetic stirrer. A 100 µl sample of freshly prepared protease (diluted in deionised water to an appropriate concentration for the assay) was added to the prehydrated substrate and reaction was carried out at 40° C. for 10 min. To terminate the reaction, 10 mL of a 2% w/Tris buffer pH 12 was added and the solution was filtered immediately through a Whatman No. 1 filter. The supernatant was collected and the absorbance at 590 nm was measured for this supernatant to quantify the product of the reaction. The absorbance from a buffer-only control was subtracted from each sample reading, and the resulting values were converted to percentages of relative activity, by defining the activity at the optimal temperature as 100%. BspAI02518 was determined to retain ≥50% activity over the temperature range of 30–65° C., and BspU02193 was determined to retain ≥50% activity over the temperature range of 60–80° C., under the conditions of this assay.

Example 6

Cleaning Performance of BspAI02518 and BspU02193

The cleaning performance of BspAI02518 and BspU02103 was tested on BMI (blood/milk/ink on cotton) microswatches (EMPA-116, Center for Testmaterials, The Netherlands) for laundry based applications, and on egg yolk (egg yolk on polyacryl fabric, aged and colored with carbon black dye) microswatches (PAS-38, Center for Testmaterials, The Netherlands) for dish based applications. MTPs (Corning 3641) containing pre-punched (to fit on MTP) swatches, were rinsed, and filled with detergent prior to enzyme addition. Commercial detergents were heat-inactivated to remove existing enzyme activity and dosed as described on Table 6-1.

Heavy duty liquid (HDL) laundry detergents were inactivated by heating at 95° C. for 4 hours in a water bath. Heavy duty dry (HDD) laundry detergents were inactivated by preparing a 10% w/v solution and heating at 95° C. for 4 hours. After heating both HDD and HDL detergents for 4 hours, protease activity was determined to be non-existent.

Following inactivation of existing detergent proteases, activity of test proteases was assayed using a suc-AAPF-pNA (AAPF) substrate. The reagent solutions used for the AAPF hydrolysis assay were: 100 mM Tris/HCl pH 8.6, containing 0.005% TWEEN®-80 (Tris dilution buffer); 100 mM Tris buffer pH 8.6, containing 10 mM $CaCl_2$ and 0.005% TWEEN®-80 (Tris/Ca buffer); and 160 mM suc-AAPF-pNA in DMSO (suc-AAPF-pNA stock solution) (Sigma: S-7388). To prepare a substrate working solution, 1 ml suc-AAPF-pNA stock solution was added to 100 ml Tris/Ca buffer and mixed well. An enzyme sample was added to a MTP plate (Greiner 781101) containing 1 mg/suc-AAPF-pNA working solution and assayed for activity at 405 nm over 3 min using a SpectraMax reader in kinetic mode at RT. The protease activity was expressed as mOD·min$^{-1}$.

Washing solutions with the Final Detergent Wash concentrations (g/L) described in Table 6-1 were made up and used in the cleaning performance assay.

TABLE 6-1

Detergent Conditions for Cleaning Performance Assays

| Detergent* | Type | Detergent Wash Conc. (g/L) | Hardness Conc. (ppm) | Buffer | pH |
|---|---|---|---|---|---|
| OMO color | HDD | 5.3 | 250 | 2 mM $NaCO_3$ | 10.6 |
| Kirkland Ultra | HDD | 1.09 | 150 | 2 mM $NaCO_3$ | 10.6 |
| OMO K & K | HDL | 2.8 | 250 | 5 mM Na HEPES | 8.2 |
| Kirkland Ultra | HDL | 0.71 | 150 | 5 mM Na HEPES | 8.2 |
| GSM-B 10.5 | ADW | 3 | 374 | unbuffered | ~10.5 |
| GSM-B 9 | ADW | 3 | 374 | Unbuffered 1M citrate to adjust pH | 9 |

*Detergent sources: Kirkland Ultra HDD and HDL (Sun Products) were purchased from local supermarket in the United States in 2012. OMO color HDD and OMO Klein & Krachtig (Unilever) were purchased from local supermarkets in The Netherlands in 2013. GSM-B was purchased from WFK Testgewebe GmbH, Germany.

TABLE 6-2

| GSM-B pH 10.5 Phosphate-Free ADW Detergent Ingredients | |
|---|---|
| Component | Weight % |
| Sodium citrate dehydrate | 30.0 |
| Maleic acid/acrylic acid copolymer sodium salt (SOKALAN ® CP5; BASF) | 12.0 |
| Sodium perborate monohydrate | 5.0 |
| TAED | 2.0 |
| Sodium disilicate: Protil A (Cognis) | 25.0 |
| Linear fatty alcohol ethoxylate | 2.0 |
| Sodium carbonate anhydrous | add to 100 |

Aliquots of enzyme were added to a detergent-filled microswatch plate to reach a final volume of 200 µL with a 0.04 to 10 ppm final enzyme concentration for laundry assay. Laundry cleaning assays with HDL or HDD detergents was carried out at 25° C. for 15 min, while automatic dish (ADW) assays were carried out at 40° C. for 30 min.

Figure 5A:
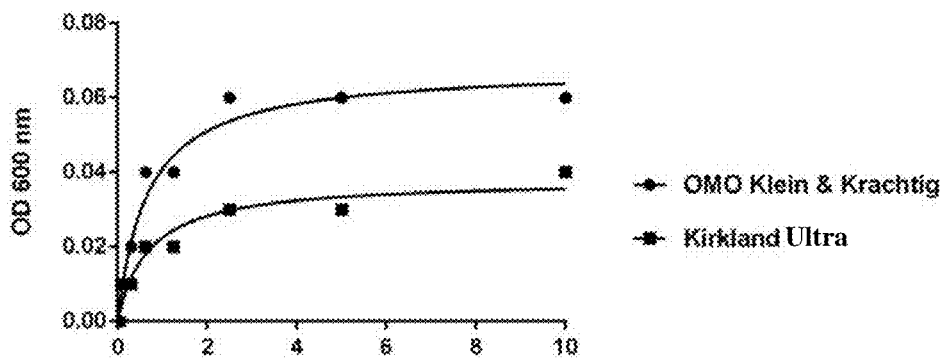
FIG. 5A provides cleaning efficiency curves of BspAI02518 in heavy duty liquid (HDL) laundry detergents.
Figure 5B:
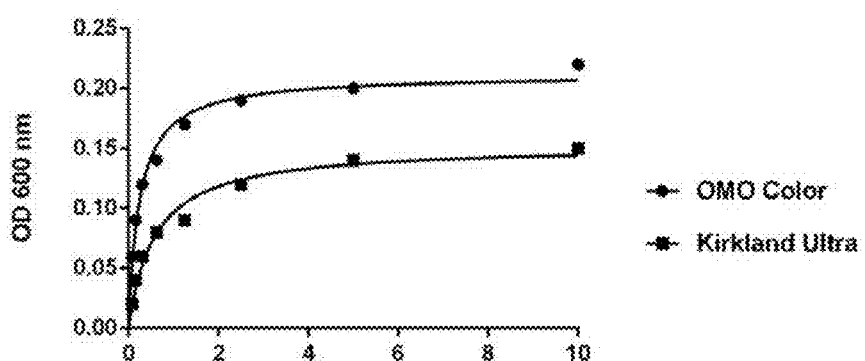
FIG. 5B provides cleaning efficiency curves of BspAI02518 in heavy duty dry (HDD) laundry detergents.
Figure 5C:
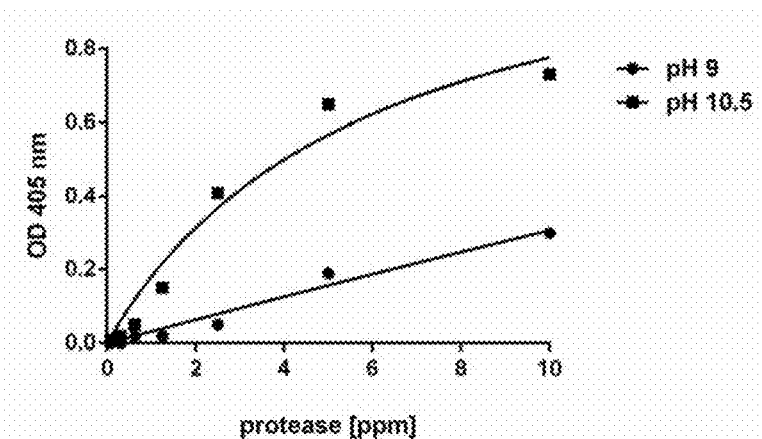
FIG. 5C provides cleaning efficiency curves of BspAI02518 in automatic dish washing (ADW) detergents.
Figure 6A:
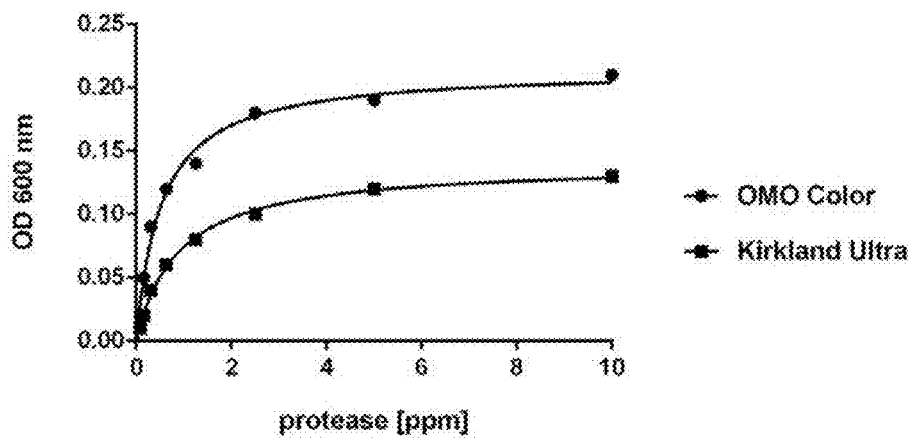
FIG. 6A provides cleaning efficiency curves of BspU02193 in heavy duty dry (HDD) laundry detergents.
Figure 6B:
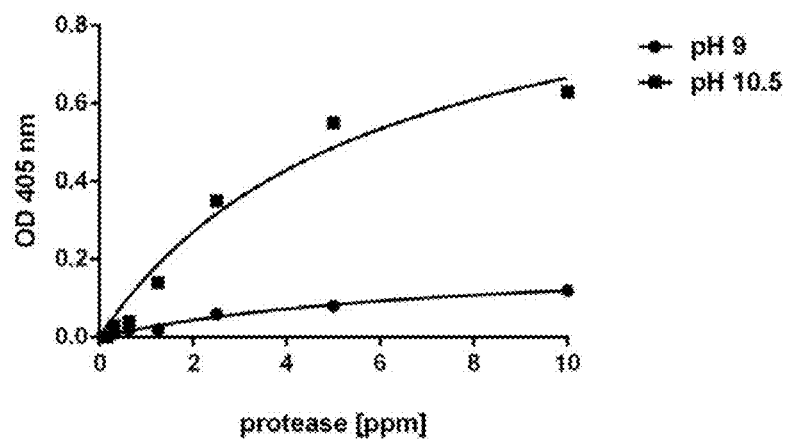
FIG. 6B provides cleaning efficiency curves of BspU02193 in automatic dish washing (ADW) detergents.

Following incubation, 100 µL of supernatant was transferred to a fresh MTP (Costar 9017) and absorbance was read at 600 nm for EMPA-116 swatches, or at 405 nm for PAS-38 swatches, using the SpectraMax plate reader. The absorbance from a buffer only control was subtracted and the resulting OD values at 600 nm (for HDL and HDD detergents) and 405 nm (for ADW detergents) were plotted as a function of protease concentration. The data was fitted using the Langmuir equation. The cleaning performance of BspAI02518 in various detergents is shown in FIG. 5A-5C, while the cleaning performance of BspU02193 in various detergents is shown in FIG. 6A-B.

Example 7

Identification of Homologous Proteases

The amino acid sequences of the mature forms of BspAI02518 (SEQ ID NO:3) and BspU02193 (SEQ ID NO:6) were subjected to a BLAST search (Altschul et al., Nucleic Acids Res, 25:3389-402, 1997) against the NCBI non-redundant protein database. A similar search was run against the Genome Quest Patent database with search parameters set to default values using SEQ ID NO:3 and SEQ ID NO:6, respectively as the query sequences. Subsets of the search results are shown in Tables 7-1 and 7-2 for BspAI02518, and Tables 7-3 and 7-4 for BspU02193. Percent identity (PID) for both search sets was defined as the number of identical residues divided by the number of aligned residues in the pairwise alignment. The column labeled "Sequence Length" refers to the length (in amino acids) of the protein sequences associated with the listed Accession Nos., while the column labeled "Aligned Length" refers to the length (in amino acids) of the aligned protein sequence used for the PID calculation.

TABLE 7-1

Percent Identity (PID) Shared by BspAI02518 with Entries in the NCBI Non-Redundant Protein Database

| Accession No. | PID | Organism | Sequence Length | Alignment Length |
| --- | --- | --- | --- | --- |
| BAA05540 | 68 | Bacillus sp.; AprM | 361 | 268 |
| BAB04574 | 68 | B. halodurans C-125 | 361 | 268 |
| ABI26631 | 68 | B. clausii | 361 | 268 |
| ADD64465 | 67 | Bacillus sp. JB99 | 361 | 268 |
| ADC49870 | 67 | B. pseudofirmus OF4 | 374 | 271 |
| BAA06157 | 64 | B. sp. Sendai [Bacillus sp. G-825-6] | 382 | 267 |
| BAD63300 | 64 | B. clausii KSM-K16 | 380 | 268 |
| AAA22212 | 63 | B. alcalophilus | 380 | 268 |
| P29600 | 63 | B. lentus | 269 | 268 |
| BAA25184 | 62 | Bacillus sp.; AprN | 379 | 267 |
| AFK08970 | 62 | B. lehensis | 378 | 267 |
| AAA87324 | 61 | B. subtilis | 378 | 267 |
| BAD11988.2 | 60 | Bacillus sp. KSM-LD1; SA-type | 376 | 273 |
| AAC43580 | 60 | Bacillus sp.; SprC | 378 | 273 |
| YP_003972439 | 60 | B. atrophaeus | 382 | 273 |
| BAD21128.1 | 60 | Bacillus sp. KSM-LD1; SB-type | 377 | 274 |
| AAC43581 | 59 | Bacillus sp.; SprD | 379 | 274 |
| WP_007497196 | 59 | B. stratosphericus LAMA 585 | 383 | 275 |
| CAJ70731 | 58 | B. licheniformis | 379 | 272 |
| ADN04910 | 58 | B. circulans | 275 | 275 |
| AFP23380 | 58 | B. lehensis | 276 | 275 |
| ADK11996 | 58 | B. pumulis | 383 | 275 |
| WP_010333625 | 58 | B. mojavensis | 381 | 273 |
| CAA74536 | 58 | B. subtilis str. 168 | 381 | 273 |
| CAA24990 | 57 | B. amyloliquefaciens | 376 | 273 |
| ABY25856 | 57 | Geobacillus stearothermophilus | 382 | 273 |
| AGC81872 | 57 | B. methylotrophicus | 382 | 273 |
| WP_010329279 | 57 | B. vallismortis | 381 | 273 |
| BAN09118 | 57 | B. subtilis | 381 | 273 |
| WP_006636716 | 55 | B. sonorensis | 378 | 272 |

TABLE 7-2

Percent Identity (PID) Shared by BspAI02518 with Entries in the Genome Quest Database

| Patent - SEQ | PID | Organism | Sequence Length | Alignment Length |
| --- | --- | --- | --- | --- |
| US20110045572-0011 | 68.5 | B. lentus | 268 | 267 |
| WO9100345-0009 | 68.5 | Synthetic | 268 | 267 |
| WO2009087508-0006 | 68.3 | B. halodurans | 301 | 268 |
| CN101270347-0003 | 68.3 | B. clausii | 360 | 268 |
| JP1994078778 | 68.3 | Bacillus sp. B18-1 | 361 | 268 |
| DE102009027540 | 68.3 | Bacillus sp. | 269 | 268 |
| DE102009027540 | 68.3 | Bacillus sp. | 269 | 268 |
| JP1998066576-0001 | 67.9 | B. subtilis | 374 | 271 |
| US20110028378-0002 | 67.8 | Bacillus sp. | 268 | 267 |
| US7449187-0009 | 67.8 | Bacillus sp. | 272 | 270 |
| US20030049619-0008 | 67.7 | Bacillus sp. | 375 | 272 |
| US20040063155-0001 | 67.5 | B. lentus | 361 | 268 |
| JP2011155932 | 67.5 | B. halodurans | 361 | 268 |

TABLE 7-2-continued

Percent Identity (PID) Shared by BspAI02518 with Entries in the Genome Quest Database

| Patent - SEQ | PID | Organism | Sequence Length | Alignment Length |
|---|---|---|---|---|
| JP2011155932 | 67.5 | B. pseudofirmus FA30-01 | 374 | 271 |
| JP2011155932 | 67.5 | Bacillus sp. NKS-21 | 374 | 271 |
| US6908991-0002 | 67.4 | Bacillus sp. | 268 | 267 |
| WO2012151480 | 64.6 | B. lentus | 269 | 268 |
| DE10064983 | 64.6 | B. alcalophilus | 269 | 268 |
| WO2010123754-0050 | 64.6 | B. clausii | 269 | 268 |
| JP2012135214-0006 | 64.6 | B. clausii KSM-K16 | 269 | 268 |
| US20130071910-0007 | 64.6 | B. lentus | 269 | 268 |
| JP2008022828 | 64.6 | B. clausii KSM-K16 | 355 | 268 |
| US20050009167-0002 | 64.6 | Bacillus sp. DSM 14390 | 380 | 268 |
| EP0415296 | 64.2 | B. alcalophilus | 269 | 268 |
| WO9402618 | 64.2 | B. novalis | 269 | 268 |
| WO2012151480 | 63.8 | B. lentus | 269 | 268 |
| WO9402618 | 63.8 | B. novalis | 269 | 268 |
| EP2100948 | 63.8 | B. alcalophilus; PB92 | 269 | 268 |
| WO9402618 | 63.4 | B. novalis | 269 | 268 |

TABLE 7-3

Percent Identity (PID) Shared by BspU02193 with Entries in the NCBI Non-Redundant Protein Database

| Accession No. | PID | Organism | Sequence Length | Alignment Length |
|---|---|---|---|---|
| ERN52602 | 66 | B. marmarensis DSM21297 | 374 | 271 |
| ADC49870 | 65 | B. pseudofirmus OF4 | 374 | 271 |
| BAB04574 | 64 | B. halodurans C-125 | 361 | 267 |
| ABI26631 | 64 | B. clausii | 361 | 267 |
| ADD64465 | 64 | Bacillus sp. JB99 | 361 | 267 |
| BAA05540 | 64 | Bacillus sp.; AprM | 361 | 267 |
| BAA25184 | 62 | Bacillus sp.; AprN | 379 | 266 |
| AFK08970 | 62 | B. lehensis | 378 | 266 |
| BAD63300 | 61 | B. clausii KSM-K16 | 380 | 266 |
| AAA22212 | 61 | B. alcalophilus | 380 | 266 |
| AAA87324 | 61 | B. subtilis | 378 | 266 |
| AAC43580 | 61 | Bacillus sp.; SprC | 378 | 272 |
| AGS78407 | 60 | B. gibsonii | 375 | 266 |
| P29600 | 60 | B. lentus | 269 | 266 |
| BAA06157 | 59 | B. sp. Sendai [Bacillus sp. G-825-6] | 382 | 267 |
| BAD11988.2 | 59 | Bacillus sp. KSM-LD1; SA type | 376 | 273 |
| YP_003972439 | 59 | B. atrophaeus | 382 | 273 |
| BAD21128.1 | 59 | Bacillus sp. KSM-LD1; SB type | 377 | 274 |
| CAJ70731 | 59 | B. licheniformis | 379 | 272 |
| WP_007497196 | 59 | B. stratosphericus LAMA 585 | 383 | 275 |
| AAC43581 | 58 | Bacillus sp.; SprD | 379 | 273 |
| WP_006636716 | 58 | B. sonorensis | 378 | 272 |
| AFP23380 | 57 | B. lehensis | 276 | 273 |
| ADK11996 | 57 | B. pumulis | 383 | 273 |
| WP_010329279 | 57 | B. vallismortis | 381 | 273 |
| ADN04910 | 56 | B. circulans | 275 | 273 |
| WP_010333625 | 56 | B. mojavensis | 381 | 273 |
| CAA74536 | 56 | B. subtilis str. 168 | 381 | 273 |
| BAN09118 | 56 | B. subtilis | 381 | 273 |
| CAA24990 | 55 | B. amyloliquefaciens | 376 | 273 |
| ABY25856 | 54 | Geobacillus stearothermophilus | 382 | 273 |
| AGC81872 | 54 | B. methylotrophicus | 382 | 273 |

TABLE 7-4

Percent Identity (PID) Shared by BspU02193 with Entries in the Genome Quest Database

| Patent - SEQ | PID | Organism | Sequence Length | Alignment Length |
|---|---|---|---|---|
| US20030049619-0008 | 65.8 | Bacillus sp. | 375 | 272 |
| JP2011155932-0012 | 66.1 | B. pseudofirmus FA30-01 | 374 | 271 |
| US7449187-0009 | 65.7 | Bacillus sp. | 272 | 271 |

TABLE 7-4-continued

Percent Identity (PID) Shared by BspU02193 with Entries in the Genome Quest Database

| Patent - SEQ | PID | Organism | Sequence Length | Alignment Length |
|---|---|---|---|---|
| JP1998066577-0001 | 65.7 | B. subtilis | 374 | 271 |
| JP2011155932 | 65.7 | Bacillus sp. NKS-21 | 374 | 271 |
| DE102009027540 | 65.2 | Bacillus sp. | 269 | 267 |
| US20110045572-0048 | 65.0 | Bacillus | 268 | 266 |
| DE102009027540 | 64.8 | Bacillus sp. | 269 | 267 |
| CN101270347-0003 | 64.8 | B. clausii | 360 | 267 |
| JP1994078778 | 64.8 | Bacillus sp; B18-1 | 361 | 267 |
| JP2011155932 | 64.4 | B. halodurans | 361 | 267 |
| US20040063155-0001 | 64.0 | B. lentus | 361 | 267 |
| US20090099056-0002 | 64.3 | Bacillus | 268 | 266 |
| US20050003504-0003 | 64.3 | B. gibsonii DSM 14391 | 269 | 266 |
| WO2012119955-0006 | 63.5 | Bacillus sp. | 269 | 266 |
| US7569226-0002 | 62.4 | Bacillus sp. DSM 14392 | 374 | 266 |
| US7642080-0002 | 62.4 | Bacillus sp. strain Zi344 | 381 | 266 |
| EP0516200 | 61.8 | Synthetic | 270 | 267 |
| WO9402618 | 61.7 | B. novalis | 269 | 266 |
| EP2100948 | 61.7 | B. alcalophilus; PB92 | 269 | 266 |
| US8460893-0043 | 61.7 | B. clausii KSM-K16 | 380 | 266 |
| WO2012151534 | 61.3 | B. lentus | 269 | 266 |
| US20130123162 | 60.9 | B. lentus | 269 | 266 |

The amino acid sequence of the mature forms of BspAI02518 protease (SEQ ID NO:3) or BspU02193 (SEQ ID NO: 6) were aligned with the amino acid sequences of multiple proteases listed in Tables 7-1 through 7-4 using CLUSTALW software (Thompson et al., Nucleic Acids Research, 22:4673-4680, 1994) with the default parameters. FIG. 7A-F shows the CLUSTAL W (1.83) multiple sequence alignment.

Figure 8:
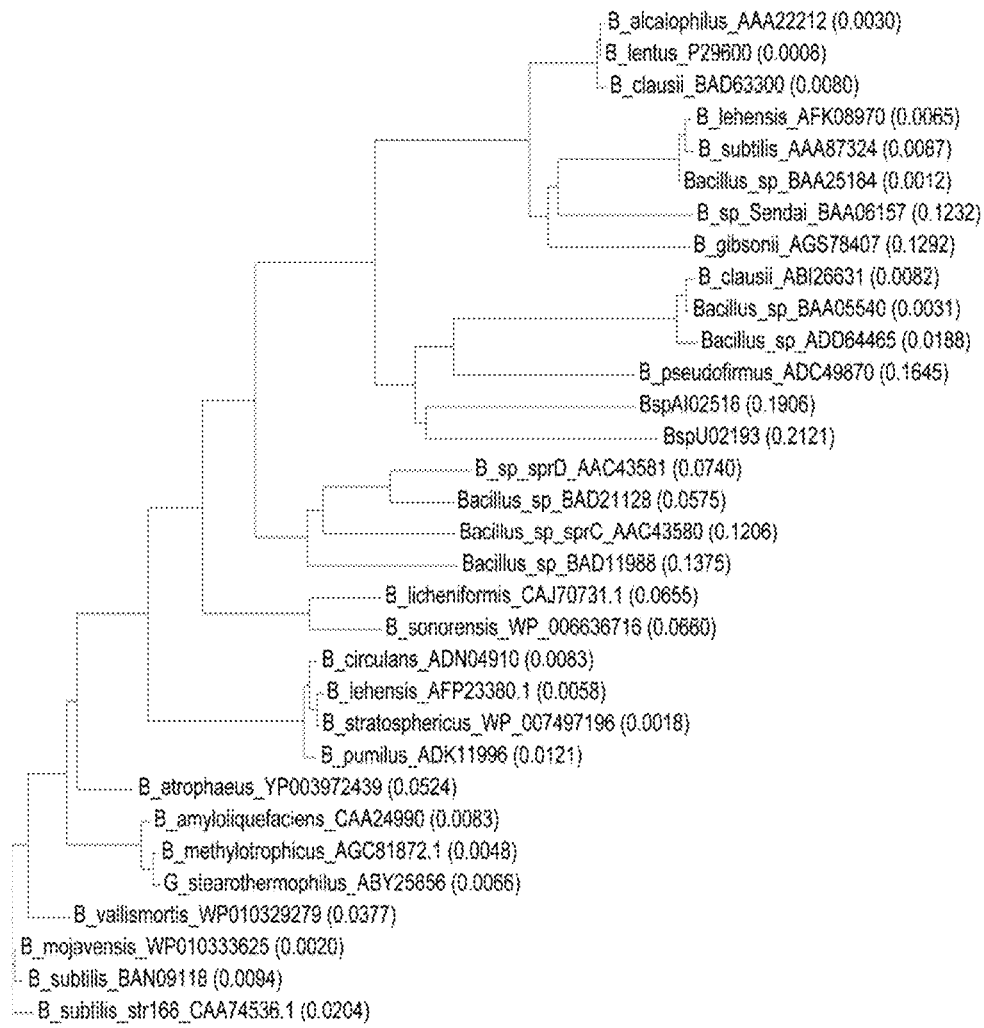
FIG. 8 provides a phylogenetic tree of BspAI02518, BspU02193 and various bacterial serine proteases.

A phylogenetic tree for amino acid sequences of the mature forms of BspAI02518 protease (SEQ ID NO:3) and BspU02193 (SEQ ID NO: 6) was built using the amino acid sequences of multiple proteases listed in Tables 7-1 through 7-4. The sequences were entered in the Vector NTI Advance suite and a Guide Tree was created using the Neighbor Joining (NJ) method (Saitou and Nei, Mol Biol Evol, 4:406-425, 1987). The NJ method works on a matrix of distances between all pairs of sequences to be analyzed. The distances are related to the degree of divergence between the sequences. The Guide Tree was calculated after the sequences were aligned. The tree construction was calculated using the following parameters: Kimura's correction for sequence distance and ignoring positions with gaps. AlignX displays the calculated distance values in parenthesis following the molecule name displayed on the tree shown in FIG. 8.

Example 8

Identification of Additional Bacillus Spp. Serine Proteases

Additional subtilisins were identified by sequencing the genomes of additional Bacillus species. B. akibai ATCC No. 43226 was obtained from the American Type Culture Collection. B. clarkii strain DSM 8720 was obtained from DSMZ (Leibniz-Institut DSMZ—Deutsche Sammlung von Mikroorganismen and Zellkulturen GmbH). B. clarkii strain SWT66_254731 was obtained from the DuPont Culture Collection. Genome sequencing, assembly and annotation were essentially as described in Example 1. All three genomes encoded proteins homologous to BspAI02518 and BspU02193.

Serine Protease Bakn00315

The nucleotide sequence of Bakn00315n is set forth as SEQ ID NO:9:

ATGCGAGTTTTGAAAGGTAACAAACTAACTGGTTTGCTTCTTGGGTTTAT

TTTAGTATTTTCTTTCGCGTTTTTATCACTATCGGTTAGCGCTAATGGCA

ACGGGAATGGCAATGGCGTAGAAAGACATGACTATTTAATAGGGTTTCAC

GAAAAGGTAGATAAAAAAGCCATTACTCAAGCAAGCGGAGAAGTAGTTCA

CGAATATCAGTATATGCCTGTTCTTCATGTGAAACTTCCAGAAAAAGCAG

CAAAAGCTTTAGAAAAAAATCCTAATATTGCTTATGTTGAAAAAGACGAA

GAGGTTACTGCTTCACAAACGGTTCCTTGGGGAATTAATCATATTCAAGC

TCCAACCGTACATTCTTGGGGGAATCGCGGAAACGGTGTTCGTGTCGCTG

TGTTAGATTCAGGGGTTGCTTCCCATGAAGATTTAAGAATTTCTGGTGGT

AGAAGTTTCATTACTAGCGAGCCTTCTTATCAAGATTATAATGGCCATGG

AACTCATGTAGCTGGTACCATCGCTGGGTTAAATAATAGTTATGGCGTAC

TTGGTGTCGCACCTAATGTTAACCTTTACGCAGTAAAAGTATTAGATCGT

AATGGAAGTGGATCTCACAGTGCGATTGCACAAGGAATTGAATGGTCTGT

TAGCAACGGTATGCATATTGTTAACATGAGCTTAGGTGGGCAACAGGTT

CAACAACGCTTCAACGTGCCGCCGATAATGCTTATAATAGAGGTGTTCTC

CTTATCGCTGCAGCTGGTAACACGGGTTCTGCCGGTATTTCCTATCCAGC

TAGATACAACTCTGTTATGGCAGTAGGTGCTGTTGACTCCAATAACAATC

GTGCTTCATTTTCAACTTTTGGAAACGAATTAGAAATTATGGCACCAGGA

GTATCCATTTTAAGCACACACCTTTCAAATCAATATGTTTCTTTAAACGG

TACATCAATGGCAAGTCCACATGTTGCTGGTGTTGCAGCTTTGGTGAAAG

CTCAATATCCAAGTGCGACTAATGCCCAAATCAGACAAAGACTAAGAGAT

ACTGCCACACCACTTGGTAGTTCATATTACTTTGGAAATGGTTTAGTGCA

TGCTGCTAGAGCGGCGAAT.

The amino acid sequence of the preproenzyme encoded by Bakn00315n is set forth as SEQ ID NO:10 and entered in the NCBI Non-Redundant Protein Database February 2014 under Accession number GAE36608:

*MRVLKGNKLTGLLLGFILVFSFAFLSLSVSA*NGNGNGNGVER-
HDYLIGFHEKVDKKAITQASGE

VVHEYQYMPVLHVKLPEKAAKALEKNPNIAYVEKDEEVTASQTVPWGINH

IQAPTVHSWGNRGNGVRVAVLDSGVASHEDLRISGGRSFITSEPSYQDYN

GHGTHVAGTIAGLNNSYGVLGVAPNVNLYAVKVLDRNGSGSHSAIAQGIE

WSVSNGMHIVNMSLGGPTGSTTLQRAADNAYNRGVLLIAAAGNTGSAGIS

YPARYNSVMAVGAVDSNNNRASFSTFGNELEIMAPGVSILSTHLSNQYVS

LNGTSMASPHVAGVAALVKAQYPSATNAQIRQRLRDTATPLGSSYYFGNG

LVHAARAAN.

At the N-terminus, the preproenzyme has a signal peptide with a predicted length of 31 amino acids (in bold italics in SEQ ID NO:10) as determined using SignalP-NN (Emanuelsson et al., Nature Protocols, 2:953-971, 2007). The presence of a signal peptide sequence indicates that this serine protease is a secreted enzyme. Like other serine proteases, the enzyme has a pro-sequence with a predicted length of 73 amino acids (in italics in SEQ ID NO:10). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, Bakn00315 (269 amino acids), is set forth as SEQ ID NO:11:

SQTVPWGINHIQAPTVHSWGNRGNGVRVAVLDSGVASHEDLRISGGRSFI

TSEPSYQDYNGHGTHVAGTIAGLNNSYGVLGVAPNVNLYAVKVLDRNGSG

SHSAIAQGIEWSVSNGMHIVNMSLGGPTGSTTLQRAADNAYNRGVLLIAA

AGNTGSAGISYPARYNSVMAVGAVDSNNNRASFSTFGNELEIMAPGVSIL

STHLSNQYVSLNGTSMASPHVAGVAALVKAQYPSATNAQIRQRLRDTATP

LGSSYYFGNGLVHAARAAN.

Serine Protease Bcl04009

The nucleotide sequence of Bcl04009n is set forth as SEQ ID NO:12:

ATGAAGAATATGAGGTTCATAGGGTTTATTGTTGGGTTTTTACTAGCTTT

CACATTCACTTTTTCAGCGGTGAGTGCAGATAGCAAAGGTGTCGAAAAGT

TTGATTACTTAATTGGTTTTAAAGACAAAGTTAATGAGAACACAGTTACC

CAGCTTGGCGGCGATGTCCAGCATGAATACGAGTATATGGAGGTTCTCCA

TGTAACCTTGCCGGAAAAAGCTGCGGCAGCACTGAAAAAGAATCCGAACA

TTGCCTTTGTGGAAAAAGACGAAGAAGTAACGGCCAGCCAGACCATTCCT

TGGGGCATAAACCGTGTTCAGGCACCAACCGTCCATTCCTGGGGAGCCCG

CGGTAACGGAGTAAGAGTTGCTGTTCTTGATACTGGTATTGCAAGCCACG

AAGATTTAAGAATTTCTGGAGGAGCCAGTTTTATCAGCTCGGAACCTTCC

TACAACGACCTTAATGGCCATGGAACGCATGTGGCTGGAACAATAGCTGC

CCGGGATAACAGTTATGGAGTTCTTGGGGTGGCGCCAAACGTTGATCTTT

ACGCTGTTAAAGTTCTTGACAGAAACGGCAGCGGTTCACTTAGCGGTATT

GCCCGTGGTATTGAGTGGGCTATTACAAATAATATGGATATAGTCAATAT

GAGTTTAGGTGGTTCGACTGGATCTACTGCATTAAGACAAGCTGCTGATA

ATGCTTATAACAGAGGCATTTTACTTGTGGCAGCTGCTGGTAATACAGGC

TCTGCAGGGATTTCCTTCCCAGCTCGGTATAATTCTGTTATGGCAGTAGG

TGCTACAGACTCTAACAACAACCGCGCGTCTTTTTCAACATTTGGAAATG

AACTGGAGATAATGGCTCCAGGTGTATCTGTATTAAGTACTTACCCTACT

AACAGATATGTTTCACTTAATGGAACGTCAATGGCAAGCCCTCACGTCGC

TGGTGTCGCAGCATTAGTAAAATCACGCTATCCAAACGCCACCAATGTCC

AAATAAGAAACAGACTGAACAGTACAGCCACTAATCTGGGAAGCTCTTAC

TATTTCGGTAATGGTCTCGTTAACGCTGCAAGAGCTGCGAAT.

The amino acid sequence of the preproenzyme encoded by Bcl04009 is set forth as SEQ ID NO:13:

*MKNMRFIGFIVGFLLAFTFTFSAVSA*DSKGVEKFDYLIGFKDKV-
NENTVTQLGGDVQHEYEYME

VLHVTLPEKAAAALKKNPNIAFVEKDEEVTASQTIPWGINRVQAPTVHSW

GARGNGVRVAVLDTGIASHEDLRISGGASFISSSEPSYNDLNGHGTHVAGT

IAARDNSYGVLGVAPNVDLYAVKVLDRNGSGSLSGIARGIEWAITNNMDI

VNMSLGGSTGSTALRQAADNAYNRGILLVAAAGNTGSAGISFPARYNSVM

AVGATDSNNNRASFSTFGNELEIMAPGVSVLSTYPTNRYVSLNGTSMASP

HVAGVAALVKSRYPNATNVQIRNRLNSTATNLGSSYYFGNGLVNAAR

AAN.

At the N-terminus, the preproenzyme has a signal peptide with a predicted length of 26 amino acids (in bold italics in SEQ ID NO:13) as determined using SignalP-NN (Emanuelsson et al., Nature Protocols, 2:953-971, 2007). The presence of a signal peptide indicates that this serine protease is a secreted enzyme. Like other serine proteases, the enzyme has a pro-sequence with a predicted length of 69 amino acids (in italics in SEQ ID NO:13). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, Bcl04009 (269 amino acids) is set forth as SEQ ID NO: 14:

SQTIPWGINRVQAPTVHSWGARGNGVRVAVLDTGIASHEDLRISGGASFI

SSEPSYNDLNGHGTHVAGTIAARDNSYGVLGVAPNVDLYAVKVLDRNGSG

SLSGIARGIEWAITNNMDIVNMSLGGSTGSTALRQAADNAYNRGILLVAA

AGNTGSAGISFPARYNSVMAVGATDSNNNRASFSTFGNELEIMAPGVSVL

STYPTNRYVSLNGTSMASPHVAGVAALVKSRYPNATNVQIRNRLNSTATN

LGSSYYFGNGLVNAARAAN.

Serine Protease SWT66_254731

The nucleotide sequence of SWT66_254731n is set forth as SEQ ID NO:15:

ATGAAGAATATGAGGTTTATAGGGTTTATTGTAGTGTTTTTACTAGCTTT

CACATTCACTTTTTCAGCGGTGAGTGCAGATAGCAAAGGCGTGGAAAAGT

TTGATTACTTAATTGGTTTTAAAGACAAAGTTAATGAGAACGCAGTTACC

CAGCTTGGCGGCGATGTCCAGCATGAATACGAGTACATGGAGGTTCTCCA

TGTAACCTTGCCGGAAAAAGCTGCGGCAGCACTGAAAAGAATCCGAACA

TTGCTTTTGTGGAAAAAGACGAAGAAGTAACGGCCAGCCAGACCGTTCCC

TGGGGCATTAACCGTGTTCAGGCACCAACCGTCCATTCCTGGGGAGCCCG

CGGTAACGGAGTAAGAGTTGCTGTTCTTGATACTGGAATTGCAAGCCACG

AAGATTTAAGGATTTCCGGAGGAGCCAGTTTTATCAGCTCGGAACCTTCC

TACAACGACCTTAATGGCCATGGAACGCATGTGGCTGGAACAATAGCTGC

CCGGGATAACAGTTATGGAGTTCTTGGTGTGGCGCCAAACGTTAATCTTT

ATGCAGTTAAAGTTCTTGACAGAAACGGCAGCGGTTCACTTAGCGGCATT

GCCCGGGGTATTGAGTGGGCTATTACAAATAATATGGATATAGTCAATAT

GAGTTTAGGTGGTTCAACCGGATCCACTGCATTAAGACAAGCTGCTGATA

ACGCGTATAACAGGGGAATTTACTTGTTGCTGCCGCTGGTAATACAGGC

TCTGCAGGAATCTCCTTCCCGGCTCGGTATAATTCAGTTATGGCAGTAGG

GGCTACAGACTCTAACAACAACCGCGCGTCTTTTTCAACATTTGGAAATG

AACTGGAGATAATGGCTCCAGGTGTATCTGTATTAAGTACTTACCCAACT

AACAGATATGTTTCACTTAATGGGACATCAATGGCAAGCCCTCACGTCGC

TGGTGTCGCAGCATTAGTAAAATCACGCTATCCACACGCAACCAATGTCC

AAATAAGAAACAGACTGAACAGTACAGCCACCAATCTGGGAAGCTCTTAC

TATTTCGGAAATGGACTCGTTAACGCTGCGAGAGCGGCGAAT.

The amino acid sequence of the preproenzyme encoded by SWT66_254731n is set forth as SEQ ID NO. 16:

MKNMRFIGFIVVFLLAFTFTFSAVSADSKGVEKFDYLIGFKDKVNE-
NAVTQLGGDVQHEYEYME

VLHVTLPEKAAAALKKNPNIAFVEKDEEVTASQTVPWGINRVQAPTVHSW

GARGNGVRVAVLDTGIASHEDLRISGGASFISSEPSYNDLNGHGTHVAGT

IAARDNSYGVLGVAPNVNLYAVKVLDRNGSGSLSGIARGIEWAITNNMDI

VNMSLGGSTGSTALRQAADNAYNRGILLVAAAGNTGSAGISFPARYNSVM

AVGATDSNNNRASFSTFGNELEIMAPGVSVLSTYPTNRYVSLNGTSMASP

HVAGVAALVKSRYPHATNVQIRNRLNSTATNLGSSYYFGNGLVNAAR

AAN.

At the N-terminus, the preproenzyme has a signal peptide with a predicted length of 26 amino acids (in bold italics in SEQ ID NO:16) as determined using SignalP-NN (Emanuelsson et al., Nature Protocols, 2:953-971, 2007). The presence of a signal peptide indicates that this serine protease is a secreted enzyme. Like other serine proteases, the enzyme has a pro-sequence, with a predicted length of 69 amino acids (in italics in SEQ ID NO: 16). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, SWT66_254731, in some instances referred to as SWT66, (269 amino acids), is set forth as SEQ ID NO: 17:

SQTVPWGINRVQAPTVHSWGARGNGVRVAVLDTGIASHEDLRISGGASFI

SSEPSYNDLNGHGTHVAGTIAARDNSYGVLGVAPNVNLYAVKVLDRNGSG

SLSGIARGIEWAITNNMDIVNMSLGGSTGSTALRQAADNAYNRGILLVAA

AGNTGSAGISFPARYNSVMAVGATDSNNNRASFSTFGNELEIMAPGVSVL

STYPTNRYVSLNGTSMASPHVAGVAALVKSRYPHATNVQIRNRLNSTATN

LGSSYYFGNGLVNAARAAN.

An alignment of the amino acid sequences of the mature forms of the BspAI02518, BspU02193, Bakn00315, Bcl04009 and SWT66_254731 subtilisins with the sequences of the mature forms of subtilisins from *B. amyloliquefaciens*, *B. lentus*, *B. licheniformis*, *Bacillus* sp. LG12, and *B. pseudofirmus* (NCBI Accession Nos. CAA24990, P29600, CAJ70731, AAC43580, and ADC49870 respectively) is shown in FIG. 9A-B. The sequences were aligned using CLUSTALW software (Thompson et al., Nucleic Acids Research, 22:4673-4680, 1994) with the default parameters.

TABLE 8-1

| | Percent Identity (PID) Shared by *Bacillus* Subtilases | | | | | | | | | |
|---|---|---|---|---|---|---|---|---|---|---|
| | 1 | 2 | 3 | 4 | 5 | 6 | 7 | 8 | 9 | 10 |
| 1 SWT66_254731 | 100 | 84 | 99 | 74 | 74 | 67 | 63 | 64 | 65 | 58 |
| 2 Bakn00315 | | 100 | 84 | 80 | 75 | 71 | 61 | 64 | 59 | 57 |
| 3 Bcl04009 | | | 100 | 74 | 74 | 66 | 63 | 64 | 65 | 58 |
| 4 BspAI02518 | | | | 100 | 68 | 68 | 64 | 60 | 58 | 59 |
| 5 BspU02193 | | | | | 100 | 66 | 60 | 62 | 59 | 56 |
| 6 Bps_ADC49870 | | | | | | 100 | 63 | 62 | 62 | 57 |
| 7 Ble_P29600 | | | | | | | 100 | 64 | 62 | 61 |
| 8 Bsp_AAC43580 | | | | | | | | 100 | 71 | 65 |
| 9 Bli_CAJ70731.1 | | | | | | | | | 100 | 70 |
| 10 Bam_CAA24990 | | | | | | | | | | 100 |

Figure 10:
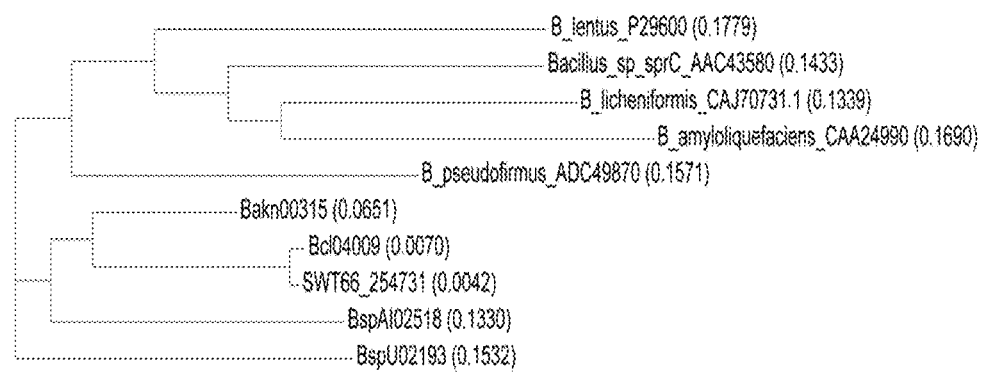
FIG. 10 provides a phylogenetic tree of BspAI02518, BspU02193, Bakn00315, Bcl04009, SWT66_254731 and various other bacterial serine proteases.
Figure 11A:
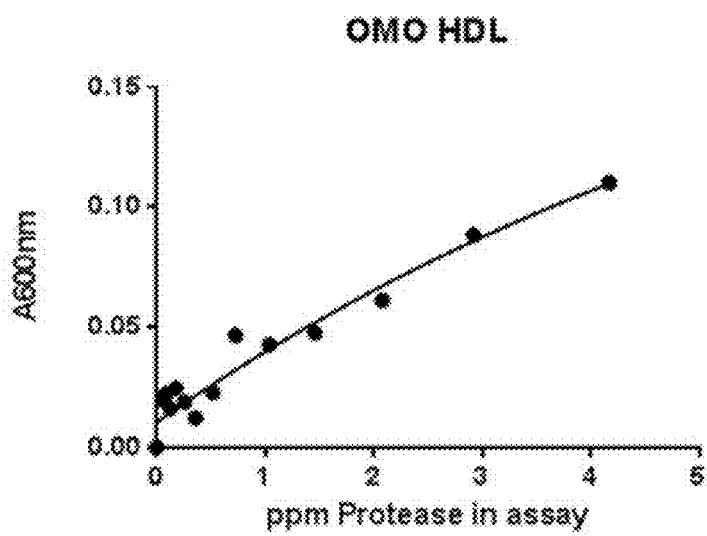
FIG. 11A provides cleaning efficiency curves of SWT66_254731 in OMO heavy duty liquid (HDL) laundry detergent.
Figure 11B:
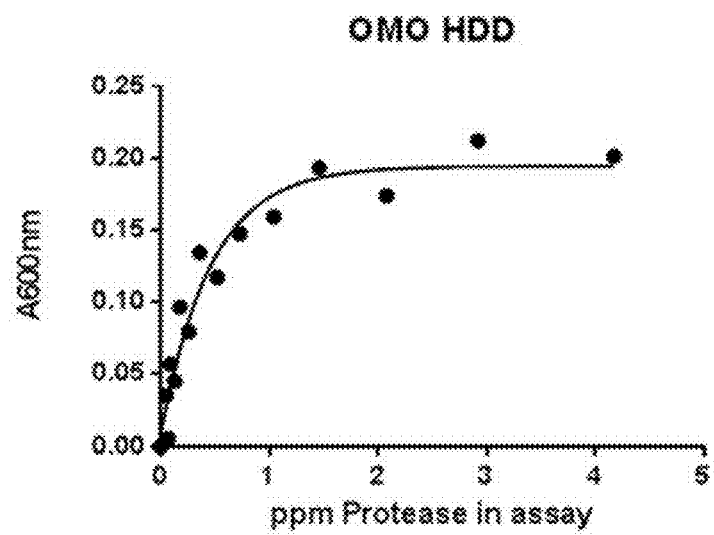
FIG. 11B provides cleaning efficiency curves of SWT66_254731 in OMO in heavy duty dry (HDD) laundry detergent.
Figure 11C:
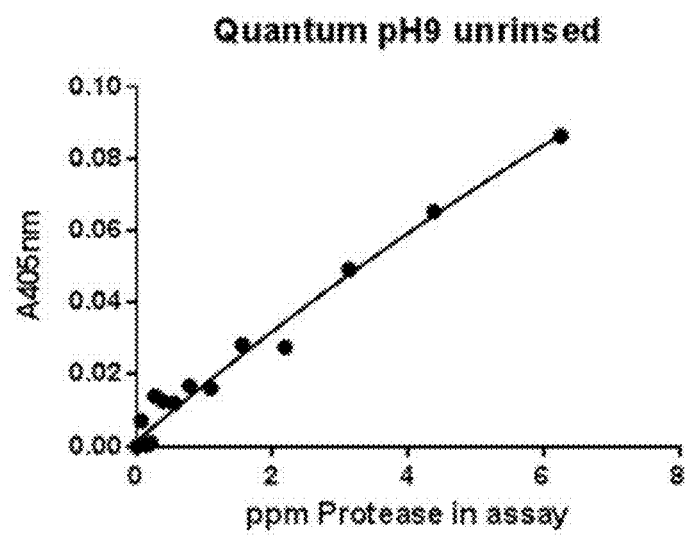
FIG. 11C provides cleaning efficiency curves of SWT66_254731 in Quantum automatic dish washing (ADW) detergent at pH 9, using unrinsed swatches.
Figure 11D:
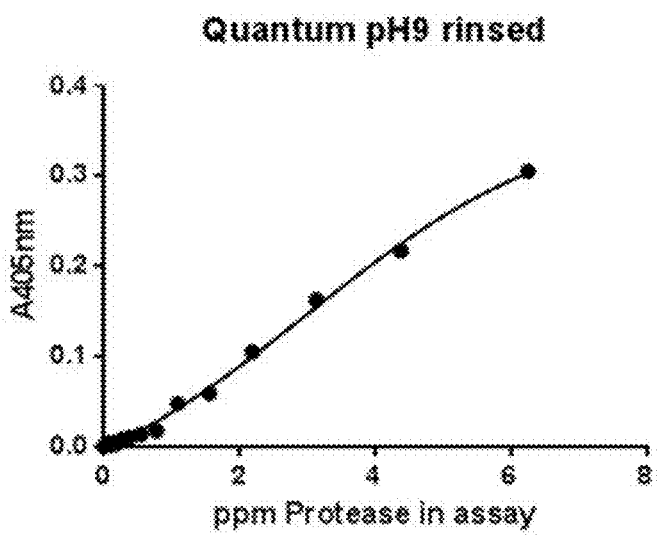
FIG. 11D provides cleaning efficiency curves of SWT66_254731 in Quantum automatic dish washing (ADW) detergent at pH 9, using rinsed swatches.
Figure 11E:
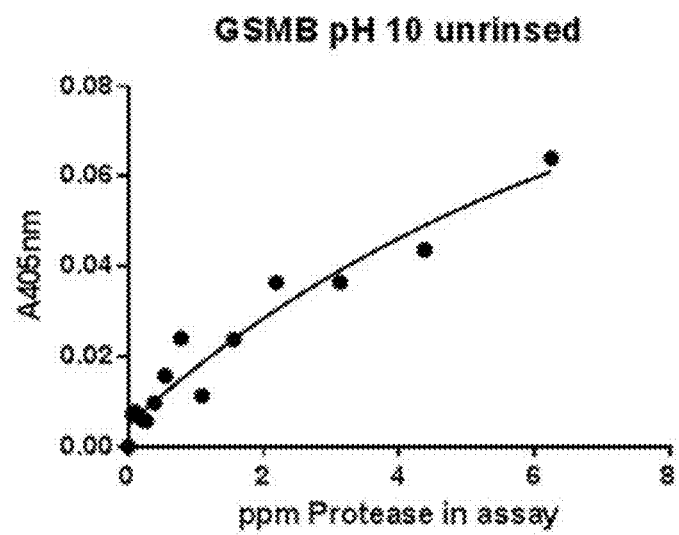
FIG. 11E provides cleaning efficiency curves of SWT66_254731 in GSMB automatic dish washing (ADW) detergent at pH 10, using unrinsed swatches.
Figure 11F:
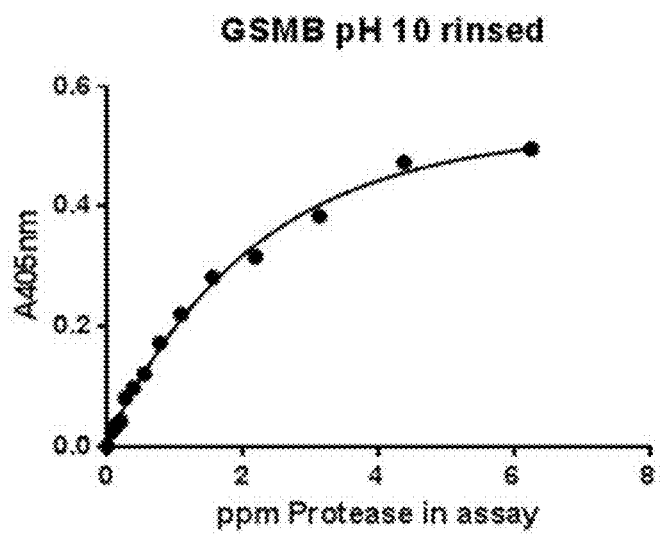
FIG. 11F provides cleaning efficiency curves of SWT66_254731 in GSMB automatic dish washing (ADW) detergent at pH 10, using rinsed swatches.

A phylogenetic tree for amino acid sequences of the mature forms of the subtilisins of Table 8-1 was built. The sequences were entered in the Vector NTI Advance suite and a Guide Tree was created using the Neighbor Joining (NJ) method (Saitou and Nei, Mol Biol Evol, 4:406-425, 1987). The tree construction was calculated using the following parameters: Kimura's correction for sequence distance and ignoring positions with gaps. AlignX displays the calculated distance values in parenthesis following the molecule name displayed on the tree shown in FIG. 10.

Example 9

Cleaning Performance of SWT66_254731 Subtilisin

The cleaning performance of SWT66_254731 subtilisin was tested on BMI (blood/milk/ink on cotton) microswatches (EMPA-116, Center for Testmaterials, The Netherlands) for laundry based applications, and on egg yolk (egg yolk on polyacryl fabric, aged and colored with carbon black dye) microswatches (PAS-38, Center for Testmaterials, The Netherlands) for dish based applications as described in Example 6. MTPs (Corning 3641) containing pre-punched (to fit on MTP) swatches, were either rinsed or unrinsed for the ADW assays, and filled with detergent prior to enzyme addition. One microswatch was used in HDD and 2 microswatches were used in HDL assays. The cleaning performance of SWT66_254731 subtilisin in various detergents is shown in FIGS. 11A-11F.

Example 10

Identification of Additional *B. akibai* Serine Proteases

Additional subtilisins were identified by sequencing the genomes of additional *B. akibai* species. *B. akibai* strains ACB102_2847966, COG104_4065768, ACB83_2687815, ACB90_2720294, ACB82_2683104, ACB89_2715301, ACB92_2732966, and DETPh35_2828044 were obtained from the DuPont Culture Collection. Genome sequencing, assembly and annotation were essentially as described in Example 1. All genomes encoded proteins homologous to BspAI02518 and BspU02193.

Serine Protease ACB102_

The nucleotide sequence of ACB102_2847966.n is set forth as SEQ ID NO:18:

ATGAAAATGAAATGGTCACGTTTAATTTTAACCCTAGTTCTCGTATTGAG

TTTTGTATTCCCATCTATGACAAGTGCAAACTCCGCTGTAGAAAAAGAGG

ATTATCTGATCGGTTTTAAGCAGAAAGGGAATGTTAGTGCACAAGTTGTG

AATATGAGTGGAGGAGAAGTCGTACATGAATATGAACATATGCCAGTCTT

GCACGTTAAATTACCTCCACAAGCTGCTAAAGCGTTAGAAAAGAACCCAA

ATATTGAATACATCGAAAAAGATGAAAAAGTCCAAGCTACAGCACAATCG

ACACCTTGGGGGATTTCACGTATTAATGCTCCTGCTGTTCACTCGACTGG

TAATTTTGGACAAGGTGTCCGAGTTGCCGTTTTAGATAGTGGAGTTGCTT

CTCATGAAGACTTACGGATTGCTGGGGGAGTGAGCTTTGTCGCTTCAGAA

CCTAGTTATCAAGATTATAATGGTCACGGAACACATGTTGCTGGAACCAT

TGCTGGTTTAAATAATAGTGTTGGGGTCCTTGGTGTAGCTCCATCTGTCC

AATTATATGCGGTTAAGGTGTTGGATCGTAATGGCGGGGGGAATCATAGT

GACATTGCTAGAGGAATTGAGTGGTCAGTTAATAATGGAATGCATGTGGT

GAATATGAGTTTAGGTGGACCAACAGGGTCAACGACTCTTCAACGAGCAG

CGGATAATGCTTATAACAGAGGAGTTCTTTTAATTGCCGCAGCTGGTAAC

ACGGGAACTAGTGGGGTTAGCTTCCCTGCGCGTTATAGCTCTGTAATGGC

AGTAGCCGCAACAGACTCTAATAATAACCGTGCTTCATTTTCAACTTATG

GTCCAGAAATTGAAATTTCAGCACCTGGAGTTGGCATTAATAGCACGTAT

CCAACGAATCGTTATTCAAGCTTAAATGGAACATCAATGGCTTCACCTCA

TGTCGCTGGTGTAGCAGCTCTTGTGAAGGCGAGATATCCAAGTGCGACGA

ATGCTCAGATTAGACAACATCTTCGTAGCACTTCTACGTATCTAGGAAAC

TCAACTTACTATGGTAGTGGTTTAGTTGATGCACAGCGTGCAGCTAAC

TAA.

The amino acid sequence of the preproenzyme encoded by ACB102_2847966.n is set forth as SEQ ID NO:19:

**MKMKWSRLILTLVLVLS*FVFPSMTSANSA*VEKED*YLIGFKQKGNVSAQVV NMSGGEVVH***

*EYEHMPVLHVKLPPQAAKALEKNPNIEYIEKDEKVQATAQSTPWGISRIN*

APAVHSTGNFGQGVRVAVLDSGVASHEDLRIAGGVSFVASEPSYQDYNGH

GTHVAGTIAGLNNSVGVLGVAPSVQLYAVKVLDRNGGGNHSDIARGIEWS

VNNGMHVVNMSLGGPTGSTTLQRAADNAYNRGVLLIAAAGNTGTSGVSFP

ARYSSVMAVAATDSNNNRASFSTYGPEIEISAPGVGINSTYPTNRYSSLN

GTSMASPHVAGVAALVKARYPSATNAQIRQHLRSTSTYLGNSTYYGSGLV

DAQRAAN.

At the N-terminus, the preproenzyme has a signal peptide with a predicted length of 29 amino acids (in bold italics in SEQ ID NO:19) as determined using SignalP-NN (Emanuelsson et al., Nature Protocols, 2:953-971, 2007). The presence of a signal peptide indicates that this serine protease is a secreted enzyme. Like other serine proteases, the enzyme has a pro-sequence, with a predicted length of 68 amino acids (in italics in SEQ ID NO: 19). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, ACB102, (269 amino acids), is set forth as SEQ ID NO: 20:

AQSTPWGISRINAPAVHSTGNFGQGVRVAVLDSGVASHEDLRIAGGVSFV

ASEPSYQDYNGHGTHVAGTIAGLNNSVGVLGVAPSVQLYAVKVLDRNGGG

NHSDIARGIEWSVNNGMHVVNMSLGGPTGSTTLQRAADNAYNRGVLLIAA

AGNTGTSGVSFPARYSSVMAVAATDSNNNRASFSTYGPEIEISAPGVGIN

STYPTNRYSSLNGTSMASPHVAGVAALVKARYPSATNAQIRQHLRSTSTY

LGNSTYYGSGLVDAQRAAN.

Serine Protease COG104

The nucleotide sequence of COG104_4065768.n is set forth as SEQ ID NO:21:

ATGAAAATGAAATGGTCACGTTTAATTTTAACCCTGGTTCTCGTATTCAG

TTTTGTATTCCCATCTATGACAAGTGCAAACTCCGCTGTAGAAAAAGAGG

ACTATCTGATCGGTTTTAAACAGAAAGGGAATGTTAGTGCACAAGTTGTG

AATATGAGTGGAGGAGAAGTCGTCCATGAATATGAACATATGCCAGTCTT

GCACGTTAAATTACCTTCACAAGCTGCTAAAGCGTTAGAAAAGAACCCCA

ATATTGAATACATTGAAAAAGATGAAAAAGTCCAAGCAACAGCACAATCG

ACACCTTGGGGAATTTCACGTATTAATGCTCCTGCTGTTCACTCGACTGG

TAATTTTGGACAAGGTGTCCGAGTTGCGGTTTTAGATAGTGGAGTTGCTT

CTCATGAAGACTTACGGATTGCTGGGGAGTGAGCTTTGTCGCTTCAGAA

CCTAGTTATCAAGATTATAATGGTCACGGAACACATGTTGCTGGAACCAT

TGCTGGTTTAAATAATAGTGTTGGGGTCCTTGGTGTAGCTCCATCTGTCC

AATTATATGCGGTTAAGGTGTTGGATCGTAATGGCGGGGGAAATCATAGT

GACATTGCTAGAGGAATTGAGTGGTCAGTTAATAATGGAATGCATGTGGT

GAATATGAGTTTAGGTGGACCAACAGGGTCAACTACTCTTCAACGAGCAG

CGGATAATGCTTATAACAGAGGAGTTCTTTTAATTGCCGCAGCTGGGAAC

ACGGGAACTAGTGGAGTTAGCTTCCCTGCGCGTTACAGCTCAGTAATGGC

AGTAGCCGCAACAGATTCTAATAATAACCGTGCTTCATTTTCAACTTATG

GAACACAAATTGAAATTTCAGCACCTGGAGTTGGCATTAATAGCACGTAT

CCAACGAATCGTTATTCAAGTTTAAATGGAACATCAATGGCTTCACCTCA

TGTAGCTGGTGTAGCGGCCCTAGTGAAGGCGAGATATCCAAGTGCGACGA

ATGCTCAGATTAGACAACATCTTCGTAGCACTTCTACGTATCTAGGAAAC

TCAACTTACTATGGTAGTGGTCTAGTTGATGCACAACGTGCAGCTAAC

TAA.

The amino acid sequence of the preproenzyme encoded by COG104_4065768.n is set forth as SEQ ID NO:22:

MKMKWSRLILTLVLVFSFVFPSMTSANSAVEKEDYLIGFKQKGNVSAQVVNMSG-
GEVVHE

YEHMPVLHVKLPSQAAKALEKNPNIEYIEKDEKVQATAQSTPWGISRINA

PAVHSTGNFGQGVRVAVLDSGVASHEDLRIAGGVSFVASEPSYQDYNGHG

THVAGTIAGLNNSVGVLGVAPSVQLYAVKVLDRNGGGNHSDIARGIEWSV

NNGMHVVNMSLGGPTGSTTLQRAADNAYNRGVLLIAAAGNTGTSGVSFPA

RYSSVMAVAATDSNNNRASFSTYGTQIEISAPGVGINSTYPTNRYSSLNG

TSMASPHVAGVAALVKARYPSATNAQIRQHLRSTSTYLGNSTYYGSGLVD

AQRAAN.

At the N-terminus, the preproenzyme has a signal peptide with a predicted length of 29 amino acids (in bold italics in SEQ ID NO:22) as determined using SignalP-NN (Emanuelsson et al., Nature Protocols, 2:953-971, 2007). The presence of a signal peptide indicates that this serine protease is a secreted enzyme. Like other serine proteases, the enzyme has a pro-sequence, with a predicted length of 68 amino acids (in italics in SEQ ID NO: 22). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, COG104, (269 amino acids), is set forth as SEQ ID NO: 23:

AQSTPWGISRINAPAVHSTGNFGQGVRVAVLDSGVASHEDLRIAGGVSFV

ASEPSYQDYNGHGTHVAGTIAGLNNSVGVLGVAPSVQLYAVKVLDRNGGG

NHSDIARGIEWSVNNGMHVVNMSLGGPTGSTTLQRAADNAYNRGVLLIAA

AGNTGTSGVSFPARYSSVMAVAATDSNNNRASFSTYGTQIEISAPGVGIN

STYPTNRYSSLNGTSMASPHVAGVAALVKARYPSATNAQIRQHLRSTSTY

LGNSTYYGSGLVDAQRAAN.

Serine Protease ACB83

The nucleotide sequence of ACB83_2687815.n is set forth as SEQ ID NO:24:

ATGAAAATGAAATGGTCACGTTTAATTTTAACCCTAGTTCTCGTATTCAG

TTTTGTATTCCCATCTATGACAAGTGCAAACTTCGCTGTAGAAAAAGAGG

ATTATCTCATCGGTTTTAAGCAGAAAGGGAATGTTAGTGCACAAGTTGTG

AATATGAGTGGAGGAGAAGTCGTCCATGAATATGAACATATGCCAGTCTT

GCACGTGAAATTACCTCCGCAAGCTGCTAAAGCGTTAGAAAAGAACCCAA

ATATTGAATACATCGAAAAAGATGAAAAGGTCCAAGCTACAGCACAATCG

ACACCTTGGGGGATTTCACGTATTAATGCTCCTGCTGTTCACTCGACTGG

TAATTTGGGACAAGGTGTCCGAGTTGCCGTTTTAGATAGTGGAGTTGCTT

CTCATGAAGACTTACGGATTGCTGGGGAGTGAGCTTTGTCGCTTCAGAA

CCTAGTTATCAAGATTATAATGGTCACGGAACACATGTTGCTGGAACCAT

TGCTGGTTTAAATAATAGTGTTGGGGTCCTTGGTGTAGCTCCATCTGTCC

AATTATATGCGGTTAAGGTGTTGGATCGTAATGGCGGGGGAAATCATAGT

GACATTGCTAGAGGAATTGAGTGGTCAGTTAATAATGGAATGCATGTGGT

GAATATGAGTTTAGGTGGACCAACAGGGTCAACGACTCTGCAACGAGCAG

CGGATAATGCTTATAACAGAGGAGTTCTTTTAATTGCCGCAGCTGGTAAC

ACGGGAACTAGTGGGGTTAGCTTCCCTGCGCGTTATAGCTCAGTAATGGC

AGTAGCCGCAACAGACTCTAATAATAACCGTGCTTCATTTTCAACTTATG

GTCCAGAAATTGAAATTTCAGCACCTGGAGTTGGCATTAATAGCACGTAT

CCAACGAATCGTTATTCAAGCTTAAATGGAACATCAATGGCTTCACCTCA

TGTCGCTGGTGTAGCAGCTCTTGTGAAGGCGAGATATCCAAGTGCGACGA

ATGCTCAGATTAGACAACATCTTCGTAGCACTTCTACGAATCTAGGAAAC

TCAACTTACTATGGTAGTGGTCTAGTTAATGCACAGCGTGCAGCTAAC

TAA.

The amino acid sequence of the preproenzyme encoded by ACB83_2687815.n is set forth as SEQ ID NO:25:

MKMKWSRLILTLVLVFSFVFPSMTSANFAVEKEDYLIGFKQKGNVSAQVV NMSGGEVVH

EYEHMPVLHVKLPPQAAKALEKNPNIEYIEKDEKVQATAQSTPWGISRIN

APAVHSTGNLGQGVRVAVLDSGVASHEDLRIAGGVSFVASEPSYQDYNGH

GTHVAGTIAGLNNSVGVLGVAPSVQLYAVKVLDRNGGGNHSDIARGIEWS

VNNGMHVVNMSLGGPTGSTTLQRAADNAYNRGVLLIAAAGNTGTSGVSFP

ARYSSVMAVAATDSNNNRASFSTYGPEIEISAPGVGINSTYPTNRYSSLN

GTSMASPHVAGVAALVKARYPSATNAQIRQHLRSTSTNLGNSTYYGSGLV

NAQRAAN.

At the N-terminus, the preproenzyme has a signal peptide with a predicted length of 29 amino acids (in bold italics in SEQ ID NO:25) as determined using SignalP-NN (Emanuelsson et al., Nature Protocols, 2:953-971, 2007). The presence of a signal peptide indicates that this serine protease is a secreted enzyme. Like other serine proteases, the enzyme has a pro-sequence, with a predicted length of 68 amino acids (in italics in SEQ ID NO: 25). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, ACB83, (269 amino acids), is set forth as SEQ ID NO: 26:

AQSTPWGISRINAPAVHSTGNLGQGVRVAVLDSGVASHEDLRIAGGVSFV

ASEPSYQDYNGHGTHVAGTIAGLNNSVGVLGVAPSVQLYAVKVLDRNGGG

NHSDIARGIEWSVNNGMHVVNMSLGGPTGSTTLQRAADNAYNRGVLLIAA

AGNTGTSGVSFPARYSSVMAVAATDSNNNRASFSTYGPEIEISAPGVGIN

STYPTNRYSSLNGTSMASPHVAGVAALVKARYPSATNAQIRQHLRSTSTN

LGNSTYYGSGLVNAQRAAN.

Serine Protease ACB90

The nucleotide sequence of ACB90_2720294.n is set forth as SEQ ID NO:27:

ATGAAAATGAAATGGTCACGTTTAATTTTAACCCTAGTTCTCGTATTCAG

TTTTGTATTCCCATCTATGACAAGTGCAAACTCCGCTGTAGAAAAAGAGG

ATTATCTCATCGGTTTTAAGCAGAAAGGGAATGTTAGTGCACAAGTTGTG

AATATGAGTGGAGGAGAAGTCGTCCATGAATATGAACATATGCCAGTCTT

GCACGTGAAATTACCTCCGCAAGCTGCTAAAGCGTTAGAAAAGAACCCAA

ATATTGAATACATCGAAAAAGATGAAAAGGTCCAAGCTACAGCACAATCG

ACACCTTGGGGGATTTCACGTATTAATGCTCCTGCTGTTCACTCGACTGG

TAATTTGGGACAAGGTGTCCGAGTTGCCGTTTTAGATAGTGGAGTTGCTT

CTCATGAAGACTTACGGATTGCTGGGGAGTGAGCTTTGTCGCTTCAGAA

CCTAGTTATCAAGATTATAATGGTCACGGAACACATGTTGCTGGAACCAT

TGCTGGTTTAAATAATAGTGTTGGGGTCCTTGGTGTAGCTCCATTTGTCC

AATTATATGCGGTTAAGGTGTTGGATCGTAATGGCGGGGGAAATCATAGT

GACATTGCTAGAGGAATTGAGTGGTCAGTTAATAATGGAATGCATGTGGT

GAATATGAGTTTAGGTGGACCAACAGGGTCAACGACTCTGCAACGAGCAG

CGGATAATGCTTATAACAGAGGAGTTCTTTTAATTGCCGCAGCTGGTAAC

ACGGGAACTAGTGGGGTTAGCTTCCCTGCGCGTTATAGCTCAGTAATGGC

AGTAGCCGCAACAGACTCTAATAATAACCGTGCTTCATTTTCAACTTATG

GTCCAGAAATTGAAATTTCAGCACCTGGAGTTGGCATTAATAGCACGTAT

CCAACGAATCGTTATTCAAGCTTAAATGGAACATCAATGGCTTCACCTCA

TGTCGCTGGTGTAGCAGCTCTTGTGAAGGCGAGATATCCAAGTGCGACGA

ATGCTCAGATTAGACAACATCTTCGTAGCACTTCTACGAATCTAGGAAAC

TCAACTTACTATGGTAGTGGTCTAGTTAATGCACAGCGTGCAGCTAACTA

A.

The amino acid sequence of the preproenzyme encoded by ACB90_2720294.n is set forth as SEQ ID NO:28:

MKMKWSRLILTLVLVFSFVFPSMTSANSAVEKEDYLIGFKQKGNVSAQVV NMSGGEVVHE

YEHMPVLHVKLPPQAAKALEKNPNIEYIEKDEKVQATAQSTPWGISRINA

PAVHSTGNLGQGVRVAVLDSGVASHEDLRIAGGVSFVASEPSYQDYNGHG

THVAGTIAGLNNSVGVLGVAPFVQLYAVKVLDRNGGGNHSDIARGIEWSV

NNGMHVVNMSLGGPTGSTTLQRAADNAYNRGVLLIAAAGNTGTSGVSFPA

RYSSVMAVAATDSNNNRASFSTYGPEIEISAPGVGINSTYPTNRYSSLNG

TSMASPHVAGVAALVKARYPSATNAQIRQHLRSTSTNLGNSTYYGSGLVN

AQRAAN.

At the N-terminus, the preproenzyme has a signal peptide with a predicted length of 29 amino acids (in bold italics in SEQ ID NO:28) as determined using SignalP-NN (Emanuelsson et al., Nature Protocols, 2:953-971, 2007). The presence of a signal peptide indicates that this serine protease is a secreted enzyme. Like other serine proteases, the enzyme has a pro-sequence, with a predicted length of 68 amino acids (in italics in SEQ ID NO: 28). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, ACB90, (269 amino acids), is set forth as SEQ ID NO: 29:

AQSTPWGISRINAPAVHSTGNLGQGVRVAVLDSGVASHEDLRIAGGVSFV

ASEPSYQDYNGHGTHVAGTIAGLNNSVGVLGVAPFVQLYAVKVLDRNGGG

NHSDIARGIEWSVNNGMHVVNMSLGGPTGSTTLQRAADNAYNRGVLLIAA

AGNTGTSGVSFPARYSSVMAVAATDSNNNRASFSTYGPEIEISAPGVGIN

STYPTNRYSSLNGTSMASPHVAGVAALVKARYPSATNAQIRQHLRSTSTN

LGNSTYYGSGLVNAQRAAN.

Serine Protease ACB82

The nucleotide sequence of ACB82_2683104.n is set forth as SEQ ID NO:30:

ATGAGAGTTTTAAAAGGTACCAAACTTACCGGTTTACTTCTTGGGTTTAT

TTTATTATTTTCTTTCACCTTTTTGTCATTATCGGTTAGTGCTAACGGGA

ATGGAGTAGAAAGACATGACTATTTAATAGGGTTTCACGAAAAGGTAGAT

AAAAAAGCCATAACTCAAGCAAGCGGAGAAGTAGTTCACGAATATCAGTA

TATGCCTGTTCTTCATGTAAAGCTTCCAGAAAAAGCAGCAAAAGCTTTAG

AAAAAAATCCTAATATTGCTTATGTTGAAAAAGACGAAGAGGTTACTGCT

TCACAAACGGTTCCTTGGGGAATTAATCATATTCAAGCTCCAACTGTACA

TTCTTGGGGGAATCGCGGAAACGGTGTTCGTGTCGCTGTGCTAGATTCAG

GGGTTGCTTCCCATGAAGATTTAAGAATTTCTGGTGGTAGAAGTTTTATT

ACTAGCGAGCCTTCTTATCAAGATTATAATGGCCATGGAACTCATGTAGC

TGGTACCATCGCTGGGTTAAATAATAGTTACGGTGTACTTGGTGTCGCAC

CTAATGTTAATCTTTACGCAGTAAAAGTATTAGATCGTAATGGAAGTGGA

TCTCACAGTGCGATTGCACAAGGGATTGAATGGTCTGTTAGCAACGGTAT

GCATATTGTTAACATGAGCTTAGGTGGGCCAACTGGTTCAACAACTCTTC

AACGTGCCGCAGATAATGCTTATAATAGAGGTGTTCTTCTTATCGCTGCA

GCTGGAAACACGGGTTCTGCTGGTATTTCCTATCCAGCTAGATACAACTC

TGTTATGGCTGTAGGTGCCGTTGACTCCAATAATAATCGTGCTTCATTCT

CGACTTTTGGAAACGAATTAGAAATTATGGCACCAGGAGTATCAATATTA

AGCACACACCTTTCAAATCAATATGTTTCTTTAAACGGTACATCTATGGC

AAGTCCTCATGTAGCTGGTGTTGCAGCTTTGGTGAAAGCTCAATATCCAA

GTGCAACTAATGCCCAAATCAGACAAAGACTAAGAGATACTGCCACTCCA

CTTGGTAGTTCATATTACTTTGGAAATGGTTTAGTGCATGCTACTAGAGC

CGCTAATTAA.

The amino acid sequence of the preproenzyme encoded by ACB82_2683104.n is set forth as SEQ ID NO:31:

*MRVLKGTKLTGLLLGFILLFSFTFLSLSVSA**NGNGVERHDYLIGFHEK-VDKKAITQASGEV*

*VHEYQYMPVLHVKLPEKAAKALEKNPNIAYVEKDEEVTA*SQTVPWGINHI

QAPTVHSWGNRGNGVRVAVLDSGVASHEDLRISGGRSFITSEPSYQDYNG

HGTHVAGTIAGLNNSYGVLGVAPNVNLYAVKVLDRNGSGSHSAIAQGIEW

SVSNGMHIVNMSLGGPTGSTTLQRAADNAYNRGVLLIAAAGNTGSAGISY

PARYNSVMAVGAVDSNNNRASFSTFGNELEIMAPGVSILSTHLSNQYVSL

NGTSMASPHVAGVAALVKAQYPSATNAQIRQRLRDTATPLGSSYYFGNGL

VHATRAAN.

At the N-terminus, the preproenzyme has a signal peptide with a predicted length of 31 amino acids (in bold italics in SEQ ID NO:31) as determined using SignalP-NN (Emanuelsson et al., Nature Protocols, 2:953-971, 2007). The presence of a signal peptide indicates that this serine protease is a secreted enzyme. Like other serine proteases, the enzyme has a pro-sequence, with a predicted length of 69 amino acids (in italics in SEQ ID NO: 31). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, ACB82, (269 amino acids), is set forth as SEQ ID NO: 32:

SQTVPWGINHIQAPTVHSWGNRGNGVRVAVLDSGVASHEDLRISGGRSFI

TSEPSYQDYNGHGTHVAGTIAGLNNSYGVLGVAPNVNLYAVKVLDRNGSG

SHSAIAQGIEWSVSNGMHIVNMSLGGPTGSTTLQRAADNAYNRGVLLIAA

AGNTGSAGISYPARYNSVMAVGAVDSNNNRASFSTFGNELEIMAPGVSIL

STHLSNQYVSLNGTSMASPHVAGVAALVKAQYPSATNAQIRQRLRDTATP

LGSSYYFGNGLVHATRAAN.

Serine Protease ACB89

The nucleotide sequence of ACB89_2715301.n is set forth as SEQ ID NO:33:

ATGAGAGTTTTGAAAGGTAACAAACTTACCGGTTTACTTCTTGGGTTTAT

TTTAGTATTTTCTTTCACCTTTTTGTCATTATCGGTTAGTGCTAACGGGA

ATGGCAATGGCAATGGAGTAGAGAGACATGACTATTTAATAGGG

TTTCACGAAAAGGTAGATAAAAAAGCCATAACTCAAGCAAGCGGAGAAGT

AGTTCACGAATATCAGTATATGCCTGTTCTTCATGTAAAGCTTCCAGAAA

AAGCAGCAAAAGCTTTAGAAAAAAATCCTAATATTGCTTATGTTGAAAAA

GACGAAGAGGTTACTGCTTCACAAACGGTTCCTTGGGGAATTAATCATAT

TCAAGCTCCAACTGTACATTCTTGGGGGAATCGTGGAAACGGCGTTCGTG

TTGCTGTGTTAGATTCAGGGGTTGCTTCCCATGAAGATTTAAGAATTTTT

GGTGGTAGAAGTTTCATTACTAGCGAGCCTTCTTATCAAGATTATAATGG

CCATGGAACTCATGTCGCCGGAACCATCGCTGGGTTAAATAATAGTTACG

GTGTACTTGGTGTTGCACCTAATGTTAATCTTTACGCAGTAAAAGTATTA

GATCGTAACGGAAGTGGATCTCACAGTGCGATTGCACAAGGGATTGAATG

GTCTGTTAGCAACGGTATGCATATTGTTAACATGAGCTTAGGTGGGCCAA

CAGGTTCAACAACTCTTCAACGTGCCGCTGATAATGCTTATAATAGAGGT

GTTCTCCTTATCGCTGCAGCTGGTAACACGGGTTCTGCTGGTATTTCCTA

TCCAGCTAGATACAACTCTGTTATGGCTGTAGGTGCCGTTGACTCCAATA

ATAATCGTGCTTCATTCTCGACTTTTGGAAACGAATTAGAAATTATGGCA

CCAGGAGTATCAATTTTAAGCACGCACCTTTCAAATCAATATGTTTCTTT

AAACGGTACATCTATGGCAAGTCCTCATGTAGCTGGTGTTGCAGCTTTGG

TGAAAGCTCAATATCCAAGTGCAACTAATGCCCAAATCAGACAAAGACTA

AGAGATACTGCCACTCCACTTGGTAGTTCATATTACTTTGGAAATGGTTT

AGTGCATGCTGCTAGAGCCGCTAATTAA.

The amino acid sequence of the preproenzyme encoded by ACB89_2715301.n is set forth as SEQ ID NO:34:

*MRVLKGNKLTGLLLGFILVFSFTFLSLSVSA**NGNGNGNGNGVER-HDYLIGFHEKVDKKAI*

*TQASGEWHEYQYMPVLHVKLPEKAAKALEKNPNIAYVEKDEEVTASQTVP*

*WGINHIQAPTVHSWGNRGNGVRVAVLDSGVASHEDLRIFGGRSFITSEPS*

*YQDYNGHGTHVAGTIAGLNNSYGVLGVAPNVNLYAVKVLDRNGSGSHSAI*

*AQGIEWSVSNGMHIVNMSLGGPTGSTTLQRAADNAYNRGVLLIAAAGNTG*

*SAGISYPARYNSVMAVGAVDSNNNRASFSTFGNELEIMAPGVSILSTHLS*

*NQYVSLNGTSMASPHVAGVAALVKAQYPSATNAQIRQRLRDTATPLGSSY*

*YFGNGLVHAARAAN.*

At the N-terminus, the preproenzyme has a signal peptide with a predicted length of 31 amino acids (in bold italics in SEQ ID NO:34) as determined using SignalP-NN (Emanuelsson et al., Nature Protocols, 2:953-971, 2007). The presence of a signal peptide indicates that this serine protease is a secreted enzyme. Like other serine proteases, the enzyme has a pro-sequence, with a predicted length of 75 amino acids (in italics in SEQ ID NO: 34). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, ACB89, (269 amino acids), is set forth as SEQ ID NO: 35:

SQTVPWGINHIQAPTVHSWGNRGNGVRVAVLDSGVASHEDLRIFGGRSFI

TSEPSYQDYNGHGTHVAGTIAGLNNSYGVLGVAPNVNLYAVKVLDRNGSG

SHSAIAQGIEWSVSNGMHIVNMSLGGPTGSTTLQRAADNAYNRGVLLIAA

AGNTGSAGISYPARYNSVMAVGAVDSNNNRASFSTFGNELEIMAPGVSIL

STHLSNQYVSLNGTSMASPHVAGVAALVKAQYPSATNAQIRQRLRDTATP

LGSSYYFGNGLVHAARAAN.

Serine Protease ACB92

The nucleotide sequence of ACB92_2732966.n is set forth as SEQ ID NO:36:

ATGCGAGTTTTAAAAGGTACCAAACTTACTGGTTTACTTCTTGGGTTTAT

TTTAGTATTTTCTTTCGCTTTTTTATCACTATCGGTTAGTGCTAATGGCA

ATGGCGTAGAAAGACATGACTATTTAATAGGGTTTCACGAAAAGGTAGAT

AAAAAAGCCATAACTCAAGCAAGCGGAGAAGTAGTTCACGAATATCAGTA

TATGCCTGTTCTTCATGTAAAGCTTCCAGAAAAAGCAGCAAAAGCTTTAG

AAAAAAATCCTAATATTGCTTATGTTGAAAAAGACGAAGAGGTTACTGCT

TCACAAACGGTTCCTTGGGGAATTAATCATATTCAAGCTCCAACTGTACA

TTCTTGGGGGAATCGTGGAAACGGCGTTCGTGTTGCTGTGTTAGATTCAG

GGGTTGCTTCCCATGAAGATTTAAGAATTTCTGGTGGTAGAAGTTTCATT

ACTAGCGAGCCTTCTTATCAAGATTATAATGGCCATGGAACTCATGTCGC

CGGAACCATCGCTGGGTTAAATAATAGTTACGGTGTACTTGGTGTTGCAC

CTAATGTTAATCTTTACGCTGTAAAAGTATTAGATCGTAACGGAAGTGGA

TCTCACAGTGCGATTGCACAAGGGATTGAATGGTCTGTTAGCAACGGTAT

GCATATTGTTAACATGAGCTTAGGTGGGCCAACTGGTTCAGCAACTCTTC

AACGTGCCGCAGATAATGCTTATAATAGAGGTGTGCTTCTGATTGCTGCA

GCTGGAAATACGGGTTCTGCTGGTATTTCCTATCCAGCAAGATACAATTC

TGTTATGGCTGTAGGTGCCGTTGACTCCAATAACAATCGTGCTTCATTCT

CGACTTTTGGAAACGAATTAGAAATTATGGCACCAGGAGTATCCATTTTA

AGCACACACCTTTCAAATCAATATATTTCTTTAAACGGTACATCTATGGC

AAGTCCACATGTAGCTGGTGTTGCAGCTTTGGTGAAAGCTCAATATCCAA

GTGCGACTAATGCCCAAATCAGACAAAGACTAAGAGACACCGCTACTCCA

CTTGGTAGCTCATATTACTTTGGCAATGGTTTAGTGCACGCTGCTAGAGC

CGCTAATTAA.

The amino acid sequence of the preproenzyme encoded by ACB92_2732966.n is set forth as SEQ ID NO. 37:

*MRVLKGTKLTGLLLGFILVFSFAFLSLSVSA**NGNGVERHDYLIGFHEK-VDKKAITQASGEV*

*VHEYQYMPVLHVKLPEKAAKALEKNPNIAYVEKDEEVTASQTVPWGINHI*

*QAPTVHSWGNRGNGVRVAVLDSGVASHEDLRISGGRSFITSEPSYQDYNG*

*HGTHVAGTIAGLNNSYGVLGVAPNVNLYAVKVLDRNGSGSHSAIAQGIEW*

*SVSNGMHIVNMSLGGPTGSATLQRAADNAYNRGVLLIAAAGNTGSAGISY*

*PARYNSVMAVGAVDSNNNRASFSTFGNELEIMAPGVSILSTHLSNQYISL*

*NGTSMASPHVAGVAALVKAQYPSATNAQIRQRLRDTATPLGSSYYFGNGL*

*VHAARAAN.*

At the N-terminus, the preproenzyme has a signal peptide with a predicted length of 31 amino acids (in bold italics in SEQ ID NO:37) as determined using SignalP-NN (Emanuelsson et al., Nature Protocols, 2:953-971, 2007). The presence of a signal peptide indicates that this serine protease is a secreted enzyme. Like other serine proteases, the enzyme has a pro-sequence, with a predicted length of 69 amino acids (in italics in SEQ ID NO: 37). The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, ACB92, (269 amino acids), is set forth as SEQ ID NO: 38:

SQTVPWGINHIQAPTVHSWGNRGNGVRVAVLDSGVASHEDLRISGGRSFI

TSEPSYQDYNGHGTHVAGTIAGLNNSYGVLGVAPNVNLYAVKVLDRNGSG

SHSAIAQGIEWSVSNGMHIVNMSLGGPTGSATLQRAADNAYNRGVLLIAA

AGNTGSAGISYPARYNSVMAVGAVDSNNNRASFSTFGNELEIMAPGVSIL

STHLSNQYISLNGTSMASPHVAGVAALVKAQYPSATNAQIRQRLRDTATP

LGSSYYFGNGLVHAARAAN.

Serine Protease DETPh35

The nucleotide sequence of DETPh35_2828044.n is set forth as SEQ ID NO:39:

ATGAGAGTTTTGAAAGGTAACAAACTTACCGGTTTACTTCTTGGGTTTAT

TTTAGTATTTTCTTTCACCTTTTTGTCATTATCGGTTAGTGCTAACGGGA

ATGGCAATGGAGTAGAAAGACATGACTATTTAATAGGGTTTCACGAAAAG

GTAGATAAAAAAGCCATAACTCAAGCAAGCGGAGAAGTAGTTCACGAATA

TCAGTATATGCCTGTTCTTCATGTAAAGCTTCCAGAAAAAGCAGCAAAAG

CTTTAGAAAAAAATCCTAATATTGCTTATGTTGAAAAAGACGAAGAGGTT

ACTGCTTCACAAACGGTTCCTTGGGGAATTAATCATATTCAAGCTCCAAC

TGTACATTCTTGGGGAATCGTGGAAACGGCGTTCGTGTTGCTGTGTTAG

ATTCAGGGGTTGCTTCCCATGAAGATTTAAGAATTTCTGGTGGTAGAAGT

TTCATTACTAGCGAGCCTTCTTATCAAGATTATAATGGCCATGGAACTCA

TGTCGCCGGAACCATCGCTGGGTTAAATAATAGTTACGGTGTACTTGGTG

TTGCACCTAATGTTAATCTTTACGCTGTAAAAGTATTAGATCGTAACGGA

AGTGGATCTCACAGTGCGATTGCACAAGGGATTGAATGGTCTGTTAGCAA

CGGTATGCATATTGTTAACATGAGCTTAGGTGGGCCAACTGGTTCAGCAA

CTCTTCAACGTGCCGCAGATAATGCTTATAATAGAGGTGTGCTTCTGATT

GCTGCAGCTGGAAATACGGGTTCTGCTGGTATTTCCTATCCAGCAAGATA

CAATTCTGTTATGGCTGTAGGTGCCGTTGACTCCAATAACAATCGTGCTT

CATTCTCGACTTTTGGAAACGAATTAGAAATTATGGCACCAGGAGTATCC

ATTTTAAGCACACACCTTTCAAATCAATATGTTTCTTTAAACGGTACATC

TATGGCAAGTCCACATGTAGCTGGTGTTGCAGCTTTGGTGAAGGCTCAAT

ATCCAAGTGCGACTAATGCCCAAATCAGACAAAGACTAAGAGACACCGCT

ACTCCACTTGGTAGCTCATATTACTTTGGCAATGGTTTAGTGCACGCTGC

TAGAGCCGCTAATTAA.

The amino acid sequence of the preproenzyme encoded by DETPh35_2828044.n is set forth as SEQ ID NO:40:

MRVLKGNKLTGLLLGFILVFSFTFLSLSVSA NGNGNGVERHDYLIGFHEK-
VDKKAITQASG

EVVHEYQYMPVLHVKLPEKAAKALEKNPNIAYVEKDEEVTASQTVPWGIN

HIQAPTVHSWGNRGNGVRVAVLDSGVASHEDLRISGGRSFITSEPSYQDY

NGHGTHVAGTIAGLNNSYGVLGVAPNVNLYAVKVLDRNGSGSHSAIAQGI

EWSVSNGMHIVNMSLGGPTGSATLQRAADNAYNRGVLLIAAAGNTGSAGI

SYPARYNSVMAVGAVDSNNNRASFSTFGNELEIMAPGVSILSTHLSNQYV

SLNGTSMASPHVAGVAALVKAQYPSATNAQIRQRLRDTATPLGSSYYFGN

GLVHAARAAN.

At the N-terminus, the preproenzyme has a signal peptide with a predicted length of 31 amino acids (in bold italics in SEQ ID NO:40) as determined using SignalP-NN (Emanuelsson et al., Nature Protocols, 2:953-971, 2007). The presence of a signal peptide indicates that this serine protease is a secreted enzyme. Like other serine proteases, the enzyme has a pro-sequence, with a predicted length of 71 amino acids (in italics in SEQ ID NO: 40).

The pro-sequence prediction was based on knowledge of the pro-mature junction in homologous serine proteases such as BPN' (Wells et al., Nucleic Acids Res, 11:7911-25, 1983) and PB92 protease (van der Laan et al., Appl Environ Microbiol, 57:901-909, 1991).

The amino acid sequence of the fully processed mature enzyme, DETPh35, (269 amino acids), is set forth as SEQ ID NO: 41:

SQTVPWGINHIQAPTVHSWGNRGNGVRVAVLDSGVASHEDLRISGGRSFI

TSEPSYQDYNGHGTHVAGTIAGLNNSYGVLGVAPNVNLYAVKVLDRNGSG

SHSAIAQGIEWSVSNGMHIVNMSLGGPTGSATLQRAADNAYNRGVLLIAA

AGNTGSAGISYPARYNSVMAVGAVDSNNNRASFSTFGNELEIMAPGVSIL

STHLSNQYVSLNGTSMASPHVAGVAALVKAQYPSATNAQIRQRLRDTATP

LGSSYYFGNGLVHAARAAN.

An alignment of the amino acid sequences of the mature forms of the BspAI02518 (SEQ ID NO:3), BspU02193 (SEQ ID NO:6), Bakn00315 (SEQ ID NO:11), Bcl04009 (SEQ ID NO:14), SWT66_254731 (SEQ ID NO:17), ACB102 (SEQ ID NO:20), COG104 (SEQ ID NO:23), ACB83 (SEQ ID NO:26), ACB90 (SEQ ID NO:29), ACB82 (SEQ ID NO:32), ACB89 (SEQ ID NO:35), ACB92 (SEQ ID NO:38), and DETPh35 (SEQ ID NO:41) subtilisins with the sequences of the mature forms of subtilisins from *B. amyloliquefaciens, B. lentus, B. licheniformis, Bacillus* sp. LG12, and *B. pseudofirmus* (NCBI Accession Nos. CAA24990, P29600, CAJ70731, AAC43580, and ADC49870 respectively) is shown in FIG. 12. The sequences were aligned using the AlignX module of Vector NTI Advance® Software (Life Technologies) with the default parameters.

TABLE 10-1

Percent Identity (PID) Shared by Various *Bacillus* Subtilases

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 1 Bsp__AAC43580 | 100 | 65 | 71 | 64 | 62 | 62 | 60 | 60 | 60 | 61 | 61 | 64 | 64 | 64 | 64 | 64 | 64 | 64 |
| 2 Bam__CAA24990 | | 100 | 70 | 61 | 57 | 56 | 60 | 59 | 59 | 60 | 60 | 58 | 58 | 57 | 57 | 58 | 58 | 57 |
| 3 Bli__CAJ70731.1 | | | 100 | 62 | 62 | 59 | 59 | 58 | 59 | 59 | 59 | 65 | 65 | 59 | 59 | 59 | 59 | 59 |
| 4 Ble__P29600 | | | | 100 | 63 | 60 | 63 | 64 | 63 | 64 | 63 | 63 | 63 | 61 | 61 | 62 | 62 | 61 |
| 5 Bps__ADC49870 | | | | | 100 | 66 | 68 | 68 | 68 | 67 | 67 | 66 | 67 | 71 | 71 | 71 | 71 | 71 |
| 6 BspU02193 | | | | | | 100 | 69 | 68 | 68 | 68 | 68 | 74 | 74 | 75 | 75 | 75 | 75 | 75 |

TABLE 10-1-continued

Percent Identity (PID) Shared by Various *Bacillus* Subtilases

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 7 ACB102 | | | | | | | 100 | 98 | 99 | 99 | 98 | 75 | 75 | 81 | 81 | 80 | 80 | 81 |
| 8 BspAI02518 | | | | | | | | 100 | 99 | 97 | 97 | 74 | 74 | 80 | 80 | 80 | 80 | 80 |
| 9 COG104 | | | | | | | | | 100 | 98 | 98 | 74 | 74 | 80 | 80 | 80 | 80 | 80 |
| 10 ACB83 | | | | | | | | | | 100 | 99.6 | 75 | 75 | 81 | 81 | 80 | 80 | 81 |
| 11 ACB90 | | | | | | | | | | | 100 | 75 | 75 | 81 | 81 | 80 | 80 | 81 |
| 12 Bcl04009 | | | | | | | | | | | | 100 | 99 | 83 | 83 | 83 | 83 | 84 |
| 13 SWT66_254731 | | | | | | | | | | | | | 100 | 84 | 84 | 84 | 84 | 84 |
| 14 ACB82 | | | | | | | | | | | | | | 100 | 99 | 99 | 99 | 99.6 |
| 15 ACB89 | | | | | | | | | | | | | | | 100 | 99 | 99 | 99.6 |
| 16 ACB92 | | | | | | | | | | | | | | | | 100 | 99.6 | 99 |
| 17 DETPh35 | | | | | | | | | | | | | | | | | 100 | 99.6 |
| 18 Bakn00315 | | | | | | | | | | | | | | | | | | 100 |

Figure 13:
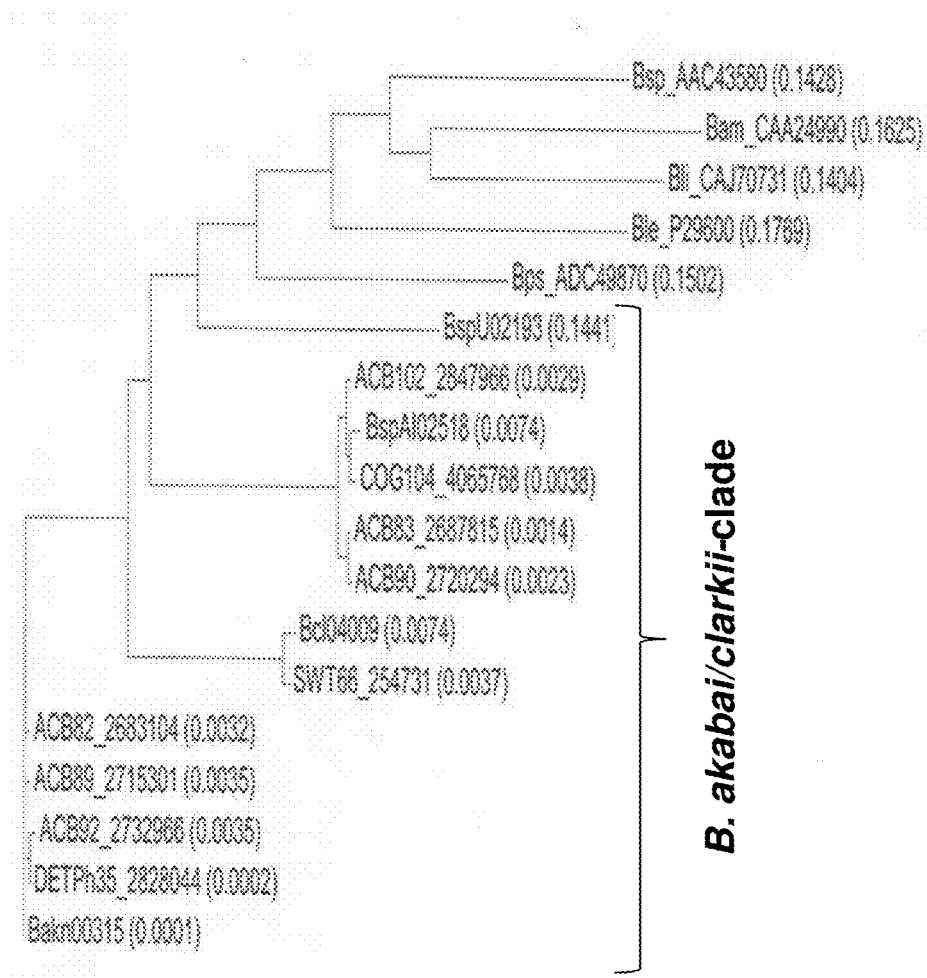
FIG. 13 provides a phylogenetic tree of BspAI02518 (SEQ ID NO: 3), BspU02193 (SEQ ID NO: 6), Bakn00315 (SEQ ID NO: 11), Bcl04009 (SEQ ID NO: 14), SWT66_254731 (SEQ ID NO: 17), ACB102 (SEQ ID NO: 20), COG104 (SEQ ID NO: 23), ACB83 (SEQ ID NO: 26), ACB90 (SEQ ID NO: 29), ACB82 (SEQ ID NO: 32), ACB89 (SEQ ID NO: 35), ACB92 (SEQ ID NO: 38), DETPh35 (SEQ ID NO: 41), and various other bacterial serine proteases with a bracket denoting the sequences encompassing the B. akibai/clarkii-clade subtilisins.

A phylogenetic tree for amino acid sequences of the mature forms of the subtilisins of Table 10-1 was built. The sequences were entered in the Vector NTI Advance suite and a Guide Tree was created using the Neighbor Joining (NJ) method (Saitou and Nei, Mol Biol Evol, 4:406-425, 1987). The tree construction was calculated using the following parameters: Kimura's correction for sequence distance and ignoring positions with gaps. AlignX displays the calculated distance values in parenthesis following the molecule name displayed on the tree shown in FIG. 13.

Example 11

Unique Features of *B. akibai/clarkii*-Clade Subtilisins

A structure based alignment (FIG. 14) was performed using the "align" option in the Molecular Operating Environment (MOE) software (Chemical Computing Group, Montreal, Quebec, Canada) to look for structural similarities. The amino acid sequences of the mature forms of BspAI02518 (SEQ ID NO:3), BspU02193 (SEQ ID NO:6), Bakn00315 (SEQ ID NO:11), Bcl04009 (SEQ ID NO:14), SWT66_254731 (SEQ ID NO:17), ACB102 (SEQ ID NO:20), COG104 (SEQ ID NO:23), ACB83 (SEQ ID NO:26), ACB90 (SEQ ID NO:29), ACB82 (SEQ ID NO:32), ACB89 (SEQ ID NO:35), ACB92 (SEQ ID NO:38), and DETPh35 (SEQ ID NO:41) subtilisins, were aligned with BPN' subtilisin from *B. amyloliquefaciens* (pdb entry 2STI), Carlsberg from *B. licheniformis* (pdb entry 3UNX), *B. lentus* subtilisin (pdb entry 1JEA) and the proprietary structure of subtilisin LG12 (PCT Patent Application No. PCT/US2014/55223, filed Sep. 11, 2014). The alignment applies conserved structural motifs as an additional guide to conventional sequence alignment. This alignment was performed using standard program defaults present in the 2012.10 distribution of MOE. As shown in FIG. 14, the structural alignment of subtilisins BspAI02518, BspU02193, Bakn00315, Bcl04009, SWT66_254731, ACB82, ACB83, ACB89, ACB90, ACB92, ACB102, COG104, and DETPh35 sequences show that these *B. akibai/clarkii*-clade sequences have a segment of three conserved amino acids: Asp-Arg-Asn (DRN) at residues 95-97 (based on BspAI02518 SEQ ID NO:3 sequence numbering) (hereafter referred to as the "DRN motif") that is unique to these subtilisins as compared to other subtilisin enzymes. The DRN motif is flanked on both sides by amino acids that are highly conserved across most *Bacillus* subtilisins. The conserved flanking residues are KVL at the N-terminus and GG/SG at the C-terminus. In place of DRN, the commercial subtilisins BPN' and *B. lentus* have GAS/N at these positions, while Carlsberg subtilisin has NNS.

The *B. akibai/clarkii*-clade subtilisin sequence DRN motif can be defined as VKVLDRNGR$^1$G, wherein R$^1$ is selected from G or S (SEQ ID NO:42), VKVLDRNGGG (SEQ ID NO:43), or VKVLDRNGSG (SEQ ID NO:44). The *B. akibai/clarkii*-clade subtilisin sequence DRN motif can further be defined as D95R96N97 (SEQ ID NO:45), V91K92V93L94D95R96N97G98G/S99G100 (SEQ ID NO:46), V91K92V93L94D95R96N97G98G99G100 (SEQ ID NO:47), or V91K92V93L94D95R96N97G98S99G100 (SEQ ID NO:48). The sequence numbering set forth in SEQ ID NOs:45, 46, 47, and 48 is based on BspAI02518 SEQ ID NO:3 sequence numbering.

Figure 15:
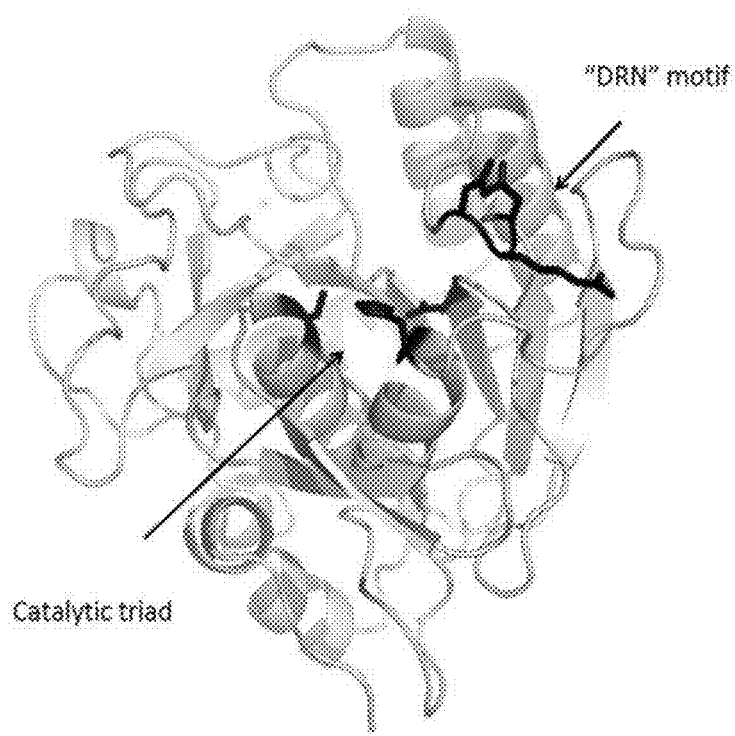
FIG. 15 shows the expected location of the DRN motif in the main chain fold of the B. akibai/clarkii-clade subtilisins modeled on the B. lentus subtilisin (pdb entry 1JEA) structure with respect to the catalytic triad. Residue side chains of the catalytic triad common to all serine proteases are colored in black.

FIG. 15 shows where the catalytic triad and DRN motif are located in the *B. akibai/clarkii*-clade subtilisin protease as modeled onto the three-dimensional structure of *B. lentus* subtilisin (pdb entry 1JEA) protease. In this structural alignment the characteristic catalytic triad residues Asp32, His62 and Ser215 are seen to be conserved along with Asn153 which forms the equally characteristic "oxyanion hole" of subtilisin-like proteases. In the alignment, we also find the prediction of a common deletion observed in *B. lentus* subtilisin between residues 156 and 157 of the *B. akibai/clarkii*-clade sequences relative to commercial subtilisins Carlsberg and BPN' and proprietary subtilisin LG12. In the alignment, we also find that in contrast to the commercial and proprietary subtilisin proteases that the *B. akibai/clarkii*-clade sequences contain a DRN motif. The D95R96N97 residues of the *B. akibai/clarkii*-clade sequences are located in a tight loop leading into the substrate binding site formed in part by residues 99-102 in the linear sequence of BspAI02518. It is expected that this motif could modulate the interaction of the *B. akibai/clarkii*-clade subtilisins with the substrate in a beneficial way.

Structural Implications of the DRN Motif:

There are no crystallographic structures of the *B. akibai/clarkii*-clade subtilisin-like proteases. Instead, FIG. 15 uses the structure of *B. lentus* susbtilisin as a surrogate to show the potential importance of the DRN motif in the performance of *B. akibai/clarkii*-clade subtilisin like proteases. The schematic representation of the overall main chain folding is shown in light gray. Also shown is the location of the side chains of the catalytic triad residues Asp32, His62 and Ser 215, as black sticks. The residues in the DRN motif have been modelled on the *B. lentus* structure at the homologous positions. It can be seen that these residues determine the loop leading in the substrate binding residues 99-102 and also are forming the leading edge of the substrate binding site and thereby in a position to modulate substrate binding.

SEQUENCE LISTING

<160> NUMBER OF SEQ ID NOS: 85

<210> SEQ ID NO 1
<211> LENGTH: 1098
<212> TYPE: DNA
<213> ORGANISM: B. akibai
<220> FEATURE:
<221> NAME/KEY: misc_feature
<222> LOCATION: (1)..(1098)
<223> OTHER INFORMATION: nucleotide sequence of BspAI02518n, B. akibai
    C-M-2-3

<400> SEQUENCE: 1

```
atgaaaatga aatggtcacg tttacttta actctagttc tcgtattcag ttttgtattc      60
ccatctatga caagtgcaaa ctcagctgta gaaaagagg actatctgat cggttttaag     120
cagaaaggga atgttagtgc acaagttgtg aatatgagtg gaggagaagt cgtccatgaa    180
tatgaacata tgccagtctt gcacgttaaa ttacctccac aagctgctaa agctttagaa    240
aagaaccgaa atattgaata catcgaaaaa gatgaaaaag tccaagcaac agcacaatcg    300
acaccttggg ggatttcacg tattaatgct cctgctgttc actcgactgg taattttgga    360
caaggtgtcc gagttgccgt tttagatagt ggagttgctt ctcatgaaga cttacggatt    420
gctgggggag tgagctttgt cgcttcagaa cctagttatc aagattataa tggtcacgga    480
acacatgttg ctggaaccat tgctggttta aataatagtg ttggggtcct tggtgtagct    540
ccatctgtcc aattatatgc ggttaaggtg ttggatcgta atggcgggg aaatcatagt    600 gacattgcta gaggaattga gtggtcagtt aataatggta tgcatgtggt gaatatgagt    660
ttaggtggac caacagggtc aaccactctt caacgagcag cggataatgc ttataataga    720
ggagttcttt taattgctgc ggctggtaac acgggaacta gtggagttag cttccctgcg    780
cgttacagct cagtaatggc agtagccgca acagattcta ataataaccg tgcttcattt    840
tcaacttatg gatcacaaat tgaaatttca gcacctggag ttggcattaa tagcacgtat    900
ccaacgaatg ttattcaag tttaaatgga acatcaatgg cttcacctca tgtcgctggt    960
gtagcggccc tagtgaaggc gagatatcca agtgcgacga atgctcagat tagacaacat   1020
cttcgtagca cttctacgta tctaggaaac tcaacttact atggtagtgg tctagttgat   1080
gcacagcgtg caactaac                                                 1098
```

<210> SEQ ID NO 2
<211> LENGTH: 366
<212> TYPE: PRT
<213> ORGANISM: B. akibai
<220> FEATURE:
<221> NAME/KEY: misc_feature
<222> LOCATION: (1)..(366)
<223> OTHER INFORMATION: amino acid sequence of the preproenzyme encoded
    by BspAI02518n, B. akibai C-M-2-3

<400> SEQUENCE: 2

Met Lys Met Lys Trp Ser Arg Leu Leu Leu Thr Leu Val Leu Val Phe
1               5                   10                  15

Ser Phe Val Phe Pro Ser Met Thr Ser Ala Asn Ser Ala Val Glu Lys
            20                  25                  30

Glu Asp Tyr Leu Ile Gly Phe Lys Gln Lys Gly Asn Val Ser Ala Gln
        35                  40                  45

Val Val Asn Met Ser Gly Gly Glu Val Val His Glu Tyr Glu His Met
    50                  55                  60

Pro Val Leu His Val Lys Leu Pro Pro Gln Ala Ala Lys Ala Leu Glu

```
                65                  70                  75                  80
Lys Asn Arg Asn Ile Glu Tyr Ile Glu Lys Asp Glu Lys Val Gln Ala
                    85                  90                  95

Thr Ala Gln Ser Thr Pro Trp Gly Ile Ser Arg Ile Asn Ala Pro Ala
            100                 105                 110

Val His Ser Thr Gly Asn Phe Gly Gln Gly Val Arg Val Ala Val Leu
            115                 120                 125

Asp Ser Gly Val Ala Ser His Glu Asp Leu Arg Ile Ala Gly Gly Val
            130                 135                 140

Ser Phe Val Ala Ser Glu Pro Ser Tyr Gln Asp Tyr Asn Gly His Gly
145                 150                 155                 160

Thr His Val Ala Gly Thr Ile Ala Gly Leu Asn Asn Ser Val Gly Val
                165                 170                 175

Leu Gly Val Ala Pro Ser Val Gln Leu Tyr Ala Val Lys Val Leu Asp
                180                 185                 190

Arg Asn Gly Gly Gly Asn His Ser Asp Ile Ala Arg Gly Ile Glu Trp
                195                 200                 205

Ser Val Asn Asn Gly Met His Val Val Asn Met Ser Leu Gly Gly Pro
                210                 215                 220

Thr Gly Ser Thr Thr Leu Gln Arg Ala Ala Asp Asn Ala Tyr Asn Arg
225                 230                 235                 240

Gly Val Leu Leu Ile Ala Ala Gly Asn Thr Gly Thr Ser Gly Val
                245                 250                 255

Ser Phe Pro Ala Arg Tyr Ser Ser Val Met Ala Val Ala Ala Thr Asp
                260                 265                 270

Ser Asn Asn Asn Arg Ala Ser Phe Ser Thr Tyr Gly Ser Gln Ile Glu
                275                 280                 285

Ile Ser Ala Pro Gly Val Gly Ile Asn Ser Thr Tyr Pro Thr Asn Gly
                290                 295                 300

Tyr Ser Ser Leu Asn Gly Thr Ser Met Ala Ser Pro His Val Ala Gly
305                 310                 315                 320

Val Ala Ala Leu Val Lys Ala Arg Tyr Pro Ser Ala Thr Asn Ala Gln
                325                 330                 335

Ile Arg Gln His Leu Arg Ser Thr Ser Thr Tyr Leu Gly Asn Ser Thr
                340                 345                 350

Tyr Tyr Gly Ser Gly Leu Val Asp Ala Gln Arg Ala Thr Asn
                355                 360                 365

<210> SEQ ID NO 3
<211> LENGTH: 269
<212> TYPE: PRT
<213> ORGANISM: B. akibai
<220> FEATURE:
<221> NAME/KEY: misc_feature
<222> LOCATION: (1)..(269)
<223> OTHER INFORMATION: amino acid sequence of the fully processed
      mature enzyme, BspAI02518 (269 amino acids), B. akibai C-M-2-3

<400> SEQUENCE: 3

Ala Gln Ser Thr Pro Trp Gly Ile Ser Arg Ile Asn Ala Pro Ala Val
1               5                   10                  15

His Ser Thr Gly Asn Phe Gly Gln Gly Val Arg Val Ala Val Leu Asp
                20                  25                  30

Ser Gly Val Ala Ser His Glu Asp Leu Arg Ile Ala Gly Gly Val Ser
            35                  40                  45

Phe Val Ala Ser Glu Pro Ser Tyr Gln Asp Tyr Asn Gly His Gly Thr
```

|   |   |   |   |   |   |   |   |   |   |
|---|---|---|---|---|---|---|---|---|---|
|   |   | 50 |   |   | 55 |   |   | 60 |   |
| His | Val | Ala | Gly | Thr | Ile | Ala | Gly | Leu | Asn | Asn | Ser | Val | Gly | Val | Leu |
| 65 |   |   |   | 70 |   |   |   | 75 |   |   |   |   | 80 |

His Val Ala Gly Thr Ile Ala Gly Leu Asn Asn Ser Val Gly Val Leu
65                  70                  75                  80

Gly Val Ala Pro Ser Val Gln Leu Tyr Ala Val Lys Val Leu Asp Arg
                85                  90                  95

Asn Gly Gly Gly Asn His Ser Asp Ile Ala Arg Gly Ile Glu Trp Ser
            100                 105                 110

Val Asn Asn Gly Met His Val Val Asn Met Ser Leu Gly Gly Pro Thr
        115                 120                 125

Gly Ser Thr Thr Leu Gln Arg Ala Ala Asp Asn Ala Tyr Asn Arg Gly
    130                 135                 140

Val Leu Leu Ile Ala Ala Gly Asn Thr Gly Thr Ser Gly Val Ser
145                 150                 155                 160

Phe Pro Ala Arg Tyr Ser Ser Val Met Ala Val Ala Ala Thr Asp Ser
                165                 170                 175

Asn Asn Asn Arg Ala Ser Phe Ser Thr Tyr Gly Ser Gln Ile Glu Ile
            180                 185                 190

Ser Ala Pro Gly Val Gly Ile Asn Ser Thr Tyr Pro Thr Asn Gly Tyr
    195                 200                 205

Ser Ser Leu Asn Gly Thr Ser Met Ala Ser Pro His Val Ala Gly Val
    210                 215                 220

Ala Ala Leu Val Lys Ala Arg Tyr Pro Ser Ala Thr Asn Ala Gln Ile
225                 230                 235                 240

Arg Gln His Leu Arg Ser Thr Ser Thr Tyr Leu Gly Asn Ser Thr Tyr
                245                 250                 255

Tyr Gly Ser Gly Leu Val Asp Ala Gln Arg Ala Thr Asn
                260                 265

<210> SEQ ID NO 4
<211> LENGTH: 1098
<212> TYPE: DNA
<213> ORGANISM: B. akibai
<220> FEATURE:
<221> NAME/KEY: misc_feature
<222> LOCATION: (1)..(1098)
<223> OTHER INFORMATION: nucleotide sequence of BspU02193n, B. akibai
      GICC 2089392

<400> SEQUENCE: 4
atgagtaaaa tgaagtttac tagtttgttg ttagggttgg ttgtggcgtt tgtctttgtc      60
ttctcgactc tgtcagtcag tgcgaatgga aaaggtgctg agcgtcttga ttatttagtt     120
gggtttaaag agaagccgaa tgcacaagtg atggcgcagt ctggtggcga ggtggttcat     180
gagtttgaat atatgaatgt cgttcatatg aaacttccag agcaagcagc aaaagctctt     240
gagaagaacc cgaacattgc gtttgttgag cgtgatgaga aggtcgaagc gactcaaacg     300
gttccttggg gaatcaatca tgtgaaagct ccgactgttc ataactgggg caatgttgga     360
acgggcgtga aggtggcggt gcttgataca ggaatcgcgt ctcacccgga tttacgtgtg     420
tctggtggag cgagcttcat tccatctgag cctacgattc aagatttcaa cggacacgga     480
acgcatgtgg cggggacagt cgctgcgtta aataatagca ttggtgtgct tggtgtcgcg     540
ccgaatgttc aattatatgg tgtaaaggtt ttagatcgta acggtggcgg atctcatagt     600
gcgattgctc aagggattga gtggtcgatt tcaaatggga tggatgttgt gaatatgagt     660
ttaggtggag cgactagttc aacgcgcgtta agccaagcgg tagcgaatgc gagtaaccgc     720
gggattttat taattgcggc gtctggtaac acagggcgcg cgggcattca gttccctgct     780

```
cgttatagcc aagtgatggc tgttggagcg gtcgatcaga acaaccgtct ggcttcattc    840
tcaacatttg aaacgagca agaaattgtg gctcccggtg taggtattca gagcacatac    900
ttaaacaacg gatattcttc attaaacggt acatcaatgg ctgctcctca cgtggcaggt    960
gtcgcggcac ttgtgatgag cgagtaccca tgggcaacag cacctcaagt acgcggacgt   1020
ctaaatgata cagccattcc actaggtaac gcgtattact tcgggaacgg attggtggac   1080
gcttcaagag ccgcgtat                                                 1098
```

<210> SEQ ID NO 5
<211> LENGTH: 366
<212> TYPE: PRT
<213> ORGANISM: B. akibai
<220> FEATURE:
<221> NAME/KEY: misc_feature
<222> LOCATION: (1)..(366)
<223> OTHER INFORMATION: amino acid sequence of the preproenzyme encoded
      by BspU02193n, B. akibai GICC 2089392

<400> SEQUENCE: 5

```
Met Ser Lys Met Lys Phe Thr Ser Leu Leu Gly Leu Val Val Ala
1               5                   10                  15

Phe Val Phe Val Phe Ser Thr Leu Ser Val Ser Ala Asn Gly Lys Gly
                20                  25                  30

Ala Glu Arg Leu Asp Tyr Leu Val Gly Phe Lys Glu Lys Pro Asn Ala
            35                  40                  45

Gln Val Met Ala Gln Ser Gly Gly Glu Val Val His Glu Phe Glu Tyr
        50                  55                  60

Met Asn Val Val His Met Lys Leu Pro Glu Gln Ala Ala Lys Ala Leu
65                  70                  75                  80

Glu Lys Asn Pro Asn Ile Ala Phe Val Glu Arg Asp Glu Lys Val Glu
                85                  90                  95

Ala Thr Gln Thr Val Pro Trp Gly Ile Asn His Val Lys Ala Pro Thr
            100                 105                 110

Val His Asn Trp Gly Asn Val Gly Thr Gly Val Lys Val Ala Val Leu
        115                 120                 125

Asp Thr Gly Ile Ala Ser His Pro Asp Leu Arg Val Ser Gly Gly Ala
    130                 135                 140

Ser Phe Ile Pro Ser Glu Pro Thr Ile Gln Asp Phe Asn Gly His Gly
145                 150                 155                 160

Thr His Val Ala Gly Thr Val Ala Ala Leu Asn Asn Ser Ile Gly Val
                165                 170                 175

Leu Gly Val Ala Pro Asn Val Gln Leu Tyr Gly Val Lys Val Leu Asp
            180                 185                 190

Arg Asn Gly Gly Gly Ser His Ser Ala Ile Ala Gln Gly Ile Glu Trp
        195                 200                 205

Ser Ile Ser Asn Gly Met Asp Val Val Asn Met Ser Leu Gly Gly Ala
    210                 215                 220

Thr Ser Ser Thr Ala Leu Ser Gln Ala Val Ala Asn Ala Ser Asn Arg
225                 230                 235                 240

Gly Ile Leu Leu Ile Ala Ala Ser Gly Asn Thr Gly Arg Ala Gly Ile
                245                 250                 255

Gln Phe Pro Ala Arg Tyr Ser Gln Val Met Ala Val Gly Ala Val Asp
            260                 265                 270

Gln Asn Asn Arg Leu Ala Ser Phe Ser Thr Phe Gly Asn Glu Gln Glu
        275                 280                 285
```

```
Ile Val Ala Pro Gly Val Gly Ile Gln Ser Thr Tyr Leu Asn Asn Gly
    290                 295                 300

Tyr Ser Ser Leu Asn Gly Thr Ser Met Ala Ala Pro His Val Ala Gly
305                 310                 315                 320

Val Ala Ala Leu Val Met Ser Glu Tyr Pro Trp Ala Thr Ala Pro Gln
                325                 330                 335

Val Arg Gly Arg Leu Asn Asp Thr Ala Ile Pro Leu Gly Asn Ala Tyr
            340                 345                 350

Tyr Phe Gly Asn Gly Leu Val Asp Ala Ser Arg Ala Ala Tyr
            355                 360                 365

<210> SEQ ID NO 6
<211> LENGTH: 269
<212> TYPE: PRT
<213> ORGANISM: B. akibai
<220> FEATURE:
<221> NAME/KEY: misc_feature
<222> LOCATION: (1)..(269)
<223> OTHER INFORMATION: amino acid sequence of the fully processed
      mature enzyme, BspU02193 (269 amino acids), B. akibai GICC 2089392

<400> SEQUENCE: 6

Thr Gln Thr Val Pro Trp Gly Ile Asn His Val Lys Ala Pro Thr Val
1               5                   10                  15

His Asn Trp Gly Asn Val Gly Thr Gly Val Lys Val Ala Val Leu Asp
            20                  25                  30

Thr Gly Ile Ala Ser His Pro Asp Leu Arg Val Ser Gly Gly Ala Ser
        35                  40                  45

Phe Ile Pro Ser Glu Pro Thr Ile Gln Asp Phe Asn Gly His Gly Thr
    50                  55                  60

His Val Ala Gly Thr Val Ala Ala Leu Asn Asn Ser Ile Gly Val Leu
65                  70                  75                  80

Gly Val Ala Pro Asn Val Gln Leu Tyr Gly Val Lys Val Leu Asp Arg
                85                  90                  95

Asn Gly Gly Gly Ser His Ser Ala Ile Ala Gln Gly Ile Glu Trp Ser
            100                 105                 110

Ile Ser Asn Gly Met Asp Val Asn Met Ser Leu Gly Gly Ala Thr
        115                 120                 125

Ser Ser Thr Ala Leu Ser Gln Ala Val Ala Asn Ala Ser Asn Arg Gly
    130                 135                 140

Ile Leu Leu Ile Ala Ala Ser Gly Asn Thr Gly Arg Ala Gly Ile Gln
145                 150                 155                 160

Phe Pro Ala Arg Tyr Ser Gln Val Met Ala Val Gly Ala Val Asp Gln
                165                 170                 175

Asn Asn Arg Leu Ala Ser Phe Ser Thr Phe Gly Asn Glu Gln Glu Ile
            180                 185                 190

Val Ala Pro Gly Val Gly Ile Gln Ser Thr Tyr Leu Asn Asn Gly Tyr
        195                 200                 205

Ser Ser Leu Asn Gly Thr Ser Met Ala Ala Pro His Val Ala Gly Val
    210                 215                 220

Ala Ala Leu Val Met Ser Glu Tyr Pro Trp Ala Thr Ala Pro Gln Val
225                 230                 235                 240

Arg Gly Arg Leu Asn Asp Thr Ala Ile Pro Leu Gly Asn Ala Tyr Tyr
                245                 250                 255

Phe Gly Asn Gly Leu Val Asp Ala Ser Arg Ala Ala Tyr
            260                 265
```

<210> SEQ ID NO 7
<211> LENGTH: 93
<212> TYPE: DNA
<213> ORGANISM: Artificial Sequence
<220> FEATURE:
<223> OTHER INFORMATION: Synthetic: terminator sequence

<400> SEQUENCE: 7

```
ggttaccttg aatgtatata aacattctca aagggatttc taataaaaaa cgctcggttg      60
ccgccgggcg ttttttatgc atcgatggaa ttc                                   93
```

<210> SEQ ID NO 8
<211> LENGTH: 21
<212> TYPE: DNA
<213> ORGANISM: Artificial Sequence
<220> FEATURE:
<223> OTHER INFORMATION: Synthetic: linker sequence

<400> SEQUENCE: 8

```
ggatcctgac tgcctgagct t                                                21
```

<210> SEQ ID NO 9
<211> LENGTH: 1119
<212> TYPE: DNA
<213> ORGANISM: B. akibai
<220> FEATURE:
<221> NAME/KEY: misc_feature
<222> LOCATION: (1)..(1119)
<223> OTHER INFORMATION: nucleotide sequence of Serine Protease
      Bakn00315, B. akibai ATCC No. 43226

<400> SEQUENCE: 9

```
atgcgagttt tgaaaggtaa caaactaact ggtttgcttc ttgggtttat tttagtattt      60
tctttcgcgt ttttatcact atcggttagc gctaatggca acgggaatgg caatggcgta     120
gaaagacatg actatttaat agggtttcac gaaaaggtag ataaaaaagc cattactcaa     180
gcaagcggag aagtagttca cgaatatcag tatatgcctg ttcttcatgt gaaacttcca     240
gaaaaagcag caaaagcttt agaaaaaaat cctaatattg cttatgttga aaagacgaa      300 gaggttactg cttcacaaac ggttccttgg ggaattaatc atattcaagc tccaaccgta     360
cattcttggg ggaatcgcgg aaacggtgtt cgtgtcgctg tgttagattc aggggttgct     420
tcccatgaag atttaagaat ttctggtggt agaagtttca ttactagcga gccttcttat     480
caagattata atggccatgg aactcatgta gctggtacca cgctgggt aaataatagt       540 tatgcgtac ttggtgtcgc acctaatgtt aacctttacg cagtaaaagt attagatcgt      600
aatggaagtg atctcacag tgcgattgca caaggaattg aatggtctgt tagcaacggt      660
atgcatattg ttaacatgag cttaggtggg ccaacaggtt caacaacgct tcaacgtgcc     720
gccgataatg cttataatag aggtgttctc cttatcgctg cagctggtaa cacgggttct     780
gccggtattt cctatccagc tagatacaac tctgttatgg cagtaggtgc tgttgactcc     840
aataacaatc gtgcttcatt ttcaactttt ggaaacgaat tagaaattat ggcaccagga     900
gtatccattt taagcacaca cctttcaaat caatatgttt ctttaaacgg tacatcaatg     960
gcaagtccac atgttgctgg tgttgcagct ttggtgaaag ctcaatatcc aagtgcgact    1020
aatgcccaaa tcagacaaag actaagagat actgccacac cacttggtag ttcatattac    1080
tttggaaatg gtttagtgca tgctgctaga gcggcgaat                           1119
```

```
<210> SEQ ID NO 10
<211> LENGTH: 373
<212> TYPE: PRT
<213> ORGANISM: B. akibai
<220> FEATURE:
<221> NAME/KEY: misc_feature
<222> LOCATION: (1)..(373)
<223> OTHER INFORMATION: amino acid sequence of the preproenzyme encoded
      by Bakn00315n, B. akibai ATCC No. 43226

<400> SEQUENCE: 10
```

| | | | | | | | | | | | | | | | |
|---|---|---|---|---|---|---|---|---|---|---|---|---|---|---|---|
| Met | Arg | Val | Leu | Lys | Gly | Asn | Lys | Leu | Thr | Gly | Leu | Leu | Gly | Phe | |
| 1 | | | | 5 | | | | | 10 | | | | | 15 | |
| Ile | Leu | Val | Phe | Ser | Phe | Ala | Phe | Leu | Ser | Leu | Ser | Val | Ser | Ala | Asn |
| | | 20 | | | | | 25 | | | | | 30 | | | |
| Gly | Asn | Gly | Asn | Gly | Asn | Gly | Val | Glu | Arg | His | Asp | Tyr | Leu | Ile | Gly |
| | | 35 | | | | | 40 | | | | | 45 | | | |
| Phe | His | Glu | Lys | Val | Asp | Lys | Lys | Ala | Ile | Thr | Gln | Ala | Ser | Gly | Glu |
| | 50 | | | | | 55 | | | | | 60 | | | | |
| Val | Val | His | Glu | Tyr | Gln | Tyr | Met | Pro | Val | Leu | His | Val | Lys | Leu | Pro |
| 65 | | | | | 70 | | | | | 75 | | | | | 80 |
| Glu | Lys | Ala | Ala | Lys | Ala | Leu | Glu | Lys | Asn | Pro | Asn | Ile | Ala | Tyr | Val |
| | | | | 85 | | | | | 90 | | | | | 95 | |
| Glu | Lys | Asp | Glu | Glu | Val | Thr | Ala | Ser | Gln | Thr | Val | Pro | Trp | Gly | Ile |
| | | | 100 | | | | | 105 | | | | | 110 | | |
| Asn | His | Ile | Gln | Ala | Pro | Thr | Val | His | Ser | Trp | Gly | Asn | Arg | Gly | Asn |
| | | 115 | | | | | 120 | | | | | 125 | | | |
| Gly | Val | Arg | Val | Ala | Val | Leu | Asp | Ser | Gly | Val | Ala | Ser | His | Glu | Asp |
| | 130 | | | | | 135 | | | | | 140 | | | | |
| Leu | Arg | Ile | Ser | Gly | Gly | Arg | Ser | Phe | Ile | Thr | Ser | Glu | Pro | Ser | Tyr |
| 145 | | | | | 150 | | | | | 155 | | | | | 160 |
| Gln | Asp | Tyr | Asn | Gly | His | Gly | Thr | His | Val | Ala | Gly | Thr | Ile | Ala | Gly |
| | | | | 165 | | | | | 170 | | | | | 175 | |
| Leu | Asn | Asn | Ser | Tyr | Gly | Val | Leu | Gly | Val | Ala | Pro | Asn | Val | Asn | Leu |
| | | | 180 | | | | | 185 | | | | | 190 | | |
| Tyr | Ala | Val | Lys | Val | Leu | Asp | Arg | Asn | Gly | Ser | Gly | Ser | His | Ser | Ala |
| | | 195 | | | | | 200 | | | | | 205 | | | |
| Ile | Ala | Gln | Gly | Ile | Glu | Trp | Ser | Val | Ser | Asn | Gly | Met | His | Ile | Val |
| | 210 | | | | | 215 | | | | | 220 | | | | |
| Asn | Met | Ser | Leu | Gly | Gly | Pro | Thr | Gly | Ser | Thr | Thr | Leu | Gln | Arg | Ala |
| 225 | | | | | 230 | | | | | 235 | | | | | 240 |
| Ala | Asp | Asn | Ala | Tyr | Asn | Arg | Gly | Val | Leu | Leu | Ile | Ala | Ala | Ala | Gly |
| | | | | 245 | | | | | 250 | | | | | 255 | |
| Asn | Thr | Gly | Ser | Ala | Gly | Ile | Ser | Tyr | Pro | Ala | Arg | Tyr | Asn | Ser | Val |
| | | | 260 | | | | | 265 | | | | | 270 | | |
| Met | Ala | Val | Gly | Ala | Val | Asp | Ser | Asn | Asn | Asn | Arg | Ala | Ser | Phe | Ser |
| | | 275 | | | | | 280 | | | | | 285 | | | |
| Thr | Phe | Gly | Asn | Glu | Leu | Glu | Ile | Met | Ala | Pro | Gly | Val | Ser | Ile | Leu |
| | 290 | | | | | 295 | | | | | 300 | | | | |
| Ser | Thr | His | Leu | Ser | Asn | Gln | Tyr | Val | Ser | Leu | Asn | Gly | Thr | Ser | Met |
| 305 | | | | | 310 | | | | | 315 | | | | | 320 |
| Ala | Ser | Pro | His | Val | Ala | Gly | Val | Ala | Ala | Leu | Val | Lys | Ala | Gln | Tyr |
| | | | | 325 | | | | | 330 | | | | | 335 | |
| Pro | Ser | Ala | Thr | Asn | Ala | Gln | Ile | Arg | Gln | Arg | Leu | Arg | Asp | Thr | Ala |
| | | | 340 | | | | | 345 | | | | | 350 | | |
| Thr | Pro | Leu | Gly | Ser | Ser | Tyr | Tyr | Phe | Gly | Asn | Gly | Leu | Val | His | Ala |

Ala Arg Ala Ala Asn
370

<210> SEQ ID NO 11
<211> LENGTH: 269
<212> TYPE: PRT
<213> ORGANISM: B. akibai
<220> FEATURE:
<221> NAME/KEY: misc_feature
<222> LOCATION: (1)..(269)
<223> OTHER INFORMATION: amino acid sequence of the fully processed mature enzyme, Bakn00315 (269 amino acids), B. akibai ATCC No. 43226

<400> SEQUENCE: 11

Ser Gln Thr Val Pro Trp Gly Ile Asn His Ile Gln Ala Pro Thr Val
1               5                   10                  15

His Ser Trp Gly Asn Arg Gly Asn Gly Val Arg Val Ala Val Leu Asp
            20                  25                  30

Ser Gly Val Ala Ser His Glu Asp Leu Arg Ile Ser Gly Gly Arg Ser
        35                  40                  45

Phe Ile Thr Ser Glu Pro Ser Tyr Gln Asp Tyr Asn Gly His Gly Thr
    50                  55                  60

His Val Ala Gly Thr Ile Ala Gly Leu Asn Asn Ser Tyr Gly Val Leu
65                  70                  75                  80

Gly Val Ala Pro Asn Val Asn Leu Tyr Ala Val Lys Val Leu Asp Arg
                85                  90                  95

Asn Gly Ser Gly Ser His Ser Ala Ile Ala Gln Gly Ile Glu Trp Ser
            100                 105                 110

Val Ser Asn Gly Met His Ile Val Asn Met Ser Leu Gly Gly Pro Thr
        115                 120                 125

Gly Ser Thr Thr Leu Gln Arg Ala Ala Asp Asn Ala Tyr Asn Arg Gly
    130                 135                 140

Val Leu Leu Ile Ala Ala Ala Gly Asn Thr Gly Ser Ala Gly Ile Ser
145                 150                 155                 160

Tyr Pro Ala Arg Tyr Asn Ser Val Met Ala Val Gly Ala Val Asp Ser
                165                 170                 175

Asn Asn Asn Arg Ala Ser Phe Ser Thr Phe Gly Asn Glu Leu Glu Ile
            180                 185                 190

Met Ala Pro Gly Val Ser Ile Leu Ser Thr His Leu Ser Asn Gln Tyr
        195                 200                 205

Val Ser Leu Asn Gly Thr Ser Met Ala Ser Pro His Val Ala Gly Val
    210                 215                 220

Ala Ala Leu Val Lys Ala Gln Tyr Pro Ser Ala Thr Asn Ala Gln Ile
225                 230                 235                 240

Arg Gln Arg Leu Arg Asp Thr Ala Thr Pro Leu Gly Ser Ser Tyr Tyr
                245                 250                 255

Phe Gly Asn Gly Leu Val His Ala Arg Ala Ala Asn
            260                 265

<210> SEQ ID NO 12
<211> LENGTH: 1092
<212> TYPE: DNA
<213> ORGANISM: B. clarkii
<220> FEATURE:
<221> NAME/KEY: misc_feature
<222> LOCATION: (1)..(1092)
<223> OTHER INFORMATION: nucleotide sequence of serine protease Bcl04009n, B. clarkii strain DSM 8720

<400> SEQUENCE: 12

```
atgaagaata tgaggttcat agggtttatt gttgggtttt tactagcttt cacattcact    60
ttttcagcgg tgagtgcaga tagcaaaggt gtcgaaaagt ttgattactt aattggtttt   120
aaagacaaag ttaatgagaa cacagttacc cagcttggcg gcgatgtcca gcatgaatac   180
gagtatatgg aggttctcca tgtaaccttg ccggaaaaag ctgcggcagc actgaaaaag   240
aatccgaaca ttgcctttgt ggaaaaagac gaagaagtaa cggccagcca gaccattcct   300
tggggcataa accgtgttca ggcaccaacc gtccattcct ggggagcccg cggtaacgga   360
gtaagagttg ctgttcttga tactggtatt gcaagccacg aagatttaag aatttctgga   420
ggagccagtt ttatcagctc ggaaccttcc tacaacgacc ttaatggcca tgaacgcat    480
gtggctggaa caatagctgc ccgggataac agttatggag ttcttggggt ggcgccaaac   540
gttgatcttt acgctgttaa agttcttgac agaaacggca gcggttcact tagcggtatt   600
gcccgtggta ttgagtgggc tattacaaat aatatggata tagtcaatat gagtttaggt   660
ggttcgactg gatctactgc attaagacaa gctgctgata atgcttataa cagaggcatt   720
ttacttgtgg cagctgctgg taatacaggc tctgcaggga tttccttccc agctcggtat   780
aattctgtta tggcagtagg tgctacagac tctaacaaca accgcgcgtc tttttcaaca   840
tttggaaatg aactggagat aatggctcca ggtgtatctg tattaagtac ttaccctact   900
aacagatatg tttcacttaa tggaacgtca atggcaagcc ctcacgtcgc tggtgtcgca   960
gcattagtaa aatcacgcta tccaaacgcc accaatgtcc aaataagaaa cagactgaac  1020
agtacagcca ctaatctggg aagctcttac tatttcggta atggtctcgt taacgctgca  1080
agagctgcga at                                                      1092
```

<210> SEQ ID NO 13
<211> LENGTH: 364
<212> TYPE: PRT
<213> ORGANISM: B. clarkii
<220> FEATURE:
<221> NAME/KEY: misc_feature
<222> LOCATION: (1)..(364)
<223> OTHER INFORMATION: amino acid sequence of the preproenzyme encoded
      by Bcl04009, B. clarkii strain DSM 8720

<400> SEQUENCE: 13

```
Met Lys Asn Met Arg Phe Ile Gly Phe Ile Val Gly Phe Leu Leu Ala
1               5                   10                  15

Phe Thr Phe Thr Phe Ser Ala Val Ser Ala Asp Ser Lys Gly Val Glu
            20                  25                  30

Lys Phe Asp Tyr Leu Ile Gly Phe Lys Asp Lys Val Asn Glu Asn Thr
        35                  40                  45

Val Thr Gln Leu Gly Gly Asp Val Gln His Glu Tyr Glu Tyr Met Glu
    50                  55                  60

Val Leu His Val Thr Leu Pro Glu Lys Ala Ala Ala Leu Lys Lys
65                  70                  75                  80

Asn Pro Asn Ile Ala Phe Val Glu Lys Asp Glu Glu Val Thr Ala Ser
                85                  90                  95

Gln Thr Ile Pro Trp Gly Ile Asn Arg Val Gln Ala Pro Thr Val His
            100                 105                 110

Ser Trp Gly Ala Arg Gly Asn Gly Val Arg Val Ala Val Leu Asp Thr
        115                 120                 125
```

Gly Ile Ala Ser His Glu Asp Leu Arg Ile Ser Gly Ala Ser Phe
            130                 135                 140

Ile Ser Ser Glu Pro Ser Tyr Asn Asp Leu Asn Gly His Gly Thr His
145                 150                 155                 160

Val Ala Gly Thr Ile Ala Ala Arg Asp Asn Ser Tyr Gly Val Leu Gly
                165                 170                 175

Val Ala Pro Asn Val Asp Leu Tyr Ala Val Lys Val Leu Asp Arg Asn
            180                 185                 190

Gly Ser Gly Ser Leu Ser Gly Ile Ala Arg Gly Ile Glu Trp Ala Ile
        195                 200                 205

Thr Asn Asn Met Asp Ile Val Asn Met Ser Leu Gly Gly Ser Thr Gly
210                 215                 220

Ser Thr Ala Leu Arg Gln Ala Ala Asp Asn Ala Tyr Asn Arg Gly Ile
225                 230                 235                 240

Leu Leu Val Ala Ala Ala Gly Asn Thr Gly Ser Ala Gly Ile Ser Phe
                245                 250                 255

Pro Ala Arg Tyr Asn Ser Val Met Ala Val Gly Ala Thr Asp Ser Asn
            260                 265                 270

Asn Asn Arg Ala Ser Phe Ser Thr Phe Gly Asn Glu Leu Glu Ile Met
        275                 280                 285

Ala Pro Gly Val Ser Val Leu Ser Thr Tyr Pro Thr Asn Arg Tyr Val
290                 295                 300

Ser Leu Asn Gly Thr Ser Met Ala Ser Pro His Val Ala Gly Val Ala
305                 310                 315                 320

Ala Leu Val Lys Ser Arg Tyr Pro Asn Ala Thr Asn Val Gln Ile Arg
                325                 330                 335

Asn Arg Leu Asn Ser Thr Ala Thr Asn Leu Gly Ser Ser Tyr Tyr Phe
            340                 345                 350

Gly Asn Gly Leu Val Asn Ala Ala Arg Ala Ala Asn
        355                 360

<210> SEQ ID NO 14
<211> LENGTH: 269
<212> TYPE: PRT
<213> ORGANISM: B. clarkii
<220> FEATURE:
<221> NAME/KEY: misc_feature
<222> LOCATION: (1)..(269)
<223> OTHER INFORMATION: amino acid sequence of the fully processed
      mature enzyme, Bcl04009 (269 amino acids), B. clarkii strain DSM
      8720

<400> SEQUENCE: 14

Ser Gln Thr Ile Pro Trp Gly Ile Asn Arg Val Gln Ala Pro Thr Val
1               5                   10                  15

His Ser Trp Gly Ala Arg Gly Asn Gly Val Arg Val Ala Val Leu Asp
                20                  25                  30

Thr Gly Ile Ala Ser His Glu Asp Leu Arg Ile Ser Gly Gly Ala Ser
            35                  40                  45

Phe Ile Ser Ser Glu Pro Ser Tyr Asn Asp Leu Asn Gly His Gly Thr
        50                  55                  60

His Val Ala Gly Thr Ile Ala Ala Arg Asp Asn Ser Tyr Gly Val Leu
65                  70                  75                  80

Gly Val Ala Pro Asn Val Asp Leu Tyr Ala Val Lys Val Leu Asp Arg
                85                  90                  95

Asn Gly Ser Gly Ser Leu Ser Gly Ile Ala Arg Gly Ile Glu Trp Ala
            100                 105                 110

Ile Thr Asn Asn Met Asp Ile Val Asn Met Ser Leu Gly Gly Ser Thr
            115                 120                 125

Gly Ser Thr Ala Leu Arg Gln Ala Ala Asp Asn Ala Tyr Asn Arg Gly
        130                 135                 140

Ile Leu Leu Val Ala Ala Gly Asn Thr Gly Ser Ala Gly Ile Ser
145                 150                 155                 160

Phe Pro Ala Arg Tyr Asn Ser Val Met Ala Val Gly Ala Thr Asp Ser
                165                 170                 175

Asn Asn Asn Arg Ala Ser Phe Ser Thr Phe Gly Asn Glu Leu Glu Ile
            180                 185                 190

Met Ala Pro Gly Val Ser Val Leu Ser Thr Tyr Pro Thr Asn Arg Tyr
        195                 200                 205

Val Ser Leu Asn Gly Thr Ser Met Ala Ser Pro His Val Ala Gly Val
    210                 215                 220

Ala Ala Leu Val Lys Ser Arg Tyr Pro Asn Ala Thr Asn Val Gln Ile
225                 230                 235                 240

Arg Asn Arg Leu Asn Ser Thr Ala Thr Asn Leu Gly Ser Ser Tyr Tyr
                245                 250                 255

Phe Gly Asn Gly Leu Val Asn Ala Ala Arg Ala Ala Asn
            260                 265

<210> SEQ ID NO 15
<211> LENGTH: 1092
<212> TYPE: DNA
<213> ORGANISM: B. clarkii
<220> FEATURE:
<221> NAME/KEY: misc_feature
<222> LOCATION: (1)..(1092)
<223> OTHER INFORMATION: nucleotide sequence of serine protease
      SWT66_254731n, B. clarkii strain SWT66_254731

<400> SEQUENCE: 15

```
atgaagaata tgaggtttat agggtttatt gtagtgtttt tactagcttt cacattcact      60
ttttcagcgg tgagtgcaga tagcaaaggc gtggaaaagt ttgattactt aattggtttt     120
aaagacaaag ttaatgagaa cgcagttacc cagcttggcg gcgatgtcca gcatgaatac     180
gagtacatgg aggttctcca tgtaaccttg ccggaaaaag ctgcggcagc actgaaaaag     240
aatccgaaca ttgcttttgt ggaaaaagac gaagaagtaa cggccagcca gaccgttccc     300
tggggcatta ccgtgttca ggcaccaacc gtccattcct ggggagcccg cggtaacgga     360
gtaagagttg ctgttcttga tactggaatt gcaagccacg aagatttaag gatttccgga     420
ggagccagtt ttatcagctc ggaaccttcc tacaacgacc ttaatggcca tggaacgcat     480
gtggctggaa caatagctgc ccgggataac agttatggag ttcttggtgt ggcgccaaac     540
gttaatcttt atgcagttaa agttcttgac agaaacggca gcggttcact tagcggcatt     600
gcccggggta ttgagtgggc tattacaaat aatatggata tagtcaatat gagtttaggt     660
ggttcaaccg gatccactgc attaagacaa gctgctgata cgcgtataa caggggaatt     720 ttacttgttg ctgccgctgg taatacaggc tctgcaggaa tctccttccc ggctcggtat     780
aattcagtta tggcagtagg ggctacagac tctaacaaca accgcgcgtc ttttcaaca     840 tttggaaatg aactggagat aatggctcca ggtgtatctg tattaagtac ttacccaact     900
aacagatatg tttcacttaa tgggacatca atggcaagcc ctcacgtcgc tggtgtcgca     960
gcattagtaa aatcacgcta tccacacgca accaatgtcc aaataagaaa cagactgaac    1020
agtacagcca ccaatctggg aagctcttac tatttcggaa atggactcgt taacgctgcg    1080
```

-continued agagcggcga at     1092

<210> SEQ ID NO 16
<211> LENGTH: 364
<212> TYPE: PRT
<213> ORGANISM: B. clarkii
<220> FEATURE:
<221> NAME/KEY: misc_feature
<222> LOCATION: (1)..(364)
<223> OTHER INFORMATION: amino acid sequence of the preproenzyme encoded
      by SWT66_254731n, B. clarkii strain SWT66_254731

<400> SEQUENCE: 16

```
Met Lys Asn Met Arg Phe Ile Gly Phe Ile Val Val Phe Leu Leu Ala
1               5                   10                  15

Phe Thr Phe Thr Phe Ser Ala Val Ser Ala Asp Ser Lys Gly Val Glu
            20                  25                  30

Lys Phe Asp Tyr Leu Ile Gly Phe Lys Asp Lys Val Asn Glu Asn Ala
        35                  40                  45

Val Thr Gln Leu Gly Gly Asp Val Gln His Glu Tyr Glu Tyr Met Glu
    50                  55                  60

Val Leu His Val Thr Leu Pro Glu Lys Ala Ala Ala Leu Lys Lys
65                  70                  75                  80

Asn Pro Asn Ile Ala Phe Val Glu Lys Asp Glu Glu Val Thr Ala Ser
                85                  90                  95

Gln Thr Val Pro Trp Gly Ile Asn Arg Val Gln Ala Pro Thr Val His
            100                 105                 110

Ser Trp Gly Ala Arg Gly Asn Gly Val Arg Val Ala Val Leu Asp Thr
        115                 120                 125

Gly Ile Ala Ser His Glu Asp Leu Arg Ile Ser Gly Gly Ala Ser Phe
    130                 135                 140

Ile Ser Ser Glu Pro Ser Tyr Asn Asp Leu Asn Gly His Gly Thr His
145                 150                 155                 160

Val Ala Gly Thr Ile Ala Ala Arg Asp Asn Ser Tyr Gly Val Leu Gly
                165                 170                 175

Val Ala Pro Asn Val Asn Leu Tyr Ala Val Lys Val Leu Asp Arg Asn
            180                 185                 190

Gly Ser Gly Ser Leu Ser Gly Ile Ala Arg Gly Ile Glu Trp Ala Ile
        195                 200                 205

Thr Asn Asn Met Asp Ile Val Asn Met Ser Leu Gly Gly Ser Thr Gly
    210                 215                 220

Ser Thr Ala Leu Arg Gln Ala Ala Asp Asn Ala Tyr Asn Arg Gly Ile
225                 230                 235                 240

Leu Leu Val Ala Ala Gly Asn Thr Gly Ser Ala Gly Ile Ser Phe
                245                 250                 255

Pro Ala Arg Tyr Asn Ser Val Met Ala Val Gly Ala Thr Asp Ser Asn
            260                 265                 270

Asn Asn Arg Ala Ser Phe Ser Thr Phe Gly Asn Glu Leu Glu Ile Met
        275                 280                 285

Ala Pro Gly Val Ser Val Leu Ser Thr Tyr Pro Thr Asn Arg Tyr Val
    290                 295                 300

Ser Leu Asn Gly Thr Ser Met Ala Ser Pro His Val Ala Gly Val Ala
305                 310                 315                 320

Ala Leu Val Lys Ser Arg Tyr Pro His Ala Thr Asn Val Gln Ile Arg
                325                 330                 335
```

-continued

```
Asn Arg Leu Asn Ser Thr Ala Thr Asn Leu Gly Ser Ser Tyr Tyr Phe
            340                 345                 350

Gly Asn Gly Leu Val Asn Ala Ala Arg Ala Ala Asn
            355                 360

<210> SEQ ID NO 17
<211> LENGTH: 269
<212> TYPE: PRT
<213> ORGANISM: B. clarkii
<220> FEATURE:
<221> NAME/KEY: misc_feature
<222> LOCATION: (1)..(269)
<223> OTHER INFORMATION: amino acid sequence of the fully processed
      mature enzyme, SWT66_254731, B. clarkii strain SWT66_254731

<400> SEQUENCE: 17

Ser Gln Thr Val Pro Trp Gly Ile Asn Arg Val Gln Ala Pro Thr Val
1               5                   10                  15

His Ser Trp Gly Ala Arg Gly Asn Gly Val Arg Val Ala Val Leu Asp
            20                  25                  30

Thr Gly Ile Ala Ser His Glu Asp Leu Arg Ile Ser Gly Gly Ala Ser
        35                  40                  45

Phe Ile Ser Ser Glu Pro Ser Tyr Asn Asp Leu Asn Gly His Gly Thr
    50                  55                  60

His Val Ala Gly Thr Ile Ala Ala Arg Asp Asn Ser Tyr Gly Val Leu
65                  70                  75                  80

Gly Val Ala Pro Asn Val Asn Leu Tyr Ala Val Lys Val Leu Asp Arg
                85                  90                  95

Asn Gly Ser Gly Ser Leu Ser Gly Ile Ala Arg Gly Ile Glu Trp Ala
            100                 105                 110

Ile Thr Asn Asn Met Asp Ile Val Asn Met Ser Leu Gly Gly Ser Thr
        115                 120                 125

Gly Ser Thr Ala Leu Arg Gln Ala Ala Asp Asn Ala Tyr Asn Arg Gly
    130                 135                 140

Ile Leu Leu Val Ala Ala Ala Gly Asn Thr Gly Ser Ala Gly Ile Ser
145                 150                 155                 160

Phe Pro Ala Arg Tyr Asn Ser Val Met Ala Val Gly Ala Thr Asp Ser
                165                 170                 175

Asn Asn Asn Arg Ala Ser Phe Ser Thr Phe Gly Asn Glu Leu Glu Ile
            180                 185                 190

Met Ala Pro Gly Val Ser Val Leu Ser Thr Tyr Pro Thr Asn Arg Tyr
        195                 200                 205

Val Ser Leu Asn Gly Thr Ser Met Ala Ser Pro His Val Ala Gly Val
    210                 215                 220

Ala Ala Leu Val Lys Ser Arg Tyr Pro His Ala Thr Asn Val Gln Ile
225                 230                 235                 240

Arg Asn Arg Leu Asn Ser Thr Ala Thr Asn Leu Gly Ser Ser Tyr Tyr
                245                 250                 255

Phe Gly Asn Gly Leu Val Asn Ala Ala Arg Ala Ala Asn
            260                 265

<210> SEQ ID NO 18
<211> LENGTH: 1101
<212> TYPE: DNA
<213> ORGANISM: B. akibai
<220> FEATURE:
<221> NAME/KEY: misc_feature
<222> LOCATION: (1)..(1101)
<223> OTHER INFORMATION: nucleotide sequence of serine protease
```

ACB102_2847966.n

<400> SEQUENCE: 18

```
atgaaaatga aatggtcacg tttaattta accctagttc tcgtattgag ttttgtattc      60
ccatctatga caagtgcaaa ctccgctgta gaaaaagagg attatctgat cggttttaag    120
cagaaaggga atgttagtgc acaagttgtg aatatgagtg gaggagaagt cgtacatgaa    180
tatgaacata tgccagtctt gcacgttaaa ttacctccac aagctgctaa agcgttagaa    240
aagaacccaa atattgaata catcgaaaaa gatgaaaaag tccaagctac agcacaatcg    300
acaccttggg ggatttcacg tattaatgct cctgctgttc actcgactgg taattttgga    360
caaggtgtcc gagttgccgt tttagatagt ggagttgctt tcatgaaga cttacggatt    420
gctgggggag tgagctttgt cgcttcagaa cctagttatc aagattataa tggtcacgga    480
acacatgttg ctggaaccat tgctggttta ataatagtg ttggggtcct tggtgtagct    540
ccatctgtcc aattatatgc ggttaaggtg ttggatcgta atggcggggg gaatcatagt    600
gacattgcta gaggaattga gtggtcagtt aataatggaa tgcatgtggt gaatatgagt    660
ttaggtggac caacagggtc aacgactctt caacgagcag cggataatgc ttataacaga    720
ggagttcttt taattgccgc agctggtaac acgggaacta gtggggttag cttccctgcg    780
cgttatagct ctgtaatggc agtagccgca acagactcta ataataaccg tgcttcattt    840
tcaacttatg gtccagaaat tgaaatttca gcacctggga ttggcattaa tagcacgtat    900
ccaacgaatc gttattcaag cttaaatgga acatcaatgg cttcacctca tgtcgctggt    960
gtagcagctc ttgtgaaggc gagatatcca agtgcgacga atgctcagat tagacaacat   1020
cttcgtagca cttctacgta tctaggaaac tcaacttact atggtagtgg tttagttgat   1080
gcacagcgtg cagctaacta a                                             1101
```

<210> SEQ ID NO 19
<211> LENGTH: 366
<212> TYPE: PRT
<213> ORGANISM: B. akibai
<220> FEATURE:
<221> NAME/KEY: misc_feature
<222> LOCATION: (1)..(366)
<223> OTHER INFORMATION: amino acid sequence of the preproenzyme encoded by ACB102_2847966.n

<400> SEQUENCE: 19

```
Met Lys Met Lys Trp Ser Arg Leu Ile Leu Thr Leu Val Leu Val Leu
1               5                   10                  15

Ser Phe Val Phe Pro Ser Met Thr Ser Ala Asn Ser Ala Val Glu Lys
            20                  25                  30

Glu Asp Tyr Leu Ile Gly Phe Lys Gln Lys Gly Asn Val Ser Ala Gln
        35                  40                  45

Val Val Asn Met Ser Gly Gly Glu Val Val His Glu Tyr Glu His Met
    50                  55                  60

Pro Val Leu His Val Lys Leu Pro Pro Gln Ala Ala Lys Ala Leu Glu
65                  70                  75                  80

Lys Asn Pro Asn Ile Glu Tyr Ile Glu Lys Asp Glu Lys Val Gln Ala
                85                  90                  95

Thr Ala Gln Ser Thr Pro Trp Gly Ile Ser Arg Ile Asn Ala Pro Ala
            100                 105                 110

Val His Ser Thr Gly Asn Phe Gly Gln Gly Val Arg Val Ala Val Leu
        115                 120                 125
```

Asp Ser Gly Val Ala Ser His Glu Asp Leu Arg Ile Ala Gly Gly Val
        130                 135                 140

Ser Phe Val Ala Ser Glu Pro Ser Tyr Gln Asp Tyr Asn Gly His Gly
145                 150                 155                 160

Thr His Val Ala Gly Thr Ile Ala Gly Leu Asn Asn Ser Val Gly Val
                165                 170                 175

Leu Gly Val Ala Pro Ser Val Gln Leu Tyr Ala Val Lys Val Leu Asp
            180                 185                 190

Arg Asn Gly Gly Asn His Ser Asp Ile Ala Arg Gly Ile Glu Trp
        195                 200                 205

Ser Val Asn Asn Gly Met His Val Val Asn Met Ser Leu Gly Gly Pro
210                 215                 220

Thr Gly Ser Thr Thr Leu Gln Arg Ala Ala Asp Asn Ala Tyr Asn Arg
225                 230                 235                 240

Gly Val Leu Leu Ile Ala Ala Gly Asn Thr Gly Thr Ser Gly Val
                245                 250                 255

Ser Phe Pro Ala Arg Tyr Ser Ser Val Met Ala Val Ala Ala Thr Asp
            260                 265                 270

Ser Asn Asn Asn Arg Ala Ser Phe Ser Thr Tyr Gly Pro Glu Ile Glu
        275                 280                 285

Ile Ser Ala Pro Gly Val Gly Ile Asn Ser Thr Tyr Pro Thr Asn Arg
290                 295                 300

Tyr Ser Ser Leu Asn Gly Thr Ser Met Ala Ser Pro His Val Ala Gly
305                 310                 315                 320

Val Ala Ala Leu Val Lys Ala Arg Tyr Pro Ser Ala Thr Asn Ala Gln
                325                 330                 335

Ile Arg Gln His Leu Arg Ser Thr Ser Thr Tyr Leu Gly Asn Ser Thr
            340                 345                 350

Tyr Tyr Gly Ser Gly Leu Val Asp Ala Gln Arg Ala Ala Asn
        355                 360                 365

<210> SEQ ID NO 20
<211> LENGTH: 269
<212> TYPE: PRT
<213> ORGANISM: B. akibai
<220> FEATURE:
<221> NAME/KEY: misc_feature
<222> LOCATION: (1)..(269)
<223> OTHER INFORMATION: amino acid sequence of the fully processed
      mature enzyme, ACB102, (269 amino acids)

<400> SEQUENCE: 20

Ala Gln Ser Thr Pro Trp Gly Ile Ser Arg Ile Asn Ala Pro Ala Val
1               5                   10                  15

His Ser Thr Gly Asn Phe Gly Gln Gly Val Arg Val Ala Val Leu Asp
            20                  25                  30

Ser Gly Val Ala Ser His Glu Asp Leu Arg Ile Ala Gly Gly Val Ser
        35                  40                  45

Phe Val Ala Ser Glu Pro Ser Tyr Gln Asp Tyr Asn Gly His Gly Thr
    50                  55                  60

His Val Ala Gly Thr Ile Ala Gly Leu Asn Asn Ser Val Gly Val Leu
65                  70                  75                  80

Gly Val Ala Pro Ser Val Gln Leu Tyr Ala Val Lys Val Leu Asp Arg
                85                  90                  95

Asn Gly Gly Gly Asn His Ser Asp Ile Ala Arg Gly Ile Glu Trp Ser
            100                 105                 110

Val Asn Asn Gly Met His Val Val Asn Met Ser Leu Gly Gly Pro Thr
            115                 120                 125

Gly Ser Thr Thr Leu Gln Arg Ala Ala Asp Asn Ala Tyr Asn Arg Gly
130                 135                 140

Val Leu Leu Ile Ala Ala Gly Asn Thr Gly Thr Ser Gly Val Ser
145                 150                 155                 160

Phe Pro Ala Arg Tyr Ser Ser Val Met Ala Val Ala Thr Asp Ser
                165                 170                 175

Asn Asn Asn Arg Ala Ser Phe Ser Thr Tyr Gly Pro Glu Ile Glu Ile
            180                 185                 190

Ser Ala Pro Gly Val Gly Ile Asn Ser Thr Tyr Pro Thr Asn Arg Tyr
            195                 200                 205

Ser Ser Leu Asn Gly Thr Ser Met Ala Ser Pro His Val Ala Gly Val
            210                 215                 220

Ala Ala Leu Val Lys Ala Arg Tyr Pro Ser Ala Thr Asn Ala Gln Ile
225                 230                 235                 240

Arg Gln His Leu Arg Ser Thr Ser Thr Tyr Leu Gly Asn Ser Thr Tyr
                245                 250                 255

Tyr Gly Ser Gly Leu Val Asp Ala Gln Arg Ala Ala Asn
            260                 265

<210> SEQ ID NO 21
<211> LENGTH: 1101
<212> TYPE: DNA
<213> ORGANISM: B. akibai
<220> FEATURE:
<221> NAME/KEY: misc_feature
<222> LOCATION: (1)..(1101)
<223> OTHER INFORMATION: nucleotide sequence of serine protease
      COG104_4065768.n

<400> SEQUENCE: 21
atgaaaatga aatggtcacg tttaatttta accctggttc tcgtattcag ttttgtattc     60
ccatctatga caagtgcaaa ctccgctgta gaaaagagg actatctgat cggttttaaa    120
cagaaaggga atgttagtgc acaagttgtg aatatgagtg gaggagaagt cgtccatgaa    180
tatgaacata tgccagtctt gcacgttaaa ttaccttcac aagctgctaa agcgttagaa    240
aagaacccca atattgaata cattgaaaaa gatgaaaaag tccaagcaac agcacaatcg    300
acaccttggg gaatttcacg tattaatgct cctgctgttc actcgactgg taattttgga    360
caaggtgtcc gagttgcggt tttagatagt ggagttgctt ctcatgaaga cttacggatt    420
gctgggggag tgagctttgt cgcttcagaa cctagttatc aagattataa tggtcacgga    480
acacatgttg ctggaaccat tgctggttta aataatagtg ttggggtcct tggtgtagct    540
ccatctgtcc aattatatgc ggttaaggtg ttggatcgta atggcggggg aaatcatagt    600
gacattgcta gaggaattga gtggtcagtt aataatggaa tgcatgtggt gaatatgagt    660
ttaggtggac caacagggtc aactactctt caacgagcag cggataatgc ttataacaga    720
ggagttcttt taattgccgc agctgggaac acgggaacta gtggagttag cttccctgcg    780
cgttacagct cagtaatggc agtagccgca acagattcta ataataaccg tgcttcattt    840
tcaacttatg gaacacaaat tgaaatttca gcacctggag ttggcattaa tagcacgtat    900
ccaacgaatc gttattcaag tttaaatgga acatcaatgg cttcacctca tgtagctggt    960
gtagcggccc tagtgaaggc gagatatcca agtgcgacga atgctcagat tagacaacat   1020
cttcgtagca cttctacgta tctaggaaac tcaacttact atggtagtgg tctagttgat   1080
gcacaacgtg cagctaacta a                                                  1101

<210> SEQ ID NO 22
<211> LENGTH: 366
<212> TYPE: PRT
<213> ORGANISM: B. akibai
<220> FEATURE:
<221> NAME/KEY: misc_feature
<222> LOCATION: (1)..(366)
<223> OTHER INFORMATION: amino acid sequence of the preproenzyme
      encoded by COG104_4065768.n

<400> SEQUENCE: 22

Met Lys Met Lys Trp Ser Arg Leu Ile Leu Thr Leu Val Leu Val Phe
1               5                   10                  15

Ser Phe Val Phe Pro Ser Met Thr Ser Ala Asn Ser Ala Val Glu Lys
            20                  25                  30

Glu Asp Tyr Leu Ile Gly Phe Lys Gln Lys Gly Asn Val Ser Ala Gln
        35                  40                  45

Val Val Asn Met Ser Gly Gly Glu Val Val His Glu Tyr Glu His Met
    50                  55                  60

Pro Val Leu His Val Lys Leu Pro Ser Gln Ala Ala Lys Ala Leu Glu
65                  70                  75                  80

Lys Asn Pro Asn Ile Glu Tyr Ile Glu Lys Asp Glu Lys Val Gln Ala
                85                  90                  95

Thr Ala Gln Ser Thr Pro Trp Gly Ile Ser Arg Ile Asn Ala Pro Ala
            100                 105                 110

Val His Ser Thr Gly Asn Phe Gly Gln Gly Val Arg Val Ala Val Leu
        115                 120                 125

Asp Ser Gly Val Ala Ser His Glu Asp Leu Arg Ile Ala Gly Gly Val
    130                 135                 140

Ser Phe Val Ala Ser Glu Pro Ser Tyr Gln Asp Tyr Asn Gly His Gly
145                 150                 155                 160

Thr His Val Ala Gly Thr Ile Ala Gly Leu Asn Asn Ser Val Gly Val
                165                 170                 175

Leu Gly Val Ala Pro Ser Val Gln Leu Tyr Ala Val Lys Val Leu Asp
            180                 185                 190

Arg Asn Gly Gly Gly Asn His Ser Asp Ile Ala Arg Gly Ile Glu Trp
        195                 200                 205

Ser Val Asn Asn Gly Met His Val Val Asn Met Ser Leu Gly Gly Pro
    210                 215                 220

Thr Gly Ser Thr Thr Leu Gln Arg Ala Ala Asp Asn Ala Tyr Asn Arg
225                 230                 235                 240

Gly Val Leu Leu Ile Ala Ala Ala Gly Asn Thr Gly Thr Ser Gly Val
                245                 250                 255

Ser Phe Pro Ala Arg Tyr Ser Ser Val Met Ala Val Ala Ala Thr Asp
            260                 265                 270

Ser Asn Asn Asn Arg Ala Ser Phe Ser Thr Tyr Gly Thr Gln Ile Glu
        275                 280                 285

Ile Ser Ala Pro Gly Val Gly Ile Asn Ser Thr Tyr Pro Thr Asn Arg
    290                 295                 300

Tyr Ser Ser Leu Asn Gly Thr Ser Met Ala Ser Pro His Val Ala Gly
305                 310                 315                 320

Val Ala Ala Leu Val Lys Ala Arg Tyr Pro Ser Ala Thr Asn Ala Gln
                325                 330                 335

Ile Arg Gln His Leu Arg Ser Thr Ser Thr Tyr Leu Gly Asn Ser Thr

```
                    340                 345                 350
Tyr Tyr Gly Ser Gly Leu Val Asp Ala Gln Arg Ala Ala Asn
        355                 360                 365

<210> SEQ ID NO 23
<211> LENGTH: 269
<212> TYPE: PRT
<213> ORGANISM: B. akibai
<220> FEATURE:
<221> NAME/KEY: misc_feature
<222> LOCATION: (1)..(269)
<223> OTHER INFORMATION: amino acid sequence of the fully processed
      mature enzyme, COG104, (269 amino acids)

<400> SEQUENCE: 23

Ala Gln Ser Thr Pro Trp Gly Ile Ser Arg Ile Asn Ala Pro Ala Val
1               5                   10                  15

His Ser Thr Gly Asn Phe Gly Gln Gly Val Arg Val Ala Val Leu Asp
                20                  25                  30

Ser Gly Val Ala Ser His Glu Asp Leu Arg Ile Ala Gly Gly Val Ser
            35                  40                  45

Phe Val Ala Ser Glu Pro Ser Tyr Gln Asp Tyr Asn Gly His Gly Thr
    50                  55                  60

His Val Ala Gly Thr Ile Ala Gly Leu Asn Asn Ser Val Gly Val Leu
65                  70                  75                  80

Gly Val Ala Pro Ser Val Gln Leu Tyr Ala Val Lys Val Leu Asp Arg
                85                  90                  95

Asn Gly Gly Gly Asn His Ser Asp Ile Ala Arg Gly Ile Glu Trp Ser
            100                 105                 110

Val Asn Asn Gly Met His Val Val Asn Met Ser Leu Gly Gly Pro Thr
    115                 120                 125

Gly Ser Thr Thr Leu Gln Arg Ala Ala Asp Asn Ala Tyr Asn Arg Gly
130                 135                 140

Val Leu Leu Ile Ala Ala Ala Gly Asn Thr Gly Thr Ser Gly Val Ser
145                 150                 155                 160

Phe Pro Ala Arg Tyr Ser Ser Val Met Ala Val Ala Ala Thr Asp Ser
                165                 170                 175

Asn Asn Asn Arg Ala Ser Phe Ser Thr Tyr Gly Thr Gln Ile Glu Ile
            180                 185                 190

Ser Ala Pro Gly Val Gly Ile Asn Ser Thr Tyr Pro Thr Asn Arg Tyr
    195                 200                 205

Ser Ser Leu Asn Gly Thr Ser Met Ala Ser Pro His Val Ala Gly Val
210                 215                 220

Ala Ala Leu Val Lys Ala Arg Tyr Pro Ser Ala Thr Asn Ala Gln Ile
225                 230                 235                 240

Arg Gln His Leu Arg Ser Thr Ser Thr Tyr Leu Gly Asn Ser Thr Tyr
                245                 250                 255

Tyr Gly Ser Gly Leu Val Asp Ala Gln Arg Ala Ala Asn
            260                 265

<210> SEQ ID NO 24
<211> LENGTH: 1101
<212> TYPE: DNA
<213> ORGANISM: B. akibai
<220> FEATURE:
<221> NAME/KEY: misc_feature
<222> LOCATION: (1)..(1101)
<223> OTHER INFORMATION: nucleotide sequence of serine protease
      ACB83_2687815.n
```

<400> SEQUENCE: 24

```
atgaaaatga aatggtcacg tttaatttta accctagttc tcgtattcag ttttgtattc      60
ccatctatga caagtgcaaa cttcgctgta gaaaagagg attatctcat cggttttaag     120
cagaaaggga atgttagtgc acaagttgtg aatatgagtg gaggagaagt cgtccatgaa    180
tatgaacata tgccagtctt gcacgtgaaa ttacctccgc aagctgctaa agcgttagaa    240
aagaacccaa atattgaata catcgaaaaa gatgaaaagg tccaagctac agcacaatcg    300
acaccttggg ggattcacg tattaatgct cctgctgttc actcgactgg taatttggga    360
caaggtgtcc gagttgccgt tttagatagt ggagttgctt ctcatgaaga cttacggatt    420
gctggggag tgagctttgt cgcttcagaa cctagttatc aagattataa tggtcacgga    480
acacatgttg ctggaaccat tgctggttta aataatagtg ttggggtcct tggtgtagct    540
ccatctgtcc aattatatgc ggttaaggtg ttggatcgta atggcggggg aaatcatagt    600
gacattgcta gaggaattga gtggtcagtt aataatggaa tgcatgtggt gaatatgagt    660
ttaggtggac caacagggtc aacgactctg caacgagcag cggataatgc ttataacaga    720
ggagttcttt taattgccgc agctggtaac acgggaacta gtggggttag cttccctgcg    780
cgttatagct cagtaatggc agtagccgca acagactcta ataataaccg tgcttcattt    840
tcaacttatg gtccagaaat tgaaatttca gcacctggag ttggcattaa tagcacgtat    900
ccaacgaatc gttattcaag cttaaatgga acatcaatgg cttcacctca tgtcgctggt    960
gtagcagctc ttgtgaaggc gagatatcca agtgcgacga atgctcagat tagacaacat   1020
cttcgtagca cttctacgaa tctaggaaac tcaacttact atggtagtgg tctagttaat   1080
gcacagcgtg cagctaacta a                                              1101
```

<210> SEQ ID NO 25
<211> LENGTH: 366
<212> TYPE: PRT
<213> ORGANISM: B. akibai
<220> FEATURE:
<221> NAME/KEY: misc_feature
<222> LOCATION: (1)..(366)
<223> OTHER INFORMATION: amino acid sequence of the preproenzyme encoded by ACB83_2687815.n

<400> SEQUENCE: 25

```
Met Lys Met Lys Trp Ser Arg Leu Ile Leu Thr Leu Val Leu Val Phe
1               5                   10                  15

Ser Phe Val Phe Pro Ser Met Thr Ser Ala Asn Phe Ala Val Glu Lys
            20                  25                  30

Glu Asp Tyr Leu Ile Gly Phe Lys Gln Lys Gly Asn Val Ser Ala Gln
        35                  40                  45

Val Val Asn Met Ser Gly Gly Glu Val Val His Glu Tyr Glu His Met
    50                  55                  60

Pro Val Leu His Val Lys Leu Pro Pro Gln Ala Ala Lys Ala Leu Glu
65                  70                  75                  80

Lys Asn Pro Asn Ile Glu Tyr Ile Glu Lys Asp Glu Lys Val Gln Ala
                85                  90                  95

Thr Ala Gln Ser Thr Pro Trp Gly Ile Ser Arg Ile Asn Ala Pro Ala
            100                 105                 110

Val His Ser Thr Gly Asn Leu Gly Gln Gly Val Arg Val Ala Val Leu
        115                 120                 125

Asp Ser Gly Val Ala Ser His Glu Asp Leu Arg Ile Ala Gly Gly Val
```

```
                130             135             140
Ser Phe Val Ala Ser Glu Pro Ser Tyr Gln Asp Tyr Asn Gly His Gly
145                 150                 155                 160

Thr His Val Ala Gly Thr Ile Ala Gly Leu Asn Asn Ser Val Gly Val
                165                 170                 175

Leu Gly Val Ala Pro Ser Val Gln Leu Tyr Ala Val Lys Val Leu Asp
                180                 185                 190

Arg Asn Gly Gly Asn His Ser Asp Ile Ala Arg Gly Ile Glu Trp
            195                 200                 205

Ser Val Asn Asn Gly Met His Val Val Asn Met Ser Leu Gly Gly Pro
210                 215                 220

Thr Gly Ser Thr Thr Leu Gln Arg Ala Ala Asp Asn Ala Tyr Asn Arg
225                 230                 235                 240

Gly Val Leu Leu Ile Ala Ala Gly Asn Thr Gly Thr Ser Gly Val
                245                 250                 255

Ser Phe Pro Ala Arg Tyr Ser Ser Val Met Ala Val Ala Thr Asp
                260                 265                 270

Ser Asn Asn Asn Arg Ala Ser Phe Ser Thr Tyr Gly Pro Glu Ile Glu
            275                 280                 285

Ile Ser Ala Pro Gly Val Gly Ile Asn Ser Thr Tyr Pro Thr Asn Arg
            290                 295                 300

Tyr Ser Ser Leu Asn Gly Thr Ser Met Ala Ser Pro His Val Ala Gly
305                 310                 315                 320

Val Ala Ala Leu Val Lys Ala Arg Tyr Pro Ser Ala Thr Asn Ala Gln
                325                 330                 335

Ile Arg Gln His Leu Arg Ser Thr Ser Thr Asn Leu Gly Asn Ser Thr
                340                 345                 350

Tyr Tyr Gly Ser Gly Leu Val Asn Ala Gln Arg Ala Ala Asn
                355                 360                 365

<210> SEQ ID NO 26
<211> LENGTH: 269
<212> TYPE: PRT
<213> ORGANISM: B. akibai
<220> FEATURE:
<221> NAME/KEY: misc_feature
<222> LOCATION: (1)..(269)
<223> OTHER INFORMATION: amino acid sequence of the fully processed
      mature enzyme, ACB83, (269 amino acids),

<400> SEQUENCE: 26

Ala Gln Ser Thr Pro Trp Gly Ile Ser Arg Ile Asn Ala Pro Ala Val
1               5                   10                  15

His Ser Thr Gly Asn Leu Gly Gln Gly Val Arg Val Ala Val Leu Asp
                20                  25                  30

Ser Gly Val Ala Ser His Glu Asp Leu Arg Ile Ala Gly Gly Val Ser
                35                  40                  45

Phe Val Ala Ser Glu Pro Ser Tyr Gln Asp Tyr Asn Gly His Gly Thr
            50                  55                  60

His Val Ala Gly Thr Ile Ala Gly Leu Asn Asn Ser Val Gly Val Leu
65                  70                  75                  80

Gly Val Ala Pro Ser Val Gln Leu Tyr Ala Val Lys Val Leu Asp Arg
                85                  90                  95

Asn Gly Gly Asn His Ser Asp Ile Ala Arg Gly Ile Glu Trp Ser
            100                 105                 110

Val Asn Asn Gly Met His Val Val Asn Met Ser Leu Gly Gly Pro Thr
```

```
                    115                 120                 125
        Gly Ser Thr Thr Leu Gln Arg Ala Ala Asp Asn Ala Tyr Asn Arg Gly
            130                 135                 140

Val Leu Leu Ile Ala Ala Gly Asn Thr Gly Thr Ser Gly Val Ser
        145                 150                 155                 160

Phe Pro Ala Arg Tyr Ser Ser Val Met Ala Val Ala Thr Asp Ser
                        165                 170                 175

Asn Asn Asn Arg Ala Ser Phe Ser Thr Tyr Gly Pro Glu Ile Glu Ile
                    180                 185                 190

Ser Ala Pro Gly Val Gly Ile Asn Ser Thr Tyr Pro Thr Asn Arg Tyr
                    195                 200                 205

Ser Ser Leu Asn Gly Thr Ser Met Ala Ser Pro His Val Ala Gly Val
            210                 215                 220

Ala Ala Leu Val Lys Ala Arg Tyr Pro Ser Ala Thr Asn Ala Gln Ile
        225                 230                 235                 240

Arg Gln His Leu Arg Ser Thr Ser Thr Asn Leu Gly Asn Ser Thr Tyr
                        245                 250                 255

Tyr Gly Ser Gly Leu Val Asn Ala Gln Arg Ala Ala Asn
                    260                 265

<210> SEQ ID NO 27
<211> LENGTH: 1101
<212> TYPE: DNA
<213> ORGANISM: B. akibai
<220> FEATURE:
<221> NAME/KEY: misc_feature
<222> LOCATION: (1)..(1101)
<223> OTHER INFORMATION: nucleotide sequence of serine protease
      ACB90_2720294.n

<400> SEQUENCE: 27
atgaaaatga aatggtcacg tttaatttta accctagttc tcgtattcag ttttgtattc      60
ccatctatga caagtgcaaa ctccgctgta gaaaagaggg attatctcat cggttttaag     120
cagaaaggga atgttagtgc acaagttgtg aatatgagtg gaggagaagt cgtccatgaa     180
tatgaacata tgccagtctt gcacgtgaaa ttacctccgc aagctgctaa agcgttagaa     240
aagaacccaa atattgaata catcgaaaaa gatgaaaagg tccaagctac agcacaatcg     300
acaccttggg ggatttcacg tattaatgct cctgctgttc actcgactgg taatttggga     360
caaggtgtcc gagttgccgt tttagatagt ggagttgctt ctcatgaaga cttacggatt     420
gctgggggag tgagctttgt cgcttcagaa cctagttatc aagattataa tggtcacgga     480
acacatgttg ctggaaccat tgctggttta ataatagtg ttggggtcct tggtgtagct     540
ccatttgtcc aattatatgc ggttaaggtg ttggatcgta atggcggggg aaatcatagt     600
gacattgcta gaggaattga gtggtcagtt aataatggaa tgcatgtggt gaatatgagt     660
ttaggtggac caacagggtc aacgactctg caacgagcag cggataatgc ttataacaga     720
ggagttcttt taattgccgc agctggtaac acgggaacta gtggggttag cttccctgcg     780
cgttatagct cagtaatggc agtagccgca acagactcta ataataaccg tgcttcattt     840
tcaacttatg gtccagaaat tgaaatttca gcacctggag ttggcattaa tagcacgtat     900
ccaacgaatc gttattcaag cttaaatgga acatcaatgg cttcacctca tgtcgctggt     960
gtagcagctc ttgtgaaggc gagatatcca agtgcgacga atgctcagat tagacaacat    1020
cttcgtagca cttctacgaa tctaggaaac tcaacttact atggtagtgg tctagttaat    1080
gcacagcgtg cagctaacta a                                              1101
```

```
<210> SEQ ID NO 28
<211> LENGTH: 366
<212> TYPE: PRT
<213> ORGANISM: B. akibai
<220> FEATURE:
<221> NAME/KEY: misc_feature
<222> LOCATION: (1)..(366)
<223> OTHER INFORMATION: amino acid sequence of the preproenzyme encoded
      by ACB90_2720294.n

<400> SEQUENCE: 28

Met Lys Met Lys Trp Ser Arg Leu Ile Leu Thr Leu Val Leu Val Phe
1               5                   10                  15

Ser Phe Val Phe Pro Ser Met Thr Ser Ala Asn Ser Ala Val Glu Lys
            20                  25                  30

Glu Asp Tyr Leu Ile Gly Phe Lys Gln Lys Gly Asn Val Ser Ala Gln
        35                  40                  45

Val Val Asn Met Ser Gly Gly Glu Val Val His Glu Tyr Glu His Met
    50                  55                  60

Pro Val Leu His Val Lys Leu Pro Pro Gln Ala Ala Lys Ala Leu Glu
65                  70                  75                  80

Lys Asn Pro Asn Ile Glu Tyr Ile Glu Lys Asp Glu Lys Val Gln Ala
                85                  90                  95

Thr Ala Gln Ser Thr Pro Trp Gly Ile Ser Arg Ile Asn Ala Pro Ala
            100                 105                 110

Val His Ser Thr Gly Asn Leu Gly Gln Gly Val Arg Val Ala Val Leu
        115                 120                 125

Asp Ser Gly Val Ala Ser His Glu Asp Leu Arg Ile Ala Gly Gly Val
    130                 135                 140

Ser Phe Val Ala Ser Glu Pro Ser Tyr Gln Asp Tyr Asn Gly His Gly
145                 150                 155                 160

Thr His Val Ala Gly Thr Ile Ala Gly Leu Asn Asn Ser Val Gly Val
                165                 170                 175

Leu Gly Val Ala Pro Phe Val Gln Leu Tyr Ala Val Lys Val Leu Asp
            180                 185                 190

Arg Asn Gly Gly Gly Asn His Ser Asp Ile Ala Arg Gly Ile Glu Trp
        195                 200                 205

Ser Val Asn Asn Gly Met His Val Val Asn Met Ser Leu Gly Gly Pro
    210                 215                 220

Thr Gly Ser Thr Thr Leu Gln Arg Ala Ala Asp Asn Ala Tyr Asn Arg
225                 230                 235                 240

Gly Val Leu Leu Ile Ala Ala Gly Asn Thr Gly Thr Ser Gly Val
                245                 250                 255

Ser Phe Pro Ala Arg Tyr Ser Ser Val Met Ala Val Ala Ala Thr Asp
            260                 265                 270

Ser Asn Asn Asn Arg Ala Ser Phe Ser Thr Tyr Gly Pro Glu Ile Glu
        275                 280                 285

Ile Ser Ala Pro Gly Val Gly Ile Asn Ser Thr Tyr Pro Thr Asn Arg
    290                 295                 300

Tyr Ser Ser Leu Asn Gly Thr Ser Met Ala Ser Pro His Val Ala Gly
305                 310                 315                 320

Val Ala Ala Leu Val Lys Ala Arg Tyr Pro Ser Ala Thr Asn Ala Gln
                325                 330                 335

Ile Arg Gln His Leu Arg Ser Thr Ser Thr Asn Leu Gly Asn Ser Thr
            340                 345                 350
```

```
Tyr Tyr Gly Ser Gly Leu Val Asn Ala Gln Arg Ala Ala Asn
        355                 360                 365
```

<210> SEQ ID NO 29
<211> LENGTH: 269
<212> TYPE: PRT
<213> ORGANISM: B. akibai
<220> FEATURE:
<221> NAME/KEY: misc_feature
<222> LOCATION: (1)..(269)
<223> OTHER INFORMATION: amino acid sequence of the fully processed
      mature enzyme, ACB90, (269 amino acids),

<400> SEQUENCE: 29

```
Ala Gln Ser Thr Pro Trp Gly Ile Ser Arg Ile Asn Ala Pro Ala Val
1               5                   10                  15

His Ser Thr Gly Asn Leu Gly Gln Gly Val Arg Val Ala Val Leu Asp
            20                  25                  30

Ser Gly Val Ala Ser His Glu Asp Leu Arg Ile Ala Gly Gly Val Ser
        35                  40                  45

Phe Val Ala Ser Glu Pro Ser Tyr Gln Asp Tyr Asn Gly His Gly Thr
    50                  55                  60

His Val Ala Gly Thr Ile Ala Gly Leu Asn Asn Ser Val Gly Val Leu
65                  70                  75                  80

Gly Val Ala Pro Phe Val Gln Leu Tyr Ala Val Lys Val Leu Asp Arg
                85                  90                  95

Asn Gly Gly Gly Asn His Ser Asp Ile Ala Arg Gly Ile Glu Trp Ser
            100                 105                 110

Val Asn Asn Gly Met His Val Val Asn Met Ser Leu Gly Gly Pro Thr
        115                 120                 125

Gly Ser Thr Thr Leu Gln Arg Ala Ala Asp Asn Ala Tyr Asn Arg Gly
    130                 135                 140

Val Leu Leu Ile Ala Ala Ala Gly Asn Thr Gly Thr Ser Gly Val Ser
145                 150                 155                 160

Phe Pro Ala Arg Tyr Ser Ser Val Met Ala Val Ala Ala Thr Asp Ser
                165                 170                 175

Asn Asn Asn Arg Ala Ser Phe Ser Thr Tyr Gly Pro Glu Ile Glu Ile
            180                 185                 190

Ser Ala Pro Gly Val Gly Ile Asn Ser Thr Tyr Pro Thr Asn Arg Tyr
        195                 200                 205

Ser Ser Leu Asn Gly Thr Ser Met Ala Ser Pro His Val Ala Gly Val
    210                 215                 220

Ala Ala Leu Val Lys Ala Arg Tyr Pro Ser Ala Thr Asn Ala Gln Ile
225                 230                 235                 240

Arg Gln His Leu Arg Ser Thr Ser Thr Asn Leu Gly Asn Ser Thr Tyr
                245                 250                 255

Tyr Gly Ser Gly Leu Val Asn Ala Gln Arg Ala Ala Asn
            260                 265
```

<210> SEQ ID NO 30
<211> LENGTH: 1110
<212> TYPE: DNA
<213> ORGANISM: B. akibai
<220> FEATURE:
<221> NAME/KEY: misc_feature
<222> LOCATION: (1)..(1110)
<223> OTHER INFORMATION: nucleotide sequence of serine protease
      ACB82_2683104.n

```
<400> SEQUENCE: 30
atgagagttt taaaaggtac caaacttacc ggtttacttc ttgggtttat tttattattt       60
tctttcacct ttttgtcatt atcggttagt gctaacggga atggagtaga aagacatgac      120
tatttaatag ggtttcacga aaaggtagat aaaaaagcca taactcaagc aagcggagaa      180
gtagttcacg aatatcagta tatgcctgtt cttcatgtaa agcttccaga aaaagcagca      240
aaagctttag aaaaaaatcc taatattgct tatgttgaaa agacgaaga ggttactgct       300 tcacaaacgg ttccttgggg aattaatcat attcaagctc caactgtaca ttcttggggg      360
aatcgcggaa acggtgttcg tgtcgctgtg ctagattcag gggttgcttc ccatgaagat      420
ttaagaattt ctggtggtag aagttttatt actagcgagc cttcttatca agattataat      480
ggccatggaa ctcatgtagc tggtaccatc gctgggttaa ataatagtta cggtgtactt      540
ggtgtcgcac ctaatgttaa tctttacgca gtaaaagtat tagatcgtaa tggaagtgga      600
tctcacagtg cgattgcaca agggattgaa tggtctgtta gcaacggtat gcatattgtt      660
aacatgagct taggtgggcc aactggttca acaactcttc aacgtgccgc agataatgct      720
tataatagag gtgttcttct tatcgctgca gctggaaaca cgggttctgc tggtatttcc      780
tatccagcta gatacaactc tgttatggct gtaggtgccg ttgactccaa taataatcgt      840
gcttcattct cgactttgg aaacgaatta gaaattatgg caccaggagt atcaatatta       900
agcacacacc tttcaaatca atatgtttct ttaaacggta catctatggc aagtcctcat      960
gtagctggtg ttgcagcttt ggtgaaagct caatatccaa gtgcaactaa tgcccaaatc     1020
agacaaagac taagagatac tgccactcca cttggtagtt catattactt tggaaatggt     1080
ttagtgcatg ctactagagc cgctaattaa                                      1110

<210> SEQ ID NO 31
<211> LENGTH: 369
<212> TYPE: PRT
<213> ORGANISM: B. akibai
<220> FEATURE:
<221> NAME/KEY: misc_feature
<222> LOCATION: (1)..(369)
<223> OTHER INFORMATION: amino acid sequence of the preproenzyme encoded
      by ACB82_2683104.n

<400> SEQUENCE: 31

Met Arg Val Leu Lys Gly Thr Lys Leu Thr Gly Leu Leu Leu Gly Phe
1               5                   10                  15

Ile Leu Leu Phe Ser Phe Thr Phe Leu Ser Leu Ser Val Ser Ala Asn
            20                  25                  30

Gly Asn Gly Val Glu Arg His Asp Tyr Leu Ile Gly Phe His Glu Lys
        35                  40                  45

Val Asp Lys Lys Ala Ile Thr Gln Ala Ser Gly Glu Val Val His Glu
    50                  55                  60

Tyr Gln Tyr Met Pro Val Leu His Val Lys Leu Pro Glu Lys Ala Ala
65                  70                  75                  80

Lys Ala Leu Glu Lys Asn Pro Asn Ile Ala Tyr Val Glu Lys Asp Glu
                85                  90                  95

Glu Val Thr Ala Ser Gln Thr Val Pro Trp Gly Ile Asn His Ile Gln
            100                 105                 110

Ala Pro Thr Val His Ser Trp Gly Asn Arg Gly Asn Gly Val Arg Val
        115                 120                 125

Ala Val Leu Asp Ser Gly Val Ala Ser His Glu Asp Leu Arg Ile Ser
    130                 135                 140
```

```
Gly Gly Arg Ser Phe Ile Thr Ser Glu Pro Ser Tyr Gln Asp Tyr Asn
145                 150                 155                 160

Gly His Gly Thr His Val Ala Gly Thr Ile Ala Gly Leu Asn Asn Ser
                165                 170                 175

Tyr Gly Val Leu Gly Val Ala Pro Asn Val Asn Leu Tyr Ala Val Lys
            180                 185                 190

Val Leu Asp Arg Asn Gly Ser Gly Ser His Ser Ala Ile Ala Gln Gly
            195                 200                 205

Ile Glu Trp Ser Val Ser Asn Gly Met His Ile Val Asn Met Ser Leu
210                 215                 220

Gly Gly Pro Thr Gly Ser Thr Thr Leu Gln Arg Ala Ala Asp Asn Ala
225                 230                 235                 240

Tyr Asn Arg Gly Val Leu Leu Ile Ala Ala Gly Asn Thr Gly Ser
                245                 250                 255

Ala Gly Ile Ser Tyr Pro Ala Arg Tyr Asn Ser Val Met Ala Val Gly
            260                 265                 270

Ala Val Asp Ser Asn Asn Asn Arg Ala Ser Phe Ser Thr Phe Gly Asn
            275                 280                 285

Glu Leu Glu Ile Met Ala Pro Gly Val Ser Ile Leu Ser Thr His Leu
290                 295                 300

Ser Asn Gln Tyr Val Ser Leu Asn Gly Thr Ser Met Ala Ser Pro His
305                 310                 315                 320

Val Ala Gly Val Ala Ala Leu Val Lys Ala Gln Tyr Pro Ser Ala Thr
                325                 330                 335

Asn Ala Gln Ile Arg Gln Arg Leu Arg Asp Thr Ala Thr Pro Leu Gly
                340                 345                 350

Ser Ser Tyr Tyr Phe Gly Asn Gly Leu Val His Ala Thr Arg Ala Ala
                355                 360                 365

Asn

<210> SEQ ID NO 32
<211> LENGTH: 269
<212> TYPE: PRT
<213> ORGANISM: B. akibai
<220> FEATURE:
<221> NAME/KEY: misc_feature
<222> LOCATION: (1)..(269)
<223> OTHER INFORMATION: amino acid sequence of the fully processed
      mature enzyme, ACB82, (269 amino acids),

<400> SEQUENCE: 32

Ser Gln Thr Val Pro Trp Gly Ile Asn His Ile Gln Ala Pro Thr Val
1               5                   10                  15

His Ser Trp Gly Asn Arg Gly Asn Gly Val Arg Val Ala Val Leu Asp
                20                  25                  30

Ser Gly Val Ala Ser His Glu Asp Leu Arg Ile Ser Gly Gly Arg Ser
            35                  40                  45

Phe Ile Thr Ser Glu Pro Ser Tyr Gln Asp Tyr Asn Gly His Gly Thr
        50                  55                  60

His Val Ala Gly Thr Ile Ala Gly Leu Asn Asn Ser Tyr Gly Val Leu
65                  70                  75                  80

Gly Val Ala Pro Asn Val Asn Leu Tyr Ala Val Lys Val Leu Asp Arg
                85                  90                  95

Asn Gly Ser Gly Ser His Ser Ala Ile Ala Gln Gly Ile Glu Trp Ser
            100                 105                 110
```

```
Val Ser Asn Gly Met His Ile Val Asn Met Ser Leu Gly Gly Pro Thr
            115                 120                 125
Gly Ser Thr Thr Leu Gln Arg Ala Ala Asp Asn Ala Tyr Asn Arg Gly
        130                 135                 140
Val Leu Leu Ile Ala Ala Ala Gly Asn Thr Gly Ser Ala Gly Ile Ser
145                 150                 155                 160
Tyr Pro Ala Arg Tyr Asn Ser Val Met Ala Val Gly Ala Val Asp Ser
                165                 170                 175
Asn Asn Asn Arg Ala Ser Phe Ser Thr Phe Gly Asn Glu Leu Glu Ile
            180                 185                 190
Met Ala Pro Gly Val Ser Ile Leu Ser Thr His Leu Ser Asn Gln Tyr
        195                 200                 205
Val Ser Leu Asn Gly Thr Ser Met Ala Ser Pro His Val Ala Gly Val
    210                 215                 220
Ala Ala Leu Val Lys Ala Gln Tyr Pro Ser Ala Thr Asn Ala Gln Ile
225                 230                 235                 240
Arg Gln Arg Leu Arg Asp Thr Ala Thr Pro Leu Gly Ser Ser Tyr Tyr
                245                 250                 255
Phe Gly Asn Gly Leu Val His Ala Thr Arg Ala Ala Asn
            260                 265
```

<210> SEQ ID NO 33
<211> LENGTH: 1128
<212> TYPE: DNA
<213> ORGANISM: B. akibai
<220> FEATURE:
<221> NAME/KEY: misc_feature
<222> LOCATION: (1)..(1128)
<223> OTHER INFORMATION: nucleotide sequence of serine protease ACB89_2715301.n

<400> SEQUENCE: 33

| | | | | | |
|---|---|---|---|---|---|
| atgagagttt | tgaaaggtaa | caaacttacc | ggtttacttc | ttgggtttat | tttagtattt | 60 |
| tctttcacct | ttttgtcatt | atcggttagt | gctaacggga | atggcaatgg | caatggcaat | 120 |
| ggagtagaga | gacatgacta | tttaataggg | tttcacgaaa | aggtagataa | aaaagccata | 180 |
| actcaagcaa | gcggagaagt | agttcacgaa | tatcagtata | tgcctgttct | tcatgtaaag | 240 |
| cttccagaaa | aagcagcaaa | agctttagaa | aaaaatccta | atattgctta | tgttgaaaaa | 300 |
| gacgaagagg | ttactgcttc | acaaacggtt | ccttggggaa | ttaatcatat | tcaagctcca | 360 |
| actgtacatt | cttgggggaa | tcgtggaaac | ggcgttcgtg | ttgctgtgtt | agattcaggg | 420 |
| gttgcttccc | atgaagattt | aagaattttt | ggtggtagaa | gtttcattac | tagcgagcct | 480 |
| tcttatcaag | attataatgg | ccatggaact | catgtcgccg | aaccatcgc | tgggttaaat | 540 |
| aatagttacg | tgtacttgg | tgttgcacct | aatgttaatc | tttacgcagt | aaaagtatta | 600 |
| gatcgtaacg | gaagtggatc | tcacagtgcg | attgcacaag | ggattgaatg | gtctgttagc | 660 |
| aacggtatgc | atattgttaa | catgagctta | ggtgggccaa | caggttcaac | aactcttcaa | 720 |
| cgtgccgctg | ataatgctta | taatagaggt | gttctcctta | tcgctgcagc | tggtaacacg | 780 |
| ggttctgctg | gtatttccta | tccagctaga | tacaactctg | ttatggctgt | aggtgccgtt | 840 |
| gactccaata | ataatcgtgc | ttcattctcg | acttttggaa | acgaattaga | aattatggca | 900 |
| ccaggagtat | caattttaag | cacgcacctt | tcaaatcaat | atgtttcttt | aaacggtaca | 960 |
| tctatggcaa | gtcctcatgt | agctggtgtt | gcagctttgg | tgaaagctca | aatatccaagt | 1020 |
| gcaactaatg | cccaaatcag | acaaagacta | agagatactc | ccactccact | tggtagttca | 1080 | tattactttg gaaatggttt agtgcatgct gctagagccg ctaattaa                1128

<210> SEQ ID NO 34
<211> LENGTH: 375
<212> TYPE: PRT
<213> ORGANISM: B. akibai
<220> FEATURE:
<221> NAME/KEY: misc_feature
<222> LOCATION: (1)..(375)
<223> OTHER INFORMATION: amino acid sequence of the preproenzyme encoded
      by ACB89_2715301.n

<400> SEQUENCE: 34

Met Arg Val Leu Lys Gly Asn Lys Leu Thr Gly Leu Leu Gly Phe
1               5                   10                  15

Ile Leu Val Phe Ser Phe Thr Phe Leu Ser Leu Ser Val Ser Ala Asn
                20                  25                  30

Gly Asn Gly Asn Gly Asn Gly Val Glu Arg His Asp Tyr Leu
            35                  40                  45

Ile Gly Phe His Glu Lys Val Asp Lys Lys Ala Ile Thr Gln Ala Ser
    50                  55                  60

Gly Glu Val Val His Glu Tyr Gln Tyr Met Pro Val Leu His Val Lys
65                  70                  75                  80

Leu Pro Glu Lys Ala Ala Lys Ala Leu Glu Lys Asn Pro Asn Ile Ala
                85                  90                  95

Tyr Val Glu Lys Asp Glu Glu Val Thr Ala Ser Gln Thr Val Pro Trp
                100                 105                 110

Gly Ile Asn His Ile Gln Ala Pro Thr Val His Ser Trp Gly Asn Arg
            115                 120                 125

Gly Asn Gly Val Arg Val Ala Val Leu Asp Ser Gly Val Ala Ser His
    130                 135                 140

Glu Asp Leu Arg Ile Phe Gly Gly Arg Ser Phe Ile Thr Ser Glu Pro
145                 150                 155                 160

Ser Tyr Gln Asp Tyr Asn Gly His Gly Thr His Val Ala Gly Thr Ile
                165                 170                 175

Ala Gly Leu Asn Asn Ser Tyr Gly Val Leu Gly Val Ala Pro Asn Val
            180                 185                 190

Asn Leu Tyr Ala Val Lys Val Leu Asp Arg Asn Gly Ser Gly Ser His
        195                 200                 205

Ser Ala Ile Ala Gln Gly Ile Glu Trp Ser Val Ser Asn Gly Met His
    210                 215                 220

Ile Val Asn Met Ser Leu Gly Gly Pro Thr Gly Ser Thr Thr Leu Gln
225                 230                 235                 240

Arg Ala Ala Asp Asn Ala Tyr Asn Arg Gly Val Leu Leu Ile Ala Ala
                245                 250                 255

Ala Gly Asn Thr Gly Ser Ala Gly Ile Ser Tyr Pro Ala Arg Tyr Asn
            260                 265                 270

Ser Val Met Ala Val Gly Ala Val Asp Ser Asn Asn Arg Ala Ser
    275                 280                 285

Phe Ser Thr Phe Gly Asn Glu Leu Glu Ile Met Ala Pro Gly Val Ser
290                 295                 300

Ile Leu Ser Thr His Leu Ser Asn Gln Tyr Val Ser Leu Asn Gly Thr
305                 310                 315                 320

Ser Met Ala Ser Pro His Val Ala Gly Val Ala Ala Leu Val Lys Ala
                325                 330                 335

Gln Tyr Pro Ser Ala Thr Asn Ala Gln Ile Arg Gln Arg Leu Arg Asp

```
              340                 345                 350
Thr Ala Thr Pro Leu Gly Ser Ser Tyr Tyr Phe Gly Asn Gly Leu Val
        355                 360                 365

His Ala Ala Arg Ala Ala Asn
        370                 375

<210> SEQ ID NO 35
<211> LENGTH: 269
<212> TYPE: PRT
<213> ORGANISM: B. akibai
<220> FEATURE:
<221> NAME/KEY: misc_feature
<222> LOCATION: (1)..(269)
<223> OTHER INFORMATION: amino acid sequence of the fully processed
      mature enzyme, ACB89, (269 amino acids),

<400> SEQUENCE: 35

Ser Gln Thr Val Pro Trp Gly Ile Asn His Ile Gln Ala Pro Thr Val
1               5                   10                  15

His Ser Trp Gly Asn Arg Gly Asn Gly Val Arg Val Ala Val Leu Asp
            20                  25                  30

Ser Gly Val Ala Ser His Glu Asp Leu Arg Ile Phe Gly Gly Arg Ser
        35                  40                  45

Phe Ile Thr Ser Glu Pro Ser Tyr Gln Asp Tyr Asn Gly His Gly Thr
    50                  55                  60

His Val Ala Gly Thr Ile Ala Gly Leu Asn Asn Ser Tyr Gly Val Leu
65                  70                  75                  80

Gly Val Ala Pro Asn Val Asn Leu Tyr Ala Val Lys Val Leu Asp Arg
                85                  90                  95

Asn Gly Ser Gly Ser His Ser Ala Ile Ala Gln Gly Ile Glu Trp Ser
            100                 105                 110

Val Ser Asn Gly Met His Ile Val Asn Met Ser Leu Gly Gly Pro Thr
        115                 120                 125

Gly Ser Thr Thr Leu Gln Arg Ala Ala Asp Asn Ala Tyr Asn Arg Gly
    130                 135                 140

Val Leu Leu Ile Ala Ala Ala Gly Asn Thr Gly Ser Ala Gly Ile Ser
145                 150                 155                 160

Tyr Pro Ala Arg Tyr Asn Ser Val Met Ala Val Gly Ala Val Asp Ser
                165                 170                 175

Asn Asn Asn Arg Ala Ser Phe Ser Thr Phe Gly Asn Glu Leu Glu Ile
            180                 185                 190

Met Ala Pro Gly Val Ser Ile Leu Ser Thr His Leu Ser Asn Gln Tyr
        195                 200                 205

Val Ser Leu Asn Gly Thr Ser Met Ala Ser Pro His Val Ala Gly Val
    210                 215                 220

Ala Ala Leu Val Lys Ala Gln Tyr Pro Ser Ala Thr Asn Ala Gln Ile
225                 230                 235                 240

Arg Gln Arg Leu Arg Asp Thr Ala Thr Pro Leu Gly Ser Ser Tyr Tyr
                245                 250                 255

Phe Gly Asn Gly Leu Val His Ala Ala Arg Ala Ala Asn
            260                 265

<210> SEQ ID NO 36
<211> LENGTH: 1110
<212> TYPE: DNA
<213> ORGANISM: B. akibai
<220> FEATURE:
<221> NAME/KEY: misc_feature
```

<222> LOCATION: (1)..(1110)
<223> OTHER INFORMATION: nucleotide sequence of serine protease
      ACB92_2732966.n

<400> SEQUENCE: 36

```
atgcgagttt taaaaggtac caaacttact ggtttacttc ttgggtttat tttagtattt      60
tctttcgctt ttttatcact atcggttagt gctaatggca atgcgtaga aagacatgac     120
tatttaatag ggtttcacga aaaggtagat aaaaaagcca taactcaagc aagcggagaa     180
gtagttcacg aatatcagta tatgcctgtt cttcatgtaa agcttccaga aaaagcagca     240
aaagctttag aaaaaaatcc taatattgct tatgttgaaa agacgaaga ggttactgct      300
tcacaaacgg ttccttgggg aattaatcat attcaagctc caactgtaca ttcttggggg     360
aatcgtggaa acggcgttcg tgttgctgtg ttagattcag gggttgcttc ccatgaagat     420
ttaagaattt ctggtggtag aagtttcatt actagcgagc cttcttatca agattataat     480
ggccatggaa ctcatgtcgc cggaaccatc gctgggttaa ataatagtta cggtgtactt     540
ggtgttgcac ctaatgttaa tctttacgct gtaaaagtat tagatcgtaa cggaagtgga     600
tctcacagtg cgattgcaca agggattgaa tggtctgtta gcaacggtat gcatattgtt     660
aacatgagct aggtgggcc aactggttca gcaactcttc aacgtgccgc agataatgct      720
tataatagag gtgtgcttct gattgctgca gctggaaata cgggttctgc tggtatttcc     780
tatccagcaa gatacaattc tgttatggct gtaggtgccg ttgactccaa taacaatcgt     840
gcttcattct cgacttttgg aaacgaatta gaaattatgg caccaggagt atccattta      900
agcacacacc tttcaaatca atatatttct ttaaacggta catctatggc aagtccacat     960
gtagctggtg ttgcagcttt ggtgaaagct caatatccaa gtgcgactaa tgcccaaatc    1020
agacaaagac taagagacac cgctactcca cttggtagct catattactt tggcaatggt    1080
ttagtgcacg ctgctagagc cgctaattaa                                     1110
```

<210> SEQ ID NO 37
<211> LENGTH: 369
<212> TYPE: PRT
<213> ORGANISM: B. akibai
<220> FEATURE:
<221> NAME/KEY: misc_feature
<222> LOCATION: (1)..(369)
<223> OTHER INFORMATION: amino acid sequence of the preproenzyme encoded
      by ACB92_2732966.n

<400> SEQUENCE: 37

```
Met Arg Val Leu Lys Gly Thr Lys Leu Thr Gly Leu Leu Leu Gly Phe
1               5                   10                  15

Ile Leu Val Phe Ser Phe Ala Phe Leu Ser Leu Ser Val Ser Ala Asn
            20                  25                  30

Gly Asn Gly Val Glu Arg His Asp Tyr Leu Ile Gly Phe His Glu Lys
        35                  40                  45

Val Asp Lys Lys Ala Ile Thr Gln Ala Ser Gly Glu Val Val His Glu
    50                  55                  60

Tyr Gln Tyr Met Pro Val Leu His Val Lys Leu Pro Glu Lys Ala Ala
65                  70                  75                  80

Lys Ala Leu Glu Lys Asn Pro Asn Ile Ala Tyr Val Glu Lys Asp Glu
                85                  90                  95

Glu Val Thr Ala Ser Gln Thr Val Pro Trp Gly Ile Asn His Ile Gln
            100                 105                 110

Ala Pro Thr Val His Ser Trp Gly Asn Arg Gly Asn Gly Val Arg Val
```

```
            115                 120                 125
Ala Val Leu Asp Ser Gly Val Ala Ser His Glu Asp Leu Arg Ile Ser
    130                 135                 140

Gly Gly Arg Ser Phe Ile Thr Ser Glu Pro Ser Tyr Gln Asp Tyr Asn
145                 150                 155                 160

Gly His Gly Thr His Val Ala Gly Thr Ile Ala Gly Leu Asn Asn Ser
                165                 170                 175

Tyr Gly Val Leu Gly Val Ala Pro Asn Val Asn Leu Tyr Ala Val Lys
            180                 185                 190

Val Leu Asp Arg Asn Gly Ser Gly Ser His Ser Ala Ile Ala Gln Gly
        195                 200                 205

Ile Glu Trp Ser Val Ser Asn Gly Met His Ile Val Asn Met Ser Leu
    210                 215                 220

Gly Gly Pro Thr Gly Ser Ala Thr Leu Gln Arg Ala Ala Asp Asn Ala
225                 230                 235                 240

Tyr Asn Arg Gly Val Leu Leu Ile Ala Ala Gly Asn Thr Gly Ser
                245                 250                 255

Ala Gly Ile Ser Tyr Pro Ala Arg Tyr Asn Ser Val Met Ala Val Gly
            260                 265                 270

Ala Val Asp Ser Asn Asn Arg Ala Ser Phe Ser Thr Phe Gly Asn
        275                 280                 285

Glu Leu Glu Ile Met Ala Pro Gly Val Ser Ile Leu Ser Thr His Leu
    290                 295                 300

Ser Asn Gln Tyr Ile Ser Leu Asn Gly Thr Ser Met Ala Ser Pro His
305                 310                 315                 320

Val Ala Gly Val Ala Ala Leu Val Lys Ala Gln Tyr Pro Ser Ala Thr
                325                 330                 335

Asn Ala Gln Ile Arg Gln Arg Leu Arg Asp Thr Ala Thr Pro Leu Gly
            340                 345                 350

Ser Ser Tyr Tyr Phe Gly Asn Gly Leu Val His Ala Ala Arg Ala Ala
        355                 360                 365

Asn

<210> SEQ ID NO 38
<211> LENGTH: 269
<212> TYPE: PRT
<213> ORGANISM: B. akibai
<220> FEATURE:
<221> NAME/KEY: misc_feature
<222> LOCATION: (1)..(269)
<223> OTHER INFORMATION: amino acid sequence of the fully processed
      mature enzyme, ACB92, (269 amino acids),

<400> SEQUENCE: 38

Ser Gln Thr Val Pro Trp Gly Ile Asn His Ile Gln Ala Pro Thr Val
1               5                   10                  15

His Ser Trp Gly Asn Arg Gly Asn Gly Val Arg Val Ala Val Leu Asp
            20                  25                  30

Ser Gly Val Ala Ser His Glu Asp Leu Arg Ile Ser Gly Gly Arg Ser
        35                  40                  45

Phe Ile Thr Ser Glu Pro Ser Tyr Gln Asp Tyr Asn Gly His Gly Thr
    50                  55                  60

His Val Ala Gly Thr Ile Ala Gly Leu Asn Asn Ser Tyr Gly Val Leu
65                  70                  75                  80

Gly Val Ala Pro Asn Val Asn Leu Tyr Ala Val Lys Val Leu Asp Arg
                85                  90                  95
```

Asn Gly Ser Gly Ser His Ser Ala Ile Ala Gln Gly Ile Glu Trp Ser
            100                 105                 110

Val Ser Asn Gly Met His Ile Val Asn Met Ser Leu Gly Gly Pro Thr
        115                 120                 125

Gly Ser Ala Thr Leu Gln Arg Ala Ala Asp Asn Ala Tyr Asn Arg Gly
    130                 135                 140

Val Leu Leu Ile Ala Ala Gly Asn Thr Gly Ser Ala Gly Ile Ser
145                 150                 155                 160

Tyr Pro Ala Arg Tyr Asn Ser Val Met Ala Val Gly Ala Val Asp Ser
                165                 170                 175

Asn Asn Asn Arg Ala Ser Phe Ser Thr Phe Gly Asn Glu Leu Glu Ile
            180                 185                 190

Met Ala Pro Gly Val Ser Ile Leu Ser Thr His Leu Ser Asn Gln Tyr
        195                 200                 205

Ile Ser Leu Asn Gly Thr Ser Met Ala Ser Pro His Val Ala Gly Val
    210                 215                 220

Ala Ala Leu Val Lys Ala Gln Tyr Pro Ser Ala Thr Asn Ala Gln Ile
225                 230                 235                 240

Arg Gln Arg Leu Arg Asp Thr Ala Thr Pro Leu Gly Ser Ser Tyr Tyr
                245                 250                 255

Phe Gly Asn Gly Leu Val His Ala Ala Arg Ala Ala Asn
            260                 265

<210> SEQ ID NO 39
<211> LENGTH: 1116
<212> TYPE: DNA
<213> ORGANISM: B. akibai
<220> FEATURE:
<221> NAME/KEY: misc_feature
<222> LOCATION: (1)..(1116)
<223> OTHER INFORMATION: nucleotide sequence of serine protease
    DETPh35_2828044.n

<400> SEQUENCE: 39
atgagagttt tgaaaggtaa caaacttacc ggtttacttc ttgggtttat tttagtattt     60
tctttcacct ttttgtcatt atcggttagt gctaacggga atggcaatgg agtagaaaga    120
catgactatt aatagggtt tcacgaaaag gtagataaaa aagccataac tcaagcaagc    180
ggagaagtag ttcacgaata tcagtatatg cctgttcttc atgtaaagct tccagaaaaa    240
gcagcaaaag ctttagaaaa aaatcctaat attgcttatg ttgaaaaaga cgaagaggtt    300
actgcttcac aaacggttcc ttggggaatt aatcatattc aagctccaac tgtacattct    360
tgggggaatc gtggaaacgg cgttcgtgtt gctgtgttag attcaggggt tgcttcccat    420
gaagatttaa gaatttctgg tggtagaagt ttcattacta gcgagccttc ttatcaagat    480
tataatggcc atggaactca tgtcgccgga accatcgctg ggttaaataa tagttacggt    540
gtacttggtg ttgcacctaa tgttaatctt tacgctgtaa agtattaga tcgtaacgga    600 agtggatctc acagtgcgat gcacaaggg attgaatggt ctgttagcaa cggtatgcat    660
attgttaaca tgagcttagg tgggccaact ggttcagcaa ctcttcaacg tgccgcagat    720
aatgcttata tagaggtgt gcttctgatt gctgcagctg gaaatacggg ttctgctggt    780
atttcctatc cagcaagata caattctgtt atggctgtag gtgccgttga ctccaataac    840
aatcgtgctt cattctcgac ttttggaaac gaattagaaa ttatggcacc aggagtatcc    900
attttaagca cacacctttc aaatcaatat gtttctttaa acggtacatc tatggcaagt    960

```
ccacatgtag ctggtgttgc agctttggtg aaggctcaat atccaagtgc gactaatgcc   1020
caaatcagac aaagactaag agacaccgct actccacttg gtagctcata ttactttggc   1080
aatggtttag tgcacgctgc tagagccgct aattaa                              1116
```

<210> SEQ ID NO 40
<211> LENGTH: 371
<212> TYPE: PRT
<213> ORGANISM: B. akibai
<220> FEATURE:
<221> NAME/KEY: misc_feature
<222> LOCATION: (1)..(371)
<223> OTHER INFORMATION: amino acid sequence of the preproenzyme encoded
      by DETPh35_2828044.n

<400> SEQUENCE: 40

```
Met Arg Val Leu Lys Gly Asn Lys Leu Thr Gly Leu Leu Gly Phe
1               5                   10                  15

Ile Leu Val Phe Ser Phe Thr Phe Leu Ser Leu Ser Val Ser Ala Asn
                20                  25                  30

Gly Asn Gly Asn Gly Val Glu Arg His Asp Tyr Leu Ile Gly Phe His
            35                  40                  45

Glu Lys Val Asp Lys Lys Ala Ile Thr Gln Ala Ser Gly Glu Val Val
50                  55                  60

His Glu Tyr Gln Tyr Met Pro Val Leu His Val Lys Leu Pro Glu Lys
65                  70                  75                  80

Ala Ala Lys Ala Leu Glu Lys Asn Pro Asn Ile Ala Tyr Val Glu Lys
                85                  90                  95

Asp Glu Glu Val Thr Ala Ser Gln Thr Val Pro Trp Gly Ile Asn His
            100                 105                 110

Ile Gln Ala Pro Thr Val His Ser Trp Gly Asn Arg Gly Asn Gly Val
        115                 120                 125

Arg Val Ala Val Leu Asp Ser Gly Val Ala Ser His Glu Asp Leu Arg
130                 135                 140

Ile Ser Gly Gly Arg Ser Phe Ile Thr Ser Glu Pro Ser Tyr Gln Asp
145                 150                 155                 160

Tyr Asn Gly His Gly Thr His Val Ala Gly Thr Ile Ala Gly Leu Asn
                165                 170                 175

Asn Ser Tyr Gly Val Leu Gly Val Ala Pro Asn Val Asn Leu Tyr Ala
            180                 185                 190

Val Lys Val Leu Asp Arg Asn Gly Ser Gly Ser His Ser Ala Ile Ala
        195                 200                 205

Gln Gly Ile Glu Trp Ser Val Ser Asn Gly Met His Ile Val Asn Met
210                 215                 220

Ser Leu Gly Gly Pro Thr Gly Ser Ala Thr Leu Gln Arg Ala Ala Asp
225                 230                 235                 240

Asn Ala Tyr Asn Arg Gly Val Leu Leu Ile Ala Ala Gly Asn Thr
                245                 250                 255

Gly Ser Ala Gly Ile Ser Tyr Pro Ala Arg Tyr Asn Ser Val Met Ala
            260                 265                 270

Val Gly Ala Val Asp Ser Asn Asn Arg Ala Ser Phe Ser Thr Phe
        275                 280                 285

Gly Asn Glu Leu Glu Ile Met Ala Pro Gly Val Ser Ile Leu Ser Thr
290                 295                 300

His Leu Ser Asn Gln Tyr Val Ser Leu Asn Gly Thr Ser Met Ala Ser
305                 310                 315                 320
```

```
Pro His Val Ala Gly Val Ala Leu Val Lys Ala Gln Tyr Pro Ser
            325                 330                 335

Ala Thr Asn Ala Gln Ile Arg Gln Arg Leu Arg Asp Thr Ala Thr Pro
        340                 345                 350

Leu Gly Ser Ser Tyr Tyr Phe Gly Asn Gly Leu Val His Ala Ala Arg
    355                 360                 365

Ala Ala Asn
    370

<210> SEQ ID NO 41
<211> LENGTH: 269
<212> TYPE: PRT
<213> ORGANISM: B. akibai
<220> FEATURE:
<221> NAME/KEY: misc_feature
<222> LOCATION: (1)..(269)
<223> OTHER INFORMATION: amino acid sequence of the fully processed
      mature enzyme, DETPh35, (269 amino acids)

<400> SEQUENCE: 41

Ser Gln Thr Val Pro Trp Gly Ile Asn His Ile Gln Ala Pro Thr Val
1               5                   10                  15

His Ser Trp Gly Asn Arg Gly Asn Gly Val Arg Val Ala Val Leu Asp
            20                  25                  30

Ser Gly Val Ala Ser His Glu Asp Leu Arg Ile Ser Gly Gly Arg Ser
        35                  40                  45

Phe Ile Thr Ser Glu Pro Ser Tyr Gln Asp Tyr Asn Gly His Gly Thr
    50                  55                  60

His Val Ala Gly Thr Ile Ala Gly Leu Asn Asn Ser Tyr Gly Val Leu
65                  70                  75                  80

Gly Val Ala Pro Asn Val Asn Leu Tyr Ala Val Lys Val Leu Asp Arg
                85                  90                  95

Asn Gly Ser Gly Ser His Ser Ala Ile Ala Gln Gly Ile Glu Trp Ser
            100                 105                 110

Val Ser Asn Gly Met His Ile Val Asn Met Ser Leu Gly Gly Pro Thr
        115                 120                 125

Gly Ser Ala Thr Leu Gln Arg Ala Ala Asp Asn Ala Tyr Asn Arg Gly
    130                 135                 140

Val Leu Leu Ile Ala Ala Ala Gly Asn Thr Gly Ser Ala Gly Ile Ser
145                 150                 155                 160

Tyr Pro Ala Arg Tyr Asn Ser Val Met Ala Val Gly Ala Val Asp Ser
                165                 170                 175

Asn Asn Asn Arg Ala Ser Phe Ser Thr Phe Gly Asn Glu Leu Glu Ile
            180                 185                 190

Met Ala Pro Gly Val Ser Ile Leu Ser Thr His Leu Ser Asn Gln Tyr
        195                 200                 205

Val Ser Leu Asn Gly Thr Ser Met Ala Ser Pro His Val Ala Gly Val
    210                 215                 220

Ala Ala Leu Val Lys Ala Gln Tyr Pro Ser Ala Thr Asn Ala Gln Ile
225                 230                 235                 240

Arg Gln Arg Leu Arg Asp Thr Ala Thr Pro Leu Gly Ser Ser Tyr Tyr
                245                 250                 255

Phe Gly Asn Gly Leu Val His Ala Ala Arg Ala Ala Asn
            260                 265

<210> SEQ ID NO 42
<211> LENGTH: 10
```

-continued

```
<212> TYPE: PRT
<213> ORGANISM: Artificial Sequence
<220> FEATURE:
<223> OTHER INFORMATION: Synthetic: B. akibai/clarkii-clade subtilisin
      sequence DRN motif
<220> FEATURE:
<221> NAME/KEY: misc_feature
<222> LOCATION: (9)..(9)
<223> OTHER INFORMATION: Xaa is Gly or Ser

<400> SEQUENCE: 42

Val Lys Val Leu Asp Arg Asn Gly Xaa Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic: B. akibai/clarkii-clade subtilisin
      sequence DRN motif

<400> SEQUENCE: 43

Val Lys Val Leu Asp Arg Asn Gly Gly Gly
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic: B. akibai/clarkii-clade subtilisin
      sequence DRN motif

<400> SEQUENCE: 44

Val Lys Val Leu Asp Arg Asn Gly Ser Gly
1               5                   10

<210> SEQ ID NO 45
<211> LENGTH: 3
<212> TYPE: PRT
<213> ORGANISM: Artificial

-continued

<400> SEQUENCE: 46

Val Lys Val Leu Asp Arg Asn Gly Xaa Gly
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic: B. akibai/clarkii-clade subtilisin
      sequence DRN motif
<220> FEATURE:
<221> NAME/KEY: misc_feature
<222> LOCATION: (1)..(10)
<223> OTHER INFORMATION: corresponds to positions 91 - 100 of SEQ ID NO:
      3

<400> SEQUENCE: 47

Val Lys Val Leu Asp Arg Asn Gly Gly Gly
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic: B. akibai/clarkii-clade subtilisin
      sequence DRN motif
<220> FEATURE:
<221> NAME/KEY: misc_feature
<222> LOCATION: (1)..(10)
<223> OTHER INFORMATION: corresponds to positions 91 - 100 of SEQ ID NO:
      3

<400> SEQUENCE: 48

Val Lys Val Leu Asp Arg Asn Gly Ser Gly
1               5                   10

<210> SEQ ID NO 49
<211> LENGTH: 273
<212> TYPE: PRT
<213> ORGANISM: B. pseudofirmus
<220> FEATURE:
<221> NAME/KEY: misc_feature
<222> LOCATION: (1)..(273)
<223> OTHER INFORMATION: Bps_ADC49870

<400> SEQUENCE: 49

Ala Gln Thr Val Pro Trp Gly Ile Pro Tyr Ile Tyr Ser Asp Val Val
1               5                   10                  15

His Arg Gln Gly Tyr Phe Gly Asn Gly Val Lys Val Ala Val Leu Asp
                20                  25                  30

Thr Gly Val Ala Pro His Pro Asp Leu His Ile Arg Gly Gly Val Ser
            35                  40                  45

Phe Ile Ser Thr Glu Asn Thr Tyr Val Asp Tyr Asn Gly His Gly Thr
        50                  55                  60

His Val Ala Gly Thr Val Ala Ala Leu Asn Asn Ser Tyr Gly Val Leu
65                  70                  75                  80

Gly Val Ala Pro Gly Ala Glu Leu Tyr Ala Val Lys Val Leu Asp Arg
                85                  90                  95

Asn Gly Ser Gly Ser His Ala Ser Ile Ala Gln Gly Ile Glu Trp Ala
            100                 105                 110

Met Asn Asn Gly Met Asp Ile Ala Asn Met Ser Leu Gly Ser Pro Ser
        115                 120                 125

Gly Ser Thr Thr Leu Gln Leu Ala Ala Asp Arg Ala Arg Asn Ala Gly
        130                 135                 140

Val Leu Leu Ile Gly Ala Ala Gly Asn Ser Gly Gln Gln Gly Gly Ser
145                 150                 155                 160

Asn Asn Met Gly Tyr Pro Ala Arg Tyr Ala Ser Val Met Ala Val Gly
                165                 170                 175

Ala Val Asp Gln Asn Gly Asn Arg Ala Asn Phe Ser Ser Tyr Gly Ser
            180                 185                 190

Glu Leu Glu Ile Met Ala Pro Gly Val Asn Ile Asn Ser Thr Tyr Leu
        195                 200                 205

Asn Asn Gly Tyr Arg Ser Leu Asn Gly Thr Ser Met Ala Ser Pro His
210                 215                 220

Val Ala Gly Val Ala Ala Leu Val Lys Gln Lys His Pro His Leu Thr
225                 230                 235                 240

Ala Ala Gln Ile Arg Asn Arg Met Asn Gln Thr Ala Ile Pro Leu Gly
                245                 250                 255

Asn Ser Thr Tyr Tyr Gly Asn Gly Leu Val Asp Ala Glu Tyr Ala Ala
            260                 265                 270

Gln

<210> SEQ ID NO 50
<211> LENGTH: 269
<212> TYPE: PRT
<213> ORGANISM: Bacillus sp.
<220> FEATURE:
<221> NAME/KEY: misc_feature
<222> LOCATION: (1)..(269)
<223> OTHER INFORMATION: Bacillus_sp_ADD64465

<400> SEQUENCE: 50

Ser Gln Thr Val Pro Trp Gly Ile Ser Phe Ile Ser Thr Gln Gln Ala
1               5                   10                  15

His Asn Arg Gly Ile Phe Gly Asn Gly Ala Arg Val Ala Val Leu Asp
            20                  25                  30

Thr Gly Ile Ala Ser His Pro Asp Leu Arg Ile Ala Gly Gly Ala Ser
        35                  40                  45

Phe Ile Ser Ser Glu Pro Ser Tyr His Asp Asn Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Asp Arg
                85                  90                  95

Asn Gly Ser Gly Ser Leu Ala Ser Val Ala Gln Gly Ile Glu Trp Ala
            100                 105                 110

Ile Asn Asn Asn Met His Ile Ile Asn Met Ser Leu Gly Ser Thr Ser
        115                 120                 125

Gly Ser Ser Thr Leu Glu Leu Ala Val Asn Arg Gly Asn Asn Ala Gly
    130                 135                 140

Ile Leu Leu Val Gly Ala Ala Gly Asn Thr Gly Arg Gln Gly Val Asn
145                 150                 155                 160

Tyr Pro Ala Arg Tyr Ser Gly Val Met Ala Val Ala Ala Val Asp Gln
                165                 170                 175

Asn Gly Gln Arg Ala Ser Phe Ser Thr Tyr Gly Pro Glu Ile Glu Ile
            180                 185                 190

Ser Ala Pro Gly Val Asn Val Tyr Ser Thr Tyr Thr Gly Asn Arg Tyr

```
                195                 200                 205
Val Ser Leu Ser Gly Thr Ser Met Ala Ala Pro His Val Ala Gly Thr
210                 215                 220

Ala Ala Leu Val Lys Ser Arg Tyr Pro Ser Tyr Thr Asn Asn Gln Ile
225                 230                 235                 240

Arg Gln Arg Ile Asn Gln Thr Ala Thr Tyr Leu Gly Ser Ser Asn Leu
                245                 250                 255

Tyr Gly Asn Gly Leu Val His Ala Gly Arg Ala Thr Gln
                260                 265

<210> SEQ ID NO 51
<211> LENGTH: 269
<212> TYPE: PRT
<213> ORGANISM: B. halodurans
<220> FEATURE:
<221> NAME/KEY: misc_feature
<222> LOCATION: (1)..(269)
<223> OTHER INFORMATION: B_halodurans_BAB04574

<400> SEQUENCE: 51

Ser Gln Thr Val Pro Trp Gly Ile Ser Phe Ile Asn Thr Gln Gln Ala
1               5                   10                  15

His Asn Arg Gly Ile Phe Gly Asn Gly Ala Arg Val Ala Val Leu Asp
                20                  25                  30

Thr Gly Ile Ala Ser His Pro Asp Leu Arg Ile Ala Gly Gly Ala Ser
            35                  40                  45

Phe Ile Ser Ser Glu Pro Ser Tyr His Asp Asn Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Asp Arg
                85                  90                  95

Asn Gly Ser Gly Ser Leu Ala Ser Val Ala Gln Gly Ile Glu Trp Ala
            100                 105                 110

Ile Asn Asn Asn Met His Ile Ile Asn Met Ser Leu Gly Ser Thr Ser
        115                 120                 125

Gly Ser Ser Thr Leu Glu Leu Ala Val Asn Arg Ala Asn Asn Ala Gly
    130                 135                 140

Ile Leu Leu Val Gly Ala Ala Gly Asn Thr Gly Arg Gln Gly Val Asn
145                 150                 155                 160

Tyr Pro Ala Arg Tyr Ser Gly Val Met Ala Val Ala Ala Val Asp Gln
                165                 170                 175

Asn Gly Gln Arg Ala Ser Phe Ser Thr Tyr Gly Pro Glu Ile Glu Ile
            180                 185                 190

Ser Ala Pro Gly Val Asn Val Asn Ser Thr Tyr Thr Gly Asn Arg Tyr
        195                 200                 205

Val Ser Leu Ser Gly Thr Ser Met Ala Thr Pro His Val Ala Gly Val
    210                 215                 220

Ala Ala Leu Val Lys Ser Arg Tyr Pro Ser Tyr Thr Asn Asn Gln Ile
225                 230                 235                 240

Arg Gln Arg Ile Asn Gln Thr Ala Thr Tyr Leu Gly Ser Pro Ser Leu
                245                 250                 255

Tyr Gly Asn Gly Leu Val His Ala Gly Arg Ala Thr Gln
            260                 265

<210> SEQ ID NO 52
```

```
<211> LENGTH: 269
<212> TYPE: PRT
<213> ORGANISM: Bacillus sp.
<220> FEATURE:
<221> NAME/KEY: misc_feature
<222> LOCATION: (1)..(269)
<223> OTHER INFORMATION: Bacillus_sp_BAA05540

<400> SEQUENCE: 52

Ser Gln Thr Val Pro Trp Gly Ile Ser Phe Ile Asn Thr Gln Gln Ala
1               5                   10                  15

His Asn Arg Gly Ile Phe Gly Asn Gly Ala Arg Val Ala Val Leu Asp
            20                  25                  30

Thr Gly Ile Ala Ser His Pro Asp Leu Arg Ile Ala Gly Gly Ala Ser
        35                  40                  45

Phe Ile Ser Ser Glu Pro Ser Tyr His Asp Asn Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Asp Arg
                85                  90                  95

Asn Gly Ser Gly Ser Leu Ala Ser Val Ala Gln Gly Ile Glu Trp Ala
            100                 105                 110

Ile Asn Asn Asn Met His Ile Ile Asn Met Ser Leu Gly Ser Thr Ser
        115                 120                 125

Gly Ser Ser Thr Leu Glu Leu Ala Val Asn Arg Ala Asn Asn Ala Gly
130                 135                 140

Ile Leu Leu Val Gly Ala Ala Gly Asn Thr Gly Arg Gln Gly Val Asn
145                 150                 155                 160

Tyr Pro Ala Arg Tyr Ser Gly Val Met Ala Val Ala Ala Val Asp Gln
                165                 170                 175

Asn Gly Gln Arg Ala Ser Phe Ser Thr Tyr Gly Pro Glu Ile Glu Ile
            180                 185                 190

Ser Ala Pro Gly Val Asn Val Asn Ser Thr Tyr Thr Gly Asn Arg Tyr
        195                 200                 205

Val Ser Leu Ser Gly Thr Ser Met Ala Thr Pro His Val Ala Gly Val
    210                 215                 220

Ala Ala Leu Val Lys Ser Arg Tyr Pro Ser Tyr Thr Asn Asn Gln Ile
225                 230                 235                 240

Arg Gln Arg Ile Asn Gln Thr Ala Thr Tyr Leu Gly Ser Pro Ser Leu
                245                 250                 255

Tyr Gly Asn Gly Leu Val His Ala Gly Arg Ala Thr Gln
            260                 265

<210> SEQ ID NO 53
<211> LENGTH: 269
<212> TYPE: PRT
<213> ORGANISM: B. clausii
<220> FEATURE:
<221> NAME/KEY: misc_feature
<222> LOCATION: (1)..(269)
<223> OTHER INFORMATION: B_clausii_ABI26631

<400> SEQUENCE: 53

Ser Gln Thr Val Pro Trp Gly Ile Ser Phe Ile Asn Thr Gln Gln Ala
1               5                   10                  15

His Asn Arg Gly Ile Phe Gly Asn Gly Ala Arg Val Ala Val Leu Asp
            20                  25                  30
```

-continued

Thr Gly Ile Ala Ser His Pro Asp Leu Arg Ile Ala Gly Ala Ser
 35                  40                  45

Phe Ile Ser Ser Glu Pro Ser Tyr His Asp Asn Asn Gly His Gly Thr
 50                  55                  60

His Val Ala Gly Thr Ile Ala Ala Leu Asn Asn Ser Ile Gly Val Leu
65                   70                  75                  80

Gly Val Ala Pro Ser Ala Asp Leu Tyr Ala Val Lys Val Leu Asp Arg
                 85                  90                  95

Asn Gly Ser Gly Ser Leu Ala Ser Val Ala Gln Gly Ile Glu Trp Ala
            100                 105                 110

Ile Asn Asn Met His Ile Ile Asn Met Ser Leu Gly Ser Thr Ser
        115                 120                 125

Gly Ser Ser Thr Leu Glu Leu Ala Val Asn Arg Ala Asn Asn Ala Gly
130                 135                 140

Ile Leu Leu Val Gly Ala Ala Gly Asn Thr Gly Arg Gln Gly Val Asn
145                 150                 155                 160

Tyr Pro Ala Arg Tyr Ser Gly Val Met Ala Ala Ala Val Asp Gln
                165                 170                 175

Asn Gly Gln Arg Ala Ser Phe Ser Thr Tyr Gly Pro Glu Ile Glu Ile
            180                 185                 190

Ser Ala Pro Gly Val Asn Ile Asn Ser Thr Tyr Thr Gly Asn Arg Tyr
        195                 200                 205

Glu Ser Leu Ser Gly Thr Ser Met Ala Thr Pro His Val Ala Gly Val
210                 215                 220

Ala Ala Leu Val Lys Ser Arg Tyr Pro Ser Tyr Thr Asn Asn Gln Ile
225                 230                 235                 240

Arg Gln Arg Ile Asn Gln Thr Ala Thr Tyr Leu Gly Ser Pro Ser Leu
                245                 250                 255

Tyr Gly Asn Gly Leu Val His Ala Gly Arg Ala Thr Gln
            260                 265

<210> SEQ ID NO 54
<211> LENGTH: 269
<212> TYPE: PRT
<213> ORGANISM: B. gibsonii
<220> FEATURE:
<221> NAME/KEY: misc_feature
<222> LOCATION: (1)..(269)
<223> OTHER INFORMATION: B_gibsonii_AGS78407

<400> SEQUENCE: 54

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
 50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe

```
                115                 120                 125
Pro Ser Ser Thr Leu Glu Arg Ala Val Asn Tyr Ala Thr Ser Arg Asp
130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 55
<211> LENGTH: 269
<212> TYPE: PRT
<213> ORGANISM: Bacillus sp.
<220> FEATURE:
<221> NAME/KEY: misc_feature
<222> LOCATION: (1)..(269)
<223> OTHER INFORMATION: Bacillus_sp_BAA25184

<400> SEQUENCE: 55

Met Gln Thr Val Pro Trp Gly Ile Asn Arg Val Gln Ala Pro Ile Ala
1               5                   10                  15

Gln Ser Arg Gly Phe Thr Gly Thr Gly Val Arg Val Ala Val Leu Asp
            20                  25                  30

Thr Gly Ile Ser Asn His Ala Asp Leu Arg Ile Arg Gly Gly Ala Ser
        35                  40                  45

Phe Val Pro Gly Glu Pro Asn Ile Ser Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Val Asp Leu Tyr Gly Val Lys Val Leu Gly Ala
                85                  90                  95

Ser Gly Ser Gly Ser Ile Ser Gly Ile Ala Gln Gly Leu Gln Trp Ala
            100                 105                 110

Ala Asn Asn Gly Met His Ile Ala Asn Met Ser Leu Gly Ser Ser Ala
        115                 120                 125

Gly Ser Ala Thr Met Glu Gln Ala Val Asn Gln Ala Thr Ala Ser Gly
    130                 135                 140

Val Leu Val Val Ala Ala Ser Gly Asn Ser Gly Ala Gly Asn Val Gly
145                 150                 155                 160

Phe Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Gly Val Gln Ser Thr Val Pro Gly Asn Gly Tyr
        195                 200                 205
```

```
Ser Ser Phe Asn Gly Thr Ser Met Ala Thr Pro His Val Ala Gly Val
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Asn Leu Gly Asn Thr Asn Gln
                245                 250                 255

Phe Gly Ser Gly Leu Val Asn Ala Glu Ala Ala Thr Arg
            260                 265
```

<210> SEQ ID NO 56
<211> LENGTH: 269
<212> TYPE: PRT
<213> ORGANISM: Bacillus sp. G-825-6
<220> FEATURE:
<221> NAME/KEY: misc_feature
<222> LOCATION: (1)..(269)
<223> OTHER INFORMATION: B_sp_Sendai_BAA06157

<400> SEQUENCE: 56

```
Asn Gln Val Thr Pro Trp Gly Ile Thr Arg Val Gln Ala Pro Thr Ala
1               5                   10                  15

Trp Thr Arg Gly Tyr Thr Gly Thr Gly Val Arg Val Ala Val Leu Asp
            20                  25                  30

Thr Gly Ile Ser Thr His Pro Asp Leu Asn Ile Arg Gly Gly Val Ser
        35                  40                  45

Phe Val Pro Gly Glu Pro Ser Tyr Gln Asp Gly Asn Gly His Gly Thr
    50                  55                  60

His Val Ala Gly Thr Ile Ala Ala Leu Asn Asn Ser Ile Gly Val Val
65                  70                  75                  80

Gly Val Ala Pro Asn Ala Glu Leu Tyr Ala Val Lys Val Leu Gly Ala
                85                  90                  95

Asn Gly Ser Gly Ser Val Ser Ser Ile Ala Gln Gly Leu Gln Trp Thr
            100                 105                 110

Ala Gln Asn Asn Ile His Val Ala Asn Leu Ser Leu Gly Ser Pro Val
        115                 120                 125

Gly Ser Gln Thr Leu Glu Leu Ala Val Asn Gln Ala Thr Asn Ala Gly
    130                 135                 140

Val Leu Val Val Ala Ala Thr Gly Asn Asn Gly Ser Gly Thr Val Ser
145                 150                 155                 160

Tyr Pro Ala Arg Tyr Ala Asn Ala Leu Ala Val Gly Ala Thr Asp Gln
                165                 170                 175

Asn Asn Asn Arg Ala Ser Phe Ser Gln Tyr Gly Thr Gly Leu Asn Ile
            180                 185                 190

Val Ala Pro Gly Val Gly Ile Gln Ser Thr Tyr Pro Gly Asn Arg Tyr
        195                 200                 205

Ala Ser Leu Ser Gly Thr Ser Met Ala Thr Pro His Val Ala Gly Val
    210                 215                 220

Ala Ala Leu Val Lys Gln Lys Asn Pro Ser Trp Ser Asn Thr Gln Ile
225                 230                 235                 240

Arg Gln His Leu Thr Ser Thr Ala Thr Ser Leu Gly Asn Ser Asn Gln
                245                 250                 255

Phe Gly Ser Gly Leu Val Asn Ala Glu Ala Ala Thr Arg
            260                 265
```

<210> SEQ ID NO 57
<211> LENGTH: 269

```
<212> TYPE: PRT
<213> ORGANISM: B. subtilis
<220> FEATURE:
<221> NAME/KEY: misc_feature
<222> LOCATION: (1)..(269)
<223> OTHER INFORMATION: B_subtilis_AAA87324

<400> SEQUENCE: 57
```

Met Gln Thr Val Pro Trp Gly Ile Asn Arg Val Gln Ala Pro Ile Ala
1               5                   10                  15

Gln Ser Arg Gly Phe Thr Gly Thr Gly Val Arg Val Ala Val Leu Asp
            20                  25                  30

Thr Gly Ile Ser Asn His Ala Asp Leu Arg Ile Arg Gly Gly Ala Ser
        35                  40                  45

Phe Val Pro Gly Glu Pro Asn Ile Ser Asp Gly Asn Gly His Gly Thr
    50                  55                  60

Gln Val Ala Gly Thr Ile Ala Ala Leu Asn Asn Ser Ile Gly Val Leu
65                  70                  75                  80

Gly Val Ala Pro Asn Val Asp Leu Tyr Gly Val Lys Val Leu Gly Ala
                85                  90                  95

Ser Gly Ser Gly Ser Ile Ser Gly Ile Ala Gln Gly Leu Gln Trp Ala
            100                 105                 110

Ala Asn Asn Gly Met His Ile Ala Asn Met Ser Leu Gly Ser Ser Ala
        115                 120                 125

Gly Ser Ala Thr Met Glu Gln Ala Val Asn Gln Ala Thr Ala Ser Gly
    130                 135                 140

Val Leu Val Val Ala Ala Ser Gly Asn Ser Gly Ala Gly Asn Val Gly
145                 150                 155                 160

Phe Pro Ala Arg Tyr Ala Asn Ala Met Ala Val Gly Ala Thr Asp Gln
                165                 170                 175

Asn Asn Asn Arg Ala Thr Phe Ser Gln Tyr Gly Ala Gly Leu Asp Ile
            180                 185                 190

Val Ala Pro Gly Val Gly Val Gln Ser Thr Val Pro Gly Asn Gly Tyr
        195                 200                 205

Ala Ser Phe Asn Gly Thr Ser Met Ala Thr Pro His Val Ala Gly Val
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Asn Leu Gly Asn Thr Thr Gln
                245                 250                 255

Phe Gly Ser Gly Leu Val Asn Ala Glu Ala Ala Thr Arg
            260                 265

```
<210> SEQ ID NO 58
<211> LENGTH: 269
<212> TYPE: PRT
<213> ORGANISM: B. lehensis
<220> FEATURE:
<221> NAME/KEY: misc_feature
<222> LOCATION: (1)..(269)
<223> OTHER INFORMATION: B_lehensis_AFK08970

<400> SEQUENCE: 58
```

Met Gln Thr Val Pro Trp Gly Ile Asn Arg Val Gln Ala Pro Ile Ala
1               5                   10                  15

Gln Ser Arg Gly Phe Thr Gly Thr Gly Val Arg Val Ala Val Leu Asp
            20                  25                  30

Thr Gly Ile Ser Asn His Ala Asp Leu Arg Ile Arg Gly Gly Ala Ser

```
                35                  40                  45
Phe Val Pro Gly Glu Pro Asn Ile Ser Asp Gly Asn Gly His Gly Thr
 50                  55                  60

His Val Ala Gly Thr Ile Ala Ala Leu Asn Asn Ser Ile Gly Val Ile
 65                  70                  75                  80

Gly Val Ala Pro Asn Val Asp Leu Tyr Gly Val Lys Val Leu Gly Ala
                 85                  90                  95

Ser Gly Cys Gly Ser Ile Ser Gly Ile Ala Gln Gly Leu Gln Trp Ala
            100                 105                 110

Ala Asn Asn Gly Met His Ile Ala Asn Met Ser Leu Gly Ser Ser Ala
            115                 120                 125

Gly Ser Ala Thr Met Glu Gln Ala Val Asn Gln Ala Thr Ala Ser Gly
130                 135                 140

Val Leu Val Val Ala Ala Ser Gly Asn Ser Gly Ala Gly Asn Val Gly
145                 150                 155                 160

Phe Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Gly Val Gln Ser Thr Val Pro Gly Asn Gly Tyr
            195                 200                 205

Ala Ser Phe Asn Gly Thr Ser Met Ala Thr Pro His Val Ala Gly Val
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Asn Leu Gly Asn Thr Thr Gln
                245                 250                 255

Phe Gly Ser Gly Leu Val Asn Ala Glu Ala Ala Thr Arg
            260                 265

<210> SEQ ID NO 59
<211> LENGTH: 269
<212> TYPE: PRT
<213> ORGANISM: B. clausii
<220> FEATURE:
<221> NAME/KEY: misc_feature
<222> LOCATION: (1)..(269)
<223> OTHER INFORMATION: B_clausii_BAD63300

<400> SEQUENCE: 59

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
             35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125
```

```
Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Val
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Gly Leu Gly Asn Thr Asn Leu
                245                 250                 255

Tyr Gly Ser Gly Leu Val Asn Ala Glu Ala Ala Thr Arg
            260                 265

<210> SEQ ID NO 60
<211> LENGTH: 269
<212> TYPE: PRT
<213> ORGANISM: B. lentus
<220> FEATURE:
<221> NAME/KEY: misc_feature
<222> LOCATION: (1)..(269)
<223> OTHER INFORMATION: Ble_P29600

<400> SEQUENCE: 60

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205
```

```
Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 61
<211> LENGTH: 269
<212> TYPE: PRT
<213> ORGANISM: B. alcalophilus
<220> FEATURE:
<221> NAME/KEY: misc_feature
<222> LOCATION: (1)..(269)
<223> OTHER INFORMATION: B_alcalophilus_AAA22212

<400> SEQUENCE: 61

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 62
<211> LENGTH: 275
<212> TYPE: PRT
```

```
<213> ORGANISM: Bacillus sp.
<220> FEATURE:
<221> NAME/KEY: misc_feature
<222> LOCATION: (1)..(275)
<223> OTHER INFORMATION: Bsp_AAC43580

<400> SEQUENCE: 62
```

Ala Gln Thr Val Pro Trp Gly Ile Pro His Ile Lys Ala Asp Lys Ala
1               5                   10                  15

His Ala Ala Gly Val Thr Gly Ser Gly Val Lys Val Ala Ile Leu Asp
            20                  25                  30

Thr Gly Ile Asp Ala Asn His Ala Asp Leu Asn Val Lys Gly Gly Ala
        35                  40                  45

Ser Phe Val Ser Gly Glu Pro Asn Ala Leu Gln Asp Gly Asn Gly His
    50                  55                  60

Gly Thr His Val Ala Gly Thr Val Ala Ala Leu Asn Asn Thr Thr Gly
65                  70                  75                  80

Val Leu Gly Val Ala Tyr Asn Ala Asp Leu Tyr Ala Val Lys Val Leu
                85                  90                  95

Ser Ala Ser Gly Ser Gly Thr Leu Ser Gly Ile Ala Gln Gly Ile Glu
            100                 105                 110

Trp Ser Ile Ser Asn Gly Met Asn Val Ile Asn Met Ser Leu Gly Gly
        115                 120                 125

Ser Ser Gly Ser Thr Ala Leu Gln Gln Ala Cys Asn Asn Ala Tyr Asn
    130                 135                 140

Arg Gly Ile Val Val Ile Ala Ala Ala Gly Asn Ser Gly Ser Ser Gly
145                 150                 155                 160

Asn Arg Asn Thr Met Gly Tyr Pro Ala Arg Tyr Ser Ser Val Ile Ala
                165                 170                 175

Val Gly Ala Val Ser Ser Asn Asn Thr Arg Ala Ser Phe Ser Ser Val
            180                 185                 190

Gly Ser Glu Leu Glu Val Met Ala Pro Gly Val Asn Ile Leu Ser Thr
        195                 200                 205

Thr Pro Gly Asn Asn Tyr Ala Ser Phe Asn Gly Thr Ser Met Ala Ala
    210                 215                 220

Pro His Val Ala Gly Ala Ala Ala Leu Ile Lys Ala Lys Tyr Pro Ser
225                 230                 235                 240

Met Thr Asn Val Gln Ile Arg Glu Arg Leu Lys Asn Thr Ala Thr Asn
                245                 250                 255

Leu Gly Asp Pro Phe Phe Tyr Gly Lys Gly Val Ile Asn Val Glu Ser
            260                 265                 270

Ala Leu Gln
    275

```
<210> SEQ ID NO 63
<211> LENGTH: 276
<212> TYPE: PRT
<213> ORGANISM: Bacillus sp.
<220> FEATURE:
<221> NAME/KEY: misc_feature
<222> LOCATION: (1)..(276)
<223> OTHER INFORMATION: Bacillus_sp_BAD21128

<400> SEQUENCE: 63
```

Ser Gln Thr Val Pro Tyr Gly Val Pro His Ile Lys Ala Asp Val Ala
1               5                   10                  15

His Ser Gln Asn Val Thr Gly Asn Gly Val Lys Val Ala Ile Leu Asp
            20                  25                  30

-continued

```
Thr Gly Ile Asp Ala Ala His Glu Asp Leu Arg Val Gly Gly Ala
        35                  40                  45

Ser Phe Val Ala Gly Glu Pro Asn Ala Leu Gln Asp Gly Asn Gly His
50                  55                  60

Gly Thr His Val Ala Gly Thr Val Ala Ala Leu Asn Asn Gln Val Gly
65                  70                  75                  80

Val Leu Gly Val Ala Tyr Asp Val Asp Leu Tyr Ala Val Lys Val Leu
                85                  90                  95

Gly Ala Asp Gly Ser Gly Thr Leu Ser Gly Ile Ala Gln Gly Ile Glu
            100                 105                 110

Trp Ser Ile Ala Asn Asn Met Asp Val Ile Asn Met Ser Leu Gly Gly
        115                 120                 125

Ser Thr Gly Ser Thr Thr Leu Lys Gln Ala Ala Asp Asn Ala Tyr Asn
130                 135                 140

Ser Gly Leu Val Val Ala Ala Gly Asn Ser Gly Asp Phe Phe
145                 150                 155                 160

Gly Leu Ile Asn Thr Ile Gly Tyr Pro Ala Arg Tyr Asp Ser Val Ile
                165                 170                 175

Ala Val Gly Ala Val Asp Ser Asn Asn Arg Ala Ser Phe Ser Ser
            180                 185                 190

Val Gly Ser Gln Leu Glu Val Met Ala Pro Gly Val Asn Ile Leu Ser
        195                 200                 205

Thr Leu Pro Gly Asn Ser Tyr Gly Ser Leu Asn Gly Thr Ser Met Ala
210                 215                 220

Ser Pro His Val Ala Gly Ala Ala Leu Leu Ala Gln Asp Pro
225                 230                 235                 240

Thr Leu Thr Asn Val Gln Val Arg Glu Ile Leu Arg Asp Thr Ala Thr
                245                 250                 255

Asn Leu Gly Ser Ser Phe Tyr Tyr Gly Asn Gly Val Ile Asp Val Glu
            260                 265                 270

Lys Ala Leu Gln
        275
```

<210> SEQ ID NO 64
<211> LENGTH: 275
<212> TYPE: PRT
<213> ORGANISM: Bacillus sp.
<220> FEATURE:
<221> NAME/KEY: misc_feature
<222> LOCATION: (1)..(275)
<223> OTHER INFORMATION: Bacillus_sp_BAD11988

<400> SEQUENCE: 64

```
Ala Gln Thr Thr Pro Trp Gly Val Thr His Ile Asn Ala His Arg Ala
1               5                   10                  15

His Ser Ser Gly Val Thr Gly Ser Gly Val Lys Val Ala Ile Leu Asp
                20                  25                  30

Thr Gly Ile His Ala Ser His Pro Asp Leu Asn Val Arg Gly Gly Ala
        35                  40                  45

Ser Phe Ile Ser Gly Glu Ser Asn Pro Tyr Ile Asp Ser Asn Gly His
50                  55                  60

Gly Thr His Val Ala Gly Thr Val Ala Ala Leu Asn Asn Thr Val Gly
65                  70                  75                  80

Val Leu Gly Val Ala Tyr Asn Ala Glu Leu Tyr Ala Val Lys Val Leu
                85                  90                  95
```

Ser Ala Ser Gly Ser Gly Thr Leu Ser Gly Ile Ala Gln Gly Val Glu
            100                 105                 110

Trp Ser Ile Ala Asn Lys Met Asp Val Ile Asn Met Ser Leu Gly Gly
        115                 120                 125

Ser Ser Gly Ser Thr Ala Leu Gln Arg Ala Val Asp Asn Ala Tyr Arg
    130                 135                 140

Asn Asn Ile Val Val Ala Ala Gly Asn Ser Gly Ala Gln Gly
145                 150                 155                 160

Asn Arg Asn Thr Ile Gly Tyr Pro Ala Arg Tyr Ser Ser Val Ile Ala
                165                 170                 175

Val Gly Ala Val Asp Ser Asn Asn Arg Ala Ser Phe Ser Ser Val
            180                 185                 190

Gly Ser Glu Leu Glu Val Met Ala Pro Gly Val Ser Ile Leu Ser Thr
    195                 200                 205

Val Pro Gly Ser Ser Tyr Ala Ser Tyr Asn Gly Thr Ser Met Ala Ser
        210                 215                 220

Pro His Val Ala Gly Ala Ala Leu Leu Lys Ala Lys Tyr Pro Asn
225                 230                 235                 240

Trp Ser Ala Ala Gln Ile Arg Asn Lys Leu Asn Ser Thr Thr Tyr
                245                 250                 255

Leu Gly Ser Ser Phe Tyr Tyr Gly Asn Gly Val Ile Asn Val Glu Arg
            260                 265                 270

Ala Leu Gln
        275

<210> SEQ ID NO 65
<211> LENGTH: 276
<212> TYPE: PRT
<213> ORGANISM: Bacillus sp.
<220> FEATURE:
<221> NAME/KEY: misc_feature
<222> LOCATION: (1)..(276)
<223> OTHER INFORMATION: B_sp_sprD_AAC43581

<400> SEQUENCE: 65

Ala Gln Thr Val Pro Tyr Gly Val Pro His Ile Lys Ala Asp Val Ala
1               5                   10                  15

His Ala Gln Asn Val Thr Gly Ser Gly Val Lys Val Ala Val Leu Asp
            20                  25                  30

Thr Gly Ile Asp Ala Ser His Glu Asp Leu Arg Val Gly Gly Ala
            35                  40                  45

Ser Phe Val Ser Glu Glu Pro Asp Ala Leu Thr Asp Gly Asn Gly His
    50                  55                  60

Gly Thr His Val Ala Gly Thr Ile Ala Ala Leu Asn Asn Val Gly
65                  70                  75                  80

Val Leu Gly Val Ser Tyr Asp Val Asp Leu Tyr Ala Val Lys Val Leu
                85                  90                  95

Ser Ala Gly Gly Ser Gly Thr Leu Ala Gly Ile Ala Gln Gly Ile Glu
            100                 105                 110

Trp Ala Ile Asp Asn Asn Met Asp Val Ile Asn Met Ser Leu Gly Gly
        115                 120                 125

Ser Thr Gly Ser Thr Thr Leu Lys Gln Ala Ser Asp Asn Ala Tyr Asn
    130                 135                 140

Ser Gly Ile Val Val Ile Ala Ala Gly Asn Ser Gly Ser Val Leu
145                 150                 155                 160

Gly Leu Val Asn Thr Ile Gly Tyr Pro Ala Arg Tyr Asp Ser Val Ile

```
                165                 170                 175
Ala Val Gly Ala Val Asp Ser Asn Asn Asn Arg Ala Ser Phe Ser Ser
            180                 185                 190

Val Gly Ser Gln Leu Glu Val Met Ala Pro Gly Val Ala Ile Asn Ser
        195                 200                 205

Thr Leu Pro Gly Asn Gln Tyr Gly Glu Leu Asn Gly Thr Ser Met Ala
    210                 215                 220

Ser Pro His Val Ala Gly Ala Ala Leu Leu Leu Ala Gln Asn Pro
225                 230                 235                 240

Asn Leu Thr Asn Val Gln Val Arg Glu Arg Leu Arg Asp Thr Ala Thr
                245                 250                 255

Asn Leu Gly Ser Ala Phe Asn Tyr Gly His Gly Val Ile Asn Leu Glu
            260                 265                 270

Arg Ala Leu Gln
        275

<210> SEQ ID NO 66
<211> LENGTH: 274
<212> TYPE: PRT
<213> ORGANISM: B. sonorensis
<220> FEATURE:
<221> NAME/KEY: misc_feature
<222> LOCATION: (1)..(274)
<223> OTHER INFORMATION: B_sonorensis_WP_006636716

<400> SEQUENCE: 66

Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Gly Ile Ile Asp
            20                  25                  30

Thr Gly Ile Ala Ser His Thr Asp Leu Lys Val Val Gly Gly Ala
        35                  40                  45

Ser Phe Val Ser Gly Glu Ser Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Ile Lys Val Leu Asn
                85                  90                  95

Ser Ser Gly Ser Gly Thr Tyr Ser Ala Ile Val Ser Gly Ile Glu Trp
            100                 105                 110

Ala Thr Gln Asn Gly Leu Asp Val Ile Asn Met Ser Leu Gly Gly Pro
        115                 120                 125

Ser Gly Ser Thr Ala Leu Lys Gln Ala Val Asp Lys Ala Tyr Ala Ser
    130                 135                 140

Gly Ile Val Val Val Ala Ala Ala Gly Asn Ser Gly Ser Ser Gly Ser
145                 150                 155                 160

Gln Asn Thr Ile Gly Tyr Pro Ala Lys Tyr Asp Ser Val Ile Ala Val
                165                 170                 175

Gly Ala Val Asp Ser Asn Lys Asn Arg Ala Ser Phe Ser Ser Val Gly
            180                 185                 190

Ser Glu Leu Glu Val Met Ala Pro Gly Val Ser Val Tyr Ser Thr Tyr
        195                 200                 205

Pro Ser Asn Thr Tyr Thr Ser Leu Asn Gly Thr Ser Met Ala Ser Pro
    210                 215                 220

His Val Ala Gly Ala Ala Ala Leu Ile Leu Ser Lys Tyr Pro Thr Leu
225                 230                 235                 240
```

Ser Ala Ser Gln Val Arg Asn Arg Leu Ser Ser Thr Ala Thr Asn Leu
            245                 250                 255

Gly Asp Ser Phe Tyr Tyr Gly Lys Gly Leu Ile Asn Val Glu Ala Ala
            260                 265                 270

Ala Gln

<210> SEQ ID NO 67
<211> LENGTH: 274
<212> TYPE: PRT
<213> ORGANISM: B. licheniformis
<220> FEATURE:
<221> NAME/KEY: misc_feature
<222> LOCATION: (1)..(274)
<223> OTHER INFORMATION: Bli_CAJ70731

<400> SEQUENCE: 67

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 68
<211> LENGTH: 275
<212> TYPE: PRT
<213> ORGANISM: B. pumilus

-continued

```
<220> FEATURE:
<221> NAME/KEY: misc_feature
<222> LOCATION: (1)..(275)
<223> OTHER INFORMATION: B_pumilus_ADK11996

<400> SEQUENCE: 68

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Ala Ser Gly Ser Thr Ala Leu Lys Asn Ala Val Asp Thr Ala Asn Asn
    130                 135                 140

Arg Gly Val Val Val Ala Ala Gly Asn Ser Gly Ser Ser Gly
145                 150                 155                 160

Ser Arg Ser Thr Val Gly Tyr Pro Ala Lys Tyr Glu Ser Thr Ile Ala
                165                 170                 175

Val Ala Asn Val Asn Ser Asn Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Asn Pro Asn
225                 230                 235                 240

Leu Thr Asn Ser Gln Val Arg Gln Arg Leu Glu Asn Thr Ala Thr Pro
                245                 250                 255

Leu Gly Asp Ser Phe Tyr Tyr Gly Lys Gly Leu Ile Asn Val Gln Ala
            260                 265                 270

Ala Ser Asn
        275

<210> SEQ ID NO 69
<211> LENGTH: 275
<212> TYPE: PRT
<213> ORGANISM: B. circulans
<220> FEATURE:
<221> NAME/KEY: misc_feature
<222> LOCATION: (1)..(275)
<223> OTHER INFORMATION: B_circulans_ADN04910

<400> SEQUENCE: 69

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
            20                  25                  30
```

```
Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
 50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                 85                  90                  95

Asp Arg Asn Gly Asp Gly Gln Tyr Ser Trp Ile Ile Ser Gly Ile Glu
                100                 105                 110

Trp Ala Val Ala Asn Asn Met Asp Val Ile Asn Met Ser Leu Gly Gly
            115                 120                 125

Pro Asn Gly Ser Thr Ala Leu Lys Asn Ala Val Asp Thr Ala Asn Asn
130                 135                 140

Arg Gly Val Val Val Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Arg Gly Tyr Thr Ser Tyr Thr Gly Thr Ser Met Ala Ser
210                 215                 220

Pro His Val Ala Gly Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Val Gln Ala
                260                 265                 270

Ala Ser Asn
        275

<210> SEQ ID NO 70
<211> LENGTH: 275
<212> TYPE: PRT
<213> ORGANISM: B. stratosphericus
<220> FEATURE:
<221> NAME/KEY: misc_feature
<222> LOCATION: (1)..(275)
<223> OTHER INFORMATION: B_stratosphericus_WP_007497196

<400> SEQUENCE: 70

Ala Gln Thr Val Pro Tyr Gly Ile Pro Gln Ile Lys Ala Pro Ala Val
 1               5                  10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
 50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                 85                  90                  95

Asp Arg Asn Gly Asp Gly Gln Tyr Ser Trp Ile Ile Ser Gly Ile Glu
```

```
            100                 105                 110

Trp Ala Val Ala Asn Asn Met Asp Val Ile Asn Met Ser Leu Gly Gly
        115                 120                 125

Pro Ser Gly Ser Thr Ala Leu Lys Asn Ala Val Asp Thr Ala Asn Asn
    130                 135                 140

Arg Gly Val Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Asn Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

Pro His Val Ala Gly Ala Ala Ala Leu Ile Leu Ser Lys Tyr Pro Asn
225                 230                 235                 240

Leu Ser Thr Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Val Gln Ala
            260                 265                 270

Ala Ser Asn
        275

<210> SEQ ID NO 71
<211> LENGTH: 276
<212> TYPE: PRT
<213> ORGANISM: B. lehensis
<220> FEATURE:
<221> NAME/KEY: misc_feature
<222> LOCATION: (1)..(276)
<223> OTHER INFORMATION: B_lehensis_AFP23380.1

<400> SEQUENCE: 71

Met Ala Gln Thr Val Pro Tyr Gly Ile Pro Gln Ile Lys Ala Pro Ala
1               5                   10                  15

Val His Ala Gln Gly Tyr Lys Gly Ala Asn Val Lys Val Ala Val Leu
            20                  25                  30

Asp Thr Gly Ile His Ala Ala His Pro Asp Leu Asn Val Ala Gly Gly
        35                  40                  45

Ala Ser Phe Val Pro Ser Glu Pro Asn Ala Thr Gln Asp Phe Gln Ser
    50                  55                  60

His Gly Thr His Val Ala Gly Thr Ile Ala Ala Leu Asp Asn Thr Ile
65                  70                  75                  80

Gly Val Leu Gly Val Ala Pro Ser Ala Ser Leu Tyr Ala Val Lys Val
                85                  90                  95

Leu Asp Arg Tyr Gly Asp Gly Gln Tyr Ser Trp Ile Ile Ser Gly Ile
            100                 105                 110

Glu Trp Ala Val Ala Asn Asn Met Asp Val Ile Asn Met Ser Leu Gly
        115                 120                 125

Gly Pro Asn Gly Ser Thr Ala Leu Lys Asn Ala Val Asp Thr Ala Asn
    130                 135                 140

Asn Arg Gly Val Val Val Val Ala Ala Ala Gly Asn Ser Gly Ser Thr
145                 150                 155                 160

Gly Ser Thr Ser Thr Val Gly Tyr Pro Ala Lys Tyr Asp Ser Thr Ile
                165                 170                 175
```

```
Ala Val Ala Asn Val Asn Ser Asn Asn Val Arg Asn Ser Ser Ser Ser
            180                 185                 190

Ala Gly Pro Glu Leu Asp Val Ser Ala Pro Gly Thr Ser Ile Leu Ser
            195                 200                 205

Thr Val Pro Ser Ser Gly Tyr Thr Ser Tyr Thr Gly Thr Ser Met Ala
    210                 215                 220

Ser Pro His Val Ala Gly Ala Ala Leu Ile Leu Ser Lys Tyr Pro
225                 230                 235                 240

Asn Leu Ser Thr Ser Gln Val Arg Gln Arg Leu Glu Asn Thr Ala Thr
                245                 250                 255

Pro Leu Gly Asn Ser Phe Tyr Tyr Gly Lys Gly Leu Ile Asn Val Gln
            260                 265                 270

Ala Ala Ser Asn
        275

<210> SEQ ID NO 72
<211> LENGTH: 275
<212> TYPE: PRT
<213> ORGANISM: B. atrophaeus
<220> FEATURE:
<221> NAME/KEY: misc_feature
<222> LOCATION: (1)..(275)
<223> OTHER INFORMATION: B_atrophaeus_YP003972439

<400> SEQUENCE: 72

Ala Gln Ser Val Pro Tyr Gly Ile Ser Gln Ile Lys Ala Pro Ala Val
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ser Gly Gly Ala
        35                  40                  45

Ser Phe Val Pro Ser Glu Pro Asn Pro Phe Gln Asp Gly Asn Ser His
    50                  55                  60

Gly Thr His Val Ala Gly Thr Val Ala Ala Leu Asn Asn Ser Val Gly
65                  70                  75                  80

Val Leu Gly Val Ala Pro Ser Ala Ser Leu Tyr Ala Val Lys Val Leu
                85                  90                  95

Ser Ser Ser Gly Ser Gly Asp Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Gln Gly Ser Thr Ala Leu Lys Ala Val Val Asp Lys Ala Val Ser
    130                 135                 140

Gln Gly Ile Val Val Ala Ala Ala Gly Asn Ser Gly Ser Ser Gly
145                 150                 155                 160

Ser Thr Ser Thr Val Gly Tyr Pro Ala Lys Tyr Pro Ser Val Ile Ala
                165                 170                 175

Val Gly Ala Val Asp Ser Asn Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Ser Ser Tyr Gly Ser Tyr Asn Gly Thr Ser Met Ala Ser
    210                 215                 220

Pro His Val Ala Gly Ala Ala Leu Val Leu Ser Lys His Pro Asn
225                 230                 235                 240
```

-continued

Trp Thr Asn Ser Gln Val Arg Asn Ser Leu Glu Ser Thr Ala Thr Asn
            245                 250                 255

Leu Gly Asn Ser Phe Tyr Tyr Gly Lys Gly Leu Ile Asn Val Gln Ala
        260                 265                 270

Ala Ala Gln
    275

<210> SEQ ID NO 73
<211> LENGTH: 275
<212> TYPE: PRT
<213> ORGANISM: B. amyloliquefaciens
<220> FEATURE:
<221> NAME/KEY: misc_feature
<222> LOCATION: (1)..(275)
<223> OTHER INFORMATION: Bam_CAA24990

<400> SEQUENCE: 73

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
    275

<210> SEQ ID NO 74
<211> LENGTH: 275
<212> TYPE: PRT

<213> ORGANISM: G. stearothermophilus
<220> FEATURE:
<221> NAME/KEY: misc_feature
<222> LOCATION: (1)..(275)
<223> OTHER INFORMATION: G_stearothermophilus_ABY25856

<400> SEQUENCE: 74

Ala Gln Ser Val Pro Tyr Gly Val Ser Gln Ile Lys Ala Pro Ala Leu
1               5                   10                  15

His Ser Gln Gly Phe Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Val Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Tyr Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Ile Val Val Ala Ala Ala Gly Asn Glu Gly Thr Ser Gly Ser
145                 150                 155                 160

Ser Ser Ser Thr Val Gly Tyr Pro Gly Lys Tyr Pro Ser Val Ile Ala
                165                 170                 175

Val Gly Ala Val Asn Ser Ser Asn Gln Arg Ala Ser Phe Ser Ser Val
            180                 185                 190

Gly Ser Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ala Phe Tyr Tyr Gly Lys Gly Leu Ile Asn Val Gln Ala
            260                 265                 270

Ala Ala Gln
        275

<210> SEQ ID NO 75
<211> LENGTH: 275
<212> TYPE: PRT
<213> ORGANISM: B. methylotrophicus
<220> FEATURE:
<221> NAME/KEY: misc_feature
<222> LOCATION: (1)..(275)
<223> OTHER INFORMATION: B_methylotrophicus_AGC81872.1

<400> SEQUENCE: 75

Ala Gln Ser Val Pro Tyr Gly Val Ser Gln Ile Lys Ala Pro Ala Leu
1               5                   10                  15

His Ser Gln Gly Phe Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Arg Asn Ser His
    50                  55                  60

Gly Thr His Val Ala Gly Thr Val Ala Ala Leu Asn Asn Ser Val Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
        130                 135                 140

Ser Gly Val Val Val Ala Ala Ala Gly Asn Glu Gly Thr Ser Gly Ser
145                 150                 155                 160

Gly Ser Ser Thr Val Gly Tyr Pro Gly Lys Tyr Pro Ser Val Ile Ala
                165                 170                 175

Val Gly Ala Val Asn Ser Ser Asn Gln Arg Ala Ser Phe Ser Ser Val
                180                 185                 190

Gly Ser Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ala Phe Tyr Tyr Gly Lys Gly Leu Ile Asn Val Gln Ala
            260                 265                 270

Ala Ala Gln
        275

<210> SEQ ID NO 76
<211> LENGTH: 275
<212> TYPE: PRT
<213> ORGANISM: B. vallismortis
<220> FEATURE:
<221> NAME/KEY: misc_feature
<222> LOCATION: (1)..(275)
<223> OTHER INFORMATION: B_vallismortis_WP010329279

<400> SEQUENCE: 76

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Val Ala Ala Leu Asn Asn Ser Ile Gly
65                  70                  75                  80

Val Leu Gly Val Ala Pro Asn Ala Ser Leu Tyr Ala Val Lys Val Leu
                85                  90                  95

-continued

```
Asp Ser Thr Gly Asn Gly Gln Tyr Ser Trp Ile Ile Asn Gly Ile Glu
            100                 105                 110

Trp Ala Ile Ser Asn Lys Met Asp Val Ile Asn Met Ser Leu Gly Gly
            115                 120                 125

Pro Ser Gly Ser Thr Ala Leu Lys Ser Val Val Asp Arg Ala Val Ala
            130                 135                 140

Ser Gly Ile Val Val Ala Ala Ala Gly Asn Glu Gly Thr Ser Gly
145                 150                 155                 160

Ser Ser Ser Thr Ile Gly Tyr Pro Ala Lys Tyr Pro Ser Thr Ile Ala
                165                 170                 175

Val Gly Ala Val Asn Ser Ser Asn Gln Arg Gly Ser Phe Ser Ser Val
            180                 185                 190

Gly Pro Glu Leu Asp Val Met Ala Pro Gly Val Ser Ile Gln Ser Thr
            195                 200                 205

Leu Pro Gly Gly Thr Tyr Gly Ser Tyr Asn Gly Thr Ser Met Ala Thr
            210                 215                 220

Pro His Val Ala Gly Ala Ala Leu Ile Leu Ser Lys His Pro Thr
225                 230                 235                 240

Trp Thr Asn Thr Gln Val Arg Asn Arg Leu Glu Ser Thr Thr Tyr
            245                 250                 255

Leu Gly Ser Ser Phe Tyr Tyr Gly Lys Gly Leu Ile Asn Val Gln Ala
            260                 265                 270

Ala Ala Gln
        275

<210> SEQ ID NO 77
<211> LENGTH: 275
<212> TYPE: PRT
<213> ORGANISM: B. subtilis
<220> FEATURE:
<221> NAME/KEY: misc_feature
<222> LOCATION: (1)..(275)
<223> OTHER INFORMATION: B_subtilis_str168_CAA74536.1

<400> SEQUENCE: 77

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
        50                  55                  60

Gly Thr His Val Ala Gly Thr Ile Ala Ala Leu Asn Asn Ser Ile Gly
65                  70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
            115                 120                 125

Pro Thr Gly Ser Thr Ala Leu Lys Thr Val Val Asp Lys Ala Val Ser
            130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
```

```
                    165                 170                 175
Val Gly Ala Val Asn Ser Ser Asn Gln Arg Ala Ser Phe Ser Ser Ala
                180                 185                 190

Gly Ser Glu Leu Asp Val Met Ala Pro Gly Val Ser Ile Gln Ser Thr
            195                 200                 205

Leu Pro Gly Gly Thr Tyr Gly Ala Tyr Asn Gly Thr Ser Met Ala Thr
        210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
                260                 265                 270

Ala Ala Gln
        275

<210> SEQ ID NO 78
<211> LENGTH: 275
<212> TYPE: PRT
<213> ORGANISM: B. subtilis
<220> FEATURE:
<221> NAME/KEY: misc_feature
<222> LOCATION: (1)..(275)
<223> OTHER INFORMATION: B_subtilis_BAN09118

<400> SEQUENCE: 78

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
        50                  55                  60

Gly Thr His Val Ala Gly Thr Val Ala Ala Leu Asn Asn Thr Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ala
130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
                180                 185                 190

Gly Ser Glu Leu Asp Val Met Ala Pro Gly Val Ser Ile Gln Ser Thr
            195                 200                 205

Leu Pro Gly Gly Thr Tyr Gly Ser Tyr Asn Gly Thr Ser Met Ala Thr
        210                 215                 220

Pro His Val Ala Gly Ala Ala Ala Leu Ile Leu Ser Lys His Pro Thr
225                 230                 235                 240
```

Trp Ser Asn Ala Gln Val Arg Asp Arg Leu Glu Ser Thr Ala Thr Asn
                245                 250                 255

Leu Gly Ser Ser Phe Tyr Tyr Gly Lys Gly Leu Ile Asn Val Gln Ala
            260                 265                 270

Ala Ala Gln
        275

<210> SEQ ID NO 79
<211> LENGTH: 275
<212> TYPE: PRT
<213> ORGANISM: B. mojavensis
<220> FEATURE:
<221> NAME/KEY: misc_feature
<222> LOCATION: (1)..(275)
<223> OTHER INFORMATION: B_mojavensis_WP010333625

<400> SEQUENCE: 79

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Val Ala Ala Leu Asn Asn Thr Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ala
    130                 135                 140

Ser Gly Ile Val Val Ala Ala Ala Gly Asn Glu Gly Ser Ser Gly Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Ser Ser Phe Tyr Tyr Gly Lys Gly Leu Ile Asn Val Gln Ala
            260                 265                 270

Ala Ala Gln
        275

<210> SEQ ID NO 80
<211> LENGTH: 273

```
<212> TYPE: PRT
<213> ORGANISM: B. marmarensis
<220> FEATURE:
<221> NAME/KEY: misc_feature
<222> LOCATION: (1)..(273)
<223> OTHER INFORMATION: B_marmarensis_ERN52602.1

<400> SEQUENCE: 80
```

Ala Gln Thr Val Pro Trp Gly Ile Pro Tyr Ile Tyr Ser Asp Val Val
1               5                   10                  15

His Arg Gln Gly Tyr Phe Gly Asn Gly Val Lys Val Ala Val Leu Asp
            20                  25                  30

Thr Gly Val Ala Pro His Pro Asp Leu His Ile Arg Gly Gly Val Ser
        35                  40                  45

Phe Ile Pro Thr Glu Asn Thr Tyr Val Asp Tyr Asn Gly His Gly Thr
    50                  55                  60

His Val Ala Gly Thr Val Ala Ala Leu Asn Asn Ser Tyr Gly Val Leu
65                  70                  75                  80

Gly Val Ala Pro Gly Ala Glu Leu Tyr Ala Val Lys Val Leu Asp Arg
                85                  90                  95

Asn Gly Ser Gly Ser His Ala Ser Ile Ala Gln Gly Ile Glu Trp Ala
            100                 105                 110

Met Asn Asn Gly Met Asp Ile Ala Asn Met Ser Leu Gly Ser Pro Ser
        115                 120                 125

Gly Ser Thr Thr Leu Gln Leu Ala Ala Asp Arg Ala Arg Asn Ala Gly
    130                 135                 140

Val Leu Leu Ile Gly Ala Ala Gly Asn Ser Gly Gln Gln Gly Gly Ser
145                 150                 155                 160

Asn Asn Met Gly Tyr Pro Ala Arg Tyr Ala Ser Val Met Ala Val Gly
                165                 170                 175

Ala Val Asp Gln Asn Gly Asn Arg Ala Asn Phe Ser Ser Tyr Gly Ser
            180                 185                 190

Glu Leu Glu Ile Met Ala Pro Gly Val Asn Ile Asn Ser Thr Tyr Leu
        195                 200                 205

Asn Asn Gly Tyr Arg Ser Leu Asn Gly Thr Ser Met Ala Ser Pro His
    210                 215                 220

Val Ala Gly Val Ala Ala Leu Val Lys Gln Lys His Pro His Leu Thr
225                 230                 235                 240

Ala Ala Gln Ile Arg Asn Arg Met Asn Gln Thr Ala Ile Pro Leu Gly
                245                 250                 255

Asn Ser Thr Tyr Tyr Gly Asn Gly Leu Val Asp Ala Glu Tyr Ala Ala
            260                 265                 270

Gln

```
<210> SEQ ID NO 81
<211> LENGTH: 249
<212> TYPE: PRT
<213> ORGANISM: Artificial Sequence
<220> FEATURE:
<223> OTHER INFORMATION: Synthetic: Consensus sequence

<400> SEQUENCE: 81
```

Ala Gln Thr Val Pro Trp Gly Ile Ser Ile Lys Ala Pro Ala Val His
1               5                   10                  15

Ser Gln Gly Tyr Thr Gly Ser Gly Val Lys Val Ala Val Leu Asp Thr
            20                  25                  30

Gly Ile Ala Ser Ser His Pro Asp Leu Val Gly Gly Ala Ser Phe Val

```
                35                  40                  45
Pro Ser Glu Pro Tyr Gln Asp Gly Asn Gly His Gly Thr His Val Ala
 50                  55                  60

Gly Thr Ile Ala Ala Leu Asn Asn Ser Ile Gly Val Leu Gly Val Ala
 65                  70                  75                  80

Pro Ser Ala Asp Leu Tyr Ala Val Lys Val Leu Ala Gly Ser Gly Ser
                 85                  90                  95

Tyr Ser Ile Ala Gln Gly Ile Glu Trp Ala Ile Asn Asn Met Asp Val
                100                 105                 110

Ile Asn Met Ser Leu Gly Gly Pro Ser Gly Ser Thr Thr Leu Ala Val
                115                 120                 125

Asp Ala Ala Ser Gly Val Val Val Ala Ala Gly Asn Ser Gly
                130                 135                 140

Ser Gly Thr Val Gly Tyr Pro Ala Arg Tyr Ala Ser Val Ile Ala Val
145                 150                 155                 160

Gly Ala Val Asp Ser Asn Asn Asn Arg Ala Ser Phe Ser Ser Gly Ser
                165                 170                 175

Glu Leu Asp Val Met Ala Pro Gly Val Ile Gln Ser Thr Leu Pro Gly
                180                 185                 190

Asn Tyr Gly Ser Tyr Asn Gly Thr Ser Met Ala Ser Pro His Val Ala
                195                 200                 205

Gly Ala Ala Ala Leu Val Lys Ser Lys Tyr Pro Ser Trp Thr Asn Gln
210                 215                 220

Ile Arg Asn Arg Leu Asn Thr Ala Thr Leu Gly Ser Phe Tyr Tyr Gly
225                 230                 235                 240

Gly Leu Ile Asn Val Ala Ala Thr Gln
                245

<210> SEQ ID NO 82
<211> LENGTH: 84
<212> TYPE: PRT
<213> ORGANISM: Artificial Sequence
<220> FEATURE:
<223> OTHER INFORMATION: Synthetic: GG36 pro-peptide sequence

<400> SEQUENCE: 82

Ala Glu Glu Ala Lys Glu Lys Tyr Leu Ile Gly Phe Asn Glu Gln Glu
 1                5                  10                  15

Ala Val Ser Glu Phe Val Glu Gln Val Glu Ala Asn Asp Glu Val Ala
                 20                  25                  30

Ile Leu Ser Glu Glu Glu Val Glu Ile Glu Leu Leu His Glu Phe
                 35                  40                  45

Glu Thr Ile Pro Val Leu Ser Val Glu Leu Ser Pro Glu Asp Val Asp
 50                  55                  60

Ala Leu Glu Leu Asp Pro Ala Ile Ser Tyr Ile Glu Glu Asp Ala Glu
 65                  70                  75                  80

Val Thr Thr Met

<210> SEQ ID NO 83
<211> LENGTH: 231
<212> TYPE: PRT
<213> ORGANISM: Artificial Sequence
<220> FEATURE:
<223> OTHER INFORMATION: Synthetic: consensus sequence

<400> SEQUENCE: 83

Ala Gln Thr Val Pro Trp Gly Ile Ile Ala Pro Val His Ser Gly Gly
```

```
  1               5                  10                 15
Gly Val Lys Val Ala Val Leu Asp Thr Gly Ile Ala Ser His Pro Asp
              20                 25                 30

Leu Arg Ile Gly Gly Ala Ser Phe Ser Glu Pro Ser Tyr Gln Asp Asn
              35                 40                 45

Gly His Gly Thr His Val Ala Gly Thr Ala Ala Leu Asn Asn Ser Gly
              50                 55                 60

Val Leu Gly Val Ala Pro Asn Val Leu Tyr Ala Val Lys Val Leu Asp
 65                70                 75                 80

Arg Asn Gly Ser Gly Ser Ser Ile Ala Gln Gly Ile Glu Trp Ala Ile
              85                 90                 95

Asn Gly Met Asp Val Val Asn Met Ser Leu Gly Gly Pro Gly Ser Thr
             100                105                110

Ala Leu Gln Ala Ala Asp Asn Ala Tyr Asn Arg Gly Val Leu Leu Ala
             115                120                125

Ala Ala Gly Asn Thr Gly Ser Gly Ile Ser Tyr Pro Ala Arg Tyr Ser
             130                135                140

Val Met Ala Val Gly Ala Val Asp Ser Asn Asn Asn Arg Ala Ser Phe
145                150                155                160

Ser Thr Gly Glu Leu Glu Ile Met Ala Pro Gly Val Ile Ser Thr Tyr
             165                170                175

Pro Asn Tyr Ser Leu Asn Gly Thr Ser Met Ala Ser Pro His Val Ala
             180                185                190

Gly Val Ala Ala Leu Val Lys Ser Lys Tyr Pro Ala Thr Asn Gln Ile
             195                200                205

Arg Asn Arg Leu Thr Ala Thr Leu Gly Ser Ser Tyr Tyr Gly Asn Gly
             210                215                220

Leu Val Asn Ala Arg Ala Ala
225                230

<210> SEQ ID NO 84
<211> LENGTH: 268
<212> TYPE: PRT
<213> ORGANISM: Artificial Sequence
<220> FEATURE:
<223> OTHER INFORMATION: Synthetic: amino acid sequence of the processed
      mature enzyme, BspU2193

<400> SEQUENCE: 84

Gln Thr Val Pro Trp Gly Ile Asn His Val Lys Ala Pro Thr Val His
 1               5                  10                 15

Asn Trp Gly Asn Val Gly Thr Gly Val Lys Val Ala Val Leu Asp Thr
              20                 25                 30

Gly Ile Ala Ser His Pro Asp Leu Arg Val Ser Gly Gly Ala Ser Phe
              35                 40                 45

Ile Pro Ser Glu Pro Thr Ile Gln Asp Phe Asn Gly His Gly Thr His
              50                 55                 60

Val Ala Gly Thr Val Ala Ala Leu Asn Asn Ser Ile Gly Val Leu Gly
 65                70                 75                 80

Val Ala Pro Asn Val Gln Leu Tyr Gly Val Lys Val Leu Asp Arg Asn
              85                 90                 95

Gly Gly Gly Ser His Ser Ala Ile Ala Gln Gly Ile Glu Trp Ser Ile
             100                105                110

Ser Asn Gly Met Asp Val Val Asn Met Ser Leu Gly Gly Ala Thr Ser
             115                120                125
```

```
Ser Thr Ala Leu Ser Gln Ala Val Ala Asn Ala Ser Asn Arg Gly Ile
    130                 135                 140

Leu Leu Ile Ala Ala Ser Gly Asn Thr Gly Arg Ala Gly Ile Gln Phe
145                 150                 155                 160

Pro Ala Arg Tyr Ser Gln Val Met Ala Val Gly Ala Val Asp Gln Asn
                165                 170                 175

Asn Arg Leu Ala Ser Phe Ser Thr Phe Gly Asn Glu Gln Glu Ile Val
            180                 185                 190

Ala Pro Gly Val Gly Ile Gln Ser Thr Tyr Leu Asn Asn Gly Tyr Ser
        195                 200                 205

Ser Leu Asn Gly Thr Ser Met Ala Ala Pro His Val Ala Gly Val Ala
    210                 215                 220

Ala Leu Val Met Ser Glu Tyr Pro Trp Ala Thr Ala Pro Gln Val Arg
225                 230                 235                 240

Gly Arg Leu Asn Asp Thr Ala Ile Pro Leu Gly Asn Ala Tyr Tyr Phe
                245                 250                 255

Gly Asn Gly Leu Val Asp Ala Ser Arg Ala Ala Tyr
            260                 265
```

<210> SEQ ID NO 85
<211> LENGTH: 255
<212> TYPE: PRT
<213> ORGANISM: Artificial Sequence
<220> FEATURE:
<223> OTHER INFORMATION: Synthetic: consensus sequence

<400> SEQUENCE: 85

```
Ala Gln Thr Val Pro Trp Gly Ile Ile Gln Ala Pro Val His Ser Gly
1               5                   10                  15

Asn Gly Asn Gly Val Arg Val Ala Val Leu Asp Ser Gly Val Ala Ser
                20                  25                  30

His Glu Asp Leu Arg Ile Ser Gly Gly Ser Phe Ile Ala Ser Glu Pro
            35                  40                  45

Ser Tyr Gln Asp Tyr Asn Gly His Gly Thr His Val Ala Gly Thr Ile
    50                  55                  60

Ala Gly Leu Asn Asn Ser Gly Val Leu Gly Val Ala Pro Asn Val Asn
65                  70                  75                  80

Leu Tyr Ala Val Lys Val Leu Asp Arg Asn Gly Ser Gly Ser His Ser
                85                  90                  95

Ala Ile Ala Gln Gly Ile Glu Trp Ser Val Ser Asn Gly Met His Val
            100                 105                 110

Val Asn Met Ser Leu Gly Gly Pro Thr Gly Ser Thr Thr Leu Gln Arg
        115                 120                 125

Ala Ala Asp Asn Ala Tyr Asn Arg Gly Val Leu Leu Ile Ala Ala Ala
    130                 135                 140

Gly Asn Thr Gly Ser Ala Gly Ile Ser Tyr Pro Ala Arg Tyr Ser Ser
145                 150                 155                 160

Val Met Ala Val Gly Ala Val Asp Ser Asn Asn Arg Ala Ser Phe Ser
                165                 170                 175

Ser Thr Phe Gly Glu Leu Glu Ile Met Ala Pro Gly Val Ile Asn Ser
            180                 185                 190

Thr Tyr Pro Thr Asn Tyr Ser Ser Leu Asn Gly Thr Ser Met Ala Ser
        195                 200                 205

Pro His Val Ala Gly Val Ala Ala Leu Val Lys Ala Arg Tyr Pro Ser
    210                 215                 220
```

```
Ala Thr Asn Ala Gln Ile Arg Gln Arg Leu Arg Thr Ala Thr Leu Gly
225                 230                 235                 240

Ser Ser Tyr Tyr Tyr Gly Asn Gly Leu Val Ala Arg Ala Ala Asn
                245                 250                 255
```

We claim:

1. A method for producing a recombinant polypeptide comprising:
   transforming a host cell with an expression vector comprising a polynucleotide encoding the recombinant polypeptide, wherein said recombinant polypeptide comprises an amino acid sequence having at least 90% sequence identity to the mature polypeptide SEQ ID NO: 3, or a fragment thereof, wherein said amino acid sequence or fragment has protease activity;
   cultivating said transformed host cell under conditions suitable for said host cell to produce said polypeptide; and
   recovering said polypeptide.

2. The method of claim 1, wherein said host cell is a filamentous fungus or bacterial cell.

3. The method of claim 1, wherein said host cell is selected from *Bacillus* spp., *Streptomyces* spp., *Escherichia* spp., *Aspergillus* spp., *Trichoderma* spp., *Pseudomonas* spp., *Corynebacterium* spp., *Saccharomyces* spp., and *Pichia* spp.

4. The method of claim 1, wherein said expression vector comprises a heterologous polynucleotide sequence encoding a heterologous pro-peptide.

5. The method of claim 1, wherein said expression vector comprises one or both of a heterologous promoter and a polynucleotide sequence encoding a heterologous signal peptide.

6. The method of claim 1, wherein said host cell is cultivated in a culture media or a fermentation broth.

7. The method of claim 1, wherein the amino acid sequence or fragment thereof has proteolytic activity in the presence of a surfactant.

* * * * *